US010925856B2

(12) United States Patent
Bristow et al.

(10) Patent No.: US 10,925,856 B2
(45) Date of Patent: Feb. 23, 2021

(54) METHODS AND COMPOSITIONS INVOLVING BUCINDOLOL FOR THE TREATMENT OF ATRIAL FIBRILLATION

(71) Applicant: ARCA Biopharma, Inc., Westminster, CO (US)

(72) Inventors: Michael Bristow, Englewood, CO (US); Christopher Dufton, Englewood, CO (US)

(73) Assignee: Arca Biopharma, Inc., Westminster, CO (US)

( * ) Notice: Subject to any disclaimer, the term of this patent is extended or adjusted under 35 U.S.C. 154(b) by 0 days.

(21) Appl. No.: 16/867,394

(22) Filed: May 5, 2020

(65) Prior Publication Data

US 2020/0268710 A1    Aug. 27, 2020

Related U.S. Application Data

(63) Continuation of application No. PCT/US2019/034019, filed on May 24, 2019.

(60) Provisional application No. 62/839,531, filed on Apr. 26, 2019, provisional application No. 62/676,788, filed on May 25, 2018.

(51) Int. Cl.
*A61K 31/4045* (2006.01)
*A61P 9/06* (2006.01)

(52) U.S. Cl.
CPC .......... *A61K 31/4045* (2013.01); *A61P 9/06* (2018.01)

(58) Field of Classification Search
CPC ..... A61K 8/9789; A61K 31/4045; A61P 9/04; A61P 9/06
See application file for complete search history.

(56) References Cited

U.S. PATENT DOCUMENTS

| | | | |
|---|---|---|---|
| 9,446,023 B2 | 9/2016 | Bristow et al. | |
| 9,763,916 B2 | 9/2017 | Bristow et al. | |
| 2009/0192128 A1 | 7/2009 | Worcel et al. | |
| 2015/0276717 A1* | 10/2015 | Liggett | C12Q 1/6883 435/6.12 |

OTHER PUBLICATIONS

Kao et al. (European J of Heart Failure, 2013, 15, 324-333) (Year: 2013).*
Aleong et al. (Circ Arrhythnn Electrophysiol, 2013, p. 137-143) (Year: 2013).*
Penn Medicine (https://www.pennmedicine.org/ updates/blogs/heart-and-vascular-blog/2014/october/ejection-fraction-what-the-numbers-mean, 2014). (Year: 2014).*
Black-Maier et al. (Expert Rev Cardiovasc Ther 13(6), 2015) (Year: 2015).*
Aleong, et al., "Adrenergic Receptor Polymorphisms and Prevention of Ventricular Arrhythmias with Bucindolol in Patients with Chronic Heart Failure," *Circulation: Arrhythmia and Electrophysiology*; 6(1): 137-143, 2012.
Aleong, et al., "New Onset Atrial Fibrillation Predicts Heart Failure Progression," *The American Journal of Medicine*, 127(10): 963-971, 2014.
Aleong, et al., Prevention of Atrial Fibrillation by Bucindolol is Dependent on the Beta-1 389 Arg/Gly Adrenergic Receptor Polymorphism, *JACC Heart Failure*, 1:338-44, 2013.
Aleong, et al., "Ventricular Myocardial Gene Expression in HFrEF Patients with Atrial Fibrillation (AF) vs. No AF, and Changes in Response to Beta-Blockade," *Circulation*, 136: Supp 1, A17316, 2017. (Abstract only).
Anderson, et al. "Long-Term (2 year) Beneficial Effects of Beta-Adrenergic Blockade with Bucindolol in Patients with Idiopathic Dilated Cardiomyopathy," *Journal of the American College of Cardiology*,17(6):1373-1381, 1991.
Becquemont, "Pharmacogenomics of Adverse Drug Reactions: Practical Applications and Perspectives," *Pharmacogenomics*, 10(6): 961-969, 2009.
Bradford, "CYP2D6 Allele Frequency in European Caucasians, Asians, Africans and Their Descendants," *Pharmacogenomics*, 3(2): 229-243, 2002.
Bristow, et al., "An Alpha2C-Adrenergic Receptor Polymorphism Alters the Norepinephrine-Lowering Effects and Therapeutic Response of the Beta-Blocker Bucindolol in Chronic Heart Failure," *Circulation: Heart Failure*,;3: 21-28, 2010.
Bristow, et al., "Effect of Baseline or Changes in Adrenergic Activity on Clinical Outcomes in the Beta-Blocker Evaluation of Survival Trial (BEST)," *Circulation*, 110(11):1437-1442, 2004.
Bristow, et al., "Structural and Functional Phenotyping of the Failing Heart: Is the Left Ventricular Ejection Fraction Obsolete?" *JACC-Heart Failure*, 5: 772-781, 2017.
Bunch, et al., "Increasing Time Between First Diagnosis of Atrial Fibrillation and Catheter Ablation Adversely Affects Long-Term Outcomes," *Heart Rhythm*, 10(9):1257-1262, 2013.
Butler, et al. "Developing Therapies for Heart Failure with Preserved Ejection Fraction: Current State and Future Directions," *JACC Heart Failure*, Apr. 2014; 2(2):97-112, 2014.
Butler, et al., Exploring New Endpoints for Patients with Heart Failure with Preserved Ejection Fraction. *Circulation: Heart Failure*,;9: e00358, 2016.
Chen-Scarabelli, et al., "Device-Detected Atrial Fibrillation: What To Do With Asymptomatic Patients," Journal of the American College of Cadiology, 65(3):281-294, 2015.
Cresci, et al., "Clinical and Genetic Modifiers of Long-Term Survival in Heart Failure," *Journal of the American College of Cardiology*, 54:432-444, 2009.
Davis, "Collaborative Research Group. Heart failure with Preserved and Reduced Left Ventricular Ejection Fraction in the Antihypertensive and Lipid-Lowering Treatment to Prevent Heart Attack Trial," *Circulation*,;118:2259-2267, 2008.
Dean, L. (2020). Tramadol Therapy and CYP2D6 Genotype. Medical Genetic Summaries (Internet). Retrieved Jul. 14, 2020, from: https://www.ncbi.nlm.nih.gov/books/NBK315950.

(Continued)

*Primary Examiner* — Umamaheswari Ramachandran
(74) *Attorney, Agent, or Firm* — Norton Rose Fulbright US LLP

(57) ABSTRACT

The current methods and compositions relate to treatment of atrial fibrillation with bucindolol in patients, including patients with heart failure, after being determined to be homozygous Arg389 in the $\beta_1$ adrenergic receptor gene.

24 Claims, 33 Drawing Sheets

(56) References Cited

OTHER PUBLICATIONS

Gaedigk, et al., "CYP2D6 Poor Metabolizer Status Can be Ruled Out by a Single Genotyping Assay for the −1584G Promoter Polymorphism," Clinical Chemistry, 49(6):1008-1011, 2003.

Gupta, "Heart Failure with Preserved Ejection Fraction in African Americans: The ARIC (Atherosclerosis Risk In Communities) Study," JACC: Heart Failure, 1(2):156-163, 2013.

Healey, et al., "Subclinical Atrial Fibrillation and the Risk of Stroke," New England Journal of Medicine, 366(2): 120-129, 2012.

Hussein, et al., "Radiofrequency Ablation of Persistent Atrial Fibrillation: Diagnosis-to-Ablation Time, Markers of Pathways of Atrial Remodeling, and Outcomes," Circulation: Arrhythmia and Electrophysiology, ;9(1): e003669, 2016.

International Search Report and Written Opinion Issued in Corresponding PCT Patent Application No. PCT/US2019/034019, dated Nov. 8, 2019.

Kao, et al., "Effect of Bucindolol on Heart Failure Outcomes and Heart Rate Response in Patients with Reduced Ejection Fraction Heart Failure and Atrial Fibrillation," European Journal of Heart Failure, 15:324-333, 2013.

Kotecha & Piccini, "Atrial Fibrillation in Heart Failure: What Should We Do?" European Heart Journal, 36: 3250-3257, 2015.

Kotecha, et al., "Efficacy of Beta Blockers in Patients with Heart Failure Plus Atrial Fibrillation: An Individual-Patient Data Meta Analysis," Lancet, 384:2235-2243, 2015.

Kotecha, et al., "Increased Stroke Risk in Atrial Fibrillation Patients with Heart Failure: Does Ejection Fraction Matter?" Stroke, 46: 608-609, 2015.

Kotecha et al., "Heart Failure With Preserved Ejection Fraction and Atrial Fibrillation: Vicious Twins," Journal of the American College of Cardiology, 68(20): 2217-2228, 2016.

Liggett, et al., "A Polymorphism Within a Highly Conserved Beta1-Adrenergic Receptor Motif Alters Beta-Blocker Response in Multiple Models and Human Heart Failure," PNAS, 103: 11288-11293, 2006.

Mason, et al., "A Gain-Of-Function Polymorphism in a G-Protein Coupling Domain of the Human Beta1-Adrenergic Receptor," J Biol Chem., 274:12670-12674, 1999.

Nasr, et al., "Prevention of Atrial Fibrillation Onset By Beta-Blocker Treatment in Heart Failure: A Meta-Analysis," European Heart Journal, 28: 457-462, 2007.

Nergardh, et al., "Maintenance of Sinus Rhythm with Metoprolol CR Initiated Before Cardioversion and Repeated Cardioversion of Atrial Fibrillation: A Randomized Double-Blind Placebo-Controlled Study," European Heart Journal, ;28:1351-1357, 2007.

O'Connor, et al., "Combinatorial Pharmacogenetic Interactions of Bucindolol and Beta1, a2c Adrenergic Receptor Polymorphisms," PLoS One, 7(10): e44324, 2012.

Perez, et al., "Beta 1-Adrenergic Receptor Polymorphisms Confer Differential Function and Predisposition to Heart Failure," Nature Medicine, 9:1300-1305, 2003.

Piccini, et al., "A Genotype-Directed Comparative Effectiveness Trial of Bucindolol and Metoprolol for Prevention of Symptomatic Atrial Fibrillation/Atrial Flutter in Patients with Heart Failure: Rationale and Design of the GENETIC-AF Trial,", American Heart Journal, 199: 51-58, 2018.

Ponikowski, et al., "2016 ESC Guidelines for the Diagnosis and Treatment of Acute and Chronic Heart Failure. The Task Force for the Diagnosis and Treatment of Acute and Chronic Heart Failure of the European Society of Cardiology (ESC) Developed with the Special Contribution of the Heart Failure Association," European Heart Journal, 37: 2129-2200, 2016.

Rienstra, et al., "Beta-blockers and Outcome in Heart Failure and Atrial Fibrillation: A Meta-Analysis," JACC Heart Failure, 1(1):21-28, 2013.

Sandilands, et al., "Greater Inotropic and Cyclic AMP Responses Evoked by Noradrenaline Through Arg389 Beta1-Adrenoceptors versus Gly389 Beta1-Adrenoceptors in Isolated Human Atrial Myocardium," Br J Pharmacol., ;138:386-392, 2003.

Sarkar, et al., "Burden of Atrial Fibrillation and Poor Rate Control Detected by Continuous Monitoring and the Risk for Heart Failure Hospitalization,"American Heart Journal, 164:616-624, 2012.

Taylor, et al., "Race, Genetic Variation, and Therapeutic Response Disparities in Heart Failure," JACC Heart Failure, 2:561-572, 2004.

The Beta-Blocker Evaluation of Survival Trial Investigators, "A Trial of the Beta-Adrenergic Blocker Bucindolol in Patients with Advanced Heart Failure," New England Journal of Medicine, ;344:1659-67, 2001.

Trulock, et al., "Rhythm Control in Heart Failure Patients with Atrial Fibrillation: Contemporary Challenges Including the Role of Ablation," Journal of the American College of Cardiology, ;64(7):710-721,2014.

Turagam, et al., "Catheter Ablation of Atrial Fibrillation in Patients With Heart Failure: A Meta-analysis of Randomized Controlled Trials," Annals of Internal Medicine, 170(1):41-50, 2018.

Van Veldhuisen, et al., "Presence and development of atrial fibrillation in chronic heart failure. Experiences from the MERIT-HF Study," European Journal of Heart Failure, 8(5):539-46, 2006.

Wennerholm, et al., "Characterization of the CYP2D6*29 Allele Commonly Present in a Black Tanzanian Population Causing Reduced Catalytic Activity," Pharmacogenetics, 11(5):417-427, 2001.

White, et al., "An Evaluation of the Beta-1 Adrenergic Receptor Arg389Gly Polymorphism in Individuals with Heart Failure: a MERIT-HF Sub-Study," European Journal of Heart Failure, 5:463-468, 2003.

Yancy, et al., 2013 ACCF/AHA Guideline for the Management of Heart Failure, Circulation, 128(16): e240-e327, 2013.

\* cited by examiner

Revised entry criteria supports High likelihood of Phase 3 Success

| Population | | Time to AF/AFL/ACM | | |
|---|---|---|---|---|
| Subpopulation | N | Hazard Ratio (95% conf. int.) | P-value |
|---|---|---|---|
| All Patients (LVEF 40% to 53%) | 267 | 1.01 (0.71, 1.42) | 0.961 |
| < 12 years HF and AF | 230 | 0.68 (0.45, 1.02) | 0.064 |
| AF not > 2 years prior to HF | 196 | 0.54 (0.33, 0.87) | 0.011 |
| LVEF ≥ 40% | 91 | 0.42 (0.21, 0.86) | 0.017 |
| LVEF ≥ 45% | 57 | 0.39 (0.15, 1.00) | 0.049 |

Stratified Cox proportional hazards model with adjustment for: 1) HF etiology, 2) LVEF, 3) rhythm at randomization, 4) device type, and 5) previous Class 3 AA use (subpopulations only).

Fig. 31

METHODS AND COMPOSITIONS INVOLVING BUCINDOLOL FOR THE TREATMENT OF ATRIAL FIBRILLATION

CROSS REFERENCE TO RELATED APPLICATIONS

This application is a continuation of International Application No. PCT/US2019/034019 filed May 24, 2019, which claims priority to U.S. Provisional Application No. 62/676,788, filed May 25, 2018, and U.S. Provisional Application No. 62/839,531, filed Apr. 26, 2019, The entire contents of each of the above-referenced disclosures are specifically incorporated herein by reference without disclaimer.

BACKGROUND OF THE INVENTION

1. Field of the Invention

The present disclosure relates generally to the fields of molecular biology and medicine. Particularly, it concerns methods and compositions involving treating or preventing cardiac arrhythmias by beta-blockers/vasodilators. More particularly the present invention relates to methods and compositions involving bucindolol for the treatment and prevention of heart conditions, including atrial fibrillation (AF) in heart failure.

2. Description of Related Art

Atrial fibrillation (AF) is a common and serious medical problem associated with significant morbidity and mortality, especially in patients with heart failure (HF) (89). Development of AF is associated with increased risk of adverse cardiovascular outcomes, and when AF occurs in patients with HF these adverse effects are accentuated (90,2). AF and HF often co-exist and have common risk factors, as well as overlapping pathophysiologies (2). Therefore, there is a strong rationale to minimize the occurrence of AF in patients with HF. Antiarrhythmic drugs can reduce AF burden but have many side effects including proarrhythmia, with many agents being contraindicated in HF patients (89). Although catheter ablation shows promise for preventing recurrent AF in HF patients with reduced ejection fraction (HFrEF) (91,92), it may not be suitable or practical for many patients. Thus, there is an unmet need for safe and effective drugs to reduce AF in patients with HF. Beta-blockers are first-line therapy for HFrEF due to their benefits in reducing morbidity and mortality and are widely used in HF patients with AF to control ventricular response rate. In addition, beta-blockers have modest AF prevention effects in HFrEF patients (11).

Although AF increases stroke risk above an already increased risk in HFrEF, because this risk can be mitigated by administration of oral anticoagulants and <5% of deaths in HFrEF are from stroke (5) the increased risk of major morbidity and mortality conferred by new onset AF in HF is of major concern, creating a further increase in the risk of mortality and hospitalization (2,3). AF, like HF but unlike other cardiovascular disorders, is increasing in prevalence and is projected to reach 12 million people in the U.S by 2030, from the current 6.1 million (1).

Prevention and treatment of AF in heart failure is a major unmet need (5). In the U.S. drug therapy is confined to the Class 3 antiarrhythmic agents amiodarone and dofetilide, and amiodarone is not approved for this indication. In addition, amiodarone has multiple toxicities, plus is pro-arrhythmic and likely increases mortality in HFrEF (6,7).[7] Although the pro-arrhythmia of dofetilide can be reduced by in-hospital monitoring of QT interval on institution of therapy (8), this is a requirement of dofetilide use (9) and does not preclude drug induced Torsades de Pointes (10).

Bucindolol is a non-selective beta-blocker with mild vasodilator properties and two unique antiadrenergic properties; a moderate sympatholytic effect (22) and inverse agonism for the ADRB1 Arg389 major allele gene product (17), a property which promotes inactivation of constitutively active beta1-adrenergic receptors. The treatment effects of bucindolol appear to be enhanced in patients homozygous for ADRB1 Arg389 (ADRB1 Arg389Arg) (17, 19). In advanced HFrEF patients with this genotype, a 74% reduction in the development of AF was observed for patients in sinus rhythm at baseline who received bucindolol compared to placebo (13). Metoprolol and carvedilol do not appear to confer similar clinical benefits in patients with an ADRB1 Arg389Arg genotype (26,25).

There is a need for improved methods and compositions for the treatment of AF and other heart diseases in heart failure patients, including in patients with HFrEF and in patients with heart failure with mid-range or higher left ventricle ejection fraction (i.e., a left ventricle ejection fraction (LVEF) of 0.40 or higher). Beta-blockers have not been shown to be effective in heart failure patients with mid-range or higher LVEF, and there are no approved therapies available for reducing mortality, morbidity, or hospitalizations for these patients (5, 33, 106, 107, 108, 109, 110). Indeed, Butler et al. state, "The burden of heart failure with preserved ejection fraction (HFpEF) is considerable is is projected to worsen. To date, there are no approved therapies available for reducing mortality or hospitalizations for these patients." (106). Butler et al. also state that "[n]o specific treatment for HFpEF is established and management is limited to diuretics and treatment of comorbidities," and that "β-blockers have not shown benefits in HFpEF." (106). Likewise, Kotecha et al. state that "Heart Failure with preserved ejection fraction (HFpEF) and atrial fibrillation (AF) are common conditions that are increasing in prevalence and are associated with increased morbidity and mortality compared with patients without these diagnoses. HFpEF is as common as heart failure with reduced ejection fraction (HfrEF), and patients experience similar symptoms, yet lack therapeutic options with proven efficacy." (108).

SUMMARY OF THE DISCLOSURE

The inventors have discovered treatment methods that meet the needs described above. Described herein are ways to provide therapeutic benefits to patients with heart failure, atrial fibrillation, other cardiac arrhythmia, and other cardiovascular conditions and diseases through the identification of those patients whose therapeutic outcome can be achieved with bucindolol, including particular dosage regimens of bucindolol.

In addition, methods disclosed herein are based on the surprising discovery that bucindolol is effective for treatment and prevention of heart diseases including atrial fibrillation in patients having mid-range and higher LVEF. The inventors also surprisingly discovered that bucindolol has enhanced efficacy in patients who have been initially diagnosed with heart failure and cardiac arrhythmia relatively recently (for example, within about 12 years) and close in time to one another (for example, within 2 years of each other). Thus, methods disclosed herein meet significant unmet needs in treatment of heart diseases.

Embodiments are provided as methods and uses involving bucindolol. Methods and uses include those that can be implemented for treating atrial fibrillation, heart failure, heart failure with atrial fibrillation, heart failure with reduced ejection fraction, heart failure with mid-range ejection fraction, heart failure with preserved ejection fraction, atrial flutter, ventricular tachycardia, ventricular fibrillation, chronic heart failure, cardiac arrhythmia, dilated cardiomyopathy, ischemic heart disease, hypertension, ischemic heart disease, angina and/or myocardial infarction, for identifying a patient to be treated with bucindolol, for determining bucindolol dosage for a patient, for treating a patient with bucindolol, for maximizing bucindolol treatment, for identifying a patient for bucindolol treatment, for excluding a patient from treatment with bucindolol, and/or for reducing risk of bucindolol side effects.

Methods and uses involve one or more of the following steps: administering to a patient a composition comprising bucindolol, an effective amount of a composition comprising bucindolol, or a composition with 2-20 mg of bucindolol; assaying a sample from a patient to determine whether a patient has one or more CYP2D6 polymorphisms, to determine whether the patient is a poor metabolizer of bucindolol, to determine whether the patient is an intermediate metabolizer of bucindolol, to determine whether the patient is an extensive metabolizer of bucindolol, and/or to determine whether the patient is an ultra metabolizer of bucindolol; measuring LVEF; determining when the patient presented with atrial fibrillation; determining when the patient presented with heart failure; or determining when the patient presented with atrial fibrillation relative to presenting with heart failure (or vice versa).

Patients in the embodiments disclosed herein include a human patient, a patient with one or more symptoms of heart failure, a patient with one or more symptoms of atrial fibrillation, a patient with one or more symptoms of cardiac arrhythmia, a patient diagnosed with heart failure, a patient diagnosed with atrial fibrillation, a patient diagnosed with cardiac arrhythmia, a patient determined to have moderate or mild heart failure, a patient with HFfEF, a patient measured for LVEF, a patient genotyped for one or more polymorphisms in a CYP2D6 allele, a patient assayed for CYP2D6 activity, a patient qualified as a poor, intermediate, extensive and.or ultra metabolizer of bucindolol, a patient assayed for one or more polymorphisms in CYP2D6, a patient tested and determined to be homozygous for Arg389 in the $\beta_1$AR gene, and/or a patient with a particular Left Ventricular Ejection Fraction (LVEF) profile. In particular embodiments, a patient may have an LVEF (rounded) of about, at least about, or at most about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37. 0.38, 0.39, 0.40. 0.41, 0.42, 0.43, 0.44, 0.45, 0.46, 0.47, 0.48, 0.49, 0.50 or greater (or any range derivable therein), wherein the LVEF is measured within 1, 2, 3, 4, 5, 6, 7 days, and/or 1, 2, 3, 4 weeks of being administered bucindolol. In particular embodiments, the patient has reduced LVEF, wherein the LVEF is 0.40 or below or between 0.41 and 0.49 It is contemplated that bucindolol is not administered until a patient's LVEF has been measured and/or taken into consideration prior to prescribing and/or administering the bucindolol. In some embodiments, a patient presents with atrial fibrillation less than 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day(s) (or any range derivable therein) before presenting with heart failure. In certain embodiments, the patient does not present with atrial fibrillation before presenting with heart failure. In other embodiments, the patient does not present with atrial fibrillation more than 29 days before presenting with heart failure. In some embodiments, a patient is measured for an LVEF (rounded) that is about, at least about, or at most about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37. 0.38, 0.39, 0.40. 0.41, 0.42, 0.43, 0.44, 0.45, 0.46, 0.47, 0.48, 0.49, 0.50 or greater (or any range derivable therein), wherein the LVEF is measured within 1, 2, 3, 4, 5, 6, 7 days, and/or 1, 2, 3, 4 weeks of being administered bucindolol, and the patient presents with atrial fibrillation less than 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day(s) (or any range derivable therein) before presenting with heart failure.

In particular cases, a patient has symptoms of or has been diagnosed with heart failure. The heart failure may be considered advanced heart failure, though in certain embodiments, methods exclude a patient with advanced heart failure. The term "advanced heart failure" is used according to its ordinary and plain meaning in the field of cardiology. In some embodiments, a patient being prescribed bucindolol may have or may exclude class III or class IV heart failure according to the NYHA classification system. Patients may be classified by another such system. It is further contemplated that patients may be classified by a different methodology but that embodiments would be implemented similarly. In other embodiments, a patient may have signs or symptoms of heart failure but not advanced heart failure. In such a situation the patient may have been or may be characterized as a class I or II heart failure patient according to the NYHA classification system.

In certain embodiments, there are methods of treating with bucindolol a patient who has been genotyped or assayed for at least one polymorphism in one or both CYP2D6 allele(s). In some embodiments, at least one polymorphism is genotyped or assayed in a CYP2D6 duplicate gene in addition to genotyping or assaying one or both CYP2D6 alleles. In further embodiments, a patient is genotyped or assayed for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polymorphisms (or any range derivable therein) in one or both CYP2D6 alleles, and optionally, in a CYP2D6 duplicate gene. In particular embodiments, a patient genotyped or assayed for a CYP2D6 polymorphism has been assayed or genotyped for, for at least, or for at most 1, 2, 3, 4, 5, 6, 7, 8, 9, 10, 11, 12, 13, 14, 15 or 16 of the following CYP2D6 genotypes: *1, *2, *3, *4, *5, *6, *7, *8, *9, *10, *11, *15, *17, *29, *35, or *41. In certain embodiments, a patient has been genotyped for all of the following CYP2D6 genotypes: *1, *2, *3, *4, *5, *6, *7, *8, *9, *10, *11, *15, *17, *29, *35, or *41. In other embodiments, additional CYP2D6 polymorphisms are genotyped or assayed in the patient.

In certain embodiments, CYP2D6 genotyping identifies a patient is determined as a Poor Metabolizer, a Poor/Intermediate Metabolizer, an Intermediate/Extensive Metabolizer, an Extensive Metabolizer, an Extensive/Ultra Metabolizer, or an Ultra Metabolizer of bucindolol. In particular embodiments, such a patient or any patient is administered or is administered at least or at most about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 mg of bucindolol (or any range derivable therein) in 2, 4, 6, 8, 10, 12, 24, 36, 48, 60, 72, 84, 96, 108 hours and/or 1, 2, 3, 4, 5, 6, or 7 days (or any range derivable therein). The patient may be administered a composition comprising about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 mg of bucindolol (or any range derivable therein). A composition may be administered 1, 2, 3, 4, 5, 6, 7, 8, 9, 10, 11, 12, 13, 14, 15, 16, 17, 18, 19, 20 or more times; it may be administered every 1, 2, 3, 4, 5, 6, 7, 8, 9, 10, 11, 12, 13, 14, 15, 16, 17, 18, 19, 20, 21, 22, 23, 24 hours, and for 1, 2, 3, 4, 5, 6, 7 days, or 1, 2, 3, 4, 5 weeks, or 1, 2, 3, 4, 5, 6, 7, 8, 9, 10, 11, 12 months or more (and any range derivable therein). In other embodiments, such a patient or any patient is administered or is administered at least or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mg/kg/day (or any range derivable therein) of bucindolol.

In certain embodiments, a patient is determined to be an Ultra, Extensive or Intermediate metabolizer (or a combination thereof) based on the CYP2D6 genotyping. Such a patient may be administered any dose of bucindolol described herein. In some embodiments, such patient is administered 12.5 mg-200 mg of bucindolol a day. Alternatively, such a patient is administered 0.15-2.5 mg/kg/day.

In some embodiments, a patient is determined to be an Intermediate metabolizer based on CYP2D6 genotyping; such a patient may be given less bucindolol than they might have been given if they were an Ultra and/or Extensive Metabolizer.

In additional embodiments, a patient is determined to be a Poor Metabolizer based on CYP2D6 polymorphisms or genotypes. In some embodiments, the patient is administered a dose less than the dose administered to a patient determined to be an Ultra, Extensive and/or Intermediate metabolizer (or a combination thereof) based on the CYP2D6 genotyping. Such a patient may be given less bucindolol than they might have been given if they were an Ultra and/or Extensive Metabolizer or an Intermediate Metabolizer.

In certain embodiments, a patient has been genotyped as not having at least any of the following CYP2D6 genotypes in one or both CYP2D6 alleles: *2, *3, *4, *5, *6, *7, *8, *9, *10, *11, *15, *17, *29, *35, and *41.

In specific embodiments, a patient has been genotyped for *1 in one or both alleles of CYP2D6. In some embodiments, a patient has been genotyped for a CYP2D6 duplicate with respect to genotype *1. In further embodiments, the patient is identified as an Extensive and/or an Ultra metabolizer based on genotype *1 in one or both CYP2D6 alleles and/or in a CYP2D6 duplicate gene. In particular embodiments, patient with a *1 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *2 in one or both alleles of CYP2D6. In some embodiments, a patient has been genotyped for a CYP2D6 duplicate with respect to genotype *2. In further embodiments, the patient is identified as an Extensive and/or an Ultra metabolizer based on genotype *2 in one or both CYP2D6 alleles and/or in a CYP2D6 duplicate gene. In particular embodiments, patient with a *2 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *35 in one or both alleles of CYP2D6. In some embodiments, a patient has been genotyped for a CYP2D6 duplicate with respect to genotype *35. In further embodiments, the patient is identified as an Extensive and/or an Ultra metabolizer based on genotype *35 in one or both CYP2D6 alleles and/or in a CYP2D6 duplicate gene. In particular embodiments, patient with a *35 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *9 in one or both alleles of CYP2D6. In some embodiments, a patient has been genotyped for a CYP2D6 duplicate with respect to genotype *9. In further embodiments, the patient is identified as an Intermediate and/or an Extensive metabolizer based on genotype *9 in one or both CYP2D6 alleles and/or in a CYP2D6 duplicate gene. In particular embodiments, patient with a *9 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *10 in one or both alleles of CYP2D6. In some embodiments, a patient has been genotyped for a CYP2D6 duplicate with respect to genotype *10. In further embodiments, the patient is identified as an Intermediate and/or an Extensive metabolizer based on genotype *10 in one or both CYP2D6 alleles and/or in a CYP2D6 duplicate gene. In particular embodiments, patient with a *10 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *17 in one or both alleles of CYP2D6. In some embodiments, a patient has been genotyped for a CYP2D6 duplicate with respect to genotype *17. In further embodiments, the patient is identified as an Intermediate and/or an Extensive metabolizer based on genotype *17 in one or both CYP2D6 alleles and/or in a CYP2D6 duplicate gene. In particular embodiments, patient with a *17 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *29 in one or both alleles of CYP2D6. In some embodiments, a patient has been genotyped for a CYP2D6 duplicate with respect to genotype *29. In further embodiments, the patient is identified as an Intermediate and/or an Extensive metabolizer based on genotype *29 in one or both CYP2D6 alleles and/or in a CYP2D6 duplicate gene. In particular embodiments, patient with a *29 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *41 in one or both alleles of CYP2D6. In some embodiments, a patient has been genotyped for a CYP2D6 duplicate with respect to genotype *41. In further embodiments, the patient is identified as an Intermediate and/or an Extensive metabolizer based on genotype *41 in one or both CYP2D6 alleles and/or in a CYP2D6 duplicate gene. In particular embodiments, patient with a *41 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *3 in one or both alleles of CYP2D6. In some embodiments, a patient has been genotyped for a CYP2D6 duplicate with respect to genotype *3. In further embodiments, the patient is identified as an Intermediate and/or an Poor metabolizer based on genotype *3 in one or both CYP2D6 alleles and/or in a CYP2D6 duplicate gene. In particular embodiments, patient with a *3 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *4 in one or both alleles of CYP2D6. In some embodiments, a patient has been genotyped for a CYP2D6 duplicate with respect to genotype *4. In further embodiments, the patient is identified as an Intermediate and/or an Poor metabolizer based on genotype *4 in one or both CYP2D6 alleles and/or in a CYP2D6 duplicate gene. In particular embodiments, patient with a *4 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *5 in one or both alleles of CYP2D6. In some embodiments, a patient has been genotyped for a CYP2D6 duplicate with respect to genotype *5. In further embodiments, the patient is identified as an Intermediate and/or an Poor metabolizer based on genotype *5 in one or both CYP2D6 alleles and/or in a CYP2D6 duplicate gene. In particular embodiments, patient with a *5 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *6 in one or both alleles of CYP2D6. In some embodiments, a patient has been genotyped for a CYP2D6 duplicate with respect to genotype *6. In further embodiments, the patient is identified as an Intermediate and/or an Poor metabolizer based on genotype *6 in one or both CYP2D6 alleles and/or in a CYP2D6 duplicate gene. In particular embodiments, patient with a *6 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *7 in one or both alleles of CYP2D6. In some embodiments, a patient has been genotyped for a CYP2D6 duplicate with respect to genotype *7. In further embodiments, the patient is identified as an Intermediate and/or an Poor metabolizer based on genotype *7 in one or both CYP2D6 alleles and/or in a CYP2D6 duplicate gene. In particular embodiments, patient with a *7 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *8 in one or both alleles of CYP2D6. In some embodiments, a patient has been genotyped for a CYP2D6 duplicate with respect to genotype *8. In further embodiments, the patient is identified as an Intermediate and/or an Poor metabolizer based on genotype *8 in one or both CYP2D6 alleles and/or in a CYP2D6 duplicate gene. In particular embodiments, patient with a *8 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *11 in one or both alleles of CYP2D6. In some embodiments, a patient has been genotyped for a CYP2D6 duplicate with respect to genotype *11. In further embodiments, the patient is identified as an Intermediate and/or an Poor metabolizer based on genotype *11 in one or both CYP2D6 alleles and/or in a CYP2D6 duplicate gene. In particular embodiments, patient with a *11 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

In specific embodiments, a patient has been genotyped for *15 in one or both alleles of CYP2D6. In some embodiments, a patient has been genotyped for a CYP2D6 duplicate with respect to genotype *15. In further embodiments, the patient is identified as an Intermediate and/or an Poor metabolizer based on genotype *15 in one or both CYP2D6 alleles and/or in a CYP2D6 duplicate gene. In particular embodiments, patient with a *15 genotype in one or both CYP2D6 alleles or also in a CYP2D6 duplicate gene is administered between 12.5 mg-200 mg of bucindolol per day and/or between 0.15-2.5 mg/kg/day or any other dosage described herein.

The table provided herein shows which genotypes are associated with which levels of metabolization depending on the number of alleles having that genotype and whether there is a duplicate allele. CYP2D6 genotypes with normal activity are: *1, *2, and *35. CYP2D6 genotypes with reduced activity are: *9, *10, *17, *29, *41. CYP2D6 genotypes with nonfunctional activity are: *3, *4, *5, *6, *7, *8, *11, *15. Two normal alleles are seen in Extensive metabolizers. Two reduced alleles are seen in Intermediate Metabolizers. Two nonfunctional alleles are seen in Poor metabolizers. Two normal alleles plus a duplicate normal allele is an Ultra metabolizer. One normal allele and a reduced allele plus a duplicate normal or a duplicate reduced is an Extensive metabolizer. One normal allele and a nonfunctional allele plus a duplicate normal or nonfunctional allele is an Extensive metabolizer. Two reduced alleles plus a duplicate reduced allele is an Intermediate-Extensive metabolizer. One reduced allele and one nonfunctional allele plus a duplicate allele is an Intermediate metabolizer. Two nonfunctional alleles plus a duplicate nonfunctional allele is a Poor metabolizer.

It is specifically contemplated that any single polymorphism in a genotype * described herein may be assayed or genotyped separately from the genotype. Any 1, 2, 3, and/or 4 of the polymorphisms in genotype *2 (−1584>G, 1661G>C, 2850C>T, 4180G>C) may be assayed or genotyped. The polymorphism in genotype *3 (2549A>del) may be assayed or genotyped. Any 1, 2, 3, 4, and/or 5 of the polymorphisms in genotype *4 (100C>T, 1661G>C, 1846G>A, 4180G>C, 2850C>T) may be assayed or genotyped. The polymorphism in genotype *5 (deletion) may be assayed or genotyped. One or both polymorphisms in genotype *6 (1707T>del, 4180G>C) may be genotyped or assayed. The polymorphism of genotype *7 (2935A>C) may be assayed or genotyped. Any 1, 2, 3, and/or 4 of the polymorphisms of genotype *8 (1661G>C, 1758G>T, 2850C>T, 4180G>C) may be assayed or genotyped. The polymorphism of genotype *9 (2613delAGA) may be assayed or genotyped. Any 1, 2, and/or 3 of the polymorphisms of genotype *10 (100C>T, 1661G>C, 4180G>C) may be assayed or genotyped. Any 1, 2, 3, and/or 4 of the polymorphisms of genotype *11 (883G>C, 1661G>C, 2850C>T, 4180G>C) may be genotyped or assayed. The polymorphism of genotype *15 (138insT) may be genotyped or assayed. Any 1, 2, 3, and/or 4 polymorphisms of genotype *17 (1023C>T, 1661G>C, 2850C>T, 4180G>C) may be assayed or genotyped. Any 1, 2, 3, 4, and/or 5 polymorphisms of genotype *29 (1659G>A, 1661G>C, 2850C>T, 3183G>A, 4180G>C) may be assayed or genotyped. Any 1, 2, 3, 4, and/or 5 polymorphisms of genotype *35 (−1584C>G, 31G>A, 1661G>C, 2850C>T, 4180G>C) may be genotyped or assayed. Any 1, 2, 3, and/or 4 of the polymorphisms of genotype *41 (1661G>C, 2850C>T, 2988G>A, 4180G>C) nay be genotyped or assayed.

In certain embodiments, a patient is also assessed for one or more polymorphisms in the $\beta_1$AR gene. In particular embodiments, the patient is homozygous Arg389, meaning the patient is homozygous for a cytosine at position 1165 in the nucleotide coding sequence of both $\beta_1$AR alleles.

Genotyping is physical and/or chemical alteration of a nucleic acid to determine its sequence. In certain embodiments, genotyping comprises sequencing, nucleic acid amplification, hybridization, and/or transcription, or a combination thereof.

In certain embodiments, a composition is a racemic mixture of S-bucindolol and R-bucindolol. In other embodiments, it comprises substantially more of one enantiomer than the other. In specific embodiments, a composition comprises a ratio of S-bucindolol to R-bucindolol of at least 99:1 by weight of bucindolol in the composition.

In certain embodiments, there are methods for treating atrial fibrillation in heart failure with bucindolol comprising administering a composition comprising bucindolol to a patient who has been genotyped for at least one CYP2D6 polymorphism in at least one allele prior to being administered the composition comprising bucindolol, wherein the patient has also been tested and determined to be homozygous for Arg389 in the $\beta_1$AR gene. In additional embodiments, there are methods for determining a dosage of bucindolol for treating heart failure with atrial fibrillation in a patient comprising administering to the patient a composition comprising bucindolol after the patient has been genotyped for one or more polymorphisms in one or both alleles of the CYP2D6 gene, and optionally, in a duplicate CYP2D6 gene, wherein the patient has also been tested and determined to be homozygous for Arg389 in the $\beta_1$AR gene.

In additional embodiments, there are uses of bucindolol for the treatment of heart failure with atrial fibrillation in a patient genotyped for one or more polymorphisms in CYP2D6 and wherein the patient has determined to be homozygous for Arg389 in the $\beta_1$AR gene.

The present disclosure also provides information about the interplay between heart failure and atrial fibrillation. In some embodiments, there are methods for treating a patient with atrial fibrillation and/or heart failure or atrial fibrillation in heart heart failure comprising administering an effective amount of a composition comprising bucindolol to a patient after measuring an LVEF of <0.40 or to a patient after measuring an LVEF of ≥0.40 but after determining the patient presented with atrial fibrillation no more than 29 days prior to presenting with heart failure. Alternatively, methods may include treating a patient with atrial fibrillation and/or heart failure or atrial fibrillation in heart heart failure comprising administering an effective amount of a composition comprising bucindolol to a patient after measuring an LVEF of <0.40 or to a patient after measuring an LVEF of ≥0.40 but after diagnosing the patient with atrial fibrillation no more than 29 days prior to diagnosing the patient with heart failure.

In some embodiments, a patient is measured for an LVEF (rounded) that is about, at least about, or at most about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37. 0.38, 0.39, 0.40. 0.41, 0.42, 0.43, 0.44, 0.45, 0.46, 0.47, 0.48, 0.49, 0.50 or greater (or any range derivable therein), wherein the LVEF is measured within 1, 2, 3, 4, 5, 6, 7 days, and/or 1, 2, 3, 4 weeks of being administered bucindolol, and the patient presents or is diagnosed with atrial fibrillation less than 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day(s) (or any range derivable therein) before presenting with or being diagnosed with heart failure.

Presentation of heart failure may include or include at least 1, 2, 3, 4, 5, or 6 of the following signs or symptoms: breathlessness, exertional dyspnea, orthopnea, paroxysmal nocturnal dyspnea, dyspnea at rest, or acute pulmonary edema. There may be other cardiac symptoms of heart failure such as chest pain/pressure and palpitations. Common noncardiac signs and symptoms of heart failure include anorexia, nausea, weight loss, bloating, fatigue, weakness, oliguria, nocturia, and cerebral symptoms of varying severity, ranging from anxiety to memory impairment and confusion. Findings from the Framingham Heart Study supported the idea that subclinical cardiac dysfunction and noncardiac comorbidities are associated with increased incidence of heart failure, supporting the concept that heart failure is a progressive syndrome and that noncardiac factors are very relevant. Presentation of cardiac arrhythmia may be or be at least 1, 2, 3, 4, 5, 6, 7, 8, 9, or 10 of the following signs or symptoms: palpitations, dyspnea, fatigue, dizziness, angina, decompensated heart failure, hemodynamic dysfunction, tachycardia-induced cardiomyopathy, and systemic thromboembolism.

To achieve these methods, a doctor, medical practitioner, or their staff may obtain a biological sample for evaluation. The sample may be analyzed by the practitioner or their staff, or it may be sent to an outside or independent laboratory. The medical practitioner may be cognizant of whether the test is providing information regarding the patient's CYP2D6 and/or $\beta_1$AR genes, or the medical practitioner may be aware only that the test indicates directly or indirectly that the genotype of the patient reflects a particular genotype or genotypes.

In any of these circumstances, the medical practitioner "knows" or identifies indirectly the relevant information that will allow him or her to determine whether bucindolol is an appropriate medical treatment. It is contemplated that, for example, a laboratory conducts the test to determine that patient's genotype such its personnel also know the appropriate information. They may report back to the practitioner with the specific result of the test performed or the laboratory may simply report that bucindolol is an appropriate drug based on the laboratory results. Moreover, through these different channels, the patient's genotype at any particular polymorphim and/or genotype can be known.

Certain embodiments are directed to a tangible, computer-readable medium comprising a genotype profile of a subject, wherein the genotype profile exhibits the sequence at one or more polymorphisms in one or both alleles of the CYP2D6 gene and/or a $\beta_1AR$ gene. In certain aspects the medium comprising the genotype profile of the subject exhibits the patient is homozygous Arg389 in the $\beta_1AR$ gene and/or an Ultra, Extensive, and/or Intermediate metabolizer of bucindolol.

Also disclosed herein is a method of treating, preventing, delaying onset of, or reducing the risk of a heart disease, the method comprising administering an effective amount of bucindolol to a patient who: (a) has been diagnosed with heart failure; (b) has been tested and found to have a left ventricle ejection fraction of at least 0.40; and (c) has been genotyped and found to be homozygous for Arg389 in the $\beta_1AR$ gene. In some embodiments, the heart disease that is treated, prevented, or whose onset is delayed or whose risk is reduced is heart failure, including in some embodiments chronic heart failure, or new onset, recurrent, or ongoing atrial fibrillation, atrial flutter, ventricular fibrillation, ventricular tachycardia, heart failure with reduced ejection fraction (HFrEF), heart failure with mid-range ejection fraction (HFmrEF), heart failure with preserved ejection fraction (HFpEF), tachycardia, or cardiac arrhythmia. In some embodiments, the LVEF is at least about or about 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, or 0.70, or is between any two of these values. For example, in some embodiments, the LVEF is greater than or equal to 0.40 and less than 0.50, greater than or equal to 0.45 and less than 0.50, greater than or equal to 0.40 and less than 0.60, is greater than or equal to 0.40, 0.45, 0.50, or 0.60. In some embodiments, the LVEF test of step (b) was performed less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days before the administering, or less than 1, 2, 3, 4, 5, 6, 7, 8, 9, 10, 11, or 12 months before the administering.

A person of ordinary skill in the art will recognize that there are a number of ways of measuring LVEF, including echocardiogram, MRI, or a nuclear stress test (nuclear medicine scan (multiple gated acquisition MUGA)), with the most common way being echocardiogram.

In some embodiments, the patient was initially diagnosed with heart failure less than 1, 2, 3, 4, 5, 6, 7, 8, 9, 10, 11, or 12 years before the administering, or less than 1, 2, 3, 4, 5, 6, 7, 8, 9, 10, 11, 12, 13, 14, 15, 16, 17, 18, 19, 20, 21, 22, 23, or 24 months before the administering, or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 90, 120, 150, or 180 days before the administering. In some embodiments, the patient initially developed heart failure less than 1, 2, 3, 4, 5, 6, 7, 8, 9, 10, 11, or 12 years before the administering, or less than 1, 2, 3, 4, 5, 6, 7, 8, 9, 10, 11, 12, 13, 14, 15, 16, 17, 18, 19, 20, 21, 22, 23, or 24 months before the administering, or less than 30, 60, 90, 120, 150, or 180 days before the administering.

As used herein, a patient is "initially diagnosed" with a disease when that the patient is diagnosed with the disease for the first time. As used herein, a diagnosis occurs at the time that a healthcare provider, after concluding that the patient has a disease or condition, either (1) documents such conclusion in a medical record, (2) communicates to the patient such conclusion, or (3) prescribes a medication to treat the disease or condition.

In some embodiments, the patient has further been diagnosed with atrial fibrillation or atrial flutter. In some embodiments, the patient was initially diagnosed with atrial fibrillation or atrial flutter between or less than 1, 2, 3, 4, 5, 6, 7, 8, 9, 10, 11, 12, 13, 14, 15, 16, 17, 18, 19, or 20 years before the administering (or any range derivable therein), or between or less than 1, 2, 3, 4, 5, 6, 7, 8, 9, 10, 11, 12, 13, 14, 15, 16, 17, 18, 19, 20, 21, 22, 23, or 24 months (or any range derivable therein) before the administering, or less than 30, 60, 90, 120, 150, or 180 days before the administering. In some embodiments, the patient developed or was initially diagnosed atrial fibrillation or atrial flutter less than 12 years before administering bucindolol. In some embodiments, a patient has been diagnosed with both heart failure and atrial fibrillation (or atrial flutter). In some embodiments, the patient initially developed atrial fibrillation or atrial flutter less than 1, 2, 3, 4, 5, 6, 7, 8, 9, 10, 11, or 12 years before the administering, or less than 1, 2, 3, 4, 5, 6, 7, 8, 9, 10, 11, 12, 13, 14, 15, 16, 17, 18, 19, 20, 21, 22, 23, or 24 months before the administering, or less than 30, 60, 90, 120, 150, or 180 days before the administering. In some embodiments in which the patient has been diagnosed with both heart failure and atrial fibrillation, the respective diagnoses occurred contemporaneously or within a relatively short time of each other. In some embodiments, the patient was diagnosed at different times. In some embodiments, the patient was initially diagnosed with atrial fibrillation less than 2 years before or after initially being diagnosed with heart failure. In some embodiments, the patient was initially diagnosed with atrial fibrillation less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months (or any range derivable therein) before or after initially being diagnosed with heart failure.

In some embodiments, the patient is in sinus rhythm at the time that bucindolol is administered. In some embodiments, the patient has been tested and found to be in sinus rhythm within or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days (or any range derivable therein) before the bucindolol is administered.

In some embodiments, the patient is administered about 12.5 to 200 mg of bucindolol per day. In some embodiments, the patient is administered at least about, at most about, or about 5, 7.5, 10, 12.5, 15, 20, 25, 30, 40, 50, 60, 70, 80, 90, 100, 110, 120, 130, 140, 150, 160, 170, 180, 190, 200, 210, 220, 230, 240, or 250 mg of bucindolol per day, or between any two of these values. In some embodiments, the patient is administered bucindolol in a dosage of about 0.15 to 5 mg/kg per day. In some embodiments, the patient is administered bucindolol in a dosage of at least about, at most about, or about 0.05, 0.10, 0.15, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mg/kg per day, or between any two of these values.

Also disclosed is a method of treating, preventing, or delaying onset of atrial fibrillation, the method comprising administering an effective amount of bucindolol to a patient who: (a) has been tested and found to have a left ventricle ejection fraction of at least 0.40; and (b) has been genotyped and found to be homozygous for Arg389 in the $\beta_1AR$ gene. In some embodiments, the atrial fibrillation is new onset atrial fibrillation; that is, the patient has not previously been diagnosed with atrial fibrillation or has not previously experienced symptoms of atrial fibrillation. In some embodiments, administering bucindolol prevents, delays onset of, and/or reduces the risk of developing atrial fibrillation for the first time. In some embodiments, the atrial fibrillation is recurrent atrial fibrillation; that is, the patient has previously been diagnosed with atrial fibrillation, which may include symptomatic and/or paroxysmal atrial fibrillation. In some embodiments, administering bucindolol prevents, delays onset of, and/or reduces the risk of developing recurrent atrial fibrillation. In some embodiments, administering bucindolol prevents, delays onset of, and/or reduces the risk of developing other heart diseases, including, for example, atrial flutter, new onset atrial flutter, recurrent atrial flutter, a cardia arrhythmia, new onset cardiac arrhythmia, or recurrent cardiac arrhythmia. In some embodiments, the patient has further been diagnosed with heart failure. In some embodiments, the patient was initially diagnosed with heart failure less than 12 years before the administering. In some embodiments, the patient has further been diagnosed with atrial fibrillation. In some embodiments, the patient was initially diagnosed with atrial fibrillation less than 12 years before the administering. In some embodiments, the patient was initially diagnosed with atrial fibrillation less than 2 years before, less than 2 years after, or less than 2 years before or after being initially diagnosed with heart failure. In some embodiments, the patient has been tested and found to have an LVEF of at least 0.45, 0.50, 0.55, or 0.60. In some embodiments, the patient further has been tested and found to be in sinus rhythm at the time of the administering or less than 1 day before the administering. In some embodiments, the patient is administered about 12.5 to 200 mg of bucindolol per day. In some embodiments, the patient is administered about 0.15 to 5 mg/kg of bucindolol per day.

Also disclosed is a method of treating, preventing, delaying onset of, or reducing the risk of atrial fibrillation in a patient, the method comprising: (a) obtaining the results of a test showing that the patient has a left ventricle ejection fraction of at least 0.40; and (b) administering an effective amount of bucindolol to the patient after step (a). In some embodiments, the patient has further been genotyped and found to be homozygous for Arg389 in the $\beta_1AR$ gene before the administering of step (b).

Also disclosed is a method of treating, preventing, delaying onset of, or reducing the risk of atrial fibrillation, the method comprising administering an effective amount of bucindolol to a patient after determining that the patient (a) has a left ventricle ejection fraction of at least 0.40; and (b) is homozygous for Arg389 in the $\beta_1AR$ gene.

Also disclosed is a method of treating heart failure, the method comprising administering an effective amount of bucindolol to a patient who: (a) has been tested and found to have a left ventricle ejection fraction of at least 0.40; and (b) has been genotyped and found to be homozygous for Arg389 in the $\beta_1AR$ gene. In some embodiments, the patient has further been initially diagnosed with heart failure less than 12 years before the administering. In some embodiments, the patient has further been initially diagnosed with atrial fibrillation less than 12 years before the administering and less than 2 years before or after being initially diagnosed with heart failure.

It will be understood that being initially diagnosed with atrial fibrillation less than 2 years before or after being initially diagnosed with heart failure means the patient has been initially diagnosed with atrial fibrillation within 2 years of having been initially diagnosed with heart failure. Embodiments concern patients 1) initially diagnosed with atrial fibrillation less than 2 years before being initially diagnosed with heart failure; 2) initially diagnosed with atrial fibrillation less than 2 years after being initially diagnosed with heart failure; and/or 3) initially diagnosed with atrial fibrillation within 2 years of being initially diagnosed with heart failure.

Also disclosed is a method of treating, preventing, delaying the onset of, or reducing the risk of recurrent or new onset atrial flutter, the method comprising administering an effective amount of bucindolol to a patient who: (a) has been tested and found to have a left ventricle ejection fraction of at least 0.40; and (b) has been genotyped and found to be homozygous for Arg389 in the $\beta_1AR$ gene. In some embodiments, the patient has further been initially diagnosed with heart failure less than 12 years before the administering. In some embodiments, the patient has further been initially diagnosed with atrial fibrillation less than 12 years before the administering and less than 2 years before or after being initially diagnosed with heart failure.

Also disclosed is a method of treating, preventing, delaying the onset of, or reducing the risk of a recurrent or new onset cardiac arrhythmia, the method comprising administering an effective amount of bucindolol to a patient who: (a) has been tested and found to have a left ventricle ejection fraction of at least 0.40; and (b) has been genotyped and found to be homozygous for Arg389 in the $\beta_1AR$ gene. In some embodiments, the patient has further been initially diagnosed with heart failure less than 12 years before the administering. In some embodiments, the patient has further been initially diagnosed with atrial fibrillation less than 12 years before the administering and less than 2 years before or after being initially diagnosed with heart failure.

Also disclosed is a method of maintaining a normal sinus rhythm, the method comprising administering an effective amount of bucindolol to a patient who: (a) has been tested and found to have a left ventricle ejection fraction of at least 0.40; and (b) has been genotyped and found to be homozygous for Arg389 in the $\beta_1AR$ gene. In some embodiments, the patient has further been initially diagnosed with heart failure less than 12 years before the administering. In some embodiments, the patient has further been initially diagnosed with atrial fibrillation less than 12 years before the administering and less than 2 years before or after being initially diagnosed with heart failure.

Also disclosed is a method of maintaining a normal sinus rhythm, the method comprising administering an effective amount of bucindolol to a patient who: (a) has been diagnosed with heart failure; (b) has been diagnosed with symptomatic atrial fibrillation or atrial flutter; (c) has been tested and found to have a left ventricle ejection fraction of greater than or equal to 0.40 and less than 0.50; (d) is in sinus rhythm at the time of the administering; and (e) has been genotyped and found to be homozygous for Arg389 in the $\beta_1AR$ gene. In some embodiments, maintaining a normal sinus rhythm comprises causing a delay in time to recurrence of atrial fibrillation or atrial flutter. In some embodiments, maintaining a normal sinus rhythm comprises reducing the risk of new onset or recurrent atrial fibrillation or atrial flutter.

Also disclosed is a method of treating, preventing, delaying onset of, or reducing the risk of a heart disease, the method comprising administering an effective amount of bucindolol to a patient after determining that the patient: (a) has heart failure; (b) has a left ventricle ejection fraction of at least 0.40; and (c) has been genotyped and found to be homozygous for Arg389 in the $\beta_1AR$ gene.

Also disclosed is a method of treating, preventing, or delaying onset of a heart disease in a patient, the method comprising: (a) obtaining the results of a test or tests showing that the patient has heart failure with a left ventricle ejection fraction of at least 0.40; and (b) administering an effective amount of bucindolol to the patient after step (a). In some embodiments, the method further comprises obtaining the results of a test showing that the patient is homozygous for Arg389 in the $\beta_1AR$ gene before the administering of step (b).

Also disclosed is a method of treating, preventing, delaying onset of, or reducing the risk of a heart disease, the method comprising administering an effective amount of bucindolol to a patient who has been tested and found to have a left ventricle ejection fraction of at least 0.40. In some embodiments, the heart disease is heart failure or new onset, recurrent, or ongoing atrial fibrillation, atrial flutter, tachycardia, or cardiac arrhythmia. In some embodiments, the patient has further been genotyped and found to be homozygous for Arg389 in the $\beta_1AR$ gene. In some embodiments, the patient has further been diagnosed with heart failure. In some embodiments, the patient has been further diagnosed with atrial fibrillation. In some embodiments, the patient was initially diagnosed with atrial fibrillation less than 2 years before or after being initially diagnosed with heart failure. In some embodiments, the patient was initially diagnosed with atrial fibrillation less than 12 years before the administering and was initially diagnosed with heart failure less than 12 years before the administering.

Also disclosed is a method of preventing or delaying onset of atrial fibrillation in a patient, the method comprising administering an effective amount of bucindolol to a patient who: (a) has been initially diagnosed with heart failure less than 12 years before the administering; (b) has been initially diagnosed with atrial fibrillation less than 12 years before the administering; (c) has been tested and found to have a left ventricle ejection fraction less than 0.50 within 12 months before the administering; and (d) has been genotyped and found to be homozygous for Arg389 in the $\beta_1AR$ gene. In some embodiments, the left ventricle ejection fraction is equal to or greater than 0.40 and less than 0.50 or is less than 0.40. In some embodiments, the patient was initially diagnosed with atrial fibrillation within 2 years of being initially diagnosed with heart failure. In some embodiments, the patient was initially diagnosed with atrial fibrillation less than 2 years before being initially diagnosed with heart failure. In some embodiments, the patient was diagnosed with atrial fibrillation before being diagnosed with heart failure. In some embodiments, the patient is in a sinus rhythm at the time of the administering. In some embodiments, the patient has further been diagnosed with or had symptoms of persistent or paroxysmal atrial fibrillation prior to the administering. In some embodiments, the atrial fibrillation was documented by electrocardiogram, electrocardiogram patch, transtelephonic monitor, or an implanted device. In some embodiments, the atrial fibrillation caused new or worsening symptoms. In some embodiments, the heart failure diagnosis was based on one or more of the following signs or symptoms: breathlessness, fatigability, paroxysmal nocturnal dyspnea, orthopnea, and volume overload. In some embodiments, the patient has further been tested and found to have at least one of the following: (a) a blood concentration of B-type natriuretic peptide of at least about 100 pg/ml; (b) a blood concentration of N-terminal pro B-type natriuretic peptide of at least about 125 pg/ml, wherein the patient is 75 years old or younger; or (c) a blood concentration of N-terminal pro B-type natriuretic peptide of at least about 400 pg/ml, wherein the patient is more than 75 years old; or the patient has been hospitalized for heart failure. In some embodiments, the blood concentration of B-type natriuretic peptide is at least about 490 pg/ml or the blood concentration of N-terminal pro B-type natriuretic peptide is at least about 3460 pg/ml, and the patient is of any age. In some embodiments, the patient is not presently taking a combination of sacubitril and valsartan or has not taken a combination of sacubitril and valsartan within 1 month of when the blood concentration of B-type natriuretic or N-terminal pro B-type natriuretic was tested in the patient. In some embodiments, at the time of administering, the patient has a resting heart rate below 120 bpm. In some embodiments, at the time of administering, the patient has a systolic blood pressure between 90 and 150 mmHg. In some embodiments, the method further comprises administering electrical cardioversion to cause the patient to have a sinus rhythm before the administering. In some embodiments, the patient is taking a prescribed anticoagulant. In some embodiments, the patient is administered about 12.5 to 200 mg of bucindolol per day. In some embodiments, the patient is administered about 0.15 to 5 mg/kg of bucindolol per day.

Also disclosed is a method of treating, preventing, delaying onset of, or reducing the risk of heart disease in a patient, the method comprising administering an effective amount of bucindolol to a patient who: (a) has been initially diagnosed with heart failure less than 12 years before the administering; (b) has been initially diagnosed with atrial fibrillation less than 12 years before the administering and less than 2 years before being diagnosed with heart failure; (c) has been tested and found to have a left ventricle ejection fraction equal to or greater than 0.40 and less than 0.50; (d) is in sinus rhythm; and (e) has been genotyped and found to be homozygous for Arg389 in the $\beta_1AR$ gene. In some embodiments, the heart disease is heart failure or new onset or recurrent atrial fibrillation, atrial flutter, tachycardia, or cardiac arrhythmia.

Also disclosed is a method of treating, preventing, delaying onset of, or reducing the risk of a heart disease in a patient, the method comprising administering an effective amount of bucindolol to a patient after determining that the patient: (a) was initially diagnosed with heart failure less than 12 years before the administering; (b) was initially diagnosed with symptomatic atrial fibrillation less than 12 years before the administering and less than 2 years before being diagnosed with heart failure; (c) had a left ventricle ejection fraction equal to or greater than 0.40 and less than 0.50 within 12 months before the administering; (d) is in sinus rhythm; and (e) is homozygous for Arg389 in the $\beta_1AR$ gene. In some embodiments, the heart disease is heart failure or new onset or recurrent atrial fibrillation, atrial flutter, tachycardia, or cardiac arrhythmia.

Also disclosed is a method of treating, preventing, delaying onset of, or reducing the risk of a heart disease in a patient, the method comprising administering an effective amount of bucindolol to a patient who: (a) has been initially diagnosed with heart failure less than 12 years before the administering; (b) has been initially diagnosed with atrial fibrillation less than 12 years before the administering and less than 2 years before or within being diagnosed with heart failure; (c) has been tested and found to have a left ventricle ejection fraction equal to or greater than 0.40, 0.45, or 0.50;

(d) is in sinus rhythm; and (e) has been genotyped and found to be homozygous for Arg389 in the $\beta_1$AR gene. In some embodiments, the heart disease is heart failure, atrial fibrillation, atrial flutter, recurrent atrial fibrillation, recurrent atrial flutter, or new onset atrial flutter.

Also disclosed is a method of reducing a patient's risk of developing atrial fibrillation, the method comprising administering an effective amount of bucindolol to a patient who: (a) has been tested and found to have a left ventricle ejection fraction of at least 0.40; and (b) has been genotyped and found to be homozygous for Arg389 in the $\beta_1$AR gene.

Also disclosed is a method of treating, preventing, delaying on set of, or reducing the risk of atrial fibrillation, the method comprising administering an effective amount of bucindolol to a patient who (a) has been diagnosed with atrial fibrillation less than 10, 20, 30, 40, 50, or 60 days before the administering, or less than 1, 2, 3, 4, 5, 6, 7, 8, 9, 10, 11, or 12 months before the administering, or less than 1, 2, 3, 4, 5, 6, 7, 8, 9, 10, 11, or 12 years before the administering; and (b) has been genotyped and found to be homozygous for Arg389 in the $\beta_1$AR gene.

In any method disclosed herein in which a patient's characteristics are described, such as a patient having a disease or condition (e.g., heart failure, atrial fibrillation, an LVEF value, a genotype, etc.), it is contemplated that an embodiment of such a method may include administering an effective amount of bucindolol to a patient that has the disease or condition or to a patient that has been diagnosed with the disease or condition. It is further contemplated that embodiments of such methods may additionally or alternatively include administering bucindolol to a patient after determining or ascertaining that the patient has the disease or condition or has been diagnosed with the disease or condition. It is still further contemplated that embodiments may also additionally or alternatively include first obtaining the results of a test or evaluation that shows or indicates that the patient has the disease or condition, and administering bucindolol to the patient only after obtaining such results.

Multiple embodiments of the invention are discussed throughout this application. Any embodiment discussed with respect to one aspect applies to other aspects as well and vice versa. Each embodiment described herein is understood to be applicable to all aspects. It is contemplated that any embodiment discussed herein can be implemented with respect to any method or composition, and vice versa. For example, in describing certain embodiments herein, there are values disclosed such as time from diagnosis of a disease or condition, time between diagnoses of heart failure and atrial fibrillation, LVEF values, timing of LVEF testing and testing for arrhythmia, and dosage of bucindolol, among others. Various patient characteristics, such as having or having been diagnosed with a certain disease or condition, are also disclosed in certain embodiments. It is contemplated that the values, patient characteristics, and other features discussed in the context of one embodiment can also be incorporated into any other embodiment disclosed herein. Furthermore, compositions and kits can be used to achieve methods disclosed herein.

In embodiments of the methods involving administering bucindolol disclosed herein, the administering has 1, 2, 3, 4, 5, 6, 7, 8, 9, 10 or more (or any range derivable therein) of the following effects: reduced risk of all-cause mortality; reduced risk death caused by heart failure; reduced risk of hospitalization; reduced risk of hospitalization for heart failure; reduced hospitalization for heart failure; reduced risk of stroke; reduced risk of new onset or recurrent atrial fibrillation, atrial flutter, ventricular tachycardia, ventricular fibrillation, tachycardia, or cardiac arrhythmia; reduced risk of needing therapies such as cardiac ablation or anti-arrhythmic medication; increased delay in onset of new onset or recurrent atrial fibrillation or atrial flutter; or improved quality of life. In some embodiments in which a reduced risk of an event or condition is achieved, the risk is reduced by at least 5, 10, 15, 20, 25, 30, 35, 40, 45, 50, 55, 60, 65, 70, 75, 80, 85, 90, or 95%. In some embodiments in which the length of a hospital stay is reduced, the hospital stay is reduced by at least or by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days (or any range derivable therein).

The terms "effective amount" or "therapeutically effective amount" refer to that amount of a composition of the disclosure that is sufficient to effect treatment, as defined herein, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

The "numerical values" and "ranges" provided for the various substituents are intended to encompass all integers within the recited range.

The term "optional" or "optionally" means that the subsequently described event or circumstance may or may not occur, and that the description includes instances where said event or circumstance occurs and instances in which it does not.

As used herein, "pharmaceutically acceptable carrier" or "pharmaceutically acceptable excipient" includes any and all solvents, dispersion media, coatings, antibacterial and antifungal agents, isotonic and absorption delaying agents and the like. In several embodiments, these media and agents can be used in combination with pharmaceutically active substances. Except insofar as any conventional media or agent is incompatible with the active ingredient, its use in the therapeutic compositions is contemplated. Supplementary active ingredients can also be incorporated into the compositions.

The term "treatment" or "treating" means any treatment of a disease or disorder in a mammal, including inhibiting the disease or disorder, arresting or suppressing the development of clinical symptoms; improving one or more physiological effects of the disease or disorder; reducing the severity or risk of an adverse event; reducing mortality from the disease or disorder; reducing the risk of mortality from the disease or disorder; reduced need for additional or alternative therapies such as cardiac ablation or use of anti-arrhythmic medication due to the disease or disorder; reduced risk of new-onset or recurrent atrial fibrillation, atrial flutter, ventricular tachycardia, ventricular fibrillation, or cardiac arrhythmia associated with the disease or disorder; reduced risk of hospitalization from the disease or disorder; reduced time of hospitalization from the disease or disorder; an increase in the delay of the onset of one or more symptoms or disorders associated with or caused by the disease or disorder; relieving the disease or disorder; and/or causing the regression of clinical symptoms from the disease or disorder.

Methods may involve multiple administrations of one or more compounds, compositions, and/or agents. In certain embodiments, cells or a subject are provided with a tolerance inducing agent prior to administering the composition for which a tolerance is being induced. It is contemplated that compounds, compositions, and/or agents may be formulated in a pharmaceutically acceptable formulation in certain embodiments of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that embodiments described in the context of the term "comprising" may also be implemented in the context of the term "consisting of" or "consisting essentially of." The compositions and methods can "comprise," "consist essentially of," or "consist of" particular elements, components, method steps, etc., disclosed throughout the specification.

It is contemplated that any method or composition described herein can be implemented with respect to any other method or composition described herein and that different embodiments may be combined.

Use of the one or more compositions may be employed based on methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 31. Likelihood of phase 3 success based on entry criteria.

DESCRIPTION OF ILLUSTRATIVE EMBODIMENTS

Figure 1:
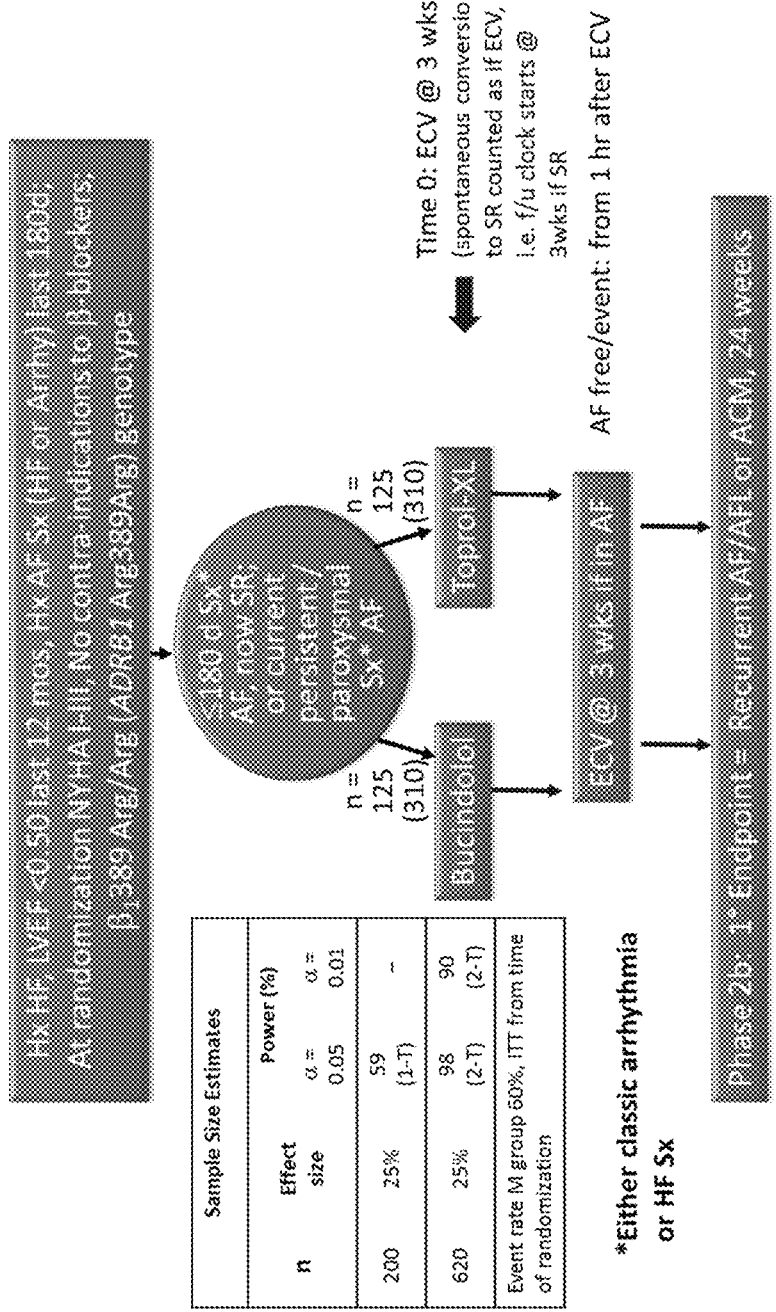
FIG. 1. Design of GENETIC-AF, a "seamless" Phase 2b→Ph 3 Adaptive Design Superiority Trial of bucindolol vs. Toprol-XL, for prevention of recurrent atrial fibrillation in HFrEF patients with the ADRB1 Arg389Arg genotype. Patients were at high-risk for recurrent AF, defined as post ECV conducted on day 0 in the trial, or with a history of an AF episode in the last 180 days. The Phase 2b stage targeted 250 evaluable patients, and the Phase 3 stage would have enrolled an additional 370 patients (620) with 330 primary events.

The current disclosure generally relates to methods, compositions and kits for treating patients with bucindolol. Pharmacogenomics and/or other criteria allow a clinician or physician to target prophylactic or therapeutic treatments to individuals who will most benefit from the treatment and to avoid treatment of individuals who will experience symptomatic side effects. Thus, a physician or clinician may consider applying knowledge obtained in relevant pharmacogenomics analysis in determining whether to administer bucindolol as well as whether to modify the dosage, regimen, and/or therapeutically effective amounts to be administered so as to attain the effect desired by the treatment. In some embodiments, a physician or clinician may alter treatment of the subject by adding an additional therapy or using an alternative therapy to treatment with bucindolol.

Bucindolol is a beta-blocker/vasodilator with unique pharmacologic properties that include sympatholysis (norepinephrine lowering) and inverse agonism for a variant of the human betas-adrenergic receptor, an arginine (Arg) at amino acid position 389. This variant is encoded by the major allele of the ADRB1 gene Arg389Gly polymorphism, with respective allele and homozygous genotype frequencies of 0.70 and 0.49 in the U.S. population. The Arg version of the encoded receptor protein has markedly higher signal transduction function and norepinephrine affinity compared to its 389Gly counterpart. In a previous 1040 patient substudy of a large placebo controlled clinical trial (BEST) conducted in advanced heart failure from reduced left ventricular ejection fraction (HFrEF), bucindolol treatment was associated with enhanced responses for prevention of arrhythmias as well as heart failure events, in patients homozygous for ADRB1 Arg389 (Arg389Arg).

A substudy was performed of 1040 patients of a large placebo controlled clinical trial (BEST) conducted in advanced heart failure from reduced left ventricular ejection fraction (HFrEF), in which bucindolol treatment was associated with enhanced responses for prevention of arrhythmias as well as heart failure events, in patients homozygous for ADRB1 Arg389 (Arg389Arg). The 1040 patient pharmacogenetic substudy of BEST included 925 patients who were randomized in sinus rhythm (SR) and at risk for developing AF. The therapeutic effect of bucindolol was found to be confined to patients who were homozygous for the major allele of the ADRB1 betas-adrenergic receptor Arg389Gly polymorphism.

Beta-blockers administered to heart failure (HF) patients with reduced ejection fraction (HFrEF) have been shown to prevent the development of AF.[11] In this meta-analysis,[11] the mean relative risk for newly developed AF comparing beta blocker against placebo was 0.73 (0.61, 0.86), with metoprolol succinate in the MERIT-HF trial[12] and bucindolol HCl in BEST[13] providing 15% and 36% of the data, respectively.

In previous studies[12,13], both beta-blockers were compared to placebo. Since metoprolol succinate has no therapeutic preference for ADRB1 Arg389 vs. Gly receptors, one can estimate the relative effectiveness of the two compounds for prevention of AF in HFrEF patients. The relative effect size (RES) formula of RES=Ln $HzR_1$/LnHzR$_2$[29] in which $HzR_1$ is the bucindolol hazard ratio for ADRB1 Arg389Arg genotype patients[13] and $HzR_2$ is the metoprolol hazard$^{ratio12,}$ [13], yields a predicted relative effect size of 2.1-fold in favor of bucindolol. This translates to a risk ratio 0.49 and an effect size of 51% in a direct comparison of bucindolol to metoprolol, in specific embodiments.

Certain embodiments concern methods and compositions involving bucindolol (2-(3-(1-(1H-indol-3-yl)-2-methylpropan-2-ylamino)-2-hydroxypropoxy)benzonitrile), which is understood to include bucindolol HCl, unless specifically excluded.

In some embodiments, methods and compositions concern bucindolol, substantially free of its R-stereoisomer. A composition is "substantially free" of R-bucindolol if it includes a mixture of S-bucindolol and (optionally) R-bucindolol wherein the weight of R-bucinolol, if present, is no more than about 20% of the total weight of S-bucindolol and R-bucindolol in the composition. In some embodiments, the composition may contain no more than about 20, 19, 18, 17, 16, 15, 14, 13, 12, 11, 10, 9, 8, 7, 6, 5, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0% or any range derivable therein by weight of R-bucindolol relative to the total weight of S-bucindolol and R-bucindolol in the composition. In some particular embodiments, the composition that is substantially free of R-bucindolol contains no more than about 20% by weight of R-bucindolol relative to the total weight of S-bucindolol and R-bucindolol in the composition. In more particular embodiments, the composition contains no more than about 10% by weight of R-bucindolol relative to the total weight of S-bucindolol and R-bucindolol in the composition. In more particular embodiments, the inventive composition contains no more than about 10% of R-bucindolol relative to the total weight of S-bucindolol and R-bucindolol in the composition. In even more particular embodiments, the inventive composition contains no more than about 1% of R-bucindolol relative to the total weight of S-bucindolol and R-bucindolol in the composition. Additional compositions and methods involving (S)-bucindolol are provided in U.S. Pat. Nos. 9,446,023, and 9,763,916, which are hereby incorporated by reference.

Administration of the β-blocker may be by any number of routes including, but not limited to, oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.). In certain embodiments bucindolol is formulated for oral administration.

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate bucindolol or other active ingredient.

In some embodiments, a patient is treated with a combination therapy that include bucindolol and another pharmaceutical agent. In certain embodiments, the pharmaceutical agent is an additional β-adrenergic receptor blocker. Non-limiting examples of beta-adrenergic receptor blockers include AC 623, acebutolol, alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrocholoride, butofilolol, carazolol, carteolol, carvedilol, celiprolol, cetamolol, cloranolol, dilevalol, esmolol, indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

In other embodiments, the composition may include a nitric oxide (NO) enhancing agent. Examples of NO enhancing agents are well known to those of ordinary skill in the art. Examples of such agents include a RAS inhibitor, a statin, a PDES inhibitor, a NO-conjugated drug, or a diazeniumdiolate. Non-limiting examples of RAS inhibitors include captopril, cilazapril, enalapril, fosinopril, lisinopril, quinapril, ramapril, zofenopril, candesartan cilexetil, eprosartan, irbesartan, losartan, tasosartan, tehnisartan, and valsartan, or a pharmaceutically acceptable salt thereof. Non-limiting examples of statins include atorvastatin, fluvastatin, lovastatin, pravastatin, rosuvastatin calcium, and simvastatin. Non-limiting examples of NO-conjugated drugs include S-NO-glutathione, NO-naproxen, NO-aspirin, NO-ibuprofen, NO-Diclofenac, NO-Flurbiprofen, NO-Ketoprofen, NO-releasing compound-7, NO-releasing compound-5, NO-releasing compound-12, or NO-releasing compound-18. Other examples of NO enhancing agents include L-arginine, arginine alpha-ketoglutarate, GEA 3175, sodium nitroprusside, glyceryl trinitrate, S-nitroso-N-acetyl-penicillamine, nitroglycerin, and diethylamine NONOate. Information concerning NO generating compounds for treating hypertension and atherosclerosis can be found in U.S. Pat. Nos. 7,396, 829, 7,348,319, 7,155,284, 7,052,695, 6,358,536, and 5,208, 233, each of which is herein specifically incorporated by reference. Information regarding nebivolol as an NO-enhancing agent can be found in U.S. Pat. No. 7,138,430, herein specifically incorporated by reference.

Administration of the pharmaceutical compositions set forth herein may be by any method known to those of ordinary skill in the art. Examples include, but are not limited to, oral, intravenous, intramuscular, intra-arterial, intramedullary, intrathecal, intraventricular, intradermal, intratracheal, intravesicular, intraocular, transdermal, subcutaneous, intraperitoneal, intranasal, enteral, topical, sublingual, or rectal administration. Further details on techniques for formulation and administration may be found in the specification below.

In some embodiments, the method further includes contacting the patient with a medical device that includes bucindolol. For example, the medical device may include a coating that includes bucindolol, a matrix that includes bucindolol, or a reservoir that includes a therapeutic composition as set forth above. The device may be inserted into the patient temporarily or implanted in the patient or placed on a body surface of the patient. Examples of such body surfaces include skin surfaces or mucosal surfaces.

The medical device may be any medical device known to those of ordinary skill in the art. Non-limiting examples of such medical devices include a stent, a graft, a heart valve, a filter, a catheter, a coil, a mesh repair material, a plate, a rod, a screw, or a suture. Embodiments also concern medical devices that include a coating, a matrix, or a chamber, wherein the coating, matrix, or chamber includes bucindolol. Non-limiting examples of such medical devices include a stent, a graft, a heart valve, a filter, a catheter, a coil, a mesh repair material, a plate, a rod, a screw, and a suture. An example of a type of filter is an inferior vena caval filter. An example of a type of catheter is a drug infusion catheter. An example of a type of coil is an embolic coil.

Detection of Polymorphisms

The CYP2D6 polymorphism described herein is present at various positions in or throughout the CYP2D6 gene. Another polymorphism is the 1165 position in the $\beta_1 AR$ gene that may give rise to an arginine or glycine amino acid residue at position 389 in the protein. The presence of the polymorphism can be determined from the sequence of the gene or by using specific characteristics of the polymorphism, e.g., restriction enzyme recognition site, hybridization, etc. As a result, a variety of different methodologies can be employed for the purpose of detecting polymorphisms in genes. Alternatively, the protein gene product can be evaluated to determine the patient's genotype.

Nucleic Acids

Certain embodiments concern various nucleic acids, including amplification primers, oligonucleotide probes, and other nucleic acid elements involved in the analysis of genomic DNA. In certain aspects, a nucleic acid comprises a wild-type, a mutant, or a polymorphic nucleic acid.

In some embodiments, nucleic acids used in embodiments comprise or are complementary to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1165, 1200, 1300, 1400, 1500, or more contiguous nucleotides, or any range derivable therein, of the human CYP2D6 gene or the human $\beta_1 AR$ gene (see U.S. Pat. No. 7,678,824, which is hereby incorporated by reference). One of skill in the art knows how to design and use primers and probes for hybridization and amplification of a sequence in the human CYP2D6 or human $\beta_1 AR$ gene. In some embodiments, the sequence is the CYP2D6 or $\beta_1 AR$ coding sequence (or its complement) or it is based on the CYP2D6 or $\beta_1 AR$ transcript, such as a cDNA of this sequence. A number of CYP2D6 genotype tests are commercially available, such as from Luminex (see Internet at luminexcorp.com/clinical/genetic-testing/pharmacogenetics/cyp2d6/, which is hereby incorporated by reference).

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

Preparation of Nucleic Acids

A nucleic acid may be made by any technique known to one of ordinary skill in the art, such as for example, chemical synthesis, enzymatic production or biological production. Non-limiting limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. In certain aspects amplification oligonucleotides can be designed on either side or overlapping with the boundaries of the insertion site. In a further aspect an oligonucleotide specific for the sequence at 894, whether a G or a T, can be designed. These oligonucleotides can varying in length from 5, 10, 15, 16, 17, 18, 19, 20, 21, 22, 23, 24, 25, 26, 27, 28, 29, 30, 50, nucleotides or more, including all values and ranges there between. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference).

In certain aspects, embodiments concern a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

Nucleic Acid Complements

Embodiments also encompass a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are used.

Nucleic Acid Detection and Evaluation

Genotyping can be performed using methods described in Small et al. (2002), which is incorporated herein by reference. It will be understood by the skilled artisan that other standard techniques are available for genotyping and any technique may be used with the embodiments described herein. General methods of nucleic acid detection methods are provided below.

In some embodiments, genotyping involves isolating from the patient a nucleic acid mixture comprising both copies of the CYP2D6 or $\beta_1$AR gene, or a fragment thereof, and determining the nucleotide sequence of one or more polymorphisms. In some embodiments, this involves determining the sequence based on the transcripts produced from both copies of the gene. Other polymorphisms, such as single nucleotide polymorphisms can be linked to and indicative of the polymorphism at positions described herein. Consequently, in some embodiments a polymorphism in linkage disequilibrium (LED or LD) with a polymorphism may be used to determine the sequence at a different position.

Those in the art will readily recognize that nucleic acid molecules may be double-stranded molecules and that reference to a particular site on one strand refers, as well, to the corresponding site on a complementary strand. Thus, in defining a polymorphic site, reference to a sequence including an adenine, a thymine (uridine), a cytosine, or a guanine at an particular site on one strand of a nucleic acid molecule is also intended to include the thymine (uridine), adenine, guanine, or cytosine (respectively) at the corresponding site on a complementary strand of a nucleic acid molecule. Thus, reference may be made to either strand and still comprise the same polymorphic site and an oligonucleotide may be designed to hybridize to either strand.

Typically, the nucleic acid mixture is isolated from a biological sample taken from the individual, such as a blood sample or tissue sample using standard techniques such as disclosed in Jones (1963) which is hereby incorporated by reference. Suitable tissue samples include whole blood, semen, saliva, tears, urine, fecal material, sweat, buccal, skin, and hair. The nucleic acid mixture may be comprised of genomic DNA.

In the genotyping methods used in embodiments, the identity of a polymorphic site may be determined by amplifying a target region containing the polymorphic site directly from one or both copies of the gene present in the individual and the sequence of the amplified region(s) determined by conventional methods or evaluated directly.

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The identity of polymorphisms may also be determined using a mismatch detection technique, including but not limited to the RNase protection method using riboprobes (Winter et al., 1985; Meyers et al., 1985) and proteins which recognize nucleotide mismatches, such as the *E. coli* mutS protein (Modrich, 1991). Alternatively, variant alleles can be identified by single strand conformation polymorphism (SSCP) analysis (Orita et al., 1989; Humphries et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. Another primer extension method is allele-specific PCR (Ruano et al., 1989; Ruano et al., 1991; WO 93/22456; Turki et al., 1995).

Polymorphic variation in genes can also be detected using differential digestion of DNA by certain restriction enzymes (Small et al., 2002) or by any other method that identifies the sequence of the polymorphic position in the gene.

In a specific example, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an Illumina forward index for MiSeq/NextSeq/HiSeq platforms) or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, and a sequence for targeting a specific target region (e.g., 16S region, 18S region, ITS region). Amplification and sequencing can further be performed on any suitable amplicon, as indicated throughout the disclosure. In the specific example, sequencing comprises Illumina sequencing (e.g., with a HiSeq platform, with a MiSeq platform, with a NextSeq platform, etc.) using a sequencing-by-synthesis technique. Additionally or alternatively, any other suitable next generation sequencing technology (e.g., PacBio platform, MinION platform, Oxford Nanopore platform, etc.) can be used. Additionally or alternatively, any other suitable sequencing platform or method can be used (e.g., a Roche 454 Life Sciences platform, a Life Technologies SOLiD platform, etc.). In examples, sequencing can include deep sequencing to quantify the number of copies of a particular sequence in a sample and then also be used to determine the relative abundance of different sequences in a sample. Deep sequencing refers to highly redundant sequencing of a nucleic acid sequence, for example such that the original number of copies of a sequence in a sample can be determined or estimated. The redundancy (i.e., depth) of the sequencing is determined by the length of the sequence to be determined (X), the number of sequencing reads (N), and the average read length (L). The redundancy is then N.times.L/X. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more.

Sequencing

Aspects of the disclosure may include sequencing nucleic acids to determine whether a gene has one or more polymorphisms. Sequencing technology that has been available for several years includes massively parallel signature sequencing (MPSS) developed in the 1990s at Lynx Therapeutics, the polony sequencing method developed by George M. Church at Harvard in 2005, and 454 pyrosequencing developed in 2006 by 454 Life Sciences (acquired by Roche Diagnostics). In some embodiments, they are superseded by new technologies, such as those disclosed below. The first next-generation sequencing technologies included Illumina (Solexa), SOLiD, Ion Torrent semiconductor, DNA nanoball, and Heliscope single molecule sequencing methods. The third generation of sequencing technologies includes single molecule real time (SMRT), Nanopore real time long read, and Illumina and 10X Genomics synthetic long read sequencing technologies.

The term "polymorphism", as used herein, refers to a difference in the nucleotide or amino acid sequence of a given nucleotide or amino acid region as compared to a nucleotide or amino acid sequence in the corresponding region of another individual of the same species. Preferably, the species is human. A polymorphism is generally defined in relation to a "reference" sequence. In the subject application, "reference" sequence and "wild type" sequence are used interchangeably. Nucleotide polymorphisms include single nucleotide differences, differences in sequence of more than one nucleotide, and single or multiple nucleotide insertions, inversions, substitutions, and deletions. Amino acid polymorphisms include single amino acid differences, differences in sequence of more than one amino acid, and single or multiple amino acid insertions, substitutions, and deletions.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term biological sample encompasses a clinical sample, and also includes cells in culture, cell supernatants, cell lysates, serum, plasma, biological fluid, and tissue samples. In one embodiment, the sample is collected by the individual. For example, an individual can collect a swap of tissue from the inside of the cheek for use as a nucleic acid sample. As known in the art, many types of samples can be used for the extraction of nucleic acids.

As used herein the term "treating" in reference to a disease or condition means a reduction in severity or elimination of one or more symptoms associated with a particular disease or condition. Therefore, treating a disorder does not necessarily mean a reduction in severity of all symptoms associated with a disorder and does not necessarily mean a complete reduction in the severity of one or more symptoms associated with a disorder. Treatment, as used in this context, covers any treatment of a symptomatic condition, such as an adverse reaction in a mammal, particularly in a human, and includes: (a) diagnosing and then preventing the adverse reaction from occurring in an individual which can be predisposed to the reaction but has not yet been diagnosed as having it; (b) inhibiting the adverse reaction, i.e., arresting its development; and (c) relieving the adverse reaction, i.e., causing regression of the reaction.

The term "therapeutically effective amount" means an amount that is effective in treating a particular disorder; that is an amount that is effective for reducing the severity of one or more symptoms associated with the particular disease or condition for which treatment is sought. The term "ameliorate," as used for instance in the amelioration of a particular condition means to make one or more symptoms of the condition at least more tolerable, if not better. The term ameliorate does not necessarily mean an increase in toleration of all symptoms associated with a disorder and does not necessarily mean a complete reduction in the severity of one or more symptoms associated with a disorder.

In another embodiment, a further step is added wherein a portion of a gene is amplified prior to the identifying step. In another embodiment, the identifying is performed by a method selected from the group consisting of a hybridization assay, a sequencing assay, a microsequencing assay, a MALDI-TOF assay, and an allele-specific amplification assay. In a further embodiment, the identifying is performed by an antibody-based assay.

Pharmacogenomics allows a clinician or physician to target prophylactic or therapeutic treatments to individuals who will most benefit from the treatment and to avoid treatment of individuals who will experience symptomatic side effects. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer bucindolol as well as tailoring the dosage, regimen, and/or therapeutically effective amounts to be administered so as to attain the effect desired by treatment with the modulator.

V. EXAMPLES

Example 1

Phase 2—Genetic AF Trial

Provided herein is an evaluation of bucindolol vs. an active beta-blocker comparator (metoprolol succinate, TOPROL XL) for the prevention of atrial fibrillation (AF), atrial flutter (AFL) or all-cause mortality (ACM). Unlike bucindolol, metoprolol succinate has not exhibited preferential treatment effects in HFrEF patients with an ADRB1 Arg389Arg genotype vs. 389Gly variants. This trial enrolled patients who had ADRB1 Arg389Arg genotype and a reduced left ventricular ejection fraction (LVEF), a history of heart failure (HF), and were at high risk for the development of recurrent AF. The primary endpoint of the trial was time to AF/AFL (symptomatic or asymptomatic) or ACM, which was assessed by symptom changes and surveillance ECGs in patients at high risk for developing recurrent AF. In order to evaluate the effect of CYP2D6 genetic variation on drug levels, safety and effectiveness, the trial included 2D6 genotyping and population PK measurements.

The trial featured an adaptive, seamless Phase 2B/Phase 3 design with an interim analysis after data were available from at least 150 evaluable patients. In this interim analysis the DSMB was charged with recommending either 1) a transition to a 620 patient Phase 3 trial with a primary endpoint of symptomatic AF/AFL or ACM, 2) continuing the trial but ending in Phase 2 with an enrollment of approximately 250 patients, or 3) discontinuing the trial immediately for futility. The recommendation was to be based primarily on Bayesian predictive probability of Phase 3 trial success (PPoS), and on other factors including data from an AF burden (AFB) continuous rhythm monitoring substudy. The interim analysis was conducted on 230 randomized patients with 103 primary events, and based on a PPoS above futility but below the Phase 3 transition boundary the DSMB recommended completing the trial in Phase 2. This disclosure includes an analysis of the 267 patients who were investigated in the Phase 2 trial, including data through the trial end.

In U.S. patients (48% of the 267 randomized patients, 51% of the primary events), the pretrial assumptions for control group event rate and effectiveness were met, with a metoprolol event rate of 60% and a hazard ratio of 0.70 (95% C.I. 0.40, 1.19). However, the entire cohort did not meet pretrial assumptions for effectiveness, with a hazard ratio of 1.01 (95% CI: 0.71,1.42). In the AF burden substudy, the hazard ratio was 0.75 (0.43,1.32) for the entire cohort (N=69) and 0.49 (0.24,1.04) for U.S. patients (N=42). Two of the five ex-U.S. countries (Hungary and Canada) exhibited marked heterogeneity for the primary endpoint with hazard ratios >1.5, and interaction p values compared to the U.S. of 0.13 and 0.008, respectively. In these two countries patients had developed their first episode of AF an average of 11 months (Canada) or 6 years (Hungary) prior to developing heart failure, compared to heart failure developing 13 months before AF in U.S. patients. In addition, patients randomized in Hungary had only mild LV dysfunction, and in both Canada and Hungary NHYA Class heart failure symptoms were either absent (Class I) or mild (Class II) at the time of randomization. In contrast, the majority of U.S. patients had either NYHA Class II or Class III symptoms.

Analysis of the data concludes that in U.S. and European HFrEF patients enrolled in countries other than Hungary, effectiveness data for bucindolol vs. metoprolol succinate are consistent with data from the BEST trial for bucindolol vs. placebo. In contrast, patients with mild LV dysfunction who were not NYHA Class II or Class III at baseline and who had developed HF many months or years after AF first presents do not respond favorably to bucindolol. This is likely due to differences in the pathophysiology of long-standing AF producing mild LV dysfunction compared to primary HFrEF pathophysiology resulting in AF.

GENETIC-AF was a trial with several firsts, including (i) the first randomized trial investigating a single pharmacologic intervention in HFrEF patients at high risk for developing recurrent AF, (ii) the first trial to compare an AF burden definition of AF to the determination of AF by symptoms/ECG criteria, (iii) the first prospectively designed, pharmacogenetically targeted cardiovascular controlled clinical trial to report data, and (iv) the first randomized beta-blocker effectiveness trial to measure CYP2D6 gene variants in every patient and compare genotype categories to drug levels, safety and effectiveness.

A. Design of The GENETIC-AF TRIAL (Phase 2 Trial)

The Genotype-Directed Comparative Effectiveness Trial of Bucindolol and Toprol-XL for Prevention of Symptomatic Atrial Fibrillation/Atrial Flutter in Patients with Heart Failure (GENETIC-AF) trial[30,31] was an adaptive, seamless design Phase 2B/3 comparative effectiveness trial conducted between 24 Jun. 2014 (first patient randomized) and Dec. 29, 2017 (last day of follow-up). The Phase 2 endpoint of the trial, time to any recurrent atrial fibrillation (AF), atrial flutter (AFL) or all-cause mortality (ACM) was evaluated in an interim analysis conducted by the DSMB on Aug. 7, 2017. Although the trial stopped in Phase 2, the Phase 3 endpoint, time to symptomatic AF/AFL or ACM, was also collected and results are presented below in section D.

GENETIC-AF was designed to evaluate the effectiveness of bucindolol HCl vs. metoprolol succinate, specifically TOPROL-XL. The preparation of study medications is given below in Example 6. GENETIC-AF was a genotype-directed, comparative effectiveness trial comparing Bucindolol to Toprol-XL for the prevention of atrial fibrillation/atrial flutter in patients with heart failure. Appropriate patients were genotyped at the screening visit and only patients who were homozygous for the B1389Arg form of the receptor were eligible to participate in the trial.

In addition to a ADRB1 Arg389Arg genotype, eligible patients had to have a reduced left ventricular ejection fraction (LVEF), a history of heart failure (HF), and be at high risk for the development of recurrent AF. High recurrent AF risk was defined as either the presence of persistent AF eligible for electrical cardioversion (ECV) to be performed after randomization, or the presence of sinus rhythm (SR) or paroxysmal AF with a documented history of AF within the past 6 months. The criteria for a reduced LVEF and a history of HF symptoms generally defined a HFrEF population. For reasons of therapeutic response differentiation and pathophysiology[32] this category has been recently subdivided into HFmrEF[33] (HF with "mid-range" LVEF, of 0.41 to 0.49) and HFrEF (HF with LVEF ≤0.40). The sample size for Phase 3 was based on a projected effect size of 25% and 330 events, corresponding to 98% power for alpha 0.05 and 90% power for alpha 0.01.

Following a screening period of up to 8 weeks, patients were randomized 1:1 to receive either Bucindolol or Toprol XL and entered a drug lead-in period during which patients were up-titrated to therapeutic dose levels. This drug lead-in period could extend up to 8 weeks but on average was 4.4 weeks and was similar for both groups. The trial also included an AF burden substudy using Medtronic LINQ and other Medtronic therapeutic devices, which could be implanted at anytime during the drug lead-in period.

After the drug lead-in period, patients who were in AF/AFL underwent electrical cardioversion to establish sinus rhythm and subsequently entered the 24-week efficacy follow-up period. Patients who were in SR and did not require ECV started the efficacy follow-up period approximately 3 weeks after initiation of study drug. Patients who failed to establish sinus rhythm or who died prior to the start of efficacy follow-up were considered an event on day 1 for the primary endpoint.

During the efficacy follow-up period, patients were seen at regular intervals, during which their heart rhythm was assessed by 12-lead ECG and they were queried for symptoms potentially related to AF and HF. After the 24-week primary endpoint period, patients entered a blinded, treatment extension period where they continued to be followed for long-term safety and clinical outcomes.

The trial also included an adaptive-design element that would allow for a seamless transition from Phase 2B to Phase 3 if certain prespecified criteria were met. This was assessed during an interim analysis conducted on 230 randomized patients and was based on the Bayesian predicted probability of success using the interim data modeled out to the Phase 3 goal of 620 patients and 330 events.

A PPoS greater than or equal to 40% would trigger a seamless transition to Phase 3 and continued enrollment of up to 620 patients. Futility was set at a PPoS <10%, which would result in immediate termination of the trial. And a PPoS between these two criteria would result in completion of the trial with the current Phase 2B population.

The PPoS was above futility but did not meet the Phase 3 criteria; therefore, the Phase 2B stage was completed and the trial results were unblinded.

It was assumed that most patients enrolled in GENETIC-AF would be receiving approved HF beta-blockers prior to enrollment. Therefore, the protocol specified that currently administered beta-blocker therapy would be discontinued at the randomization visit and patients would be allocated 1:1 to initially receive either bucindolol or metoprolol succinate at approximately 50% of the betas-adrenergic receptor (AR) blocking dose. The dose was then doubled weekly to target (or maximally tolerated dose), with a goal of having a therapeutic dose being administered in approximately 3 weeks, the protocol-recommended time point for ECV in patients in AF.

The primary efficacy follow-up period was 24 weeks, beginning at the time of ECV (Week 0) for patients in AF/AFL or approximately 3 weeks after randomization for patients in SR who did not require ECV. Week 0 could occur later for patients needing additional medical management prior to ECV, such as adjustment of oral anticoagulation. Following the 24-week efficacy follow-up period, patients entered long-term follow-up with continuation of blinded study medication and collection of endpoint and safety data until the trial completion.

The initial method for detecting rhythm events included transtelephonic monitoring (TTMs) and clinic-based ECGs. Because of impracticality in the era of smart phones as well other operational factors, TTM was abandoned on the third protocol amendment, and the frequency of clinic-based ECGs was increased accordingly. The trial had an important AF burden (AFB) substudy that was supportive of the primary endpoint. In this analysis, the definition of an AF/AFL event was prespecified as at least 6 hours of AF burden per day as recorded by an implanted or inserted device. Six hours of AF burden was selected as a surrogate endpoint for clinical AF because this amount of AF burden had previously been shown to be associated with an increased rate of hospitalization for HF.[34]

To capture primary endpoint information on every randomized subject, patients in AF at Week 0 who failed to cardiovert to SR on ECV were counted as an endpoint on day 1, as were patients who died in the study medication up-titration period prior to the start of efficacy follow-up (i.e., prior to Week 0). A diagram of the trial design is provided in FIG. 1, and an example of a schedule for trial major operational events is provided in FIG. 2.

The following three amendments were in Phase 2 as opposed to Phase 1 (the original protocol). The first amendment was released around the time of first patient randomization and generally provided procedural clarifications and modest changes to the study eligibility criteria. The second amendment was released after approximately 10 (4% of total enrollment) patients had been randomized and included more substantial changes to the study eligibility criteria to encourage enrollment. This included broader criteria for heart failure and the inclusion of paroxysmal AF, as well as patients in SR with a recent history of AF. The timing for a second rhythm assessment to confirm the presence of AF/AFL was also changed from 'at least 1 hour' to 'at least 10 minutes' after the first rhythm assessment due to operational challenges at EP clinics. The third amendment was released after approximately 55 (21% of total enrollment) patients had been randomized. This amendment included some modifications to the study eligibility criteria but was primarily focused on simplification of study procedures and site/patient burden. This included the removal of all TTM assessments and decreasing the post-ECV duration for confirmation of stable SR from 24 hours to 1 hour. Changes to the protocol are as follows:

Amendment 1/Protocol v2.0

The following changes were part of Amendment 1.

AF burden substudy that was previously required for all Phase 2B patients was now to be optional, but non-participation was capped at no more than 25% of Phase 2B population The requirement for a third rhythm assessment 7-9 days after the initial AF event for the classification of paroxysmal/persistent AF was removed.

Clarification that certain antiarrhythmic medications (i.e., amiodarone, dofetilide, flecainide, and propafenone) were allowed during the study after a patient experiences a recurrence of AF.

Clarification that a trough blood sample for the Population PK substudy only needed to be collected at Week 0 for patients who spontaneously convert to SR.

Update to emphasize that vital status (i.e., alive/dead) was to be assessed periodically during the study, including for patients who withdraw from the study who consent to periodic telephone contact.

Requirement for NYHA class II/III symptoms ≤90 days of screening visit was changed to symptomatic heart failure ≤90 days of screening visit.

Requirement for symptomatic persistent AF ≤180 days of screening visit change to requirement for symptomatic AF at screening and randomization visits determined by the Investigator to require ECV.

Left ventricular internal diameter in diastole eligibility criteria was restricted to only those patients with a LVEF ≥0.40 and <0.50.

Definition of clinical euvolemia was clarified.

Lower limit of systolic blood pressure eligibility criteria increased from 85 to 90 mmHg.

Exclusion criteria were added for permanent AF, NYHA class IV symptoms at screening, untreated second degree Mobitz II or third degree heart block, and heart rate <60 bpm or >180 bpm.

Exclusion criteria were removed for chronic use of inhaled β2-selective adrenergic agonist and evidence of paroxysmal AF during the screening period.

Modification were made to allow up-titration intervals shorter than one week in special circumstances following pre-approval by the sponsor.

Requirement was added for telephone contact within 72 hours for all patients who discontinue study drug.

Clarification provided that cardioversion or medical intervention for life-threatening AF based on a single rhythm assessment may be included as an event for the primary endpoint.

The secondary endpoint examining all-cause mortality or heart failure hospitalization was modified to include AF/AFL events.

A tertiary endpoint that explored the effects of VRR control on the all-cause hospitalization secondary endpoint was eliminated and was now to be performed as a supportive analysis for this secondary endpoint.

A supportive analysis was added for the VRR control secondary endpoint to evaluate this endpoint at the time of study drug discontinuation, as well as at the end of the study.

The duration of the Drug Titration Period was changed to 6 weeks after randomization. Previously defined as randomization through Week 8 (Week 11 post-randomization).

Consolidation of various secondary, tertiary, and safety endpoints was described.

Amendment 2/Protocol v3.0

The following are the specific changes in Amendment 2

Additional information was provided regarding the timing of study drug dosing on the day of randomization and regarding the requirement for up-titration of study drug dose to protocol-specified targets The study drug transition algorithm was updated to include guidance for immediate release metoprolol, controlled release carvedilol, and bisoprolol.

Eligibility criteria were modified to include HFREF patients currently in sinus rhythm who had experienced at least one symptomatic paroxysmal or persistent AF episode ≤120 days of the Screening Visit.

Eligibility criteria requirement for symptomatic heart failure ≤90 days of screening was modified to a history of heart failure with most recent assessment of LVEF <0.50 assessed ≤12 months of screening.

Exclusion of NYHA class IV symptoms at screening changed to exclusion for NYHA class IV symptoms at randomization.

Exclusion of patients with history of AF ablation was changed from 3 months to 30 days of screening.

Several inclusion and exclusion criteria were modified to be effective at the Randomization Visit instead of at the Screening Visit.

The schedule for clinic visits during the 24-week Follow-Up Period was modified to occur every 4 weeks. The schedule for at-home transtelephonic monitoring (TTM) assessments was modified to every 4 weeks, alternating with clinic visits to allow for heart rhythm assessments every 2 weeks during the 24-week Follow-up Period.

A requirement was added to collect two TTM recordings separated by at least 10 minutes for every TTM assessment.

The requirement for a second rhythm assessment to confirm the presence of AF/AFL was changed from 'at least 1 hour' to 'at least 10 minutes' after the first rhythm assessment.

The AFSQ was modified to assess symptom frequency and to remove/clarify potentially ambiguous questions.

The responsibility for administration of the AFSQ at the time of TTM was changed from the TTM technician to site personnel.

The timing for the first interim analysis was modified to remove the requirement for randomization of at least 200 patients.

Amendment 3/Protocol v4.0

The following are the specific changes in Amendment 3:

Concomitant administration of flecainide or propafenone with study drug after a patient reverted back to AF was no longer permitted due to the potential for CYP2D6-mediated drug interactions with study drug The sample size for Phase 2B was changed from 200 to 250 patients. The increased sample size allowed for more 24-week endpoint data to be considered for the Phase 2B interim efficacy analysis prior to meeting the Phase 2B enrollment goal. However, the overall sample size for the trial remained unchanged (i.e., 620 patients).

Previously, the most recent LVEF in the past 12 months was required to qualify the patient for the trial. Now the qualifying LVEF could be assessed at any time during the last 12 months. This change considered the potential for functional improvement following treatment for heart failure, while still defining a heart failure population with HFREF origins.

The window for qualifying AF episodes was increased from 120 days to 180 days of the Screening Visit.

The exclusionary window for previous ECV procedures was changed from 12 to 6 months and was now relative to the Randomization Visit instead of the Screening Visit.

The prohibited concomitant medication criteria were modified to only exclude frequent use of short acting nitroglycerine for the treatment of acute angina; prophylactic use of sustained release nitroglycerine for the prevention of angina was not exclusionary.

A new exclusion criterion was added for left ventricular assist devices. Added: "The presence of a left ventricular assist device (LVAD) or a condition that is likely to require LVAD placement within 6 months of the Randomization Visit."

A new exclusion criterion was added for patients with symptomatic bradycardia. Added: "History of untreated symptomatic bradycardia or if symptomatic bradycardia is likely on full dose of study drug in the opinion of the Investigator."

A new exclusion criterion was added for history of pulmonary hypertension. Added: "History of pulmonary hypertension, defined as a systolic pulmonary arterial pressure ≥70 mmHg at rest as assessed by echocardiography or right heart catheterization."

The exclusion criteria for several lab values was modified to allow for retesting during the screening period.

The maximum time period between the Screening Visit and the Randomization Visit was increased from 4 to 8 weeks to allow additional time for patient management prior to randomization.

The maximum time period between randomization and ECV was increased from 5 to 8 weeks to allow additional time for patient management prior to cardioversion.

All transtelephonic monitoring requirements were removed from the protocol and a clinic visit was now required 2 weeks after the start of efficacy follow-up (Week 2 Visit) to monitor for early AF/AFL events.

Due to the removal of TTM assessments, sites were required to make out-bound phone calls during the 24-week Follow-up Period to monitor for AF/AFL events between scheduled clinic visits. During these calls, the site was to administer the AFSQ to assess for potential changes in AF/AFL symptoms and patients were required to return to the clinic for an unscheduled visit if the investigator suspected that a new AF/AFL event had occurred between scheduled clinic visits.

Data from previously enrolled patients indicated that nearly all patients who were in SR at the Week 0 Visit were also in SR at the time of the 24-hour confirmation (only one exception); therefore the 24-hour time point was considered unnecessary and was removed to decrease patient and site burden. Therefore, the primary endpoint definition of stable sinus rhythm (SR) was changed. Stable SR was now to be defined as SR on two rhythm assessments at least 1 hour apart at the Week 0 Visit or SR at least 1 hour after electrical cardioversion (ECV).

The requirement for ECG over-read by an EP Core Lab during the 24-week Follow-up Period was removed. ECG over-read was now to be performed by the Clinical Events Committee (CEC) at the time of endpoint adjudication for both the primary and secondary rhythm endpoints.

The Phase 2B enrollment cap for patients not participating in the optional AF burden substudy was removed, making the AF burden substudy optional for all patients in both Phase 2B and Phase 3.

The randomization strata definition was updated to clarify that patients with atrial flutter (AFL) at randomization were to be included in the atrial fibrillation strata for randomization.

A supportive analysis of the primary endpoint for the Total Follow-up Period was removed because symptomatic AF/AFL events were not to be adjudicated by the CEC after Week 24.

The secondary endpoint examining ventricular rate control in periods of AF/AFL was updated to be consistent with the Clinical Event Committee charter.

A supportive analysis was added for the hospitalization secondary endpoint that was to examine the subset of heart failure related hospitalization.

The methodology for the statistical analysis of AF burden data was minimized, as a more detailed description of the analysis was already specified in the data analysis plan.

Details of the Phase 2B interim analysis were removed from the protocol, as a more detailed description was provided in the DSMB charter.

A new Phase 3 interim analysis was added to assess the absence of futility and whether an expansion of the total sample size would have been warranted. Details of the Phase 3 interim analysis were prespecified in the DSMB charter.

The trial enrolled a genotype-defined heart failure population at high risk of AF/AFL recurrence, and in particular cases, eligibility criteria were as follows:

1. History of HF with reduced left ventricle ejection fraction (HFrEF+HFmrEF)
   LVEF <0.50 within 12 months of the Screening Visit
   Excluded: NYHA class IV
   Excluded: Significant fluid overload at Randomization
2. Symptomatic paroxysmal or persistent AF episode ≤180 days of Screening Visit
   Excluded: Permanent AF >1 year
3. Possess the β1389Arg/Arg (ADRB1 Arg389Arg) genotype
4. Receiving appropriate anticoagulation therapy prior to randomization for stroke
5. Clinically appropriate for ECV if AF/AFL is present at the Week 0 Visit
   Excluded: More than 2 ECVs within 6 months of Randomization
   Excluded: Most recent ECV failed to produce sinus rhythm
6. Systolic BP >90 mmHg and <150 mmHg at Randomization
7. Heart rate ≥60 bpm (if BB naïve) and <180 bpm (all) at Randomization B. Enrollment and Randomization Metrics of The GENETIC-AF TRIAL (Phase 2 Trial)

The trial was conducted in the U.S., Canada and Europe, with an operational goal of enrolling approximately 50% of the patients in the U.S. Randomized patients (n=267) were enlisted from 110 sites, including 48 in the US, 20 in Canada, 10 in Poland, 9 in Hungary, 8 in Serbia, 8 in Bulgaria, and 7 in the Netherlands.

C. Interim Analysis for the GENETIC-AF TRIAL (Phase 2 Trial)

The interim analysis was conducted by the DSMB based on 230 randomized patients of whom 103 had AF/AFL/ACM events and 49 had completed 24 weeks of follow-up without experiencing a primary endpoint event. As this number of primary endpoint events would not provide adequate statistical power by conventional/frequentist statistical analysis, the time to primary endpoint event data were subjected to Bayesian modeling to generate "predictive probability of success" (PPoS) values, assuming the trial would go to its 620 patient/330 event Phase 3-conclusion.

The Phase 3 stage of the trial included a second interim analysis to determine if a fixed, 200-patient increase in sample size was warranted (N=820). This "Promising Zone"[37] approach was based on predefined PPoS and conditional power criteria applied to the Phase 3 primary endpoint event rates, which was to be assessed after 400 patients had been randomized.[30,35]

Figure 3:
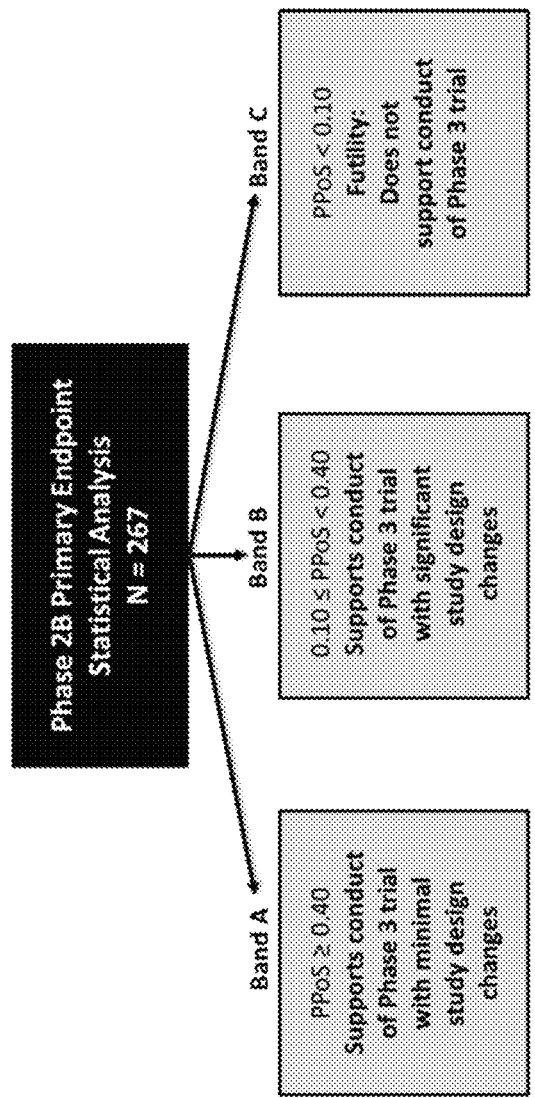
FIG. 3. Boundaries for prespecified thresholds, predictive probability of success based on Bayesian modeling of the Phase 2 primary endpoint of time to any recurrent AF/AFL or ACM.

The PPoS estimates were compared to the decision boundaries shown in FIG. 3, which created three options for the Phase 2B DSMB recommendation. For a PPoS of ≥0.40 and an adequate safety profile, the trial would convert to Phase 3, retaining all randomized patients and preceding with no substantial modification of trial design. At the other end of the spectrum was the recommendation of an immediate stop for futility, for a PPoS <0.10 or a major safety issue. The third option for consideration was an intermediate PPoS of ≥0.10 and <0.40, which would lead to a recommendation to continue and complete the trial in Phase 2, with full 24-week follow-up for most patients. The estimated size of the Phase 2 trial under these conditions was an N of 200, with evaluable data (i.e., completed 24 weeks follow-up or had an endpoint) from at least 150 patients.

The PPoS for the entire cohort was close to the futility boundary at 0.11, but the PPoS was 0.52 for the AF burden substudy endpoint with a HzR of 0.84 (95% CI: 0.45, 1.57). Further, the DSMB considered the USA results for the AF/AFL/ACM endpoint, which had a HzR of 0.73 (0.41, 1.28). While these trends were not statistically significant, they numerically favored bucindolol. As such, the DSMB recommendation based on the interim analysis was to complete the trial in Phase 2.

These interim results were consistent with the final results (Section D below), which included substantially more (by 39%) events. Based on the DSMB recommendation, ARCA stopped enrollment of the trial and informed sites to continue follow-up on all patients in the 24-week Follow-up Period. Most patients completed the 24-week Follow-up Period (mean follow-up=21.4±6.2 weeks); however, follow-up was truncated for 28 (10.5%) patients due to the operational constraints.

D. Final Results for the GENETIC-AF TRIAL (Phase 2 Trial)

1. Statistical Analysis Plan (SAP)

The original SAP was based on completion of the trial in Phase 3, with a primary endpoint of time to first symptomatic AF/AFL or ACM (Supplement, Section 7.3). When the DSMB recommended the trial be completed in Phase 2 a SAP addendum was developed (Supplement, Section 7.4) that adopted the Phase 2 DSMB methodology for the interim analysis as the SAP of record. This approach was necessary because the numbers of patients and events expected for Phase 2B was less than half of that projected for the full Phase 3 trial, resulting in inadequate power for the primary endpoint to produce a test of the null consideration based on the conventional statistical analysis described in the original SAP. Therefore, the Bayesian predictive probability construct described in FIG. 3 was applied to the final results from the entire cohort, as well as to prespecified subgroups. The latter included the four randomization stratification variables (HF etiology: ischemic vs. non-ischemic; LVEF: <0.35 vs. ≥0.35); Type of Medtronic device: Reveal vs. Non-Reveal vs. No Device, and; Rhythm status at randomization: SR vs. AF/AFL), which were also predefined subgroups in the Phase 3 SAP. In addition, history of persistent AF vs. paroxysmal AF and analysis by geographic region (U.S. vs. Canada vs. Europe) were predefined for subgroup analysis and Bayesian modeling in the SAP amendment For the conventional analyses described in the Phase 3 SAP, the log rank statistic was covariate adjusted for the four stratification factors. The Bayesian modeling was also covariate adjusted for these same variables. For conventionally constructed time to event curves we also present unadjusted analyses for the major results and for subgroup analyses with small sample sizes.

2. Baseline Characteristics i) Entire Cohort Baseline Characteristics: Table 1 gives baseline characteristics for the entire cohort and components randomized in the U.S., Canada and Europe.

TABLE 1

Baseline characteristics for the entire cohort, U.S. Canada and Europe

| Parameter | Entire Cohort n = 267 | U.S. n = 127 | Canada n = 59 | Europe n = 81 |
| --- | --- | --- | --- | --- |
| Age | 65.6 ± 10.1 | 66.3 ± 10.7 | 62.8 ± 9.8 | 66.7 ± 9.0 |
| Gender M/F (%) | 82/18 | 87/13 | 86/14 | 72/28 |
| Race/ethnicity: W/B/A/O/H (%) | 96/2/1/1/3 | 93/4/1/2/5 | 98/0/2/0/0 | 100/0/0/0/1 |
| LVEF | 0.36 ± 0.10 | 0.33 ± 0.09 | 0.35 ± 0.10 | 0.42 ± 0.08 |
| NYHA I/II/III (%) | 28/57/15 | 17/57/26 | 32/61/7 | 43/53/4 |
| Hx Ischemic/Non-Ischemic HF (%) | 32/68 | 31/69 | 29/71 | 36/64 |
| Randomized in AF/Not in AF (%) | 51/49 | 59/41 | 58/42 | 32/68 |
| Hx Persistent/Paroxysmal AF (%) | 51/49 | 52/48 | 53/47 | 48/52 |
| AF Dx to Randomization, days | 1306 ± 2240 | 1236 ± 2192 | 1249 ± 1776 | 1458 ± 2605 |

TABLE 1-continued

Baseline characteristics for the entire cohort, U.S. Canada and Europe

| Parameter | Entire Cohort n = 267 | U.S. n = 127 | Canada n = 59 | Europe n = 81 |
|---|---|---|---|---|
| HF Dx to randomization, days | 1153 ± 1909 | 1627 ± 2306 | 919 ± 1557 | 581 ± 1119 |
| DTRI* | −153 ± 2649 | 391 ± 2839 | −330 ± 1954 | −876 ± 2617 |
| sBP (mm Hg) | 123.3 ± 15.3 | 119.9 ± 15.7 | 121.8 ± 15.1 | 129.6 ± 13.0 |
| dBP (mmHg) | 75.3 ± 10.8 | 73.8 ± 11.3 | 74.6 ± 9.5 | 78.1 ± 10.5 |
| Heart Rate, bpm | 76.3 ± 17.8 | 78.4 ± 19.4 | 75.9 ± 17.3 | 73.3 ± 15.0 |
| Previous ECV (%) | 49 | 55 | 46 | 43 |
| Previous AF ablation (%) | 21 | 17 | 10 | 35 |
| Previous Class III AADs (%) | 48 | 47 | 34 | 59 |
| Device Type: ILR/CRT/ICD/PM (%) | 16/8/15/9 | 19/10/21/5 | 31/3/14/12 | 1/7/6/15 |
| Norepinephrine (pg/ml) | 673 ± 353 | 657 ± 373 | 656 ± 380 | 710 ± 298 |
| NT-proBNP (pg/ml) | 1250 ± 1596 | 1380 ± 1736 | 1471 ± 1911 | 891 ± 950 |
| HF treatment at randomization | | | | |
| Beta-blockers | 248 (93%) | 111 (87%) | 57 (97%) | 80 (99%) |
| ACEI/ARB | 205 (77%) | 94 (74%) | 43 (73%) | 168 (84%) |
| Diuretics | 158 (59%) | 81 (64%) | 33 (56%) | 44 (54%) |
| Digoxin | 43 (16%) | 25 (20%) | 11 (19%) | 7 (9%) |
| Spironolactone (MRA) | 85 (32%) | 42 (33%) | 19 (32%) | 24 (30%) |
| Sacubitril/valsartan | 11 (4%) | 5 (4%) | 6 (10%) | 0 (0%) |
| CRT-P or -D | 21 (8%) | 13 (10%) | 2 (3%) | 6 (7%) |
| ICD | 40 (15%) | 27 (21%) | 8 (14%) | 5 (6%) |
| Anticoagulation | | | | |
| Warfarin | 63 (24%) | 37 (29%) | 5 (8%) | 21 (26%) |
| Rivaroxaban | 92 (34%) | 40 (32%) | 22 (37%) | 30 (37%) |
| Apixaban | 69 (26%) | 43 (34%) | 24 (41%) | 2 (2%) |
| Dabigatran | 30 (11%) | 6 (5%) | 7 (12%) | 17 (21%) |
| Other OACs | 11 (4%) | 0 (0%) | 0 (0%) | 11 (14%) |
| None (contraindication to AC) | 2 (1%) | 1 (1%) | 1 (2%) | 0 (0%) |

*DTRI = Time (days) from 1st HF diagnosis to randomization minus time from 1st AF diagnosis to randomization (DTRI, Diagnosis To Randomization Index, negative value means AF was diagnosed first; see Supplement, 7.11.3 for graphic illustration). W/B/A/O/H = White/Black/Asian/Other/Hispanic.
Note:
mean ± standard deviations are presented unless otherwise specified.

The entire cohort was relatively young (65.6 years), had moderate LV dysfunction/remodeling (LVEF 0.36), and was predominately NYHA Class II heart failure. Most (93%) of patients were on beta-blockers at the time of randomization. Other guideline-based heart failure medications were administered as would be expected, except perhaps a relatively low diuretic use of 59% for a heart failure population (e.g. compared to 94% in BEST[14] and 90% in MERIT-HF[15]). Nearly all patients (99%) were on oral anticoagulants. Differences in baseline characteristics by region or country are described below.

ii) U.S. Baseline Characteristics and Patient Population: As seen in Table 1, differences in baseline characteristics were observed in Canada and Europe compared to the U.S. Patients in the U.S. had the lowest LVEF (0.33), the lowest systolic blood pressure (in moderate to severe LV dysfunction an index of systolic function), the highest proportion of NYHA Class III patients (26%), highest percentage of CRT/ICD devices (31%), highest proportion of diuretic use (64%) and the longest average duration of heart failure (1627 days). Importantly, the U.S. was the only major region/country where heart failure was diagnosed substantially earlier than AF, as quantified by a large, positive DTRI (391 days, see Table 1 footnote for definition). In contrast, AF diagnoses typically preceded heart failure diagnoses by a substantial period of time in the entire cohort (DTRI: −153 days) and in the other two predefined major regions (Canada: −330 days and Europe: −876 days).

These differences, allowed per the entry criteria of the trial, were likely created by the types of PI referral lines in the various regions, with U.S. sites emphasizing the recruitment of HF patients who subsequently developed AF (i.e., the intended GENETIC-AF population, based on BEST and other beta-blocker trial observations), as opposed to long-standing AF patients who subsequently developed HF. This is important to note, as duration of AF diagnosis is an important prognostic determinant in the maintenance of sinus rhythm after catheter ablation.[38,39]

iii) Canada, Europe Baseline Characteristics: Canada had the youngest patient population (62.8 years), the lowest proportion of patients that had been previously treated with Class III anti-arrhythmic drugs, the smallest number of previous AF ablation patients (10%), very few NYHA Class III patients (7%), and the negative DTRI commented on in Section 2.5.2.2. Thus, the Canadian cohort can be characterized as patients with moderate LV dysfunction, who were initially in AF and eventually developed mild heart failure symptoms.

The differences in the Europe baseline characteristics compared to the U.S. are primarily due to Hungary, whose patient demographic data are given in Table 2A and will be described below.

iv) Hungary vs. Rest of Europe Baseline Characteristics:

The differences between Europe and the other two regions shown in Table 1 are primarily due to patients enrolled in Hungary, as shown in Table 2A that includes U.S. and Europe excluding Hungary patients for comparison. As shown in Table 2A, the Hungarian cohort was dramatically different from the U.S. cohort, having a much higher LVEF (0.43 vs. 0.33), almost no Class III patients (3% vs, 26%), lower diuretic use (48% vs. 64%), a much higher systolic blood pressure (131 mm Hg vs. 120 mm Hg), an extremely high proportion of previous AF ablation patients (64% vs. 17%), a low NT-proBNP (895 pg/ml vs. 1380), and a low proportion with CRT/ICD devices (12% vs. 31%. The Hungarian cohort also had the most negative DTRI of any country (−2172, days), which was created by a large imbalance between the time of heart failure diagnoses (562 days prior to randomization) and AF diagnoses (2734 days prior to randomization). Patients randomized in Hungary were therefore longstanding AF patients who had previously experienced multiple EP procedures (e.g. ablation, ECVs) and eventually developed minimal/mild LV dysfunction and mild heart failure.

Patients randomized in the three other European countries (N=48) also had higher LVEFs (0.40), a lack of class III heart failure (4%), higher systolic blood pressure (129 mm Hg) and relatively low NT-proBNP levels (888 pg/ml) compared to the U.S. cohort. However, unlike Hungary, the other European randomized patients had very short AF diagnosis to randomization times (580 days compared to 2734 days in Hungary) and a neutral DTRI of +14 days. As such, the non-Hungary European patients are best characterized as mild LV dysfunction and mild heart failure who developed AF and HF contemporaneously.

TABLE 2A

Baseline characteristics for subjects randomized in Hungary, the rest of Europe, or the U.S.

| Parameter | Hungary n = 33 | Europe excluding Hungary, n = 48 | U.S. n = 127 |
|---|---|---|---|
| Age | 67.5 ± 7.6 | 66.2 ± 9.9 | 66.3 ± 10.7 |
| Gender M/F | 70/30 | 73/27 | 87/13 |
| LVEF | 0.43 ± 0.08 | 0.40 ± 0.08 | 0.33 ± 0.09 |
| NYHA I/II/III (%) | 42/55/3 | 44/52/4 | 17/57/26 |
| Hx Ischemic/Non-Ischemic HF (%) | 36/64 | 35/65 | 31/69 |
| Randomized in AF/Not in AF (%) | 30/70 | 33/67 | 59/41 |
| Hx Persistent/Paroxysmal AF (%) | 48/52 | 48/52 | 52/48 |
| AF Dx to Randomization, days | 2734 ± 3527 | 580 ± 1077 | 1236 ± 2192 |
| HF Dx to randomization, days | 562 ± 897 | 595 ± 1258 | 1627 ± 2306 |
| DTRI* | −2172 ± 3647 | 14.1 ± 786 | 391 ± 2839 |
| sBP (mm Hg) | 130.8 ± 11.8 | 128.8 ± 13.9 | 119.9 ± 15.7 |
| dBP (mmHg) | 79.0 ± 12.2 | 77.4 ± 9.2 | 73.8 ± 11.3 |
| Heart Rate, bpm | 73.3 ± 15.4 | 73.3 ± 14.9 | 78.4 ± 19.4 |
| Previous ECV (%) | 61 | 31 | 55 |
| Previous AF ablation (%) | 64 | 15 | 17 |
| Previous Class III AADs (%) | 58 | 60 | 47 |
| Device Type: ILR/CRT/ICD/PM (%) | 3/12/3/12 | 0/4/8/17 | 19/10/21/5 |
| Norepinephrine (pg/ml) | 703 ± 270 | 715 ± 319 | 657 ± 373 |
| NT-proBNP (pg/ml) | 895 ± 1091 | 888 ± 854 | 1380 ± 1736 |
| HF treatment at randomization | | | |
| Beta-blocker | 33 (100%) | 47 (98%) | 111 (87%) |
| ACEI/ARB | 27 (82%) | 41 (85%) | 94 (74%) |
| Diuretics | 16 (48%) | 28 (58%) | 81 (64%) |
| Digoxin | 2 (6%) | 5 (10%) | 25 (20%) |
| Spironolactone (MRA) | 8 (24%) | 16 (33%) | 42 (33%) |
| Sacubitril/valsartan | 0 (%) | 0 (0%) | 5 (4%) |
| CRT-P or -D | 4 (12%) | 2 (4%) | 13 (10%) |
| ICD | 1 (3%) | 4 (8%) | 27 (21%) |
| Anticoagulation | | | |
| Warfarin | 7 (21%) | 14 (29%) | 37 (29%) |
| Rivaroxaban | 12 (36%) | 18 (38%) | 40 (32%) |
| Apixaban | 2 (6%) | 0 (0%) | 43 (34%) |
| Dabigatran | 4 (12%) | 13 (27%) | 6 (5%) |
| Other OACs | 8 (24% | 3 (6%) | 0 (0%) |
| None (contraindication to AC) | 0 (0%) | 0 (0%) | 1 (1%) |

*DTRI = Time (days) from 1st heart failure diagnosis to randomization minus time from 1st AF diagnosis to randomization (DTRI, Diagnosis To Randomization Index, negative value means AF was diagnosed first).
Note:
mean ± standard deviations are presented unless otherwise specified.

TABLE 2B

Baseline Characteristics (±SD; *p < 0.05 vs. MET)

| Parameter | MET n = 133 | BUC N = 134 |
|---|---|---|
| Age | 65.5 ± 10.0 | 65.8 ± 10.3 |
| Gender M/F(%) | 81/19 | 83/17 |
| LVEF | 0.36 ± 0.10 | 0.36 ± 0.10 |
| NYHA I/II/III (%) | 26/54/20 | 30/60/10 |
| Hx Ischemic/Non-Ischemic HF (%) | 33/67 | 31/69 |
| Randomized in AF/Not in AF (%) | 52/48 | 49/51 |
| Hx Persistent/Paroxysmal AF (%) | 51/49 | 51/49 |
| AF Dx to Randomization, days | 1180 ± 2209 | 1431 ± 2271 |
| HF Dx to randomization, days | 1054 ±1733 | 1252 ± 2070 |
| sBP (mm Hg) | 122 ± 15.7 | 125 ± 14.9 |
| Heart Rate, bpm | 76.0 ± 17.7 | 76.5 ± 17.9 |
| Previous ECV/AF ablation/Class III AADs (%) | 50/20/46 | 49/21/50 |
| Device Type: ILR/CRT/ICD/PM (%) | 15/10/12/10 | 17/6/18/9 |
| HF Rx: b-bl/ACEI or ARB/Dig/Diuretic/MRA/Scbtl-Val (%) | 92/78/17/61/32/5 | 94/75/15/57/32/4 |
| NT-proBNP (pg/ml) | 1343 ± 1846 | 1159 ± 1306 |
| Norepinephrine (NE) (pg/ml) | 664 ± 359 | 682 ± 348 |
| Change in NE at Week 4, median (Q1, Q3) | −10 (198,121) | −101 (−241, 43)* |

Baseline characteristics for the overall study population were well-balanced between the treatment groups. However, there was some regional variability in patient characteristics that may have contributed to greater heterogeneity for the primary endpoint.

Key characteristics to highlight from Table 2B: LVEF, primarily NYHA I/II, half were in AF at rand, half had persistent AF, half had paroxysmal AF, half had previously been cardioverted, half had previously received class III AADs, 20% had previous ablations, half had implanted devices, drug therapy was typical for a HF population with more than 90% previously receiving BB therapy. NT-proBNP was elevated and consistent with HF population. Baseline NE levels were similar between groups but only decreased in the bucindolol group at week 4, which is consistent with bucindolol's unique sympatholytic effects.

3. Phase 2 Trial Primary Endpoint

There were 2 (1.5%) patients in the bucindolol group and 7 (5.3%) patients in the metoprolol group who withdrew from the study prior to the start of the 24-week efficacy follow-up period. These patients were censored at day 1 for the primary endpoint analysis, except for one death in the metoprolol group that was counted as an event on day 1. There were 143 primary endpoint events observed during the trial. Seventy-three of these events were in the bucindolol group, consisting of 64 AF/AFL events, 9 ECV failures, and no deaths. In the metoprolol group there were 70 events, consisting of 56 AF/AFL events, 11 ECV failures, and 3 deaths.

i) Bayesian Predictive Probability

The primary analysis for the Phase 2 stage of the trial was Bayesian modeling of the time to ACM or any (symptomatic or asymptomatic) AF/AFL, to yield predictive probability of success (PPoS) for a discreet Phase 3 trial of 620 patients and 330 events. The DSMB charter's Promising Zone increase in the Phase 3 sample size to 820 was also modeled (Table 3).

TABLE 3

Bayesian Predictive Probabilities (PPoS) of achieving a p < 0.05 in a 620 patient/330 events or an 820 patient/430 event trial

| | 620 patients, 330 events | | 820 patients, 430 events | |
|---|---|---|---|---|
| Analysis | Entire Cohort | U.S. | Entire Cohort | U.S. |
| Interim analysis (103 actual events) | 0.114 | NA | NA | NA |
| Completed Phase 2 (143 actual events) | 0.144 | 0.606 | 0.186 | 0.678 |

Note:
The interim analysis model assumed completion of the existing trial inclusive of the Phase 2B population; whereas, the final analysis model assumed a discreet Phase 3 trial that was not inclusive of the Phase 2B population.

Figures 4A, 4B:
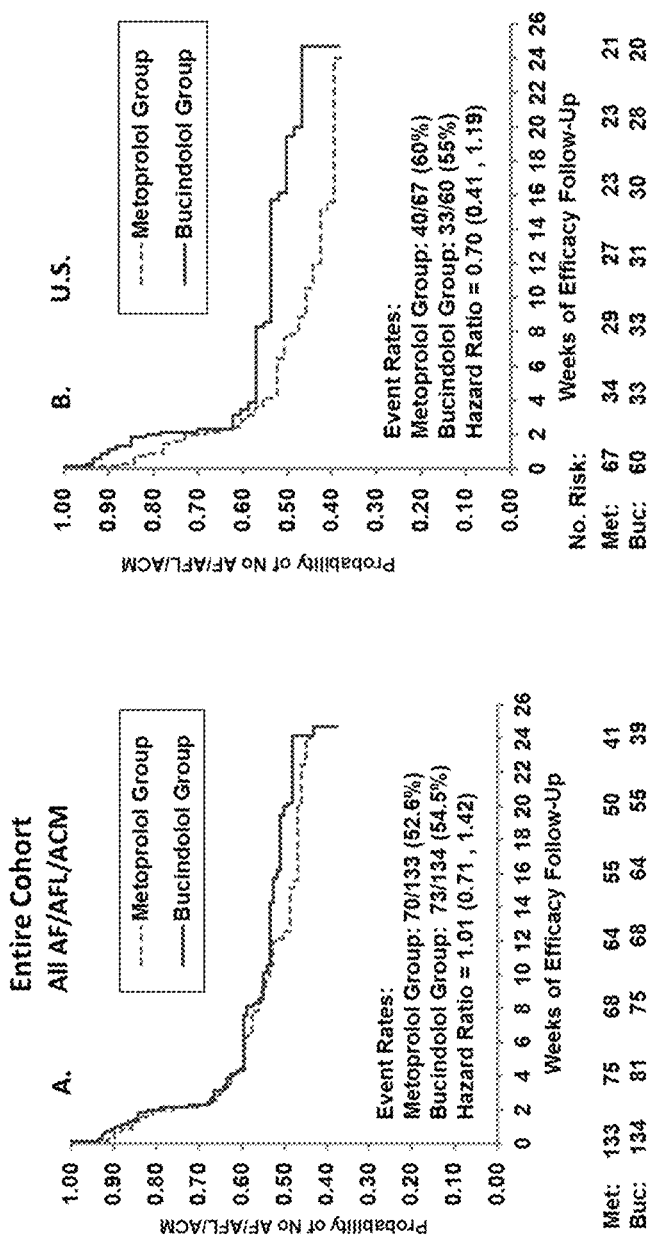
FIG. 4A-4B. Phase 2 primary endpoint in 4A., Entire Cohort, with covariate adjusted hazard ratio (unadjusted=0.96 (0.69,1.33), p=0.80; 4B., U.S. randomized patients and covariate adjusted hazard ratio, unadjusted=0.77 (0.48,1.22), p=0.27.

The amended statistical analysis plan also called for Bayesian modeling of additional subgroups, as described in aforementioned statistical analysis plan. The geographic region analysis of U.S. vs. Canada vs. Europe was only done for the U.S., and yielded a PPoS of 0.606 for a discreet 620-patient trial, and 0.678 for an 820-patient trial ii) Time to Event Analyses for Phase 2 Primary Endpoint FIG. 4A gives the time to event curves for the Phase 2 primary endpoint (any AF/AFL or ACM) in the entire cohort, with the covariate adjusted and unadjusted hazard ratios. The dip at the end of the bucindolol curves is caused by a single patient in each of the U.S., Canada, Hungary and Poland randomized cohorts having a primary endpoint between 168 and 180 days (the statistical analysis plan maximum interval for completing 24-week follow-up), where the denominators of patients at risk were small. For both the adjusted and unadjusted analysis, the time to event curves do not suggest a difference between bucindolol and metoprolol succinate for effects on the Phase 2 primary endpoint In contrast to the entire cohort data, a separation between treatment groups was observed in the U.S. cohort (FIG. 4B), with an adjusted hazard ratio of 0.70 (95% CI: 0.41,1.19; p=0.19) and an unadjusted hazard ratio of 0.77 (95% CI: 0.48,1.22; p=0.27). The Phase 2 stage of GENETIC-AF had inadequate power to achieve statistical significance based on its assumed effect size of 25%, but as indicated in Table 3, if the U.S. result had been generalized to the entire population of a discreet future trial, the predictive probability of 0.606 would have led to a recommendation to perform a subsequent Phase 3 trial with a similar target population One can interpret the data in FIG. 4 as: 1) in the entire cohort (FIG. 4A), no evidence of a difference in effectiveness between bucindolol and an approved heart failure beta-blocker that has been shown to lower the AF risk by 48% in HFrEF[12]; and 2) in U.S. patients (FIG. 4B) who have a more HFrEF-driven pathophysiology (See Section 3 iii) and Section F below), evidence for a favorable treatment effect of bucindolol vs. metoprolol succinate.

iii) Geographic Heterogeneity of Treatment Effect

Figures 5A, 5B, 5C, 5D:
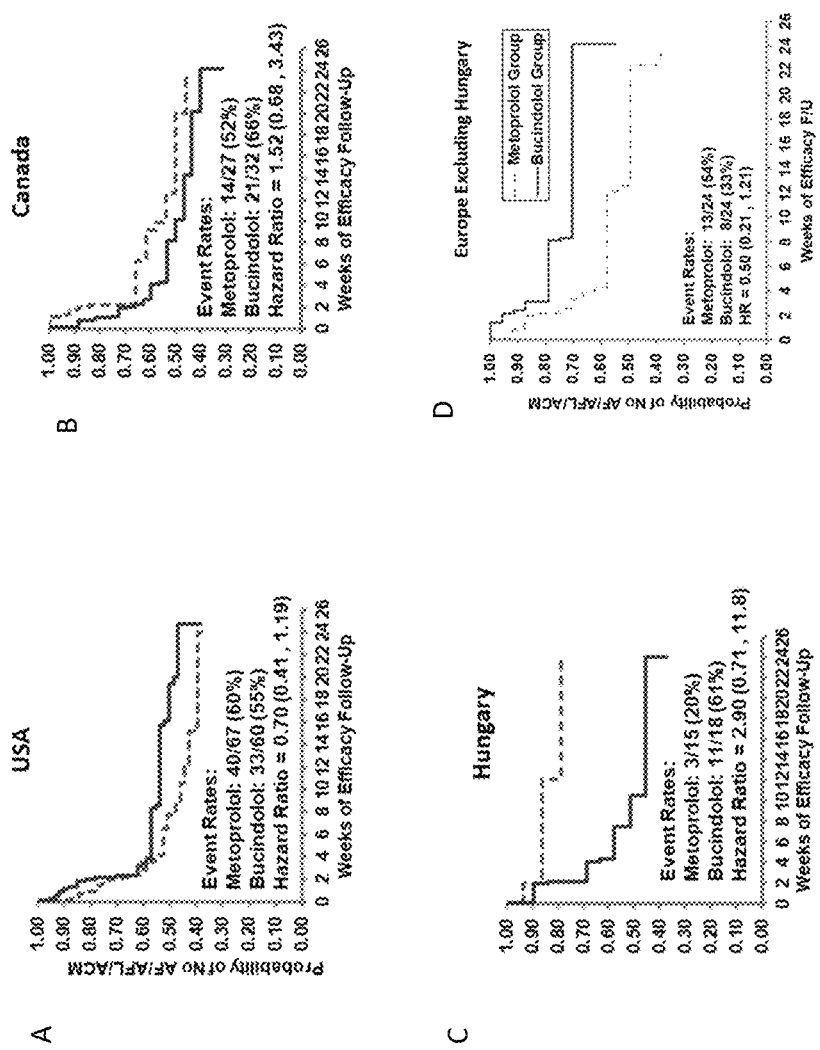
FIG. 5A-5D. Country specific heterogeneity in effects on time to time to any AF/AFL or ACM: 5A. U.S., 5B. Canada, 5C. Hungary, 5D. Europe excluding Hungary. Hazard ratios on figures are covariate adjusted; unadjusted hazard ratios are: 5A., U.S. 0.77 (0.48, 1.22): 5B., Canada 1.42 (0.72, 2.79); 5C., Hungary 3.57 (0.99, 12.9; 5D., Europe excluding Hungary 0.50 (0.21,1.21).

There was clear heterogeneity by country in the Phase 2 primary endpoint data as can be deduced from the entire cohort vs. U.S. results, with Canada and Hungary exhibiting results that were very different from those in the U.S. This is evident from the panel of time to event curves shown in FIG. 5. The hazard ratio in Hungary vs. the U.S. is strongly significant by test for interaction (p=0.008), meaning these regional differences are likely real (addressed below). The Canada hazard ratio was not significantly different from the U.S. by interaction test (p=0.13). In Europe, Hungary is a clear outlier from the other 3 countries, who have a hazard ratio of 0.50 (0.21, 1.21) (FIG. 5D) compared to 2.90 (0.70, 11.8) in Hungary (FIG. 5C) (interaction p=0.18). Furthermore, an analysis performed on the entire cohort with Hungary removed yielded a hazard ratio of 0.82 (95% CI: 0.57, 1.19; p=0.29).

iv) Cox Modeling of Phase 2B Primary Endpoint

In accordance with the SAP, Cox proportional hazards regression modeling was performed to explore significant predictors of the primary endpoint. This effort began with each predictor being examined individually as a prelude to building a multi-term model. Each predictor was examined in Cox models that included treatment and a term for treatment by predictor interaction as well as a model without the interaction term. If the treatment by predictor interaction term is not significant the results of the two-predictor model are more pertinent for selection of variables to be included in the multi-term model. The results of these initial models are summarized in Table 4.

Higher NT-proBNP at randomization
Higher NYHA Class at screening|Body Text|ZZMPTAG|
Greater time from AF diagnosis to randomization|Body Text|ZZMPTAG|

The only predictors by treatment interaction terms having p-values <0.05 are country and length of AF diagnosis. These effects are examined further in subgroup analyses presented in Section E.8 and Section F. Length of AF diagnosis is combined with another significant predictor, length of HF diagnosis (p=0.007) to create the DTRI (Example 6C). This measure proved difficult to fit into the model because of the large spread of values (minimum=−15,252, median=−1, maximum=9,533). Currently the values are translated into 3 categories and this diminishes the predictive power. The true impact of this measure is better quantified in the subgroup analyses presented in Section F.

In order to better define a responder population for future trials, the next step in the process will be to construct models

TABLE 4

Cox Modeling of Phase II Endpoint: Individual Predictor Runs

| Predictor | Values Tested for Greater Risk | 3 Predictor Model | | | 2 Predictor Model | |
| --- | --- | --- | --- | --- | --- | --- |
| | | Tx | Pred. | Tx * Pred Interaction | Tx | Pred. |
| Rhythm at Rand Strata | AF | 0.66 | <0.0001 | 0.51 | 0.83 | <0.0001 |
| Heart Rate at Rand | Higher Values | 0.96 | 0.042 | 0.99 | 0.8 | <0.000 |
| AF Type | Persistent | 0.77 | 0.061 | 0.49 | 0.72 | 0.001 |
| SBP at Randomization (Rand) | Higher Values | 0.147 | 0.63 | 0.152 | 0.84 | 0.006 |
| HF Diagnosis Days | Longer Diagnosis | 0.66 | 0.63 | 0.73 | 0.77 | 0.007 |
| Initial Study Dose Level | Higher Dose Level | 0.79 | 0.89 | 0.35 | 0.39 | 0.017 |
| ECV (prior) Count | Higher Count | 0.37 | 0.78 | 0.3 | 0.76 | 0.018 |
| HF Etiology Strata | Ischemic Etiology | 0.91 | 0.043 | 0.53 | 0.81 | 0.023 |
| NT-proBNP at Rand | Higher Values | 0.48 | 0.75 | 0.28 | 0.91 | 0.04 |
| NYHA at Screen | Higher Values | 0.59 | 0.91 | 0.57 | 0.99 | 0.043 |
| AF Diagnosis Days | Higher Values | 0.178 | 0.145 | 0.025 | 0.83 | 0.067 |
| Device Strata | NA | 0.98 | 0.77 | 0.77 | 0.72 | 0.109 |
| ECV or Ablation Y/N( prior) | History of Either | 0.51 | 0.13 | 0.52 | 0.79 | 0.134 |
| Country | NA | 0.23 | 0.105 | 0.048 | 0.88 | 0.242 |
| DBP at Rand | Higher Values | 0.18 | 0.093 | 0.159 | 0.71 | 0.279 |
| Beta Blocker Prior to Rand | NA | 0.66 | 0.68 | 0.98 | 0.84 | 0.42 |
| DTRI: <−30, −30 to 30, >30 | AF diagnosed first | 0.43 | 0.49 | 0.34 | 0.81 | 0.47 |
| Creatinine at Rand | Higher Values | 0.3 | 0.188 | 0.26 | 0.82 | 0.48 |
| ECV + Ablation Total Count | Higher Count | 0.75 | 0.64 | 0.93 | 0.74 | 0.52 |
| Ablation (prior) Count | Higher Count | 0.83 | 0.137 | 0.186 | 0.78 | 0.62 |
| LVEF | Higher Values | 0.79 | 0.96 | 0.84 | 0.8 | 0.66 |
| LVEF Strata | LVEF <35% | 0.74 | 0.89 | 0.82 | 0.8 | 0.68 |
| CYP2D6 | Lower Metabolizing | 0.21 | 0.29 | 0.174 | 0.98 | 0.93 |
| NE at Rand | Higher Values | 0.63 | 0.73 | 0.72 | 0.73 | 0.99 |

Predictors of Phase 2 primary endpoint occurrence that were identified include:
Presence of AF at randomization
Higher heart rate at randomization
History of persistent AF
Higher systolic blood pressure at randomization
Greater time from HF diagnosis to randomization
Higher initial study drug dose level
Greater number of prior ECVs
HF of ischemic etiology containing multiple terms. A challenge will be the high degree of correlation among some of these predictors. High correlation implies a high degree of overlapping information that could result in potentially over-parameterizing a model. In particular, the following set of indicators of HF severity at randomization were found to be highly correlated with one another: length of HF diagnosis; NT-proBNP; NYHA; sBP and LVEF. In addition, length of AF diagnosis and number of pre-study ECVs were found to be highly correlated, as would be expected. The sponsor will next pursue a stepwise model building process the individual predictors identified as having significant predictive power.

4. AF Burden i) Time to Event Analysis for the AF Burden Substudy

Figures 7A, 7B:
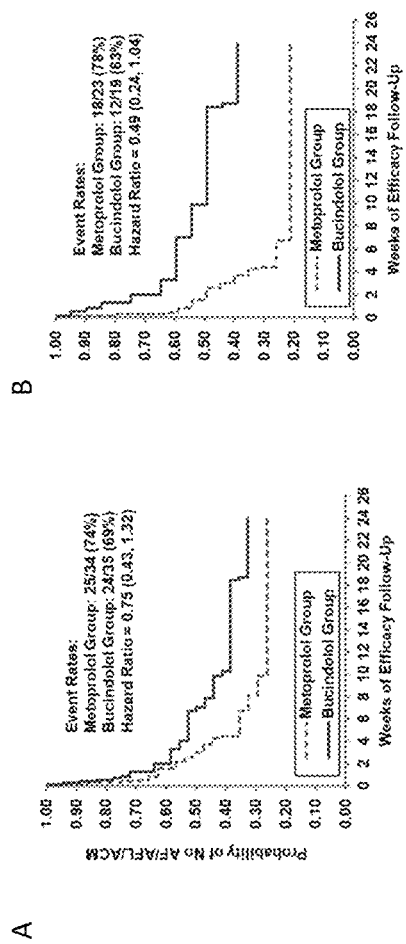
FIG. 7A-7B. Time to AF/AFL/ACM event based on continuous monitoring with implanted devices for patients in the AFB substudy (7A) and for the U.S. AFB cohort (7B).

GENETIC-AF contained a continuous monitoring substudy conducted during the 24-week primary endpoint follow-up period, using Medtronic CRT, ICD, dual chamber pacemaker, or trial-supplied implantable loop recorder (ILR). The primary purpose of the AF burden substudy, performed in collaboration with Medtronic, was to provide a measure of AF/AFL events by continuous monitoring, in order to provide a more precise measure of onset of AF/AFL compared to clinical or scheduled ECG detection. This information was also important as an aid to the DSMB in their interim analysis evaluation.[26] The baseline characteristics of AF burden substudy patients are given in Table 6.

difference could also be due to the higher % of patients randomized in AF. In general, the patient populations in the U.S. and AF burden substudy are similar, reflecting the large contribution (61%) of U.S. patients to the AF burden subpopulation FIG. 7 presents the time to AF/AFL event data based on continuous monitoring with implanted devices for patients in the AFB substudy (A) and for the U.S. cohort (B). An AF/AFL event in this analysis was based on at least 6 hours of AFB per day, which has previously been shown to be associated with an increased rate of hospitalization for HF.[24]

In the entire AFB cohort (N=69), a separation by treatment group is observed in the Kaplan-Meier curves for time to first device-detected AF/AFL/ACM event, yielding an unadjusted hazard ratio of 0.75 (95% CI: 0.43, 1.32) in favor of bucindolol. In the U.S. cohort (N=42), an even greater

TABLE 6

Baseline characteristics of the AF burden entire substudy population vs. the study entire cohort

| Parameter (±SD) | Entire Study Cohort n = 267 | U.S. Study Cohort n = 127 | AFB Substudy Cohort n = 69 |
|---|---|---|---|
| Age (years) | 65.6 ± 10.1 | 66.3 ± 10.7 | 66.1 ± 10.7 |
| Gender M/F (%) | 82/18 | 87/13 | 93/7 |
| LVEF | 0.36 ± 0.09 | 0.33 ± 0.09 | 0.34 ± 0.08 |
| NYHA I/II/III (%) | 28/57/15 | 17/57/26 | 23/57/20 |
| Hx Ischemic/Non-Ischemic HF (%) | 32/68 | 31/69 | 27/73 |
| Randomized in AF/Not in AF (%) | 51/49 | 59/41 | 65/35 |
| Hx Persistent/Paroxysmal AF (%) | 51/49 | 52/48 | 64/36 |
| AF Dx to Randomization, days | 1306 ± 2240 | 1236 ± 2192 | 1355 ± 1984 |
| HF Dx to randomization, days | 1153 ± 1909 | 1627 ± 2306 | 1168 ± 1723 |
| DTRI* | −152 ± 2649 | 391 ± 2839 | −185 ± 2558 |
| sBP (mm Hg) | 123.3 ± 15.3 | 119.9 ± 15.7 | 123.3 ± 15.1 |
| dBP (mmHg) | 75.3 ± 10.8 | 73.8 ± 11.3 | 75.0 ± 10.1 |
| Heart Rate, bpm | 76.3 ± 17.8 | 78.4 ± 19.4 | 78.4 ± 17.2 |
| Previous ECV (%) | 49 | 55 | 55 |
| Previous AF ablation (%) | 21 | 17 | 13 |
| Previous Class III AADs (%) | 48 | 47 | 54 |
| Device Type: ILR/CRT/ICD/PM (%) | 16/8/15/9 | 19/10/21/5 | 62/13/16/9 |
| Norepinephrine (pg/ml) | 673 ± 353 | 657 ± 373 | 706 ± 368 |
| NT-proBNP (pg/ml) | 1250 ± 1596 | 1380 ± 1736 | 1568 ± 2053 |

*DTRI = Time (days) from 1st HF diagnosis to randomization minus time from 1st AF diagnosis to randomization
(DTRI, Diagnosis To Randomization Index, negative value means AF was diagnosed first).
Note:
mean ± standard deviations are presented unless otherwise specified.

The baseline characteristics of the AF burden substudy cohort are similar to the study entire cohort, but the AF burden substudy cohort had slightly lower LVEFs (0.34 vs. 0.36), slightly higher proportion of NYHA class III (20% vs. 15%), a higher proportion of patients being randomized in AF (65% vs. 51%), a higher NT-proBNP (1568 pg/ml vs. 1250 pg·ml), and a somewhat smaller proportion of previous AF ablation patients (13% vs. 21%). The AF burden substudy cohort was also very similar to the U.S. study cohort, except for a slightly higher NT-proBNP (1568 pg/ml vs. 1380 pg·ml) and a negative DTRI (−185 days vs. 391 days). In AF burden substudy vs. US. patients, based on the difference in NT-proBNP it could be that the AF burden subpopulation had more advanced LV dysfunction or heart failure not captured by LVEF or NHYHA Class, but the treatment effect was observed, with a hazard ratio of 0.49 (95% CI: 0.24, 1.04). The AFB substudy population had a higher proportion of patients from the U.S., which may partially explain why a greater trend for benefit was observed in the AFB substudy cohort (HR=0.75; 95% CI: 0.43, 1.32) compared to the overall study population (HR=1.01; 95% CI: 0.71, 1.42). However, regional proportionality does not explain the greater treatment response observed in the U.S. AFB cohort (HR=0.49; 95% CI: 0.24, 1.04) compared to the results seen in the overall U.S. cohort that were based on intermittent/clinic-based ECG detection (HR=0.70; 95% CI: 0.41, 1.19). Therefore, the two rhythm assessment methods were compared in the same AFB populations to determine the effects of detection methodology on treatment benefit.

Figures 8A, 8B:
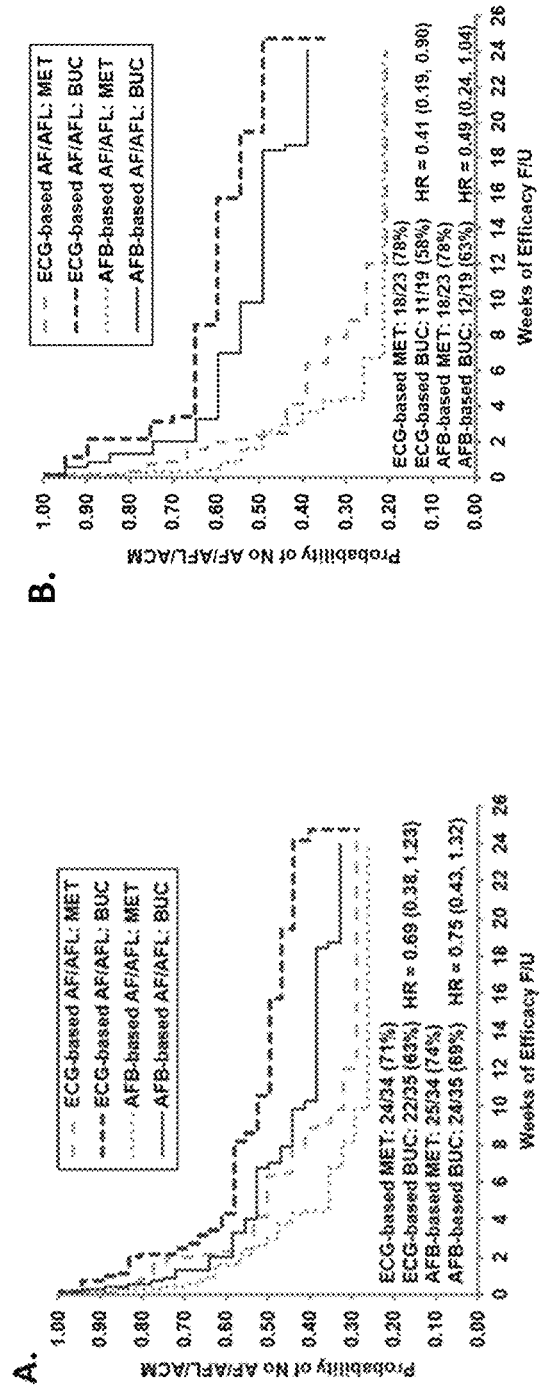
FIG. 8A-8B. AFB substudy endpoint vs. Clinical/ECG detected endpoint in 8A., Entire AFB cohort (n=69) and 8B., U.S. patients (n=42).

FIG. 8 gives the time to AF/AFL event data for patients in the AFB substudy, for both the entire cohort (A) and for U.S. patients (B). The AFB defined endpoint (i.e., 6 hours of AFB per day or ACM) and the Phase 2 endpoint (i.e., AF/AFL/ACM as determine by ECG/TTM) are presented on the same axis for comparison As shown in FIG. 8A, the AFB and ECG/TTM determined endpoints track very closely for both treatment groups, with the AFB curves being slightly steeper, likely reflecting earlier detection. The median time to event in the entire AFB cohort was 9 days for AFB detection, and 16 days for clinical/ECG determination (p<0.0001) with no difference in this interval in the AFB metoprolol (9 days) cohort vs. the bucindolol (6.5 days) group (p=0.73). Similar results were observed in the U.S. FIG. 8B, with both methodologies detecting similar treatment effects. As such, differences in methodology do not explain why the AFB population appears to respond better to bucindolol than the overall study population. The treatment effect seen in the U.S. AFB cohort (HR=0.49; 95% CI: 0.24, 1.04) was numerically quite different that seen in the ex-U.S. AFB cohort (HR=1.32; 95% CI: 0.45, 3.87); therefore, the baseline characteristics of these two groups were compared, as shown in Table 7.

advance of their AF (DTRI=393 days); whereas, the ex-U.S. cohort was comprised primarily of patients whose AF was diagnosed well in advance of their HF (DTRI=−1084 days). These characteristics are similar to those described in Section E.2 for the more responsive regional cohorts in the overall study population ii) Area Under the Curve (AUC).

AFB measured by continuous monitoring of rhythm with implantee or inserted[41] devices has been promulgated as an ideal method of measuring AF, and has been correlated with both stroke risk[42,43] and in heart failure patients, risk of heart failure hospitalization.[34] For assessment of anti-arrhythmic drug (AAD) effects, AFB is most efficiently deployed with a pretreatment control period, followed by a treatment period where each patient serves as his/her own control in a change from baseline analysis.[40,44]

AF burden data in the GENETIC-AF population tended to have a bimodal distribution,[45] i.e. either 0 hours of AFB or 24 hours of AFB per day, creating a large degree of variance that complicated the analysis. Also, a pretreatment period was not practical, as many patients had AFB measured by inserted loop recorders that were typically placed at randomization or during the uptitration period prior to the start of efficacy follow-up (usually 3 weeks after randomization).

TABLE 7

Baseline characteristics of the APB substudy population

| Parameter | AFB entire substudy n = 69 | U.S. AFB substudy n = 42 | Ex-U.S. AFB substudy n = 27 |
|---|---|---|---|
| Age (years) | 66.1 ± 10.7 | 67.4 ± 1.70 | 64.3 ± 9.9 |
| Gender M/F (%) | 93/7 | 95/5 | 89/11 |
| Race/ethnicity: W/B/A/O/H (%) | 96/1/1/1/3 | 93/2/2/2/5 | 100/0/0/0/100 |
| LVEF (%) | 0.34 ± 0.08 | 0.33 ± 0.80 | 0.37 ± 0.93 |
| NYHA I/II/III (%) | 23/57/20 | 14/52/33 | 37/63/0 |
| Hx Ischemic/Non-Ischemic HF (%) | 27/73 | 36/64 | 15/85 |
| Randomized in AF/Not in AF (%) | 65/35 | 71/29 | 56/44 |
| Hx Persistent/Paroxysmal AF (%) | 64/36 | 74/26 | 48/52 |
| AF Dx to Randomization, days | 1355 ± 1984 | 1195 ± 2005 | 1603 ± 1961 |
| HF Dx to randomization, days | 1168 ± 1723 | 1588 ± 2007 | 519 ± 822 |
| DTRI* | −185 ± 2558 | 393 ± 2650 | −1084 ± 2160 |
| sBP (mm Hg) | 123.3 ± 15.1 | 121.8 ± 16.0 | 125.6 ± 13.5 |
| dBP (mmHg) | 75.0 ± 10.1 | 74.5 ± 10.3 | 75.8 ± 10.0 |
| Heart Rate, bpm | 78.4 ± 17.2 | 77.9 ± 17.7 | 79.4 ± 16.7 |
| Previous ECV (%) | 55 | 55 | 56 |
| Previous AF ablation (%) | 13 | 10 | 19 |
| Previous Class III AADs (%) | 54 | 55 | 52 |
| Device Type: ILR/CRT/ICD/PM (%) | 62/13/16/9 | 57/14/24/5 | 70/11/4/15 |
| Norepinephrine (pg/ml) | 706 ± 368 | 660 ± 310 | 782 ± 441 |
| NT-proBNP (pg/ml) | 1568 ± 2053 | 1652 ± 2354 | 1441 ± 1530 |

*DTRI = Time (days) from 1st HF diagnosis to randomization minus time from 1st AF diagnosis to randomization (DTRI, Diagnosis To Randomization Index, negative value means AF was diagnosed first).
W/B/A/O/H = White/Black/Asian/Other/Hispanic
Note:
mean ± standard deviations are presented unless otherwise specified.

Compared to the ex-U.S. AFB cohort, the more responsive U.S. AFB cohort was slightly older, had evidence of more advanced heart failure (i.e., lower LVEF, more NYHA class III patients, higher NT-proBNP), and a higher proportion of patients with HF of ischemic etiology. The U.S. cohort also had a mean time of HF diagnosis to randomization that was 3-fold greater than that of the ex-U.S. AFB cohort and had a slightly shorter mean time of AF diagnosis to randomization. This led to a substantial difference in the DTRI score, indicating that the U.S. AFB cohort consisted primarily of patients whose HF was diagnosed well in Therefore, the AFB analysis compared two treatments in a parallel design without benefit of change from baseline calculations.

FIG. 9 presents mean AFB in 6-week intervals (i.e., quartiles) during the 24-week Follow-up Period with treatment comparisons performed via the Wilcoxon Rank Sum test.

Figures 9A, 9B:
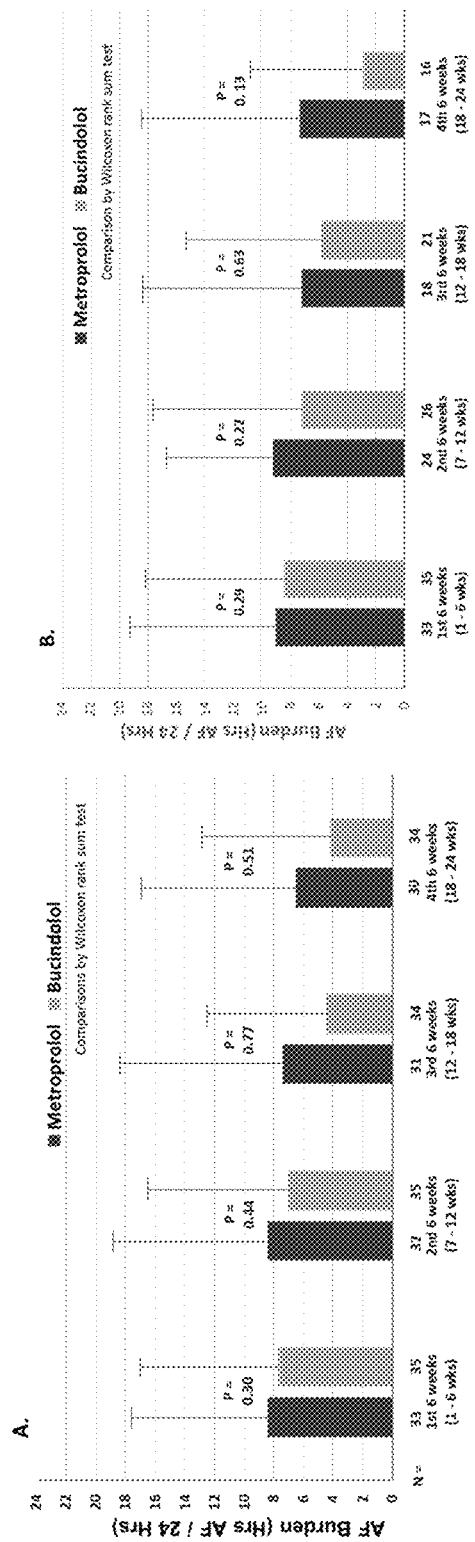
FIG. 9A-9B. AFB by 6-week intervals in GENETIC-AF, 9A., no censoring. 9B., data censored at the time of AF treatment consisting of a) electrical cardioversion (n=28, b) catheter ablation (n=5), c) Class III AADs (dofetilide, amiodarone, sotalol) (n=26) or for permanent withdrawal of study medication (n=6).

As shown in FIG. 9A, the parallel design AFB measurements have a large coefficient of variation, typically exceeding 100%. Although there are trends for a progressive reduction in AFB by bucindolol vs. metoprolol over the course of treatment, the effects are not statistically significant for any of the 6-week intervals or for the entire 24-week period (p=0.48 for all data and p=0.65 when data are censored after an intervention). A similar trend for a greater decrease in the bucindolol group is seen in FIG. 9B, which censored patients at the time they received treatment that can terminate AF, or with study drug termination.

Mean AFB by week during the 24-week Follow-up Period is given in Example 5C and Table 26 for both uncensored and censored analyses. In the censored analysis, AFB is p<0.05) in the bucindolol vs. metoprolol groups in weeks 16, 17, 20, 21, and 22.

Based on these data we cannot conclude that in a parallel design AFB has an advantage over symptom change-triggered or routine surveillance ECGs as a method of detecting treatment effects in AF. However, 6 hours of AFB per day appears to be an excellent surrogate marker for the subsequent development of clinical AF.

5. Secondary Endpoints

Protocol Secondary endpoints: Table 8 presents data on the protocol secondary endpoints.

6. Effects on Norepinephrine, NT-proBNP i) Norepinephrine

Because sympatholysis is thought to be a major mechanism by which bucindolol favorably inhibits ADRB1 Arg389 receptors,[19] peripheral venous sampled plasma norepinephrine (NE) was measured at baseline and at Week 4, 12 and 24 of efficacy follow-up.

Table 10 presents the change in NE from baseline to Week 4 of the efficacy follow-up period, as this is approximately 7 weeks after initiation of study drug when the NE lowering effects of bucindolol should be fully apparent and the analysis less influenced by confounding factors (e.g., study withdrawals, drug discontinuations). Week 12 and Week 24 data are shown in Example 5D. Sympatholytic effect of bucindolol is easily identified in Week 4 sampling, by within group reductions in NE in the entire cohort and in all countries/regions except Canada. These changes in NE in the bucindolol group were p<0.05 vs. metoprolol changes in the entire cohort and Canada, with a trend (p=0.066) in Hungary. By median values the degree of reduction was by 101 pg/ml in both the entire cohort and the U.S., by 213

TABLE 8

Secondary endpoints in the entire cohort and U.S. randomized patients

| | Entire cohort | | U.S. | |
| --- | --- | --- | --- | --- |
| Secondary endpoint | Metoprolol n = 133 | Bucindolol n = 134 | Metoprolol n = 67 | Bucindolol n = 60 |
| Symptomatic AF/AFL/ACM during the 24-Week Follow-up Period | See Section 2.5.4 (Phase 3 Primary Endpoint) | | | |
| VT, VF or Sx SVT during the 24-Week Follow-up Period, N (%) | 1 (0.8%) | 2 (1.5%) | 0 (0.0%) | 1 (1.7%) |
| Total All-cause Hospitalization during Total Study Period, days/patient | 1.7 ± 5.5 | 2.8 ± 8.1 | 2.8 ± 7.3 | 3.3 ± 9.6 |
| AF/AFL/ACM or HF Hospitalization during Total Study Period, N (%) | 78 (58.6%) | 85 (63.4%) | 46 (68.7%) | 42 (70.0%) |

Secondary endpoints involving arrhythmias other than AF/AFL and based on hospitalizations were too few to evaluate.

Heart Failure Component Endpoints: Table 9 contains heart failure endpoints collected in the Total Study Period, as components of secondary or tertiary endpoints. Again, there were relatively few events, and the data are not evaluable. However, there is no suggestion of a lesser effect of bucindolol on heart failure major outcomes.

pg/ml in Hungary and 121 pg/ml in the rest of Europe. These reductions compare to 75 pg/ml in the BEST trial at 12 weeks,[22] which had a lower baseline NE in the bucindolol group of 529 pg/ml. The very large reduction in NE in patients randomized in Hungary is within a range (<−144 pg/ml) associated with adverse outcomes in the all-genotype BEST trial entire cohort.[22] Metoprolol was not associated with a within group NE change in any of the regions at the Week 4 measurement.

TABLE 9

Heart failure endpoints in the entire cohort and U.S. randomized patients for the Total Study Period

| | Entire cohort | | U.S. | |
| --- | --- | --- | --- | --- |
| Endpoint | Metoprolol n = 133 | Bucindolol n = 134 | Metoprolol n = 67 | Bucindolol n = 60 |
| ACM | 3 (2.3%) | 3 (2.3%) | 2 (3.0%) | 3 (5.0%) |
| HF hospitalization | 11 (8.3%) | 10 (7.5%) | 9 (13.4%) | 6 (10.0%) |
| ACM or HF hospitalization | 12 (9%) | 11 (8%) | 9 (13.4%) | 8 (13.3%) |
| CV hospitalization | 15 (11.3%) | 18 (13.4%) | 12 (17.9%) | 8 (13.3%) |

At Week 12 (Table 27) the reductions in NE in the bucindolol group persisted and were to approximately the same degree in the entire cohort (p<0.0001), U.S. (p=0.011) and Hungary (p=0.022), but now Canada demonstrated a significant reduction (by 100 pg/ml, p=0.016). The reduction in Hungary is again within the range associated with adverse outcomes in the BEST. At Week 12 the GENETIC-AF entire cohort metoprolol group exhibited a significant NE reduction (by 57 pg/ml), and the between treatment group change was no longer significant (p=0.18). No individual region or country exhibited within group metoprolol NE reductions at Week 12, although the U.S. (p=0.070) and Canada (p=0.061) exhibited trends. At Week 24 (Table 27) once again the entire cohort exhibited a within bucindolol treated group NE reduction (p=0.012) but of lesser magnitude than at Weeks 4 or 12, by 47 pg/ml. The U.S. reduction was also less (by 46 pg/ml and nonsignificant (p=0.058). Hungary's bucindolol group decrease remained substantial (by 193 pg/ml) and statistically significant, and Canada's was no longer significant and much smaller than at Week 12 (by 21 pg/ml). There were no within metoprolol group changes in NE at Week 24.

have been associated with an enhanced therapeutic effect,[19] but substantially greater reductions such as occurred in Hungary carry the risk of adverse outcomes.[22]

Regarding the lack of a sympatholytic effect of bucindolol in Canada at Weeks 4 and 24, although Canada had the lowest median baseline NE levels of all countries and regions (that was not statistically significant (p=0.33) vs all other baseline values), systemic NE levels underestimate cardiac adrenergic activation. In addition, at Week 4 bucindolol did not produce a sympatholytic effect in Canadian patients who had baseline values above the median of 522 pg/ml. Possible explanations for a lack of sympatholytic effect by bucindolol in Canada are very mild heart failure (only 7% NYHA Class III, Table 1) and the trend for a lower degree of adrenergic activation. That Canadian patients did not have a sympatholytic effect from bucindolol is countered by Week 12 NE reduction in the bucindolol group, although the change was not different from the metoprolol group. Thus the sympatholytic effect of bucindolol in Canada was at a minimum less consistent than in other countries or regions.

TABLE 10

Plasma norepinephrine (NE) levels (pg/ml)

| | Entire Cohort | | U.S. | | Canada | | Hungary | | Europe excluding Hungary | |
|---|---|---|---|---|---|---|---|---|---|---|
| Parameter | Met N = 128 | Buc N = 134 | Met N = 64 | Buc N = 60 | Met N = 26 | Buc N = 32 | Met N = 15 | Buc N = 18 | Met N = 23 | Buc N = 24 |
| Baseline Mean ± SD | 664 ± 359 | 682 ± 349 | 664 ± 386 | 650 ± 362 | 674 ± 429 | 642 ± 341 | 627 ± 258 | 767 ± 270 | 675 ± 250 | 753 ± 375 |
| Baseline Median | 590 | 607 | 599 | 598 | 541 | 522 | 571 | 792 | 592 | 691 |
| Week 4 Mean ± SD | 617 ± 29 | 563 ± 25 | 616 ± 42 | 529 ± 38 | 613 ± 62 | 583 ± 52 | 530 ± 63 | 576 ± 56 | 676 ± 73 | 604 ± 60 |
| Week 4 Median | 570 | 500 | 556 | 473 | 605 | 551 | 460 | 525 | 612 | 540 |
| ⍰ Mean ±SEM | −36 ± 32 | −124 ± 26 | −18 ± 48 | −136 ± 47 | −97 ± 58 | −59 ± 44 | −35 ± 66 | −208 ± 62 | −18 ± 89 | −126 ± 53 |
| ⍰ Median | −10 | −101 | +29 | −101 | −59 | −1 | −70 | −213* | −12 | −129 |
| P value vs. Bsl*/vs. Met[†] | 0.30 | <0.001/ 0.012 | 0.96 | 0.001/ 0.015 | 0.34 | 0.30/ 0.89[†] | 0.38 | 0.003/ 0.066[†] | 0.72 | 0.021/ 0.47 |

*Wilcoxon signed rank test for within group changes;
[†]/Wilcoxon rank sum test on between group changes Thus NE data are: 1) consistent with the dual, sympatholytic/beta-blocker mechanism of action of bucindolol and its differentiation from metoprolol and other beta-blockers;[21] 2) patterns of NE change are possibly correlated with the therapeutic effects of bucindolol, where in the ADRB1 Arg389Arg genotype NE reductions in the 120 pg/ml range ii) NT-ProBNP NT-proBNP was measured at baseline, Weeks 4, 12 and 24 to assess the value of this biomarker on predicting outcomes including any treatment effects. Baseline and Week 4 NT-ProBNP values are given in. Weeks 12 and 24 data are in Example 5D, and in Table 28)

TABLE 11

NT-proBNP (pg/ml), median values

| | Entire Cohort (n = 267) | | U.S. (n = 127) | | Canada (n = 59) | | Hungary (n = 33) | | Europe excluding Hungary (n = 48) | |
|---|---|---|---|---|---|---|---|---|---|---|
| Parameter | Met 123/133 | Buc 125/134 | Met 62/67 | Buc 55/60 | Met 26/27 | Buc 29/32 | Met 14/15 | Buc 17/18 | Met 21/24 | Buc 24/24 |
| Baseline Mean ± SD | 1343 ± 1846 | 1159 ± 1306 | 1499 ± 2033 | 1245 ± 1332 | 1646 ± 2303 | 1314 ± 1503 | 781 ± 458 | 989 ± 1428 | 883 ± 880 | 893 ± 849 |
| Baseline Median | 861 | 777 | 982 | 904 | 913 | 790 | 785 | 567 | 521 | 600 |

TABLE 11-continued

| | NT-proBNP (pg/ml), median values | | | | | | | | | |
|---|---|---|---|---|---|---|---|---|---|---|
| | Entire Cohort (n = 267) | | U.S. (n = 127) | | Canada (n = 59) | | Hungary (n = 33) | | Europe excluding Hungary (n = 48) | |
| Parameter | Met 123/133 | Buc 125/134 | Met 62/67 | Buc 55/60 | Met 26/27 | Buc 29/32 | Met 14/15 | Buc 17/18 | Met 21/24 | Buc 24/24 |
| Week 4 Mean ± SD | 1212 ± 1670 | 1196 ± 2446 | 1227 ± 1136 | 1501 ± 3075 | 1715 ± 3022 | 859 ± 1135 | 812 ± 524 | 1616 ± 3522 | 820 ± 0876 | 756 ± 1108 |
| Week 4 Median | 792 | 613 | 831 | 796 | 1067 | 499 | 803 | 594 | 433 | 431 |
| ΔWeek 4 Mean ± SEM | −50 ± 96 | −0.4 ± 166 | −14 ± 162 | +182 ± 332 | −91 ± 222 | −455 ± 197 | −11 ± 152 | +461 ± 576 | −117 ± 123 | −72 ± 139 |
| ΔWeek 4 Median | −35 | −96 | −27 | −75 | −101 | −184 | −40 | −47 | −93 | −108 |
| P value vs. Bsl*/vs. Met† | 0.32 | 0.003/ 0.11† | 0.79 | 0.25/ 0.58 | 0.48 | 0.003/ 0.16 | 1.000 | 0.58/ 0.66 | 0.31 | 0.17/ 0.68 |

*Wilcoxon signed rank test;
†/Wilcoxon signed rank sum test

Compared to the U.S., combined treatment group baseline NT-proBNP values are lower in Hungary (p=0.034), and in Europe excluding Hungary (p=0.029). In addition, both Hungary and Europe excluding Hungary trend lower than Canada (respective p values 0.12 and 0.13). At Week 4, in the entire cohort a significant decrease from baseline was observed in the bucindolol group, but not in the metoprolol group. A similar but statistically nonsignificant change in the bucindolol group occurred in the U.S. cohort. In the Canadian cohort, a significant decrease from baseline was observed in the bucindolol group, which was not observed in the metoprolol group.

At Week 12 (Table 28), the entire and Canadian cohorts again demonstrated statistically significant decreases in NT-proBNP in the bucindolol group and not in the metoprolol group, as did Europe excluding Hungary. For the entire cohort, the difference in change from baseline between the bucindolol and metoprolol groups approached statistical significance (p=0.051).

At Week 24, in the entire and U.S. cohorts both treatment groups exhibited statistically significant decreases in NT-proBNP, which were numerically greater in the bucindolol group. In the Canadian cohort, a substantial decrease was observed in the bucindolol group that approached statistical significance (−39%; p=0.057) and was nearly 3-fold greater than that seen in the metoprolol group.

In HFrEF beta-blockers generally and metoprolol[46] or bucindolol[47] specifically, have not previously been associated with reductions in systemic natriuretic peptide (NP) levels despite evidence that metoprolol or carvedilol reduce myocardial NP gene expression.[48,49] AF can increase NT-proBNP or BNP levels,[50-52] but in AF complicating HFrEF BNP levels appear to be determined more by the degree of left ventricular dysfunction than by the presence or absence of AF.[53] The data in Table 11, Example 5D and Table 28 indicate that in HFrEF patients at risk for recurrent AF, bucindolol treatment is associated with a reduction in circulating NT-proBNP, to a greater extent and earlier in the treatment course than for metoprolol. However, there does not appear to be an association with reduction in NT-proBNP and effectiveness for preventing recurrent AF/AFL, as Canada patients had the greatest early (at 4 weeks of follow-up) decreases in NT-proBNP, which was associated with a hazard ratio of 1.52 (0.68, 3.43) (Table 8.B). On the other hand, the U.S. patient population, who exhibited consistently favorable treatment effects from bucindolol and the highest baseline median NT-proBNP values, was the only cohort to exhibit a statistically significant decrease in NT-proBNP at the end of the 24-week follow-up period, by the substantial amount of 33% compared to 20% for metoprolol.

In summary, the GENETIC-AF results do not provide support for the use of NT-proBNP as a biomarker for beta-blocker effectiveness in preventing AF in HFrEF patients. High vs. lower baseline values had a relationship with subsequent bucindolol treatment response in the U.S. and Hungary, but higher baseline values in Canada and lower values in Europe excluding Hungary exhibited an opposite relationship to bucindolol treatment effects. Nor does serial change in NT-proBNP appear promising as a surrogate marker of efficacy for preventing AF/AFL, as in the bucindolol treatment arm patients randomized in Canada exhibited the most consistent reduction in NT-proBNP across all time points, but no evidence of a favorable effect on recurrent AF/AFL.

7. Analysis of Country Specific Heterogeneity of Treatment Effect, Patient Characteristics and Treatment Assignment Imbalances in Covariates.

Based on results shown in FIG. 5, it is clear that the results from GENETIC-AF exhibit country specific heterogeneity of bucindolol treatment effects, which has been observed in other trials conducted in patients with heart failure[54-59] including those comparing beta-blockers to placebo.[58,59] For beta-blocker studies, both metoprolol succinate in MERIT-HF[58,59] and carvedilol in COPERNICUS[59] have exhibited evidence of less effectiveness in U.S. randomized patients. In these trials a plausible specific consideration was not offered for the possible blunting of treatment effects in the U.S., but the authors concluded that "prespecified subgroup analyses by geographical region should be incorporated", and that genetic and other biomarker data should be collected to inform any differences in biological effects.[59] In addition, their comment that "enrollment criteria must be general enough to allow broad participation such that demographics reflect a true population, however, with some specificity to ensure enrollment of true disease patients"[59] is generally accepted by the majority of clinical trialists. In GENETIC-AF the predefined geographic regions selected for analysis were the U.S., Canada and Europe, the study population was pharmacogenetically selected based on the drug target, and additional biomarker information was collected in the form of NT-proBNP and ADRA2C genotypes (Example 2 F iv). Furthermore, a pre-randomization case report form established the date of the first diagnosis of AF or heart failure, allowing the determination of the diagnosis-randomization intervals for each. Based on this information a measure was developed, Diagnosis to Randomization Index, DTRI (Table 1, and Example 6C) that could identify whether the clinical course was dominated by AF, HFrEF, or neither. This index likely has implications for differences in underlying pathophysiology (Section 2.6).

Although regional or country specific variations in treatment effects in multicenter trials are usually assumed to be due to chance,[58,60,61] a recent authoritative review on the topic of regional heterogeneity in multinational trials concluded that, "When a randomized, clinical trial shows marked variations in results among countries, one should seek supporting evidence to understand whether the observed results are likely to be real, an artifact of the design, analysis or implementation of the trial, or simply due to chance".[60] Furthermore, when an interaction test for homogeneity is highly significant, such as it was for Hungary vs. the U.S. (p=0.008, FIG. 8, Section 3iii), the likelihood of nonrandom differences increases.[60] GENETIC-AF clearly demonstrates evidence of "marked variations in results among countries", and in addition to the standard collection and analysis of baseline characteristics has a full complement of additional information that can brought to bear on analysis of this heterogeneity.

i) Differences in Baseline Characteristics

Differences in baseline characteristics have been implicated as likely causative of regional heterogeneity for outcomes in previous trials,[54-57] and some of the differences between patients randomized in Hungary vs. the U.S. or the rest of Europe shown in Table 2A suggest this possibility. Table 12 presents baseline covariates that have the potential of influencing outcomes in GENETIC-AF. These baseline covariates were either predefined for randomization stratification or subgroup analysis, have been shown to previously affect AF incidence, heart failure outcomes or were shown in the trial to have a substantial effect ($\geq 0.20$) on hazard ratio.

TABLE 12

Baseline characteristics of all patients by region with Hungary presented independent of the rest of Europe

| Parameter | U.S. N = 127 | Canada N = 59 | Hungary N = 33 | Europe excluding Hungary n = 48 | P-value[#] |
|---|---|---|---|---|---|
| Age | 66.3 ± 10.7 | 62.8 ± 9.8 | 67.5 ± 7.6 | 66.2 ± 9.9 | 0.074 |
| Gender M/F (%) | 87/13 | 86/14 | 70/30 | 73/27 | 0.034 |
| LVEF | 0.33 ± 0.09 | 0.35 ± 0.10 | 0.43 ± 0.08 | 0.40 ± 0.08 | <0.001 |
| NYHA I/II/III (%) | 17/57/26 | 32/61/7 | 42/55/3 | 44/52/4 | <0.001 |
| Hx Ischemic/Non-Ischemic HF (%) | 31/69 | 29/71 | 36/64 | 35/65 | 0.840 |
| Randomized in AF/Not in AF (%) | 59/41 | 58/42 | 30/70 | 33/67 | 0.001 |
| Hx Persistent/Paroxysmal AF (%) | 52/48 | 53/47 | 48/52 | 48/52 | 0.950 |
| AF Dx to Randomization, days | 1236 ± 2192 | 1249 ± 1776 | 2734 ± 3527 | 580 ± 1077 | 0.002 |
| HF Dx to randomization, days | 1627 ± 2306 | 919 ± 1557 | 562 ± 897 | 595 ± 1258 | 0.002 |
| DTRI* | 391 ± 2839 | −330 ± 1954 | −2172 ± 3647 | 14.1 ± 786 | <0.001 |
| sBP (mm Hg) | 119.9 ± 15.7 | 121.8 ± 15.1 | 130.8 ± 11.8 | 128.8 ± 13.9 | <0.001 |
| dBP (mmHg) | 73.8 ± 11.3 | 74.6 ± 9.5 | 79.0 ± 12.2 | 77.4 ± 9.2 | 0.035 |
| Heart Rate, bpm | 78.4 ± 19.4 | 75.9 ± 17.3 | 73.3 ± 15.4 | 73.3 ± 14.9 | 0.280 |
| Previous ECV (%) | 55 | 46 | 61 | 31 | 0.019 |
| Previous AF ablation (%) | 17 | 10 | 64 | 15 | <0.001 |
| Previous Class III AADs (%) | 47 | 34 | 58 | 60 | 0.031 |
| Device Type: ILR/CRT/ICD/PM (%) | 19/10/21/5 | 31/3/14/12 | 3/12/3/12 | 0/4/8/17 | <0.001 |
| Norepinephrine (pg/ml) | 657 ± 373 | 656 ± 380 | 703 ± 270 | 715 ± 319 | 0.230 |
| NT-proBNP (pg/ml) | 1380 ± 1736 | 1471 ± 1911 | 895 ± 1091 | 888 ± 854 | 0.055 |

*DTRI = Time (days) from 1st HF diagnosis to randomization minus time from 1st AF diagnosis to randomization (DTRI, Diagnosis To Randomization Index, negative value means AF was diagnosed first) (see graphic illustration in Supplement, 7.11.3).
Note:
mean ± standard deviations are presented unless otherwise specified.
†p < 0.05 by Wilcoxon Rank Sum test or chi-square.
[#]Test for heterogeneity between groups is Wilcoxon rank sum test for continuous variables, and Chi-sq for categorical data.

As can be observed in Table 12, patients in Hungary differ from those randomized elsewhere in several respects. Patients randomized in Hungary have: 1) a longer interval between AF diagnosis and randomization; 2) a large negative DTRI indicating that most patients had AF several years in advance of heart failure; 3) a greater percentage of patients with a history of catheter ablation and ECVs (as might be expected from longstanding AF patients); 4) higher baseline LVEFs; 5) a complete absence of NYHA Class III patients, and; 6) lower baseline NT-proBNP levels. Patients randomized in Canada also had negative DTRIs (mean −330 days), but not nearly as negative as Hungary. Otherwise patients enrolled in Canada had similar baseline characteristics to U.S. and European patients excluding Hungary. In summary, patients enrolled in Hungary are characterized by longstanding AF diagnoses that were first made several years prior to randomization, who only recently had developed heart failure symptoms (median of 99 days prior to randomization) and who had only mild LV dysfunction. Despite these differences, patients enrolled in Hungary met the entry criteria of the protocol.

ii) Possible Treatment Group Imbalances

In small sample sizes that characterize Phase 2 trials, imbalances in covariates are a potential cause of random variations in treatment effect.[62] Such differences should balance out in a large trial, but may not in a smaller Phase 2 trials such as GENETIC-AF. In order to evaluate the distribution of variables that may have affected treatment group response in individual countries or regions, analyses of the entire cohort were performed in predefined, previously demonstrated, or other subgroups that may affect beta-blocker response in HFrEF or AF incidence (Table 13).

TABLE 13

Subgroup analysis in the entire cohort of variables potentially capable of altering treatment effect, Phase 2 primary endpoint unadjusted analysis

| Subgroup | Metoprolol event rate (%) | Bucindolol event rate (%) | Hazard ratio (95% CI) |
|---|---|---|---|
| All Subjects | 70/133 (53%) | 73/134 (54%) | 0.96 (0.69, 1.33) |
| Age > 66 years[†] | 35/62 (56%) | 34/71 (48%) | 0.75 (0.47, 1.21) |
| Gender female | 11/25 (44%) | 13/23 (57%) | 1.22 (0.55, 2.74) |
| AF at Rand | 51/69 (74%) | 49/66 (74%) | 0.91 (0.62, 1.35) |
| SR at Rand | 19/64 (30%) | 24/68 (35%) | 1.13 (0.62, 2.06) |
| Persistent AF at Randomization | 36/48 (75%) | 32/45 (71%) | 0.85 (0.53, 1.37) |
| SR/Paroxysmal AF at Randomization | 34/85 (40%) | 41/89 (46%) | 1.09 (0.69, 1.73) |
| SR at FU Start | 58/113 (51%) | 64/122 (52%) | 1.00 (0.70, 1.43) |
| No previous ECV | 34/67 (51%) | 32/68 (47%) | 0.82 (0.50, 1.33) |
| Previous catheter ablation | 14/25 (56%) | 12/25 (48%) | 0.73 (0.34, 1.59) |
| Ischemic etiology | 20/44 (45%) | 18/42 (43%) | 0.79 (0.42, 1.50) |
| Non-ischemic etiology | 50/89 (56%) | 55/92 (60%) | 1.02 (0.70, 1.50) |
| LVEF < 0.39 | 35/68 (51%) | 38/69 (55%) | 1.02 (0.65, 1.62) |
| LVEF ≥ 0.39 | 35/65 (54%) | 35/65 (54%) | 0.89 (0.56, 1.43) |

TABLE 13-continued

Subgroup analysis in the entire cohort of variables potentially capable of altering treatment effect, Phase 2 primary endpoint unadjusted analysis

| Subgroup | Metoprolol event rate (%) | Bucindolol event rate (%) | Hazard ratio (95% CI) |
|---|---|---|---|
| NYHA I | 15/35 (43%) | 15/40 (38%) | 0.72 (0.35, 1.48) |
| NYHA II/III | 55/98 (56%) | 58/94 (62%) | 1.06 (0.73, 1.54) |
| LVEF ≥ 0.39, AF Dx to randomization > 321 days[†] | 19/41 (46%) | 17/30 (57%) | 1.20 (0.62, 2.31) |
| LVEF ≥ 0.39, AF Dx to randomization ≤ 321 days[†] | 16/24 (67%) | 18/35 (51%) | 0.65 (0.33, 1.27) |
| DTRI > −1 days in LVEF ≥ 0.39[†] | 10/16 (63%) | 14/28 (50%) | 0.71 (0.31, 1.63) |
| Heart rate ≤ 74[†] bpm | 25/66 (38%) | 32/70 (46%) | 1.12 (0.66, 1.90) |
| Heart rate >74[†] bpm | 45/67 (67%) | 41/64 (64%) | 0.89 (0.58, 1.35) |
| SBP < 123[†] mm Hg | 40/69 (58%) | 40/61 (66%) | 1.18 (0.76, 1.84) |
| SBP > 123[†] mm Hg | 30/64 (47%) | 33/73 (45%) | 0.82 (0.50, 1.35) |
| Norepinephrine (pg/ml) ≥ 600 pg/ml[‡] | 37/62 (60%) | 35/68 (51%) | 0.81 (0.51, 1.28) |
| NT-proBNP (pg/ml) ≥ 1131 pg/ml | 27/43 (63%) | 26/41 (63%) | 0.87 (0.47, 1.64) |
| 2D6 Poor Metabolizers (PMs) | 3/8 (38%) | 8/12 (67%) | 2.19 (0.58, 8.30) |

*DTRI = Time (days) from 1st HF diagnosis to randomization minus time from 1st AF diagnosis to randomization (DTRI, Diagnosis To Randomization Index, negative value means AF was diagnosed first) (see graphic illustration in Example 6 C.
[†]median value;
[‡]upper tertile boundary.

Table 14 presents by region some of the covariates identified in Table 13 that may affect AF recurrence or beta-blocker response, those with the potential to improve (hazard ratio ≤0.85 in Table 12) or worsen (hazard ratio ≥1.15 in Table 12) bucindolol treatment effects.

TABLE 14

Distribution by region or country and treatment group of covariates that have the potential to affect beta-blocker response, AF incidence or generalized heart failure treatment effects

| Parameter | U.S. Met N = 67 | U.S. Buc N = 60 | Canada Met N = 27 | Canada Buc N = 32 | Hungary Met N = 15 | Hungary Buc N = 18 | Europe excluding Hungary Met N = 24 | Europe excluding Hungary Buc N = 24 |
|---|---|---|---|---|---|---|---|---|
| Age >66 yrs, (%) | 46 | 50 | 48 | 38 | 67 | 72 | 33 | 67 |
| Gender, F (%) | 13 | 13 | 11 | 16 | 47 | 17 | 25 | 29 |
| Persistent AF at rand, (%) | 54 | 50 | 48 | 56 | 53 | 44 | 46 | 50 |
| Previous ECV, (%) | 55 | 55 | 44 | 47 | 73 | 50 | 25 | 38 |
| Previous ablation, (%) | 19 | 13 | 7 | 13 | 67 | 61 | 8 | 21 |
| LVEF | 0.33 ± 0.09 | 0.35 ± 0.10 | 0.36 ± 0.10 | 0.35 ± 0.10 | 0.44 ± 0.08 | 0.42 ± 0.08 | 0.42 ± 0.07 | 0.39 ± 0.09 |
| LVEF ≥0.39 and AF to rand >321 days[†], (%) | 21 | 18 | 26 | 16 | 87 | 50 | 29 | 21 |
| DTRI*, days | 323 ± 2924 | 467 ± 2764 | 102 ± 1638 | −694 ± 2143 | −2492 ± 4235 | −1905 ± 3177 | −154 ± 470 | 182 ± 991 |
| DTRI <−30 days (%) | 30 | 27 | 30 | 44 | 80 | 56 | 29 | 38 |
| NYHA I/II/III (%) | 13/55/31 | 20/60/20 | 26/59/15 | 38/63/0 | 40/53/7 | 44/56/0 | 54/46/0 | 33/58/8 |
| ISC etiology, (%) | 34 | 28 | 33 | 25 | 27 | 44 | 33 | 38 |
| median sBP ≤123 mmHg, (%) | 63 | 52 | 59 | 53 | 33 | 22 | 25 | 38 |
| NE (pg/ml) | 664 ± 386 | 650 ± 362 | 674 ± 429 | 642 ± 341 | 627 ± 258 | 767 ± 270 | 675 ± 250 | 753 ± 375 |
| NT-proBNP | 1499 ± | 1245 ± | 1646 ± | 1314 ± | 781 ± | 989 ± | 883 ± | 893 ± |

TABLE 14-continued

Distribution by region or country and treatment group of covariates that have the potential to affect beta-blocker response, AF incidence or generalized heart failure treatment effects

| | U.S. | | Canada | | Hungary | | Europe excluding Hungary | |
|---|---|---|---|---|---|---|---|---|
| Parameter | Met N = 67 | Buc N = 60 | Met N = 27 | Buc N = 32 | Met N = 15 | Buc N = 18 | Met N = 24 | Buc N = 24 |
| (pg/ml) | 2033 | 1332 | 2303 | 1503 | 458 | 428 | 880 | 849 |
| Alcohol use (%) | 55 | 59 | 37 | 56 | 47 | 50 | 54 | 57 |
| Failed ECV at day 0, (%) | 18 | 9 | 0 | 21 | 25 | 33 | 25 | 0 |
| 2D6 PMs, (%) | 11 | 7 | 0 | 16 | 0 | 6 | 4 | 10 |

*Diagnosis (Dx) to randomization (RND) index, = (HF Dx to Rnd interval-AF Dx to Rnd interval); negative value means AF Dx occurred before HF Dx, by the index # of days, >−1 days (means AF was diagnosed at same time or after HF) in LVEF ≥0.39.
Note:
mean ± standard deviations are presented unless otherwise specified.

The covariates listed in Table 14 are fairly evenly distributed between treatment groups except in Canada and to a lesser extent in Hungary. For example, in Canada the bucindolol group has a DTRI of −694 days compared to a positive DTRI of 102 days in the metoprolol group. Although not statistically significant (p=0.41) due to the large variance in the DTRI measurement, this means that the bucindolol patients in Canada had an AF diagnosis, on average, of nearly 2 years before their heart failure diagnosis, whereas the metoprolol group had their heart failure diagnosis 102 days before the AF diagnosis. 2D6 Poor Metabolizer (PM) variants, which were associated with markedly higher bucindolol plasma concentrations (Section 2.5.9.4) and hazard ratios of 2.57 (95% CI: 0.49, 13.6; adjusted) and 2.19 (95% CI: 0.58, 8.30; unadjusted), in Canada distributed to 5 PMs in the bucindolol group and none in the metoprolol group (p=0.056). No other country had such an imbalance in PMs by treatment group.

Canada also had a higher percentage of alcohol users (a known risk factor for AF) in the bucindolol group (56% vs. 37% for metoprolol, p=0.014). In the Canada bucindolol group, 4 patients failed ECV on day 0, meaning they were endpointed for not cardioverting to sinus rhythm, vs. none in the metoprolol group (p=0.11).

In contrast, patients randomized in the U.S. had no major imbalances against bucindolol. Patients randomized in Hungary are clearly different as described in the discussion of Table 11, but have no substantial treatment group imbalances. Europe excluding Hungary is also well balanced, with the exception of twice as many patients being >66 years age in the bucindolol group (p=0.021).

8. Safety i) Summary of Study Drug Exposure Nearly all randomized patients had received beta blocker therapy (92.9%) prior to enrollment. Metoprolol (succinate or tartrate) was the most common (42.7%) beta blocker previously administered, followed by bisoprolol (28.5%) and carvedilol (19.5%). The bucindolol treatment group, compared to the metoprolol treatment group, had a smaller proportion of patients who had previously received metoprolol (37% and 48%, respectively), a greater proportion who had received bisoprolol (33% and 24%, respectively) and a similar proportion who had received carvedilol (21% and 18%, respectively).

The initial dose of study drug was based on the dose of the commercial beta blocker the patient was receiving immediately prior to randomization. Nearly all patients (97%) received one of the three lower dose levels as their initial dose of study drug. These corresponded to M25B625 (i.e., 34% metoprolol 25 mg qd and 26% bucindolol 6.25 mg bid), M50B125 (i.e., 29% metoprolol 50 mg qd and 34% bucindolol 12.5 mg bid), and M100B25 (i.e., 34% metoprolol 100 mg qd and 37% bucindolol 25 mg bid). An additional 8 patients had an initial study drug dose at M200B50 (i.e., 4% metoprolol 200 mg qd and 2% bucindolol 50 mg BID).

Study drug compliance was good (~92% for both groups), with slightly more patients up-titrating to target dose in the bucindolol group (84%) compared to the metoprolol group (72%). Most patients in the bucindolol and metoprolol groups attained the target dose of study drug by day 42 (77% and 63%, respectively) and approximately half of all patients attained the target dose of study drug by the start of the efficacy follow-up period (51% and 47%, respectively).

At day 42, the mean daily dose of study drug normalized to body weight (i.e., mg/kg) was slightly higher in the metoprolol group compared to the bucindolol group (1.8 and 1.6 mg/kg, respectively). Patients who were genotyped and identified as CYP2D6 Poor Metabolizers had a slightly lower mean daily dose of study drug for both metoprolol and bucindolol groups at day 42 (1.1 and 1.4 mg/kg, respectively) compared to patients who were identified as CYP2D6 Extensive Metabolizers (1.9 and 1.7 mg/kg, respectively).

ii) Global Summary of Safety

A global summary of treatment emergent adverse events for the Total Study On-Drug Period is shown in Table 15.

TABLE 15

Global Summary of Treatment Emergent Adverse Events for the Total Study Period

| Endpoint | Metoprolol (N = 133) | Bucindolol (N = 134) |
|---|---|---|
| Any adverse event | 95 (71.4%) | 100 (74.6%) |
| Adverse event - possible/probably related to study drug | 40 (30.1%) | 32 (23.9%) |
| Adverse events leading to permanent study drug discontinuation | 11 (8.3%) | 11 (8.2%) |
| Adverse events leading to study withdrawal (excluding death) | 2 (1.5%) | 2 (1.5%) |

TABLE 15-continued

Global Summary of Treatment Emergent Adverse
Events for the Total Study Period

| Endpoint | Metoprolol (N = 133) | Bucindolol (N = 134) |
|---|---|---|
| Adverse event leading to death | 3 (2.3%) | 3 (2.3%) |
| Adverse events related to neoplasm | 9 (6.8%) | 3 (2.2%) |
| Any serious adverse event | 27 (20.3%) | 34 (25.4%) |

Data presented for Total Study On-Drug Period which starts at day of randomization and extends through 30 days after the final dose of study treatment.

The proportion of patients who experienced at least 1 AE during the study was similar in the bucindolol and metoprolol groups. AEs considered by the Investigator to be possibly or probably related to drug were slightly lower in the bucindolol group compared to the metoprolol group, as were AEs related to neoplasm events. The proportion of patients who experienced at least 1 SAE during the study was slightly greater in the bucindolol group compared to the metoprolol group; however, the two treatment groups had similar proportions of patients who had AEs leading to permanent study drug discontinuation, AEs leading to study withdrawal, and AEs leading to death.

iii) Safety During Upitration

Table 16 displays a summary of safety related endpoint for the Drug Titration Period.

TABLE 16

Titration Safety Endpoints

| Endpoint | Metoprolol (N = 133) | Bucindolol (N = 134) |
|---|---|---|
| Any serious adverse event | 10 (8%) | 8 (6%) |
| Treatment-related serious adverse event | 0 (0%) | 1 (1%) |
| Treatment-related cardiovascular serious adverse event | 0 (0%) | 0 (0%) |
| All-cause hospitalization | 9 (7%) | 7 (5%) |
| Cardiovascular hospitalization | 4 (3%) | 5 (4%) |
| Heart failure hospitalization | 4 (3%) | 1 (1%) |
| Symptomatic bradycardia | 3 (2%) | 2 (1%) |
| Asymptomatic bradycardia | 4 (3%) | 0 (0%) |
| All-cause mortality | 1 (1%) | 0 (0%) |
| AC mortality or CV hosp or treatment disc. due to AE | 6 (5%) | 5 (4%) |

Note:
Titration is defined as the first 42 days after the initial randomized study treatment dosing. Patients are counted once for each endpoint. Serious treatment-related SAE is selected with both SAE and relation CRF fields.

Safety endpoints during the Drug Titration Period were similar in the two treatment groups, although most endpoints were numerically lower in the bucindolol group compared to the metoprolol group. Most patients in the bucindolol and metoprolol groups attained the target dose of study drug by the end of the Drug Titration Period (77% and 63%, respectively).

iv) Adverse Events During Total Follow-Up Period

Treatment-emergent AEs with a frequency ≥3% in any treatment group are shown in Table 29. The proportion of patients who experienced at least 1 AE during the study was similar in bucindolol and metoprolol groups (74.6% and 71.4%, respectively). Common AEs with a frequency of ≥3% in the bucindolol group and with a frequency ≥1% greater in the bucindolol group compared to the metoprolol group were: constipation (6.0% and 1.5%), hypomagnesaemia (3.0% and 0.0%), epistaxis (3.0% and 0.0%), hematuria (3.0% and 0.0%), pneumonia (3.0% and 0.8%), chronic kidney disease (3.0% and 0.8%), hypotension (9.7% and 7.5%), upper respiratory tract infection (6.0% and 4.5%), cardiac failure (5.2% and 3.8%), and arthralgia (5.2% and 3.8%)

Higher level examination of the AE data for system organ classes (SOC) with a frequency of ≥3% in the bucindolol group and with a frequency ≥1% greater in the bucindolol group compared to the metoprolol group were: Musculoskeletal and Connective Tissue Disorders (25.4% and 15.0%), Infections and Infestations (28.4% and 21.8%), Respiratory, Thoracic and Mediastinal Disorders (15.7% and 10.5%), Investigators (12.7% and 7.5%), Eye Disorders (6.0% and 3.0%), Gastrointestinal Disorders (20.9% and 18.0%), Metabolism and Nutrition Disorders (14.2% and 12.0%), and Hepatobiliary Disorders (3.7% and 2.3%). Of note, a similar proportion of patients in the bucindolol and metoprolol groups experienced the SOCs of Renal and Urinary Disorders (10.4% and 9.8%) and Cardiac Disorders (25.4% and 26.3%); whereas, a lower proportion of patients in the bucindolol group compared to the metoprolol group experienced a SOC of Neoplasms Benign Malignant and Unspecified (2.2% and 6.8%).

The proportion of patients who experienced at least 1 serious adverse event (SAE) during the entire study was similar in bucindolol and metoprolol groups (25.4% and 20.3%, respectively) (Supplement 7.7, Table 30). The only SAEs with a frequency of ≥3% in any treatment group was Cardiac Failure Congestive (5.3% and 2.2%) and Cardiac Failure (3.0% and 2.3%). Higher level examination of the SAE data for SOCs with a frequency of ≥3% in the bucindolol group and with a frequency ≥1% greater in the bucindolol group compared to the metoprolol group were: Respiratory, Thoracic and Mediastinal Disorders (5.2% and 1.5%), Infections and Infestations (4.5% and 3.0%), and Renal and Urinary Disorders (3.0% and 1.5%).

Example 5E, Tables 31, 32, 33 and 34 respectively give selected cardiovascular events, bradycardia events, potential rhythm related events and systolic blood pressure or heart rate data. Possible differences between the two treatment groups are infrequent, and include more bradycardia events in the metoprolol group (Tables 31, 32), more coronary artery disease events and catheterizations in the bucindolol group (Table 33) and greater heart rate reduction by metoprolol at 4, 12 and 24 weeks (Table 34).

Remarkably, during full follow there were no strokes in the trial (Table 33), with 99% of patients receiving oral anticoagulants (Table 1). One patient in the metoprolol group experienced a TIA (Table 33). These data speak to the excellent care provided by trial Investigators, as well as the quality of the clinical monitoring.

v) CYP2D6 Genetic Variation Effects on Drug Levels, Efficacy and Safety

Based on FDA interactions and recommendations[63] the inventor sought to categorize CYP2D6 genetic variation in every patient in GENETIC-AF. Of the 267 randomized patients, 255 had technically adequate 2D6 genotyping. Table 17 profiles the four major 2D6 variant categories (methods in Example 6D), including the polymorphism distributions (N (%), primary endpoint event rates and hazard ratios, cardiac AEs and drug doses.

TABLE 17

CYP2D6 genetic variants in 255 GENETIC-AF patients, and primary endpoint (1EP), AE data

| CYP2D6 Variant | N (%) | Hazard Ratio Adjusted/ Unadjusted | 1EP Events (rate) | Cardiac AE* | Dose week 12 mg/kg/d | mg/d |
|---|---|---|---|---|---|---|
| Poor Metabolizer (PM) | 20 (7.8%) | — | 11 (55%) | 7 (35%) | — | — |
| Metoprolol | 8 | 2.57 (0.49, 13.6) | 3 (38%) | 4 (50%) | 1.13 ± 0.89 | 110 ± 88 |
| Bucindolol | 12 | 2.19 (0.58, 8.30) | 8 (67%) | 3 (25%) | 1.39 ± 0.94 | 124 ± 83 |
| Intermediate Metabolizer (IM) | 19 (7.5%) | — | 9 (47%) | 3 (16%) | — | — |
| Metoprolol | 10 | 0.34 (0.04, 3.10) | 7 (70%) | 3 (30%) | 1.63 ± 0.86 | 157 ± 73 |
| Bucindolol | 9 | 0.24 (0.05, 1.18) | 2 (22%) | 0 (0%) | 1.72 ± 0.84 | 157 ± 73 |
| Extensive/Ultra Metabolizer (EM/UM)* | 216 (85%) | — | 119 (55%) | 58 (27%) | — | — |
| Metoprolol | 111 | 1.01 (0.69, 1.48) | 58 (52%) | 27 (24%) | 1.95 ± 0.65 | 180 ± 47 |
| Bucindolol | 105 | 1.01 (0.70, 1.45) | 61 (58%) | 31 (30%) | 1.72 ± 0.51 | 165 ± 54 |
| Totals | 255 | — | 139 (55%) | 68 (27%) | — | — |
| Metoprolol | 129 | 1.04 (0.73, 1.48) | 68 (53%) | 34 (26%) | 1.87 ± 0.70 | 173 ± 54 |
| Bucindolol | 126 | 0.98 (0.71, 1.37) | 71 (56%) | 34 (27%) | 1.70 ± 0.59 | 161 ± 58 |
| P value M vs. B. 2D6 variant distribution P = 0.67 | — | — | — | — | — | — |

*Includes 2 patients with CYP2D6 Ultra Metabolizer genotype

As shown in Table 17 and Example 5F, Table 35, CYP2D6 Poor Metabolizers (PMs) have numerically but not statistically (p=0.39) higher cardiac AE rates than Intermediate Metabolizers (IMs) or Extensive Metabolizers (EMs) (35% vs. 16% and 27% vs. IMs and EMs, respectively). These AEs consist of heart failure or bradycardia events, which are more plentiful in the metoprolol group (50% vs. 25% with the excess due to bradycardia AEs 3 (38%) vs. none in bucindolol PMs). In bucindolol treated patients there is no difference for overall AEs between PMs (75.0% incidence) and EMs (77.1%, Table 36). For metoprolol the PM overall AE rate is numerically higher (87.5% vs. 72.1%) but not statistically significant (p=0.34). There is no obvious effect of the variants on combined treatment group event rates. As seen in Table 17, for primary endpoint event rate, PMs contain the highest rate for bucindolol (67% vs. 56% overall), while metoprolol's event rate is highest in IMs, 70% vs. 53% overall. The lowest event rates for metoprolol occur in PM variants (38%), while for bucindolol it is in IMs (22%). For hazard ratios, PMs have the highest value (2.19 (0.58,8.30) unadjusted) and IMs the lowest (0.24 (0.05,1.18) (Table 17). These are explained by the metoprolol and bucindolol's respective low and high event rates in PMs, and the opposite rates in IMs (Table 17). The hazard ratio of all 2D6 genotypes other than PMs (IMs+EMs+UMs) is 0.92 (0.65,1.38), interaction p value vs. PMs=0.18.

Given that PMs have a hazard ratio >2.0 for the Phase 2 primary endpoint and that bucindolol has a high event rate in the PM group (67%, Table 17), we looked at heart failure related endpoint event rates in the treatment groups with or without PMs included (Table 37). Of the 8 endpoints evaluated (4 each in the 24 week or full follow-up periods), removing PMs from the analysis resulted in a trivial (by 1%) reduction in event rates in 6 of the 8 categories, while for bucindolol event rates didn't change in 5 and went up 1% for 3 endpoints on removal of PMs. Thus, there is no evidence that in PMs bucindolol has any loss of efficacy for heart failure effects, or any adverse effects on cardiac AEs.

On a mg/kg or mg/day basis doses for both metoprolol and bucindolol are lower in PMs, more so for metoprolol (60% of overall/total dose in mg/kg, 64% in mg/day) compared to bucindolol's 82% of overall/total dose in mg/kg, 77% in mg/day. The greater reduction in dose in the metoprolol group may have been in response to the greater incidence of bradycardia in metoprolol PMs.

Population PK study drug plasma trough levels measured at 12 weeks in 198 GENETIC-AF patients are given in Table 18, along with 2D6 genotypes. Receptor occupancies of the human $\beta_1$-adrenergic receptor (AR) are also given, using $K_D$ ($K_A$ in the occupancy formula) values of 3.6 nM for bucindolol and 45 nM for metoprolol.[64] Assumptions used in these calculations include myocardial membrane concentration=that of plasma, and effects of competing ligands such as norepinephrine not taken into account. Although the doses of bucindolol and metoprolol succinate were similar in GENETIC-AF (Table 17) and in previous HFrEF trials, the higher bioavailability of metoprolol succinate (approximately 50%[65]) vs. approximately 30% for bucindolol[66] leads to higher plasma levels of metoprolol in EMs (by 9.2-fold, p<0.0001) and IMs (by 5.5-fold, p=0.003) but not in PMs (1.3, fold, p=0.53) (Table 18). Estimated $\beta_{11}$-AR occupancies for bucindolol are similar for all three 2D6 variants (between 85% and 99%) but are nearly identical in EMs (85.2% for bucindolol, 86.4% for metoprolol), slightly higher for bucindolol in IMs (94.6% vs, 91.2% for metoprolol, and as a result of the high bucindolol plasma concentrations in PMs there is even more of a separation in this 2D6 variant (99.0% for bucindolol, 93.4% for metoprolol). In PMs the bucindolol plasma concentration is 17.4-fold >EMs (p<0.0001) and 5.7-fold >IMs (p=0.013). In contrast, the metoprolol PM concentration is only 2.4-fold >EMs (p=0.028) and statistically different from IMs (1.3 fold higher. P=0.88). Clearly, the step up of plasma concentration for bucindolol from EMs or IMs to PMs is much greater than for metoprolol's PM levels compared to either EMs or IMs. Similar results for bucindolol and its relationship to metoprolol levels were obtained at 4 weeks follow-up, where metoprolol PM levels were higher in IMs than PMs (Example 5F, Table 38). Thus, it appears that the PM 2D6 genotype is associated with a greater relative increase in plasma levels for bucindolol compared to metoprolol.

TABLE 18

Trough bucindolol (B) and metoprolol (M) plasma concentrations and human $\beta_1$-adrenergic receptor (AR) occupancies, 2D6 genetic variants at 12 weeks of efficacy follow-up

| CYP2D6 Variant | Bucindolol plasma concentration, ng/ml | | P value vs. PM | Metoprolol plasma concentration, ng/ml | | P value vs. PM | P vs Buc, w/in variant |
|---|---|---|---|---|---|---|---|
| (N) | Mean | Median | | Mean | Median | | |
| EM (82) B (85) M | 8.3 ± 14.2 | 3.1 | <0.0001 | 76.5 ± 93.8 | 56.5 | 0.028 | <0.0001 |
| IM (7B, 8M) | 25.4 ± 25.6 | 11.1 | 0.013 | 142.9 ± 66.0 | 140 | 0.88 | 0.003 |
| PM (11B, 5M)) | 144.2 ± 120.4 | 113 | — | 185.4 ± 156.7 | 126 | — | 0.53 |

Bucindolol $\beta_1$-AR receptor occupancy, $y = [A]/(K_A + [A])$ where $K_A$ = bucindolol dissociation constant for human
$\beta_1$-ARs (3.6 nM), [A] = molar plasma concentration: EMs: 85.2%; IMs, 94.6%; PMs, 99.0%
Metoprolol $\beta_1$-AR receptor occupancy ($K_A$ = 45 nM): EMs, 86.4%; IMs 91.2%; PMs, 93.4%

The data contained in Table 17, Table 18 and S7.8.4 are the first comparison of beta-blocker plasma levels, CYP2D6 genotype, safety and efficacy in a cardiovascular comparative effectiveness trial. They support the conclusions that 1) the PM genotype exhibits greater loss of CYP2D6 metabolizing function for bucindolol metabolism compared to metoprolol; 2) the marked (by 17-fold) increase in bucindolol plasma concentrations in PMs vs. EMs is not accompanied by an increase in AEs, but is associated with a statistically nonsignificant higher hazard ratio raising the possibility of an effect of higher drug levels on bucindolol effectiveness. Bucindolol's mechanism of action for selective/enhanced effects in ADRB1 Arg389Arg genotypes is thought to be through high (low nM $K_i$ affinity antagonism of $\beta_1$-ARs, as well as $\beta_2$-ARs (likely mechanism of NE lowering, in a compound without potent effects on $\beta_1$-ARs). High drug levels in the 200-500 nM range as measured in PMs would be expected to occupy "off target" receptors, channels and other biologic binding sites. However, norepinephrine lowering from bucindolol was not different in PMs compared to EMs, so counteraction of sympatholysis by occupancy of $\alpha_{2C}$ or $\alpha_1$-ARs both of which inhibit cardiac sympathetic neurotransmission, was not involved. Of course, with a total N of 20 patients in the PM group the bucindolol hazard ratio could well be a chance finding.

E. Identification of Unresponsive Population

The AF prevention effects of bucindolol were first identified in the BEST trial[12,13] from a population with advanced HFrEF (92% NYHA Class III and 8% Class IV) with severe LV dysfunction (mean LVEF 0.23±0.07), who at the time of randomization had an increased risk of developing AF because of advanced heart failure (n=2392) or in permanent AF (n=303).

As shown in Table 1, the GENETIC-AF population primarily had mild heart failure (85% NYHA I/II) and only moderate LV dysfunction (mean LVEF 0.36±0.10, median 0.39). These patients also had a much higher risk of developing AF by virtue of being in AF and requiring ECV at the start of follow-up, or having had an AF episode in the past 180 days. Thus, BEST was an advanced heart failure, severe LV dysfunction, moderate AF risk population, while GENETIC-AF was conducted in subjects with mild-moderate heart failure, moderate LV remodeling/dysfunction and high risk for developing recurrent AF. In addition to these study population differences, BEST was placebo controlled and GENETIC-AF was a comparative effectiveness trial against a beta-blocker with substantial activity in preventing AF[13]. Finally, GENETIC-AF patients were all genotype ADRB1 Arg389Arg, while for the BEST entire cohort AF prevention data[13] approximately 48% of patients had this genotype.

Figure 17:
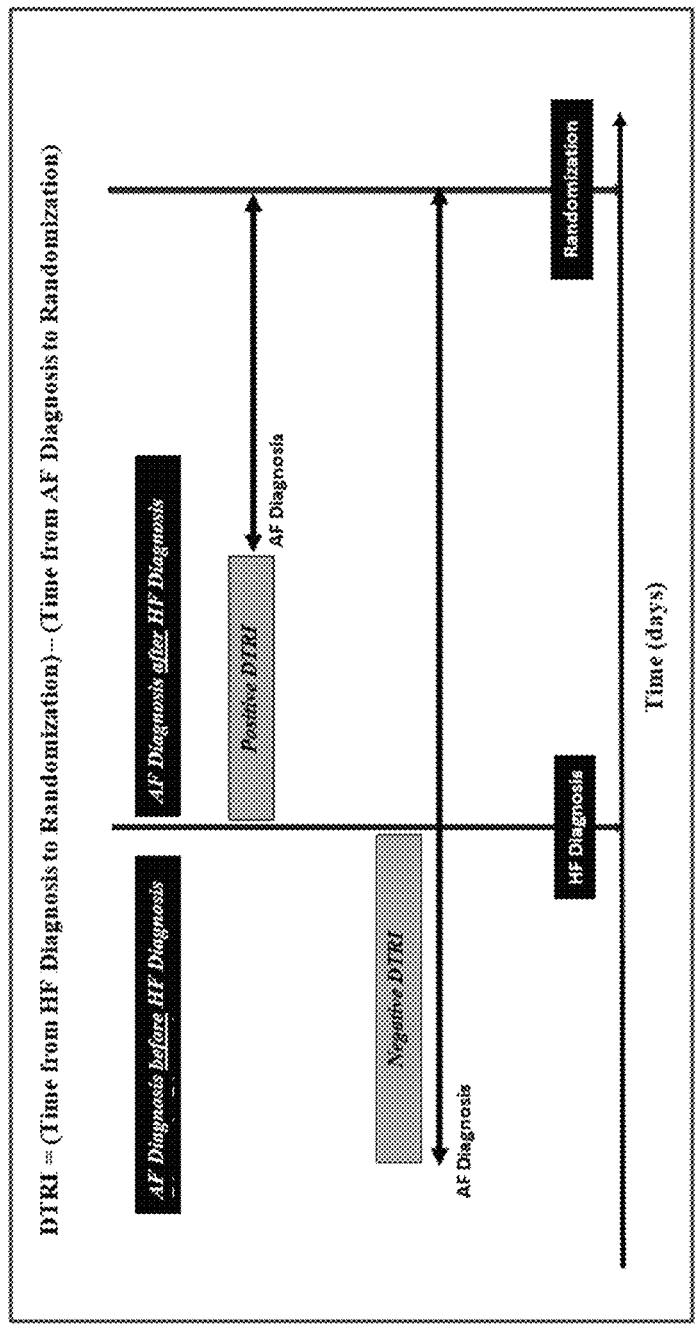
FIG. 17. One embodiment of a Diagnosis to Randomization Index (DTRI) illustrated as time from heart failure (HF) to Randomization—time from atrial fibrillation diagnosis to Randomization.

The GENETIC-AF trial included a case report form that collected the dates of diagnosis for both heart failure and AF. These data, which are used to calculate the "diagnosis to randomization index" DTRI (FIG. 17) are given in Table 19.

TABLE 19

Time in days from first diagnosis to randomization for AF ($AF_{days}$) or heart failure (HF, $HF_{days}$), and the value of $HF_{days}$-$AF_{days}$ (DTRI, diagnosis to randomization index, negative value means AF was diagnosed first (Supplement, 7.11.2))

| Cohort (n) | AF Dx to Randomization (days) | | HF Dx to Randomization (days) | | HF Dx-AF Dx (DTRI, days) | | P value vs. U.S.* |
|---|---|---|---|---|---|---|---|
| | Mean | Median | Mean | Median | Mean | Median | |
| Entire cohort (267) | 1306 | 338 | 1153 | 203 | −153 | −1.0 | — |
| USA (127) | 1236 | 366 | 1627 | 566 | 391 | 0 | — |
| Canada (59) | 1249 | 230 | 919 | 170 | −330 | −6.0 | 0.024 |
| Hungary (33) | 2734 | 1498 | 562 | 99 | −2172 | −1037 | <0.0001; (0.01 vs. Canada) |
| Poland (23) | 494 | 256 | 583 | 311 | 89 | 0 | 0.590 |
| Serbia (21) | 338 | 138 | 157 | 112 | −180 | −1.0 | 0.175 |
| Netherlands (4) | 2354 | 1383 | 2924 | 2584 | 570 | −50 | — |

*Wilcoxon rank sum

The mean duration between AF diagnosis and randomization in Hungary (~7.5 years) clearly stands out compared to the U.S. and Canada (each ~3.4 years), Serbia (~0.9 years), and Poland (1.3 years). For the mean duration between HF diagnosis and randomization, Hungary, Poland and Serbia have shortest interval, ranging from 0.4 years (Serbia) to 1.6 years (Poland); whereas the U.S. was approximately 3-fold higher (4.5 years). These data naturally lead to major differences in the DTRI ($HF_{days}-AF_{days}$), a measure of whether AF diagnosis precedes HF or vice versa, and by how much.

By DTRI the major outlier is Hungary, with a mean value of −5.95 years. This means that patients in Hungary had years of AF, and AF treatment, prior to entering the trial, at which time they had only minimal LV dysfunction (Table 2A) with average LVEFs of 0.43±0.08 and only 1 patient out of 18 with Class III heart failure. Although they all met the protocol entry criteria, the Hungary study population is best characterized as having longstanding AF and only mild or incidental HFmrEF, for which no previous bucindolol data, or in fact other beta-blocker therapeutic effects, had been investigated.

Longstanding AF that eventually leads to LV dysfunction and heart failure has a very different pathophysiology[67-69] compared to HFrEF[70] with AF developing secondarily. In short, the pathophysiology of longstanding AF is driven by MAP kinase and TGF □□signaling[67,71,72] of fibrosis and hypertrophy in the atrium and ventricle.[68,72,73] In contrast, HFrEF pathophysiology is driven by neurohormonal signaling of pathologic eccentric hypertrophy and contractile dysfunction in the ventricle[32,70] and to a lesser extent in the atrium,[73] with only minimal signaling of fibrosis in most cases.[74]

Canada also had a large, negative DTRI, whose index of −0.9 years (mean) was significantly different from the U.S. (p<0.024). As demonstrated in the Supplement 7.9, Table 39, both Hungary and Canada had predominately electrophysiology specialist (EP) PIs who randomized approximately 80% of the patients in these areas, with no heart failure specialists and no (Hungary) or few (Canada) general cardiologist PIs. The U.S., on the other hand, had physicians who care for heart failure patients as PIs or Co-Is in nearly every site, using the EP-heart failure specialist Co-PI model developed in other trials, such as MIRACLE[75] and COMPANION.[76] Despite the negative DTRI and predominance of EP PIs in Canada, patient baseline characteristics were similar to the U.S. and Europe excluding Hungary (Table 1 and Table 2A). One difference was the proportion of patients with Class III heart failure, which was 4/59 (7%) in Canada vs. 33/127 (26%) in the U.S. despite similar LVEFs (0.35±0.10 and 0.34±0.09, respectively). In addition, patients randomized in Canada tended to have lower baseline NE levels (Table 10) and, in contrast to all other countries, bucindolol did not lower mean NE plasma concentrations at Week 4 in the Canadian cohort. The trial Steering Committee Chairman (Stuart Connolly) and Canada Country PI/SC member (Jeff Healey), are EPs but were well aware of the pathophysiological preference for the heart failure phenotype, and therefore it is not surprising that the patient profile in Canada is very different from Hungary and much closer to the U.S. characteristics. In summary, the Canadian patients randomized in GENETIC-AF had on average AF diagnosed before heart failure but not nearly as extreme as in Hungary, and had moderate LV dysfunction but only mild heart failure symptoms that based on median values may have been accompanied by lower levels of adrenergic activation precluding a sympatholytic effect of bucindolol.

Based on these observations we concluded that positive DTRI values are a simple means of identifying AF-HFrEF patients whose pathophysiology is characterized by HFrEF mechanisms, including adrenergic activation similar to patients investigated in the BEST trial, as opposed to patients having predominately AF pathophysiology.

Table 20 contains data used to analyze the impact of the directionality and duration of the DTRI interval on bucindolol treatment effect, in all subjects and in patients whose LVEFs are below or above the baseline median of 0.39.

TABLE 20

DTRI values by quartiles, for all LVEFs and for above, below LVEF median of 0.39 in Entire Cohort (EC) and in U.S. patients

| LVEF Category | Cohort | All Patients/ DTRIs | Q1: −15,251 to −311 days | Q2: −310 to −1 days | Q3: 0 to +44 days | Q4: +45 to +9533 days |
|---|---|---|---|---|---|---|
| LVEF <0.39 | | | | | | |
| Met event rate | EC | 35/68 (51%) | 4/6 (67%) | 10/17 (59%) | 8/22 (36%) | 13/23 (57%) |
| | U.S. | 25/46 (54%) | 3/5 (60%) | 7/10 (70%) | 5/15 (33%) | 10/16 (63%) |
| Buc event rate | EC | 38/69 (55%) | 11/16 (69%) | 6/14 (43%) | 8/15 (53%) | 13/24 (54%) |
| | U.S. | 17/35 (49%) | 5/6 (83%) | 2/6 (33%) | 3/7 (43%) | 7/16 (44%) |
| Hazard ratio (CIs) | EC | 1.02 (0.65, 1.62) | 0.83 (0.26, 2.69) | 0.51 (0.18, 1.42) | 1.70 (0.64, 4.53) | 0.92 (0.42, 1.98) |
| | U.S. | 0.80 (0.43, 1.50) | 1.18 (0.26, 5.29) | 0.43 (0.09, 2.10) | 1.62 (0.39, 6.82) | 0.57 (0.22, 1.50) |
| LVEF >0.39 | | | | | | |
| Met event rate | EC | 35/65 (54%) | 11/26 (42%) | 14/23 (61%) | 4/6 (67%) | 6/10 (60%) |
| | U.S. | 15/21 (71%) | 4/7 (57%) | 6/9 (67%) | 1/1 (100%) | 4/4 (100%) |
| Buc event rate | EC | 35/65 (54%) | 11/19 (58%) | 10/18 (56%) | 11/19 (58%) | 3/9 (33%) |
| | U.S. | 16/25 (64%) | 4/5 (80%) | 5/8 (63%) | 4/6 (67%) | 3/6 (50%) |
| Hazard ratio (CIs) | EC | 0.89 (0.56, 1.43) | 1.52 (0.66, 3.51) | 0.63 (0.28, 1.42) | 0.83 (0.26, 2.66) | 0.48 (0.12, 1.92) |
| | U.S. | 0.57 (0.28, 1.16) | 1.04 (0.26, 4.21) | 0.54 (0.16, 1.80) | 0.70 (0.07, 6.83) | 0.35 (0.08, 1.58) |

The first three data rows in Table 20 contain DTRI data by quartile for LVEF <0.39 patients, with the first quartile (Q1) indicating that AF was initially diagnosed at least 311 days prior to the heart failure diagnosis. For LVEF <0.39, scanning through the four quartiles for either the entire cohort (EC) or U.S. data reveals no pattern of improving hazard ratio as the DTRI becomes more positive. On the other hand, the hazard ratio pattern with increasingly more positive DTRI values appears to be different in patients with LVEFs ≥0.39. In Q1 hazard ratios are >1.0 in both the entire cohort and U.S., which then decrease to well below 1.0 in Qs 2-4 as the DTRI becomes more positive.

These data, although based on relatively small numbers of events and patients in each quartile cell, fit with the construct of atrial-ventricular pathology in LVEFs <0.39 being driven by HFrEF pathophysiology, while LVEFs ≥0.39 are driven by AF pathophysiology when AF is diagnosed well before HF. These observations led us to explore exactly how far in advance of HF can AF first occur without compromising treatment effect in the ≥0.39 LVEF subgroup. DTRI intervals with lower bounds from −730 days to 0, upper bound of +9533 days were evaluated for the ≥0.39 LVEF subgroup, as shown in Table 21.

TABLE 21

Relationship of −DTRI (days) value to Phase 2 primary endpoint hazard ratio (HzR), subject population of LVEF ≥0.39 by lower bound DTRI values from ≤730 days to ≤0 days, upper bound +9533 days (most positive DTRI in the dataset)

| DTRI lower bound* | ≤−730 | ≤−365 | ≤−180 | ≤−90 | ≤−60 | ≤−30 | ≤0 |
|---|---|---|---|---|---|---|---|
| HzR (95% C.I.) | 0.73 (0.41, 1.27) | 0.61 (0.34, 1.09) | 0.69 (0.38, 1.24) | 0.65 (0.36, 1.19) | 0.58 (0.31, 1.11) | 0.54 (0.28, 1.03) | 0.56 (0.16, 1.92) |
| Ratio† | −23.4% | −8.2% | −18.8% | −13.8% | −3.4% | +3.7% | — |

*Upper bound = +9533 days;
†1-(Hazard ratio at ≤0/hazard ratio at ≤−730 or at other intervals) × 100; negative values assigned to hazard ratios >0.56 (the ≤0 hazard ratio), positive values to hazard ratios <0.56.

The data in Table 21 indicate that beginning with a DTRI interval of −29 days to +9533 days, as the lower bound becomes more negative bucindolol's treatment effect diminishes. The data in Table 20 indicate that the LVEF ≥0.39 Q1 DTRI interval hazard ratio for the entire cohort is 1.52 (0.66,3.51)), while the Q2 interval has a hazard ratio of 0.63 (0.28,1.42). These data support the conclusion that in mild LV remodeling/dysfunction, an AF diagnosis preceding HF by ≤310 days (the Q1/Q2 boundary) is associated with a more favorable treatment effect for bucindolol then in DTRIs <−310, and that within the −310 to −1 day DTRI interval, an interval up to −29 days is accompanied by gradually improving effectiveness.

FIG. 10 gives the Phase 2 primary endpoint time to event data in the study population with LVEF ≥0.39 and DTRIs <−30 days removed. For the entire cohort, the removal of the longstanding AF/mild LV dysfunction population patients results in retention of 77% of the original entire cohort, and 85% of the U.S. population. Example 5H, Table 40 gives the number of patients removed by this analysis in each country, which ranged from 15% (U.S.) to 61% (Hungary) and 23% overall. In the proposed Phase 3 trial (Section 4.1.1.1) one of the entry criteria will be exclusion of LVEF 0.40-0.49 patients with a DTRI <−30 days F. Interpretation of Results The goals of a Phase 2B drug development trial may be several, including 1) establishment of a safe and effective dose regimen, 2) determine if there is evidence of an efficacy signal, 3) gather evidence on safety, and 4) seek evidence of subgroups that may have favorable or unfavorable effectiveness responses to inform trial design for Phase 3.

We believe that all these goals were achieved in the GENETIC-AF trial: (i) Although the target dose of bucindolol in HFrEF was previously determined in a multicenter Phase 2 trial[77] and then confirmed in BEST,[14] in GENETIC-AF, the first controlled beta-blocker clinical effectiveness trial in heart failure to measure CYP2D6 genetic variants and drug levels in every patient, has provided evidence that a dose reduction of bucindolol (and metoprolol) should be considered in CYP2D6 Poor Metabolizers (PMs, Sections 8 iv) and Sections 8 iv) and on CYP2D6 genotyping below); (ii) Results in U.S. patients, the AFB substudy, and patients other than those with minimal/mild LV dysfunction and longstanding AF that precedes heart failure provide evidence for an efficacy signal vs. the active comparator metoprolol succinate; (iii) safety was comparable to metoprolol succinate, whose adverse event profile is acceptable and well established; (iv) clear evidence of a nonresponsive subgroup not previously exposed to bucindolol (see (ii)) plus a genetically defined small subpopulation that is a candidate for dose reduction (2D6 PMs) was identified, which will lead to modification of entry criteria and precision dosing in Phase 3.

The overall conclusion is that for prevention of AF in a HFrEF population at high-risk for AF, pharmacogenetically targeted bucindolol should be further investigated in ADRB1 Arg389Arg genotype patients with LVEFs <0.39 and patients with LVEFs ≥0.39 and <0.50 as long as HF has developed prior to or contemporaneously with AF (i.e., AF present <30 days days prior to the HF diagnosis). These criteria define a patient whose atrial-ventricular pathophysiology is likely to be the result of mechanisms that lead to progression of HFrEF, as opposed to an AF driven pathophysiology. Support for this consideration consists of basic work done on the distinct pathophysiologies of primary AF vs. primary HFrEF discussed in Example 2E, hazard ratios in DTRI quartiles of patients with LVEFs ≥0.39 given in Table 21, hazard ratios in patients with LVEFs <0.39 given in Table 20 and in U.S. patients in Table 22 below, and results in ADRB1 Arg389Arg patients in permanent AF in the BEST trial (presented and discussed below in Example 2F iv))

1. Relationship of Findings to the BEST Trial
   i) Phase 2 GENTECI-AF results by LVEF and NYHA Class Table 22 gives GENETIC-AF LVEF data by degree of remodeling/dysfunction and NYHA Class, for the entire cohort (A.) or U.S. randomized patients (B.). For the data in Table 22, there is no direct relationship between LVEF remodeling category or NHYA Class and event rates or hazard ratios. In both the Entire Cohort and in U.S. patients hazard ratios were lower in mild LV remodeling/dysfunction (LVEF 0.40-0.49) and asymptomatic heart failure (Class I), but in both cohorts the hazard ratios were lower in severe LV remodeling/dysfunction (LVEF <0.30) or Class III heart failure vs. moderate LV remodeling/dysfunction (LVEF 0.30-0.39). Note that in U.S. patients the LVEF subgroup (<0.30) whose mean is the same as in the BEST trial[4] (0.23) has a hazard ratio of 0.74 (0.29,1.91), while the Class III patients that overlap with BEST entry criteria (Table 23) have a hazard ratio of 0.81 (0.30,2.15).

TABLE 22

GENETIC-AF Phase 2 primary endpoint (time to any AF/AFL or ACM) by LVEF degree of remodeling/dysfunction (0.40-0.49, mild; 0.30-0.39, moderate; <0.30, severe); NYHA Class measure of heart failure severity; or BEST trial inclusion criteria for LVEF (≤0.35) and NYHA Class (III). A., Entire Cohort, B. U.S. randomized patients

| | A. Entire Cohort | | | | | |
|---|---|---|---|---|---|---|
| | LVEF | | | | NYHA Class | |
| | 0.40-0.49 | 0.30-0.39 | <0.30 | | | |
| Parameter | (mean 0.447) | (mean 0.337) | (mean 0.228) | I | II | III |
| Events/pts (%) | | | | | | |
| Metoprolol | 35/63 (56%) | 19/37 (51%) | 16/32 (50%) | 15/35 (43%) | 40/72 (56%) | 15/26 (58%) |
| Bucindolol | 33/62 (53%) | 21/36 (58%) | 17/33 (52%) | 15/40 (38%) | 51/80 (64%) | 7/14 (50%) |
| Hazard ratio (95% C.I.) | 0.84 (0.52, 1.35) | 1.13 (0.61, 2.11) | 0.95 (0.48, 1.89) | 0.72 (0.35, 1.48) | 1.12 (0.74, 1.70) | 0.83 (0.34, 2.04) |
| | B. U.S. randomized patients | | | | | |
| | LVEF | | | | NYHA Class | |
| | 0.40-0.49 | 0.30-0.39 | <0.30 | I | II | III |
| Parameter | (mean 0.443)) | (mean 0.332) | (mean 0.229) | | | |
| Events/pts (%) | | | | | | |
| Metoprolol | 15/20 (75%) | 14/23 (61%) | 11/23 (48%) | 5/9 (56%) | 23/37 (62%) | 12/21 (57%) |
| Bucindolol | 15/24 (62.5%) | 10/18 (56%) | 7/17 (41%) | 4/12 (33%) | 23/36 (64%) | 6/12 (50%) |
| Hazard ratio (95% C.I.) | 0.51 (0.25, 1.05) | 0.86 (0.37, 1.98) | 0.74 (0.29, 1.91) | 0.55 (0.15, 2.05) | 0.82 (0.46, 1.48) | 0.81 (0.30, 2.15) | ii) Characteristics of Patients Sharing BEST and GENETIC-AF Entry Criteria

The baseline characteristics of the 76 (28% of the entire cohort) GENETIC-AF patients who have a BEST trial LVEF inclusion criterion (≤0.35) are given in Table 23. In order to create a comparator data from BEST, shown in Table 23 are genetic substudy ADRB1 Arg389Arg patients from BEST who were not in AF or AFL at randomization.[3].

TABLE 23

Baseline characteristics for the study populations in FIG. 12.

| | GENETIC-AF, U.S., LVEF ≤ 0.35 | | BEST, ADRB1 Arg389Arg with no AF/AFL at randomization | |
|---|---|---|---|---|
| Parameter | Metoprolol n = 43 | Bucindolol n = 33 | Placebo n = 203 | Bucindolol n = 232 |
| Age | 66.0 ± 10.7 | 65.8 ± 10.9 | 59.7 ± 11.9 | 59.6 ± 11.9 |
| Gender M/F (%) | 81/19 | 88/12 | 76/24 | 79/21 |
| LVEF | 0.28 ± 0.06 | 0.27 ± 0.06 | 0.23 ± 0.07 | 0.23 ± 0.07 |
| NYHA I/II/III/IV (%) | 5/51/44/0 | 18/58/24/0 | 0/0/95/5 | 0/0/95/5 |
| Isc/Nonisc etiology (%) | 42/58 | 30/70 | 63/37 | 55/45 |
| SBP, mmHg | 115.8 ± 15.1 | 121.2 ± 17.2 | 118.9 ± 18.7 | 117.1 ± 18.1 |
| Heart Rate, bpm | 78.7 ± 18.8 | 83.3 ± 19.8 | 80.0 ± 12.9 | 83.0 ± 14.0 |
| AF Dx to screen visit, days | 745 ± 1749 | 1597 ± 2726 | — | — |
| HF Dx to screen visit, days | 1837.2 ± 2182.1 | 2177.5 ± 2382.7 | 1494.2 ± 1610.8 | 1419.1 ± 1504.1 |

TABLE 23-continued

Baseline characteristics for the study populations in FIG. 12.

| Parameter | GENETIC-AF, U.S., LVEF ≤ 0.35 | | BEST, ADRB1 Arg389Arg with no AF/AFL at randomization | |
|---|---|---|---|---|
| | Metoprolol n = 43 | Bucindolol n = 33 | Placebo n = 203 | Bucindolol n = 232 |
| DTRI* | 1091.7 ± 2557.5 | 580.7 ± 2931.6 | — | — |
| DTRI <−30/ ≥−30 (%) | 19/81 | 21/79 | — | — |
| Norepinephrine (pg/ml) | 659.1 ± 309.2 | 657.6 ± 366.3 | 428.8 ± 243.8 | 480.5 ± 265.8 |
| HF Rx at randomization | | | | |
| ACEI/ARB | 33 (74%) | 23 (70%) | 189 (93%) | 205 (88%) |
| Diuretics | 37 (86%) | 24 (72%) | 184 (91%) | 213 (92%) |
| Digoxin | 14 (33%) | 7 (21%) | 181 (89%) | 212 (91%) |
| Spironolactone (MRA) | 20 (47%) | 11 (33%) | 28 (14%) | 24 (10%) |
| Sacubitril/valsartan | 3 (7%) | 2 (6%) | 0 (0%) | 0 (0%) |
| Beta Blocker | 38 (88%) | 28 (85%) | 0 (0%) | 0 (0%) |
| CRT-P or -D | 8 (19%) | 4 (12%) | 0 (0%) | 0 (0%) |
| ICD | 12 (28%) | 11 (33%) | 9 (4%) | 7 (3%) |

*DTRI = (interval of 1st HF diagnosis (Dx) to randomization in days) − time of AF 1st Dx to randomization); a negative number means AF qs Dxd 1st.

Although there are overall similarities in the two trial populations in Table 23, there are some differences. The GENETIC-AF U.S. population is slightly older, LVEFs are slightly higher, the percentage of nonischemic etiology is higher as are norepinephrine levels. There are also substantial differences in the percentage of NYHA Class III (38% vs. 95% in BEST), MRA use (41% in GENETIC-AF and 12% in BEST), digoxin use (28% in GENETIC-AF and 90% in BEST), and CRTs and ICDs were used in a minority of patients in GENETIC-AF and weren't available (CRT) or used often (ICD; 3%) in BEST. Thus, with the exception of CRT devices, the same baseline characteristics were present in both cohorts, but in some cases at a different prevalence.

iii) Prevention of AF/AFL/ACM

FIG. 11 compares the AF/AFL prevention findings of GENETIC-AF to those in the BEST trial, using the Phase 2 primary endpoint of time to AF/AFL or all-cause mortality for the cohorts described in Table 23.

Figures 10A, 10B:
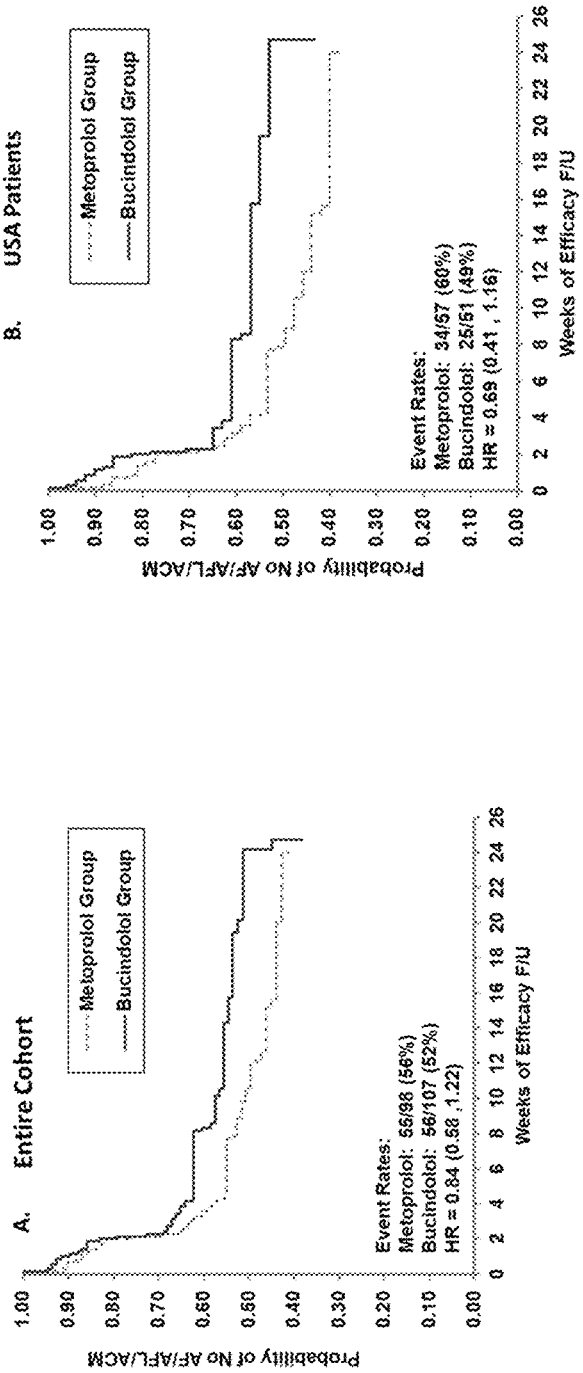
FIG. 10A-10B. Removal of patients with LVEF ≥0.39 and DTRI≤−30 days in 10A. Entire Cohort, and 10B. U.S. randomized patients. Hazard ratios on figures are not covariate adjusted.
Figures 11A, 11B:
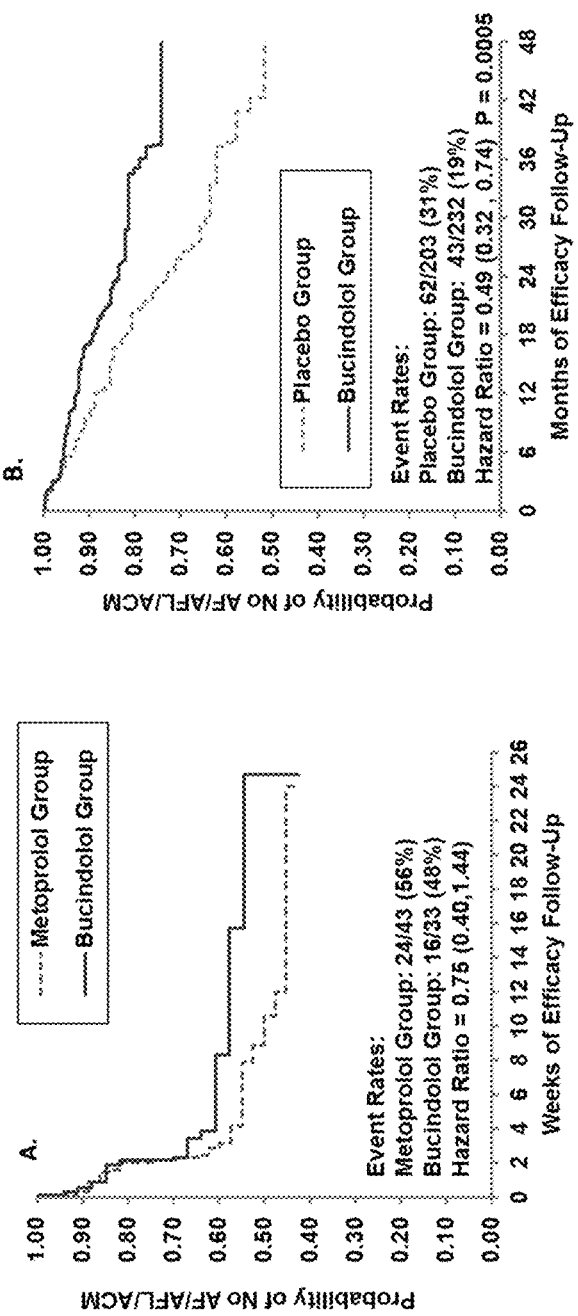
FIG. 11A-11B. Time to AF/AFL or ACM in: 11A., U.S. GENETIC-AF patients with LVEF ≤0.35, mean 0.27 (combined endpoint components are (N) AF/AFL, 64, ECV failure at start of follow-up 9, ACM 3; 11B., BEST trial DNA substudy ADRB1 Arg389Arg patients with LVEF ≤0.35, mean 0.23, no AF or AFL at randomization (combined endpoint components are AF 36, AFL 3, ACM 66). Hazard ratios for both sets of K-Ms are adjusted for randomization strata.

In FIG. 11, the BEST data compare bucindolol to placebo, while in GENETIC-AF the comparison is to metoprolol succinate. The BEST data in FIG. 11A differ from those reported[13] by including ACM in the primary endpoint, and having 6 patients removed who were in atrial flutter (AFL) at randomization. The AF/AFL endpoint in GENETIC-AF was not adjudicated for AF vs. AFL components, and BEST contained more ACM than AF/AFL component events while GENETIC-AF contained more AF/AFL than ACM. The data in FIG. 11 support the consideration that in ADRB1 Arg389Arg genotype patients with HFrEF and severe LV remodeling/dysfunction, bucindolol has a substantial effect in lowering AF/AFL/ACM risk that is markedly greater than placebo, and is highly suggestive of being greater than metoprolol succinate. The LVEF mean for the ≤0.35 data in FIG. 10A is 0.27, which is slight higher than the BEST LVEF mean of 0.23.[14] However, the U.S. LVEF <0.30 data shown in Table 22B have an identical mean (0.23) to that in BEST,[14] with a hazard ratio of 0.74 (0.29,1.91) compared to 0.75 (0.40,1.44) in FIG. 10A.

Table 24 demonstrates that the treatment effect of bucindolol in BEST is selective for the ADRB1 Arg389Arg genotype but still present when all genotypes are considered, either in the BEST entire cohort or the BEST substudy, all genotypes cohort.

TABLE 24

Event rates and hazard ratios for time to AF/AFL/ACM in BEST, entire cohort and DNA substudy.

| Parameter, Treatment Group | Entire Cohort n = 2708 | DNA substudy all genotypes n = 1040 | ADRB1 389Gly Carriers* n = 482 | ADRB1 Arg389Arg n = 435 |
|---|---|---|---|---|
| Placebo, Events/patients (rate) | 461/1182 (39.0%) | 134/457 (29.3%) | 72/254 (28.4%) | 62/203 (30.5%) |
| Bucindolol, Events/patients (rate) | 401/1193 (33.6%) | 104/460 (22.6%) | 61/228 (26.8%) | 43/232 (18.5%) |
| Hazard Ratio (95% C.I.) | 0.80 (0.70, 0.91) P = 0.0009 | 0.70 (0.54, 0.91) P = 0.007 | 0.95 (0.67, 1.34) P = 0.77 | 0.49 (0.32, 0.74)† P = 0.0005 |

*ADRB1 Gly389Gly or Arg389Gly;
†interaction p vs. 389Gly Carriers = 0.016

In a previous NDA submission a substantial proportion of patients (70%) had entered the substudy after they had been randomized in the main trial, due to delayed ethical committee approval of the DNA Bank. Under these circumstances patients who entered the trial before the DNA substudy that were available had to survive the interval to be able to sign consent for the substudy. These patients comprised a "survivor cohort" who couldn't have had the ACM primary endpoint, but also had somewhat lower hospitalization event rates. In FIG. 11B the curve separation begins to occur at 4-5 months, in part due to this phenomenon (66 of the 150 AF/AFL or ACM events were ACM). In contrast, the time to AF event curves from the BEST DNA substudy population reported[13] separate much earlier, because the endpoint could have occurred in each treatment arm during the period between randomization and entering the DNA substudy in delayed entry patients. However, delayed entry of earlier randomized patients into the BEST DNA substudy does not explain the differentiation of ADRB1 Arg389Arg genotype patients from 389Gly carriers observed in Table 24, because these genotype subgroups were investigated under the same circumstances. Also, considering the placebo control in BEST and the active comparator control in GENETIC-AF, the effects in FIG. 11A and FIG. 11B are comparable.

Finally, in the previously submitted NDA FDA reviewers maintained there was a difference in treatment effect in these late entry DNA substudy patients because they were highly selected and not representative of the general BEST trial population. The inventors performed extensive analyses relevant to this issue including a propensity score analysis of the timing of consent for the DNA substudy vs. randomization in BEST, for both the ACM BEST primary endpoint and CVM/CVH endpoint that was planned for the previously negotiated heart failure trial SPA. These analyses will be presented in the new NDA, and findings are that 1) there is increased significance of the p-value for interaction of ADRB1 genotype and treatment due to the inclusion of propensity scores, and 2) for the ADRB1 Arg389Arg genotype there is no change in the estimate of treatment effect (hazard ratio) due to the addition of propensity scores. The appearance of a decrement in treatment effect in ADRB1 Arg389Arg genotype patients was in part related to the short overall follow-up time (1.15 years vs. 2 years in the entire cohort), plus for the ACM endpoint a lesser treatment effect in all patients enrolled after the Jun. 11, 1997 date of the first DNA draw for the pharmacogenetic substudy. In regard to this, The approval of carvedilol for the treatment of HFrEF one month earlier may led to a change in the type of patient being enrolled in BEST.

iv) Effects of the ADRA2C Ins322-325Del Polymorphism on the Time to AF/AFL or ACM Endpoint in GENETIC-AF and BEST.

The $\alpha_{2C}$-adrenergic receptor (ADRA2C) is a prejunctional AR positioned on cardiac sympathetic nerve terminals that negatively regulates NE release.[78] ADRA2C has a relatively high frequency insertion/deletion polymorphism (indel) that is racially distributed (Del allele frequency 0.04 in European ancestry individuals, 0.43 in African ancestry).[79] The indel is in the third intracytoplasmic loop, a functionally important region, and deletion of the 4 amino acid segment renders the receptor nearly nonfunctional.[80]

The relationship of the ADRA2C Ins/Del polymorphism to systemic NE levels and clinical outcomes was investigated as part of the BEST trial AR polymorphism substudy. Del genotypes were found not to be associated with higher baseline NE levels compared to Ins homozygous controls, but were associated with greater NE lowering by bucindolol.[81] In addition, compared to Ins homozygotes the Del related adrenergic dysregulation was associated with loss of effectiveness for cardiovascular mortality reduction and heart failure hospitalization burden (total days of hospitalization for heart failure, patient/year).[71] These adverse effects on clinical outcomes were likely related to the greater degree of NE lowering in the bucindolol group, as the sympatholysis in Del genotypes (decrease by 153 pg/ml compared to a 50 pg/ml decrease in Ins homozygotes) was at a level shown to be associated with an increase in mortality in the larger BEST entire cohort[22] as well as in the MOXCON study investigating the sympatholytic agent moxonidine.[82]

The pharmacodynamic interaction of ADRA2C Ins/Del genetic variants with the ADRB1 Arg389Gly polymorphism were then investigated, for effects on NE lowering and clinical outcomes.[19] For both receptors the minor alleles are dominant negative, meaning that homozygotes or heterozygotes produce similar decreases in function.[17,19] The combinatorial genotype analysis showed that marked NE lowering from bucindolol in Del genotypes only produced adverse clinical effects when in combination with ADRB1 389Gly genotypes,[9] where the encoded $\beta_1$-receptor protein has markedly lower affinity for NE in addition to its compromised signal transduction capacity.[17,19] The combination genotype of {ADRB1 389Gly carrier+ADRA2C Del carrier} therefore results in markedly decreased adrenergic activity coupled with a hypofunctional, low norepinephrine affinity $\beta_1$-AR.

The combination genotype of {ADRA2C Del carrier (heterozygotes or homozygotes) and ADRB1 Arg389Arg (Arg389 homozygotes)}, present in 7% of the 1040 patient DNA substudy, exhibited no evidence of any adverse effect on effectiveness despite exhibiting a large reduction in NE (by 120 pg/ml compared to an increase of 38 pg/ml in the same combination genotype placebo group). The hazard ratios for this combination genotype were respectively 0.50 (0.12,2.05), 0.40 (0.08,2,12) and 0.60 (0.11,1.30) for ACM, CVM and heart failure hospitalization burden. On the other hand, the combination genotype of {ADRA2C Del carriers and ADRB1 389Gly carriers} (13% of the total) exhibited evidence of loss of efficacy (respective hazard ratios of 1.04 (0.43,2.54), 1.11 (0.45,2.78) and 1.19 (–0.17,2.55) for ACM, CVM and heart failure hospitalization burden.

The conclusions from the combination genotype clinical outcomes analysis coupled with the pharmacology of the ADRA2C and ADRB1 polymorphisms were that 1) the bucindolol effectiveness loss related to marked NE lowering in ADRA2C Del genotypes (Del carriers) is confined to HFrEF patients who also have ADRB1 389Gly genotypes (389Gly carriers), and 2) there is no issue of effectiveness loss in ADRA2C Del carriers if HFrEF patients also are ADRB1 Arg389 homozygotes, who can only have high functioning, high NE affinity, high constitutive activity Arg389$\beta_{11}$-ARs. In other words, the higher function and NE affinity of Arg389 $\beta_{11}$-ARs protects against cardiac function compromising marked lowering of NE in moderate-severe LV dysfunction. It is even possible that bucindolol efficacy is enhanced in {ADRA2C Del carrier+ADRB1 Arg389Arg} patients, and for these reasons we did not prospectively genotype for ADRA2C Ins322-325Del in GENETIC-AF, where all randomized subjects were ADRB1 Arg389 homozygotes. However, we did genotype retrospectively from stored DNA samples, where technically adequate results were obtained on 260 of the 267 randomized subjects (Methods in Example 6E).

Figures 12A, 12B, 12C, 12D:
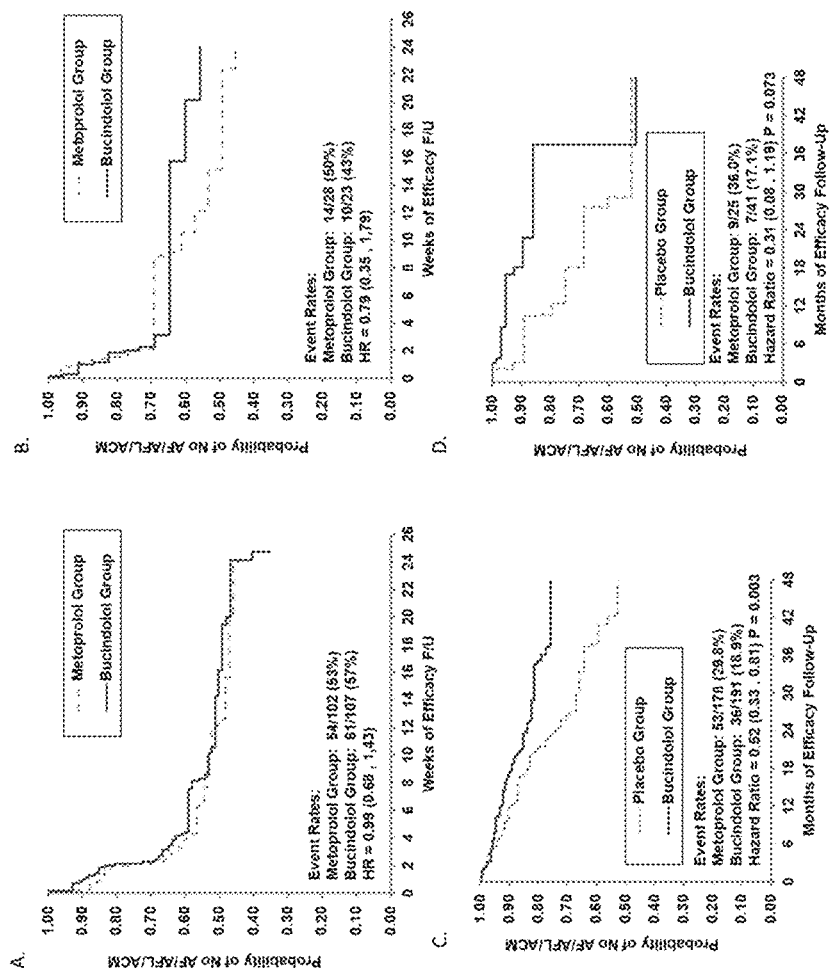
FIG. 12A-12D. 12A., Time to AF/AFL or ACM in GENETIC-AF by treatment group, ADRA2C Ins322-325Ins patients; 12B., Same endpoint, GENETIC-AF ADRA2C 322-325 Del carrier patients; 12C., Same endpoint, BEST {ADRB1 Arg389Arg+ADRA2C Ins322-325Ins} genotype; 12D., Same endpoint, BEST {ADRB1 Arg389Arg+ ADRA2C 322-325Del carrier} genotype.

FIGS. 12A and 12B give the time to event curves for AF/AFL or ACM in GENETIC-AF, for ADRA2C Ins homozygotes (16A) or Del carriers (16B). FIGS. 12C and 12B give the same endpoint by ADRA2C Ins/Del polymorphisms in the ADRB1 Arg389 homozygote subpopulation of the BEST DNA substudy. In both GENETIC-AF and BEST an ADRA2C 322-325 Del genotype is associated with a lower hazard ratio than for ADRA2C Ins homozygotes, supporting the notion that the presence of an ADRB1 Arg389Arg genotype eliminates any compromise of bucindolol effectiveness related to ADRA2C Del genotype associated marked NE lowering.

v) Heart Failure Endpoints

Table 25 compares heart failure endpoints in U.S. GENETIC-AF patients during the 24 week follow-up period, vs. the BEST Trial ADRB1 Arg389Arg patients shown in FIG. 12B.

The GENETIC-AF heart failure endpoint data in Table 25 do not have enough events to provide a valid comparison to the comparator population from BEST. The proposed Phase 3 trial in Section 3 will have a 12 month minimum follow-up, which will produce more heart failure events for evaluation.

TABLE 25

Heart failure events in U.S. LVEF ≤0.35 GENETIC-AF patients vs. the BEST trial ADRB1 Arg389Arg genetic subgroup free of AF/AFL at randomization (unadjusted log rank)

| | GENETIC-AF, n = 127 | | | BEST ADRB1 Arg389Arg, free of AF at randomization, n = 435 | | |
|---|---|---|---|---|---|---|
| Endpoint | Metoprolol Events/36 pts (%) | Bucindolol Events/29 pts (%) | HzR, p value | Placebo Events/203 pt (%)s | Bucindolol Events/232 pt (%)s | HzR, p value |
| ACM | 2 (3.0%) | 0 (0%) | — | 41 (19.9%) | 33 (14.0%) | 0.61 (0.38, 0.99) P = 0.048 |
| CVM | 0 (0%) | 0 (0%) | — | 34 (16.5%) | 25 (10.6%) | 0.54 (0.31, 0.93) P = 0.026 |
| HFH | 1 (1.5%) | 2 (3.3%) | 2.21 (0.20, 24.32) P = 0.52 | 72 (35.0%) | 65 (27.7%) | 0.70 (0.49, 0.99) P = 0.043 |
| CVH | 4 (6.0%) | 3 (5.0%) | 0.84 (0.19, 3.73) P = 0.81 | 96 (46.6%) | 88 (37.5%) | 0.69 (0.51, 0.94) P = 0.017 |
| ACM/HFH | 3 (4.5%) | 2 (3.3%) | 0.74 (0.12, 4.41) P = 0.74 | 89 (43.2%) | 82 (34.9%) | 0.69 (0.51, 0.95) P = 0.021 |
| ACM/CVH | 6 (9.0%) | 3 (5.0%) | 0.56 (0.14, 2.22) P = 0.41 | 111 (53.9%) | 106 (45.1) | 0.72 (0.55, 0.95) P = 0.021 |
| CVM/HFH | 1 (1.5%) | 2 (3.3%) | 2.21 (0.20, 24.32) P = 0.52 | 87 (42.2%) | 76 (32.3%) | 0.66 (0.48, 0.91) P = 0.011 |

Figure 13:
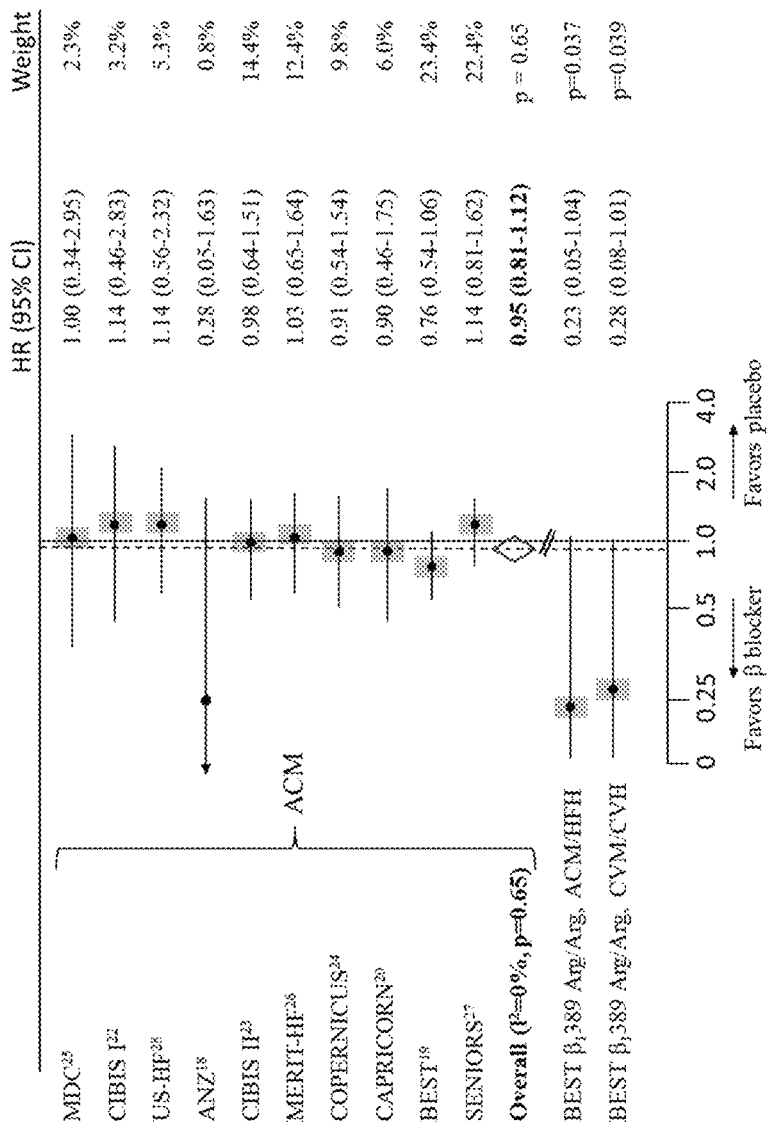
FIG. 13. Effects of beta-blockers used to treat HFrEF on patients with HFrEF and randomized against placebo while in permanent AF. ACM (All-cause mortality) data are from Kotecha et al,[28] BEST trial data in 108 ADRB1 Arg389Arg patients in permanent AF at randomization are from Kao et al.[24].

ACM = all-cause mortality,
CVM = cardiovascular mortality;
HFH = HF hospitalization,
CVH = cardiovascular hospitalization,
pt = patients vi) Permanent AF One of the recent realizations in HFrEF therapeutics is that in permanent AF current standard beta-blocker therapies have little or no therapeutic effect.[28,83,84] In GENETIC-AF, by the end of the 24 week follow-up period 24% of the GENETIC-AF study population was in AF, but based on design, trial size and length of follow-up it was not possible to investigate effects in sustained or permanent AF. However, effects on heart failure events were investigated in BEST,[24] and in the ADRB1 Arg389Arg subset the endpoints of time to all-cause mortality or heart failure hospitalization and cardiovascular mortality or cardiovascular hospitalization were p<0.05, with effect sizes exceeding 70%. FIG. 13 displays the forest plot from Kotecha et al's individual patient meta-analysis,[28] with the BEST ADRB1 Arg389Arg permanent AF patients (n=108) shown on the bottom for comparison.

The data in FIG. 13 suggest that bucindolol has promise in lowering HF event rates in HFrEF patients with permanent AF, and provide the basis for performing a dedicated trial in this patient population.

2. Overall Interpretation

The aggregate and the LVEF ≤0.35 U.S. data in the GENETIC-AF trial are in general agreement with the BEST DNA substudy data for patients with an ADRB1 Arg389Arg genotype, factoring in that GENETIC-AF was conducted with an active comparator with substantial demonstrated activity, and BEST was placebo controlled. ROW data are hampered by the enrollment of patients in Hungary who were not HFrEF patients at risk for recurrent AF, but rather were longstanding AF patients with minimal to mild remodeling/LV dysfunction. These patients would be expected to have a very different pathophysiology, and indeed had no evidence of a favorable treatment effect. Nevertheless, the inclusion of all 267 patients in GENETIC-AF produced evidence of equivalency to metoprolol, a beta blocker approved for treatment of SVT in Europe and which in the succinate formulation has substantial efficacy in preventing AF in HFrEF[12,13].

Example 2

Phase 3

Based on insights gained from GENETIC-AF, a similar trial design for Phase 3 is herewith presented with a primary endpoint of time to first symptomatic AF/AFLACM event. The proposed Phase 3 population would include the same requirements for ADRB1 Arg389Arg genotype HFrEF patients at high risk for recurrent AF. However, for patients with LVEFs ≥40 and <0.50 eligibility would be limited to patients who historically developed their first episode of AF after or contemporaneously with their heart failure diagnosis (i.e., no more than 30 days prior to their HF diagnosis). The active comparator will again be metoprolol succinate, and the period of follow-up will be 12 months rather than 24 weeks in order to better capture a likely favorable bucindolol remodeling effect on AF/AFL risk as well as to evaluate more heart failure events. The pharmacogenetic testing prior to randomization will include ADRB1 Arg389Gly genotyping to determine eligibility, and CYP2D6 genotyping to determine if the dose of both study drugs needs to be reduced in patients with Poor Metabolizer genetic variants.

Phase 3 Primary Endpoint

Figures 6A, 6B:
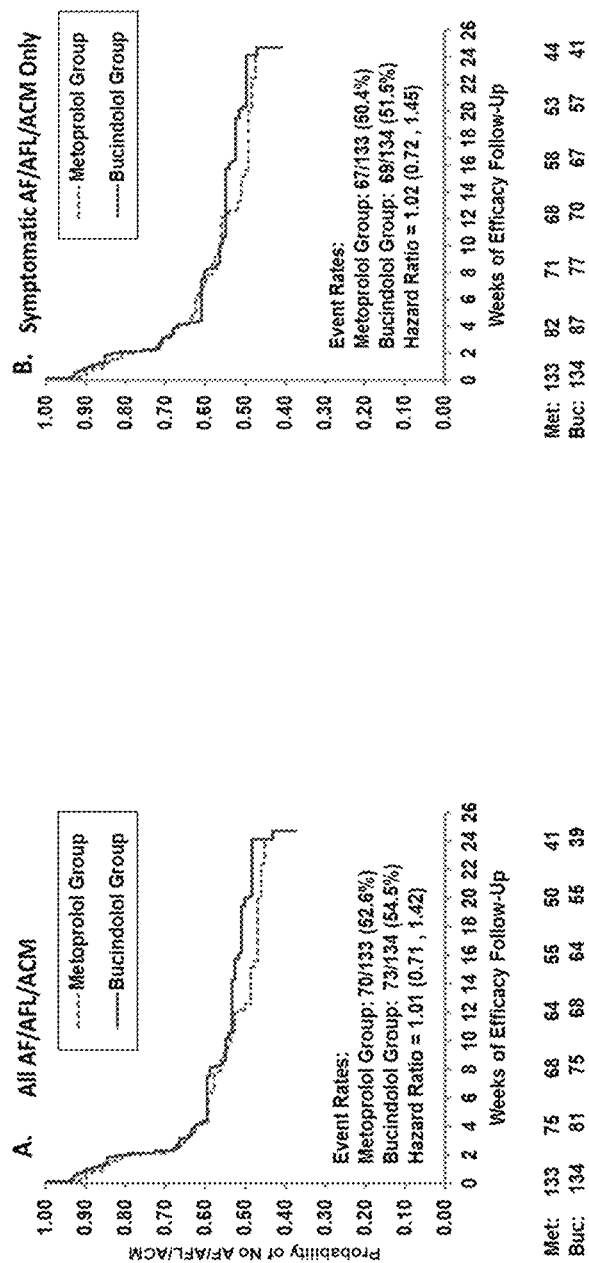
FIG. 6A-6B. 6A., Phase 2 primary endpoint (All AF/AFL (asymptomatic and symptomatic) or ACM, Entire Cohort covariate adjusted. 6B., Phase 3 primary endpoint of symptomatic AF/AFL or ACM in Entire Cohort, covariate adjusted.

Entire Cohort: FIG. 6 presents time to event curves for the Phase 2B and Phase 3 primary endpoints. These endpoints were identical except for the additional Phase 3 requirement for new or worsening symptoms at the time of the AF/AFL event. An AF/AFL event was categorized as symptomatic if there were new or worsening symptoms within ±7 days of the AF/AFL event as adjudicated by a blinded Clinical Events Committee.

All but 7 patients who had an AF/AFL event were adjudicated by the Clinical Events Committee as having a symptomatic AF/AFL event. More than 90% of these symptomatic AF/AFL events were identified on the first occurrence of AF/AFL (i.e., <10% of patients who had symptomatic AF/AFL initially had an asymptomatic event). As such, the symptomatic AF/AFL/ACM results were very similar to the Phase 2 primary endpoint.

Similar to the Phase 2 primary endpoint, the time to event curves in FIG. 6 do not suggest a difference in effectiveness of metoprolol succinate and bucindolol for prevention of AF in the entire cohort.

U.S. and Other Predefined Regions: Table 5 presents hazard ratios for the Phase 3 endpoint of time to symptomatic AF/AFL or ACM in the three regions designated for analysis in the Phase 2 statistical analysis plan, with the Phase 2 endpoint shown for comparison.

Table 5 indicates there is agreement between the Phase 2 and Phase 3 endpoints, which would be expected since 136 of 143 (95%) patients who had AF/AFL/ACM events also had symptomatic AF/AFL/ACM events.

TABLE 5

Comparison of hazard ratios (95% C.I.s) for Phase 2 (time to any AF/AFL or ACM) to Phase 3 (symptomatic AF/AFL or ACM) in the entire cohort or statistical analysis plan predefined geographic regions

| Endpoint | Entire cohort (n = 267) 143 events 136 Sx events | U.S. (n = 127) 73 events 72 Sx events | Canada (n = 59) 35 events 31 Sx events | Europe (n = 81) 35 events, 33 Sx events |
|---|---|---|---|---|
| Phase 2 | 1.01 (0.71, 1.42) | 0.70 (0.41, 1.19) | 1.52 (0.68, 3.43) | 1.01 (0.48, 2.14) |
| Phase 3 | 1.02 (0.72, 1.45) | 0.73 (0.43, 1.26) | 1.60 (0.69, 3.72) | 1.04 (0.48, 2.26) |

Sx = symptomatic;
All analyses covariate adjusted.

A. Redefinition of the Study Population i) HFrEF with High AF Risk, Definition

If a subsequent Phase 3 AF prevention trial is performed in a HFrEF population it is clear from the data presented in Section 2.5.2.1 that patients with mild LV dysfunction will need to have evidence that HF developed before or contemporaneous with AF, in order to define a patient population where atrial and ventricular pathophysiology is driven by HF and not longstanding AF. As shown in FIG. 10, HF patients with mild or minimal LV dysfunction appear to be responsive to bucindolol if AF develops after HF is identified or if the AF and HF develop contemporaneously (i.e., AF diagnosis no more than 30 days prior to HF diagnosis. For the LVEF <0.39 subpopulation, a substantially negative DTRI doesn't have the same effect (Table 19), but being randomized by sites that emphasize and care for heart failure patients does. Thus, the entry criteria for any subsequent Phase 3 trial will include patients with an LVEF <0.40, as well as LVEF ≥0.40 (for practical purposes, lower bound rounded to 0.40) and <0.50 (a quasi-HFmrEF population) and a DTRI >−30 days, meaning the initial AF diagnosis could not have developed ≥30 days prior to the HF diagnosis. The other adjustment will be that all sites will have the involvement of PIs who care for heart failure patients (following the MIRACLE[75] and COMPANION[76] trial model). These adjustments should mean that the study population will be at least 80% of what was randomized in GENETIC-AF.

Figures 14A, 14B:
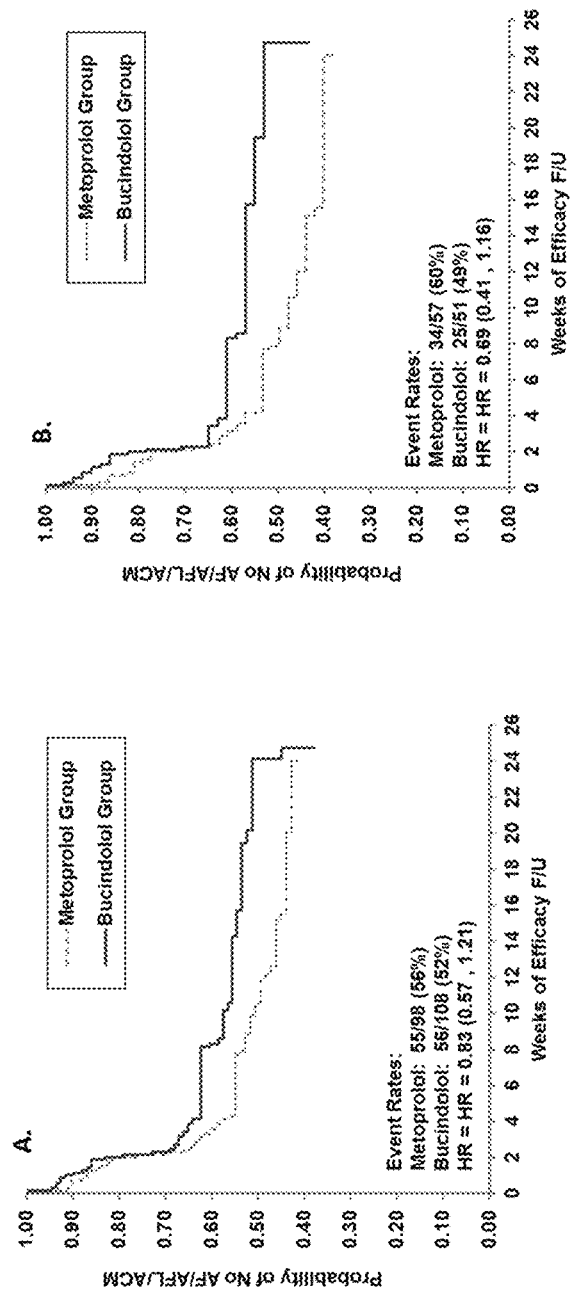
FIG. 14A-14B. GENETIC-AF patients with LVEF <0.40, or LVEF ≥0.40, <0.50 and DTRI >−30 days, 14A. entire cohort. 14B. U.S. patients. Hazard ratios on figures are not covariate adjusted.

FIG. 14 gives time to event curves for the entire cohort (17.A) and U.S. patients (17.B) using the LVEF <0.40 or LVEF ≥0.40, <0.50 and DTRI >−30 days criteria.

ii) CYP2D6 Genotyping

The other major adjustment in entry criteria that we believe should be applied to any subsequent Phase 3 trial is to add CYP2D6 genotyping to the ADRB1 Arg389Gly genetic analysis, as was done in GENETIC-AF. This would add precision dosing to precision targeting of bucindolol. This is a relatively straightforward matter since DNA is already being collected and sampled, and the turnaround for both will be less than one week, not different from ADRB1 alone. Although not associated with an increase in AEs, the markedly higher bucindolol plasma levels in PMs producing $\beta_1$-AR receptor occupancy much beyond necessary that was associated with a hazard ratio >2.0 raises the possibility that the occupancy of low affinity receptors or channel binding sites could occur and interfere with efficacy. In addition, the very high levels of bucindolol in PMs means that drug-drug interactions could occur with CYP3A4 metabolized drugs; CYP3A4 is an alternate pathway for bucindolol metabolism that likely is important when 2D6 metabolism isn't a factor.[85] In metoprolol succinate treated patients the increase plasma levels in PMs was much less, 2.4-fold >EMs. The cardiac AE rate was non-significantly higher in this group compared to the bucindolol PM group or to the metoprolol EM group, due primarily to bradycardia AEs. In addition, likely responding to symptoms and/or bradycardia, in PM genotype patients investigators in GENETIC-AF reduced metoprolol dose levels by 36% and bucindolol doses by 25%, supporting the idea that target doses of each should be reduced in this 2D6 genotype. These clinical outcome trends and pharmacokinetic effects argue for prospective 2D6 genotyping and dose reduction in PMs, if it can be practicably implemented into trial conduct.

Figures 15A, 15B:
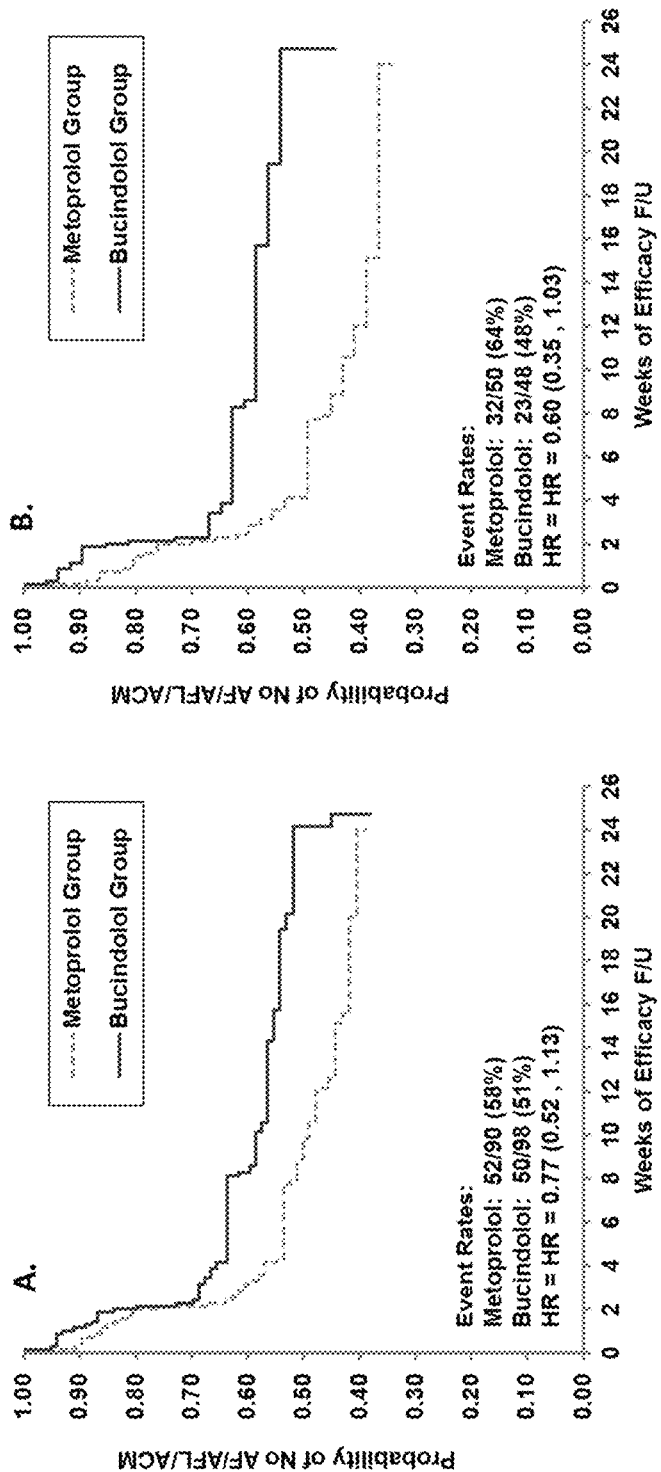
FIG. 15A-15B. GENETIC-AF data with criteria in FIG. 10 applied, plus removal of 18 CYP2D6 PMs in the entire cohort and 10 PMs in U.S. patients. 15A. entire cohort. 15B. U.S. patients. Hazard ratios on figures are not covariate adjusted.

Here the idea is not to withhold treatment in 2D6 PMs, but to reduce dose to a level that brings blood levels into the same range as IMs. It is possible or even likely that bucindolol and metoprolol could have the same proportional decrease in dose, e.g. by 50% or 75%, in the 7-8% of ADRB1 Arg389Arg patients who are 2D6 PMs. This maneuver therefore would not reduce the number of patients eligible for the trial or ultimately for commercial treatment with bucindolol, but it would guarantee that the high blood levels of bucindolol measured in GENETIC-AF PMs would not interfere with effectiveness or be associated with adverse events. A separate pharmacokinetic study in healthy volunteer PMs performed prior to Phase 3 or an adaptive design beginning with a dose reduction of both beta-blockers followed by careful monitoring of C. drug levels by the DSMB and further dose modification if necessary would be necessary, to precisely determine the required dose reduction. FIG. 15 gives the GENETIC AF Phase 2 primary endpoint time to event analysis with the PMs removed.

Figure 18:
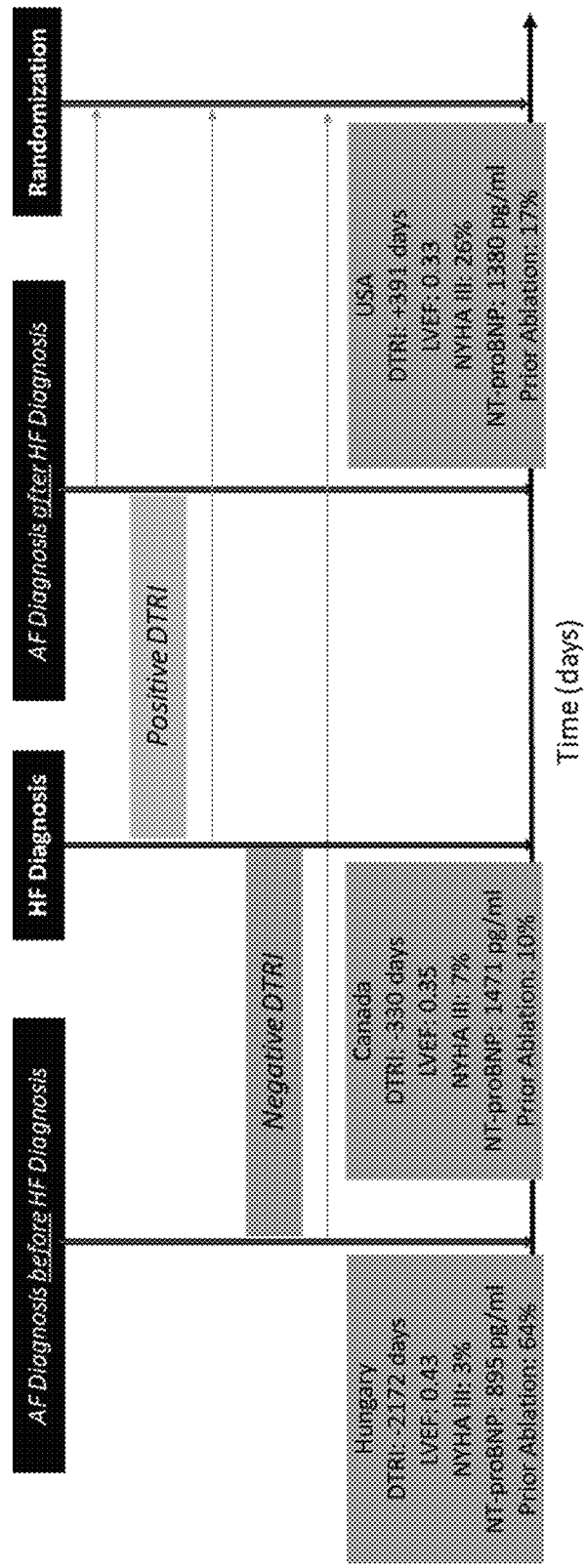
FIG. 18. Another illustration of a DTRI embodiment.
Figure 19:
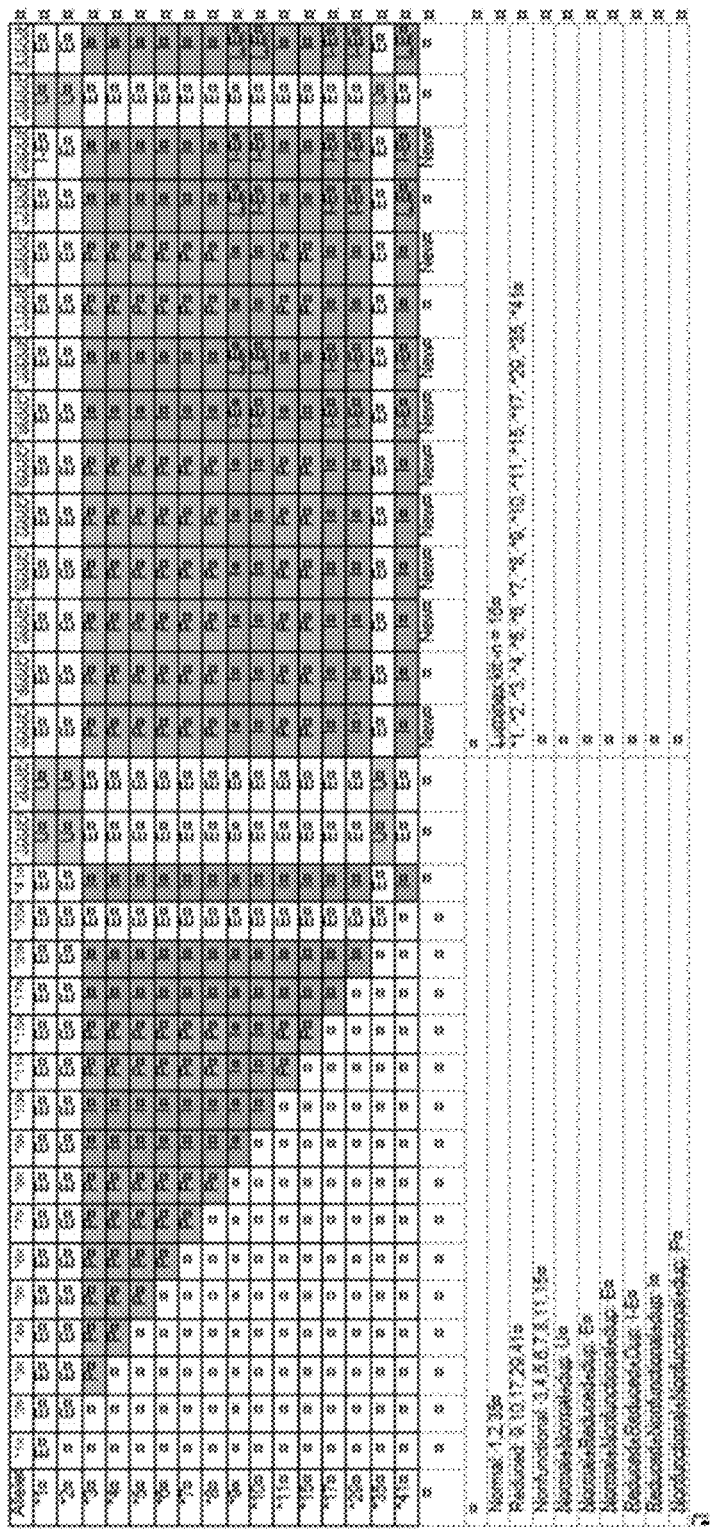
FIG. 19. provides metabolic phenotypes of particular CYP2D6 allelic variants.

B. Endpoints i) Primary Endpoint for Prevention of Recurrent Symptomatic AF/AFL/ACM The primary endpoint time to event curves (e.g., FIG. 18 and others) have a biphasic pattern consisting of an early phase over the first 2 weeks with little or no separation, followed by progressive separation out to 24 weeks. From a mechanistic point of view, this suggests time dependent remodeling of atrial fibrillation mechanisms. Such beta-blocker time dependent remodeling has been shown in the LV for structure and function,[86,87] along with molecular mechanisms that may account for such effects. Beta-blocker reverse remodeling may take at least a year to develop, and for bucindolol there is evidence that it may continue for up to 18 months. For these reasons it would be desirable to extend the period of primary endpoint follow-up from 24 weeks to 52 weeks for Phase 3.

For the primary endpoint, we plan to use the current definition of time to AF/AFL/ACM because this is a hard endpoint that cannot be affected by subjective measures, as can hospital admissions. Our symptom capture data indicate that 1) our symptom capture and adjudication methodology although somewhat unwieldy was quite sensitive, and 2) the vast majority (136 of 143) of AF/AFL events in HFrEF patients are symptomatic. Although there is an argument that the occurrence of AF/AFL is more clinically important than whether a patient has symptoms associated with it (e.g. stroke risk goes up with >6 minutes of AF/AFL on continuous monitoring),[88] and as shown in the GENETIC-AF study if one looks carefully most patients who develop incident clinical AF/AFL are symptomatic. However, ARCA proposes symptomatic AF/AFL/ACM as the primary endpoint for Phase 3, but will continue to study all AF/AFL events (i.e., asymptomatic and symptomatic) as a key secondary endpoint. Because of costs and patient inconvenience associated with the tight surveillance required to detect incident AF/AFL we would limit the primary endpoint follow-up period to 12 months, but continue to follow patients for secondary endpoints until the study is completed, as was done in GENETIC-AF.

AFB generated from a substudy in GENETIC-AF proved quite helpful in demonstrating accuracy of the clinical/ECG detection methodology, as well as showing that 6 hours of AFB is highly associated with subsequent clinical AF/AFB. However, we do not envision performing a trial that incorporates AFB into the primary endpoint, because 1) not everyone otherwise eligible for a study wants an implantable or insertable device, 2) there is a non-negligible cost to providing loop recorders, when there is no possibility of third party payment; 3) it isn't clear if FDA would accept 6 hours of AFB as a definition of AF/AFL, since it may be asymptomatic, and 4) the use of AUC AFB in a parallel design with no pretreatment individual patient control period generates high variance data that are not amenable to detecting even moderate changes by standard statistical methodology. However, we would likely conduct a substudy again, for the reasons why AFB was helpful in GENETIC-AF.

ii) Secondary Endpoints

The highest order secondary endpoint in GENETIC-AF was any (symptomatic or asymptomatic) AF/AFL or ACM, which was the Phase 2 interim and final analysis primary endpoint. If symptomatic AF remains the regulatory standard for drug approval in AF/AFL prevention, then any AF/AFL or ACM would again be the highest order secondary endpoint. Otherwise in a subsequent Phase 3 study we would focus on heart failure secondary endpoints, over the entire follow-up period. In GENETIC-AF patients who developed recurrent AF, we attempted to provide information on ventricular rate control as well as subsequent heart failure events, but for technical and sample size reasons this was not a fruitful exercise. Such a study, measuring rate control and heart failure events in a permanent AF HFrEF population, undertaken to confirm/extend results from BEST[14] (FIG. 13), will need a separate/dedicated study.

iii) Primary Endpoint for Prevention of Heart Failure Events in Permanent AF

The data in FIG. 13 offer considerable promise that in the ADRB1 Arg389Arg population that comprises approximately 50% of the U.S. population, HFrEF patients in permanent AF would benefit from bucindolol for reduction in major morbidity and mortality. Based on data shown in FIG. 13, this also would constitute addressing a major unmet medical need. Here the primary endpoint would be time to cardiovascular mortality or heart failure hospitalization, requiring 1500-2000 HFrEF and HFmrEF patients to achieve enough events. This would be a major economic endeavor, and would require a partnership with a major pharmaceutical company. However, ARCA is pursuing such a partnership and will perform this study if feasible Example 5.

Example 3

Routes to a Phase 3 Trial(s)

A. Traditional Pathway
Designs and Timelines
i) Prevention of AF/AFL or ACM

Some of the features of a subsequent Phase 3 trial have been outlined above, including the redefined patient population that will restrict entry of longstanding AF preceding heart failure in HFmrEF patients, pharmacogenetic precision dosing designed to eliminate very high drug levels and possible negative effects on efficacy and/or safety, and a longer efficacy follow-up period. The high risk of AF recurrence inclusion criteria will be similar to GENETIC-AF, but in the next study we would expect a higher proportion of post AF ablation patients. Such a study would be conducted on the MIRACLE/COMPANION model"[65,66] used in the U.S. for GENETIC-AF, whereby each site has a dedicated heart failure clinical program and both EPs and transplant/heart failure specialists are PIs or Co-Is. As for GENETIC-AF, at least 50% of the patients and events would need to be from the U.S. We would also lower the effect size for calculating sample size to 20% from 25%, which balanced against the increased follow-up period would mean a sample size in the n=500-600 range to achieve a p<0.05. We would also use Bayesian predictive probabilities for this trial, with an interim analysis at 200 evaluable patients and PPoS boundaries similar if not identical to those in FIG. 3. This trial will take approximately 3 years to complete, and we already have sites and investigators identified in the U.S. We would need to recruit some additional, heart failure PIs and Co-Is in Canada and in Europe, and may also expand to Australia where our heart failure relationships are strong. We would also likely need a co-development partner, since additional venture capital funding may not be available. A flow diagram of such a study is given in FIG. 16.

ii) Prevention of Major Heart Failure Morbidity and Mortality in HFrEF/HFmrEF

If a heart failure event reduction trial is performed in HFrEF/HFmrEF, the timeline would be longer than the Phase 3 GENETIC-AF II study and likely on the order of 4 years. The inventors have previously had extensive discussions with FDA about such a trial, and in in fact negotiated an SPA on it.[89] The difference is the SPA was for a HFrEF trial in all rhythms, rather than being in HFrEF/HFmrEF in permanent AF only. If successful, this trial would be the first to demonstrate benefit of a beta-blocker in HFrEF with permanent AF, and the first heart failure therapy of any type to demonstrate benefit in HFmrEF.

B. Expedited Pathway

I) Design and Timeline

Figure 16:
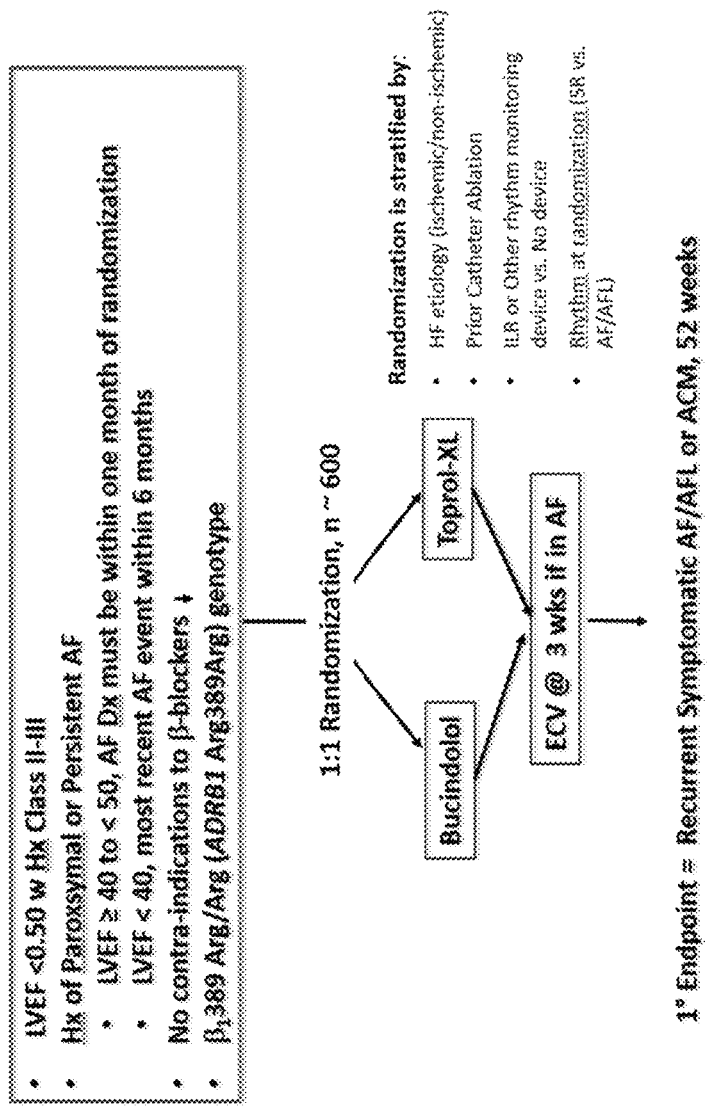
FIG. 16. Flow Diagram of GENETIC AF II trial.

This route would be to conduct the trial outlined the section above regarding traditional design and pathways and in FIG. 16, but do it under the auspices of an expedited approval pathway, namely accelerated approval. The basis for accelerated approval would be BEST trial data supported by GENETIC-AF, primarily the data generated in the U.S. which corroborates BEST data. GENETIC-AF data have addressed most of CRL issues from our last NDA submission for a heart failure approval, and could provide further documentation of that quite quickly and/or in the NDA submission. The logic for an accelerated approval pathway is based on bucindolol meeting the May, 2014 FDA guidance criteria of 1) being indicated for a serious disorder (AF-HFrEF), 2) addressing an unmet medical need in HFrEF patients with an ADRB1 Arg389Arg genotype by providing a meaningful advantage over available therapies, and 3) demonstrating an effect on an intermediate clinical endpoint (or in our case two intermediate endpoints, asymptomatic or symptomatic AF/AFL or ACM, and 6 hours of AFB) that reasonably predicts clinical benefit.

Example 5

C. AF Burden Data.
See Table 26 below.
D. Norepinephrine (NE) and NT-proBNP Data
See Tables 27 and 28 in the Appendix
E. Safety During Total Follow-Up.
See Tables 29-34 in the Appendix.
F. CYP2D6 Genetic Variation Effects on Adverse Events.
See Table 35-38 in the Appendix.
G. PI Subspecialties by Country.
See Table 39 in the Appendix and S7.9.1 below.

H. Numbers of Patients Excluded by {LVEF ≥0.39, DTRI <−30 Days}
See Table 40 in the Appendix.

Example 5

Description of Methods

A. Acquisition and Preparation of Study Medications

Toprol XL, the branded version of extended release metoprolol succinate, was procured from commercial suppliers by Patheon, ARCA's drug product CMO partner. Patheon utilized Adira Medica, LLC for these comparator sourcing activities. Patheon was also responsible for blinding both the study drug and comparator, and for primary packaging into blisters. Blinding of the bucindolol and Toprol XL tablets was accomplished by means of overencapsulation, using the same color and size of overcapsule for all study doses. Comparative dissolution studies were performed at three pH conditions (pH 1.2-2.0, 4.5 and 6.8), and demonstrated that the overencapsulation process did not alter bioavailability of the active drugs.

B. ADRB1 Arg389Gly Genotype Methodology

ADRB1 Arg389Gly genotyping was performed by Laboratory Corporation of America's National Genetics Institute in Los Angeles, Calif. by TaqMan PCR using flanking primers for the ADRB1 C to G substitution at nucleotide 1165. The assay was performed under IDE G130274, approved on Nov. 20, 2013 in support of the GENETIC-AF trial.

C. Diagnosis to Randomization Index (DTRI), Graphic Illustration
See FIGS. 17 and 18.

D. CYP2D6 Polymorphism Methodology

CYP2D6 polymorphisms were identified using the xTAG® CYP2D6 Kit v3 manufactured by Luminex Corporation, with the assay performed by Esoterix, Boulder, Colo. on DNA extracted from whole blood by LabCorp's subsid-

TABLE S7.9.1

PI subspecialties and randomizations in GENETIC-AF by Country

| PIs, Ranomized Pts/Sub-specialty | U.S. (127 Pts/43 Sites) | | Canada (59 Pts/18 Sites) | | Hungary (33 Pts/7 sites) | | Poland (23 Pts/6 sites) | | Serbia (21 pts/4 sites) | | Netherlands (4 pts/4 sites) | |
|---|---|---|---|---|---|---|---|---|---|---|---|---|
| PI Subspecialties | EP | 23 (53%) | EP | 12 (67%) | EP | 5 (71%) | EP | 1 (17%) | GC/I | 3 (75%) | GC/I | 4 (100%) |
| | HF | 13 (30%) | GC/I | 3 (17%) | Intvn | 1 (14%) | HF | 1 (17%) | Intvn | 1 (25%) | | |
| | GC/I | 6 (14%) | Intvn | 1 (11%) | Crt Cr | 1 (14%) | GC/I | 4 (66%) | | | | |
| | Intvn | 1 (2%) | Crt Cr | 1 (6%) | | | | | | | | |
| Totals, PIs | | | EP | 41 (48%) | Intvn | 4 (5%) | | | | | | |
| | | | HF | 18 (21%) | Crt Cr | 2 (2%) | | | | | | |
| | | | GC/I | 20 (24%) | | | | | | | | |
| Randomized by Subspecialty | EP | 77 (61%) | EP | 47 (80%) | EP | 26 (79%) | EP | 9 (39%) | GC/I | 20 (95%) | GC/I | 4 (100%) |
| | HF | 32 (25%) | GC/I | 9 (15%) | Intvn | 6 (18%) | HF | 4 (17%) | Intvn | 1 (5%) | | |
| | GC/I | 15 (12%) | Intvn | 2 (2%) | Crt Cr | 1 (3%) | GC/I | 10 (43%) | | | | |
| | Intvn | 3 (2%) | Crt Cr | 1 (xx) | | | | | | | | |
| Totals, Randomizations/ Subspecialty | | | EP | 159 (59.6%) | Intvn | 12 (4.5%) | | | | | | |
| | | | HF | 36 (13.5%) | Crt Cr | 2 (0.7%) | | | | | | |
| | | | GC/I | 58 (21.7%) | | | | | | | | |

EP = electrophysiologist;
HF = heart failure or HF/transplant;
GC/I = general cardiology &/or imaging;
Intvn = interventional;
Crt Cr = critical care iary Covance, of Salt Lake City, Utah See Table 41 in the Appendix for identified polymorphisms.

E. ADRA2C Ins322-325Del Methodology

ADRA2C Ins322-325Del polymorphisms were identified by RFLP-PCR and gel electrophoresis as previously described,[29] using Ddel restriction digests of the PCR product amplified by ADRA2C nucleotide +964 to 975 flanking primers. The digests were then separated by gel electrophoresis and identified by their fragments as Ins homozygotes, heterozygotes or Del homozygotes. The assay was performed in Dr. Michael Bristow's academic laboratory at the University of Colorado Medical Campus, on DNA samples from GENETIC-AF patients provided by Covance.

AF Burden Data

TABLE 26

Uncensored and censored (at ECV, AF ablation, or administration of Class 3 antiarrhythmic drugs) AFB data at weekly intervals throughout the 24 week follow-up period.

| | Uncensored | | | | Censored* | | | | |
|---|---|---|---|---|---|---|---|---|---|
| | Metoprolol N = 33 | | Bucindolol N = 35 | | Metoprolol N = 33 | | Bucindolol N = 35 | | |
| Week | N | AFB ± SD | N | AFB ± SD | P value | N | AFB ± SD | N | AFB ± SD | P value |
| 1(d1-7) | 33 | 6.8 ± 9.7 | 33 | 4.8 ± 8.3 | 0.40 | 33 | 6.8 ± 9.7 | 33 | 4.8 ± 8.3 | 0.41 |
| 2 | 33 | 8.4 ± 10.8 | 33 | 7.4 ± 10.7 | 0.38 | 32 | 7.9 ± 10.6 | 31 | 7.1 ± 10.6 | 0.45 |
| 3 | 32 | 9.3 ± 11.0 | 33 | 7.9 ± 11.0 | 0.76 | 29 | 7.9 ± 10.6 | 29 | 7.4 ± 11.2 | 0.83 |
| 4 | 32 | 9.0 ± 11.0 | 34 | 8.9 ± 11.1 | 0.44 | 26 | 6.0 ± 10.1 | 30 | 8.5 ± 11.1 | 0.80 |
| 5 | 32 | 9.7 ± 10.7 | 35 | 8.9 ± 11.0 | 0.71 | 25 | 8.7 ± 10.4 | 28 | 7.8 ± 11.3 | 0.51 |
| 6 | 32 | 8.1 ± 10.6 | 35 | 7.6 ± 10.6 | 0.38 | 24 | 8.5 ± 10.8 | 28 | 7.8 ± 11.3 | 0.44 |
| 7 | 32 | 7.8 ± 10.6 | 35 | 7.5 ± 10.4 | 0.47 | 24 | 8.4 ± 10.7 | 26 | 6.7 ± 10.7 | 0.14 |
| 8 | 32 | 8.5 ± 10.9 | 35 | 7.9 ± 10.6 | 0.55 | 24 | 8.7 ± 11.3 | 7.0 | 7.0 ± 10.7 | 0.36 |
| 9 | 32 | 9.3 ± 11.0 | 35 | 6.1 ± 9.9 | 0.14 | 24 | 9.7 ± 11.2 | 24 | 6.0 ± 10.5 | 0.11 |
| 10 | 32 | 8.4 ± 11.0 | 35 | 6.4 ± 10.0 | 0.16 | 22 | 8.0 ± 11.2 | 23 | 5.6 ± 9.9 | 0.11 |
| 11 | 32 | 8.3 ± 10.7 | 35 | 7.3 ± 10.6 | 0.24 | 19 | 8.7 ± 11.0 | 23 | 7.2 ± 10.8 | 0.18 |
| 12 | 32 | 8.3 ± 11.1 | 35 | 7.0 ± 10.8 | 0.26 | 18 | 8.3 ± 11.5 | 23 | 7.4 ± 11.2 | 0.18 |
| 13 | 31 | 7.3 ± 10.7 | 34 | 5.6 ± 9.5 | 0.53 | 18 | 6.8 ± 11.0 | 21 | 5.4 ± 9.5 | 0.60 |
| 14 | 31 | 8.3 ± 11.3 | 34 | 5.2 ± 9.1 | 0.29 | 18 | 7.8 ± 11.2 | 20 | 4.7 ± 9.6 | 0.25 |
| 15 | 31 | 7.5 ± 10.8 | 34 | 3.5 ± 8.1 | 0.19 | 17 | 7.3 ± 11.1 | 19 | 2.7 ± 7.5 | 0.21 |
| 16 | 31 | 7.1 ± 11.0 | 34 | 5.0 ± 9.6 | 0.18 | 17 | 7.2 ± 11.2 | 18 | 3.9 ± 9.0 | 0.033 |
| 17 | 31 | 7.1 ± 11.0 | 34 | 3.9 ± 8.6 | 0.15 | 17 | 7.2 ± 11.2 | 18 | 4.0 ± 9.2 | 0.012 |
| 18 | 31 | 7.1 ± 11.0 | 34 | 3.8 ± 8.0 | 0.51 | 17 | 7.2 ± 11.2 | 17 | 3.5 ± 8.1 | 0.27 |
| 19 | 30 | 6.4 ± 10.5 | 33 | 5.0 ± 9.2 | 0.85 | 17 | 7.2 ± 11.2 | 16 | 3.1 ± 7.1 | 0.33 |
| 20 | 30 | 6.4 ± 10.5 | 33 | 5.1 ± 9.9 | 0.21 | 17 | 7.1 ± 10.9 | 16 | 3.1 ± 8.2 | 0.022 |
| 21 | 30 | 6.4 ± 10.3 | 33 | 4.4 ± 9.4 | 0.29 | 17 | 7.0 ± 10.5 | 15 | 1.6 ± 6.2 | 0.015 |
| 22 | 30 | 6.6 ± 10.7 | 33 | 4.2 ± 8.9 | 0.29 | 17 | 7.3 ± 11.1 | 15 | 1.6 ± 6.2 | 0.037 |
| 23 | 30 | 6.8 ± 10.6 | 33 | 3.7 ± 8.6 | 0.28 | 17 | 7.8 ± 11.0 | 15 | 1.7 ± 6.2 | 0.050 |
| 24 | 29 | 6.9 ± 10.9 | 32 | 3.4 ± 8.0 | 0.32 | 17 | 7.2 ± 11.2 | 15 | 2.0 ± 6.2 | 0.10 |

FOR ECV, ABLATION, TREATMENT WITH CLASS 3 ANTIARRHYTHMIC DRUGS (AMIODARONE, DOFETILIDE, SOTALOL)

Additional AF Burden Data is provided in the Appendix.

An adverse event (AE) profile of bucindolol was generated. The AE profile for bucindolol is similar to metoprolol with the notable exception of bradycardia, which was significantly lower in the bucindolol group. Hospitalization rates were similar in the both groups, especially for hospitalizations related to cardiovascular and heart failure events. Mortality rates were similar as well, with 3 deaths in each group. However, all 3 deaths in the metoprolol group occurred during the first 12 weeks of the study; whereas, all 3 deaths in the bucindolol group occurred after more than a year of treatment.

AEs, Hospitalization, Stroke or Death

| Endpoint | Metoprolol (N = 133) | Bucindolol (N = 134) |
|---|---|---|
| AEs leading to permanent study drug discontinuation | 8.3% | 8.2% |
| AEs leading to study withdrawal (excluding death) | 1.5% | 1.5% |
| AEs: Bradycardia | 12.0% | 3.7% |
| AEs: Stroke (99% on OACs) | 0.0% | 0.0% |
| SAEs: Any cardiovascular event | 9.8% | 9.0% |
| All-cause hospitalization | 15.0% | 20.1% |
| Cardiovascular hospitalization | 10.5% | 12.7% |
| Heart failure hospitalization | 7.5% | 6.7% |
| All-cause mortality | 2.3% | 2.3% |
| Cardiovascular mortality | 1.5% | 0.7% |
| Heart failure mortality | 0.7% | 0.0% |

Conclusions

Pharmacogenetic guided bucindolol did not reduce AF/AFL/ACM recurrence compared to the active comparator metoprolol in the overall population. Trends for bucindolol benefit were observed in several large subpopulations, but bucindolol appears to have a similar safety profile compared to metoprolol. From these Phase 2 results, one can further investigate in a redefined population the following: HFrEF (LVEF <0.40); HFmrEF (LVEF ≥0.40 and <0.50) if DTRI >−30 days; symptomatic paroxysmal/persistent AF ≤180 days of randomization; and/or $\beta_1$389Arg/Arg genotype.

In one embodiment, a prescribing algorithm relating to AF and the timing of HF is utilized. An example of a prescribing algorithm is as follows:

In LVEFs ≥0.39 (or rounded to ≥0.40), bucindolol only used for patients who have AF presenting no more than 29 days prior to HF presentation (DTRI >−30 days). For LVEF <0.39 (or rounded to <0.40), no DTRI restriction.

DTRI (diagnosis to randomization index)=Time (days) from 1st HF diagnosis to randomization minus time from 1st AF diagnosis to randomization Example 6

GENETIC-AF and Precision Therapeutic Phenotyping: Bucindolol for the Maintenance of Sinus Rhythm in a Genotype-Defined Heart Failure Population Objective: To compare the effectiveness of bucindolol and metoprolol succinate for the maintenance of sinus rhythm in a genetically defined heart failure (HF) population with atrial fibrillation (AF).

Background: Bucindolol is a beta-blocker whose unique pharmacologic properties provide greater benefit in HF patients with reduced ejection fraction (HFrEF) who have the beta1-adrenergic receptor (ADRB1) Arg389Arg genotype.

Methods: 267 HFrEF patients with a left ventricular ejection fraction (LVEF) <0.50, symptomatic AF, and the ADRB1 Arg389Arg genotype were randomized 1:1 to bucindolol or metoprolol and up-titrated to target doses. The primary endpoint of AF/atrial flutter (AFL) or all-cause mortality (ACM) was evaluated by electrocardiogram (ECG) during a 24-week period.

Figure 30:
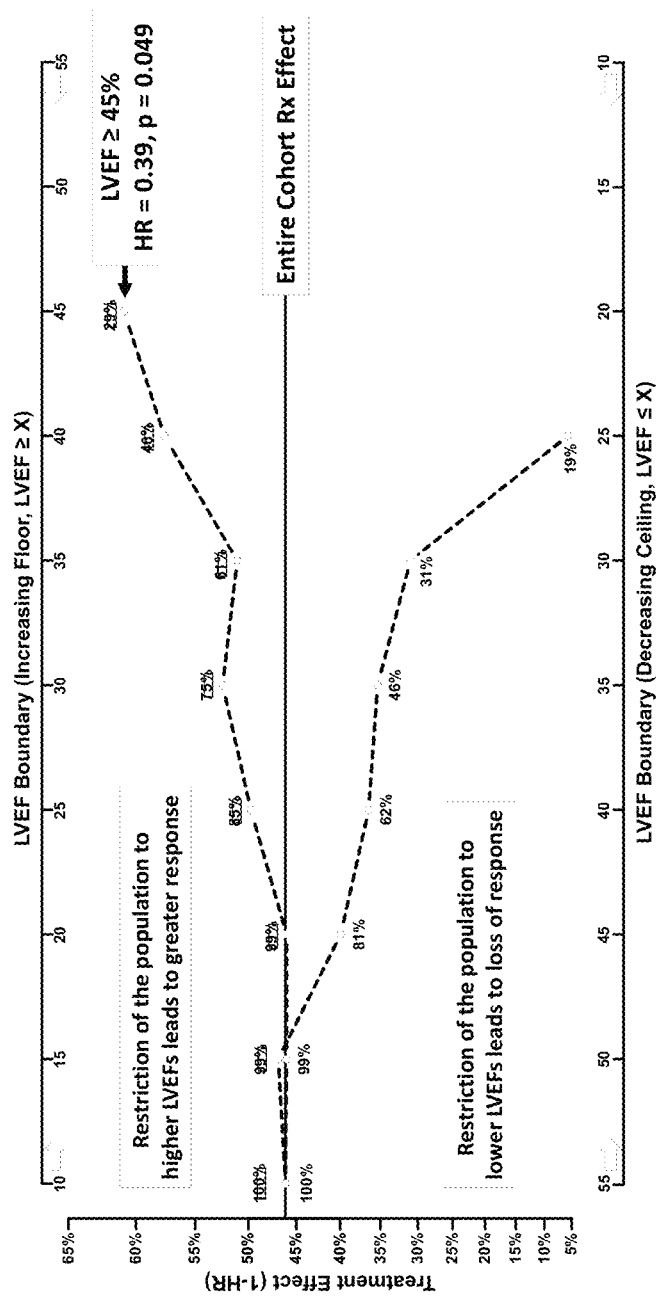
FIG. 30. Relationship between LVEF and treatment effects. X-axis displays DxT12/DTRI-2 population with restrictions on LVEF upper and lower boundary. For example, a LVEF upper boundary of 35% includes all patients with LVEF between the minimum value (12%) and 35%; a LVEF lower boundary of 35% includes all patients with LVEF between the maximum value (53%) and 35%.

Results: The hazard ratio (HR) for the primary endpoint was 1.01 (95% CI: 0.71, 1.42) but trends for bucindolol benefit were observed in several subgroups. Precision therapeutic phenotyping revealed that a differential response to bucindolol was associated with: 1) the interval of time from the initial diagnosis of HF and AF to randomization, and; 2) the onset of AF relative to initial HF diagnosis. In a cohort whose first HF and AF diagnoses were <12 years prior to randomization, in which AF onset did not precede HF by more than 2 years (N=196) the HR was 0.54 (95% CI: 0.33, 0.87; p=0.011). It was also observed that, surprisingly, effectiveness of bucindolol was higher in patient groups having higher LVEF, with the highest effectiveness in the group having LVEF between 0.45 and 0.50. FIG. 30 shows a graph demonstrating the relationship between LVEF and treatment effects and supports the use of bucindolol treatment in patients with a relatively high LVEF.

Conclusion: Pharmacogenetic-guided bucindolol therapy did not reduce the recurrence of AF/AFL/ACM compared to metoprolol in HFrEF patients, but populations were identified that merit further investigation in future Phase 3 trials.

List of Abbreviations: ADRB1=beta1-adrenergic receptor gene; AF=atrial fibrillation AFL=atrial flutter; Arg=arginine; DTRI=diagnosis to randomization index; DxT=Time for initial diagnosis to randomization; HF=heart failure; HFlrEF=HF with lower-range ejection fraction (LVEF <0.40); HFmrEF=HF with mid-range ejection fraction (0.40≤LVEF<0.50); HFrEF=HF with reduced ejection fraction (LVEF <0.50); ICM=insertable cardiac monitor A. Methods 1. Study Design GENETIC-AF was a multicenter, randomized, double-blind, comparative efficacy trial in a genotype-defined population with HFrEF, defined as a left ventricular ejection fraction (LVEF)<0.50 and AF. The trial had an adaptive design allowing for seamless transition from Phase 2B to Phase 3 based on review of interim data. The rationale and design of the trial have been previously reported (31).

Patients were randomly assigned to receive bucindolol or metoprolol and were up-titrated to target doses (Table 45).

TABLE 45

Study Drug Titration Schedule

| Previous Commercial Beta-blocker Dose[1] | | | | | | | | | | | | Randomized Beta-blocker Dose | |
|---|---|---|---|---|---|---|---|---|---|---|---|---|---|
| Metoprolol XL/CR (mg QD) | | Metoprolol IR (mg BID) | | Carvedilol CR (mg QD) | | Carvedilol IR (mg BID) | | Bisoprolol (mg QD) | | Nebivolol (mg QD) | | Metoprolol XL (mg QD) | Bucindolol (mg BID) |
| > | ≤ | > | ≤ | > | ≤ | > | ≤ | > | ≤ | > | ≤ | = | = |
| — | 50 | — | 25 | — | 20 | — | 6.25 | — | 2.5 | — | 1.25 | 25 | 6.25 |
| 50 | 100 | 25 | 50 | 20 | 40 | 6.25 | 12.5 | 2.5 | 5 | 1.25 | 2.5 | 50 | 12.5 |
| 100 | 200 | 50 | 100 | 40 | 80 | 12.5 | 25 | 5 | 10 | 2.5 | 5 | 100 | 25 |
| 200[3] | — | 100[3] | — | 80[3] | — | 25[3] | — | 10[3] | — | 5 | 10[3] | 200 | 50 |
| — | — | — | — | — | — | — | — | — | — | — | — | 200 | 100[2] |
| Transition to Starting Dose of Study Drug ➔➔➔ | | | | | | | | | | | | Up-titration ↓ | |

[1]Transition from β-blockers other than those above requires approval from the Sponsor or its designee prior to randomization.
[2]Patients who weigh <75 kg at randomization will receive a maximum bucindolol dose of 50 mg BID.
[3]Patients receiving commercial β-blocker doses higher than those currently approved will require pre-approval from the Sponsor or its designee prior to randomization.

Figure 2:
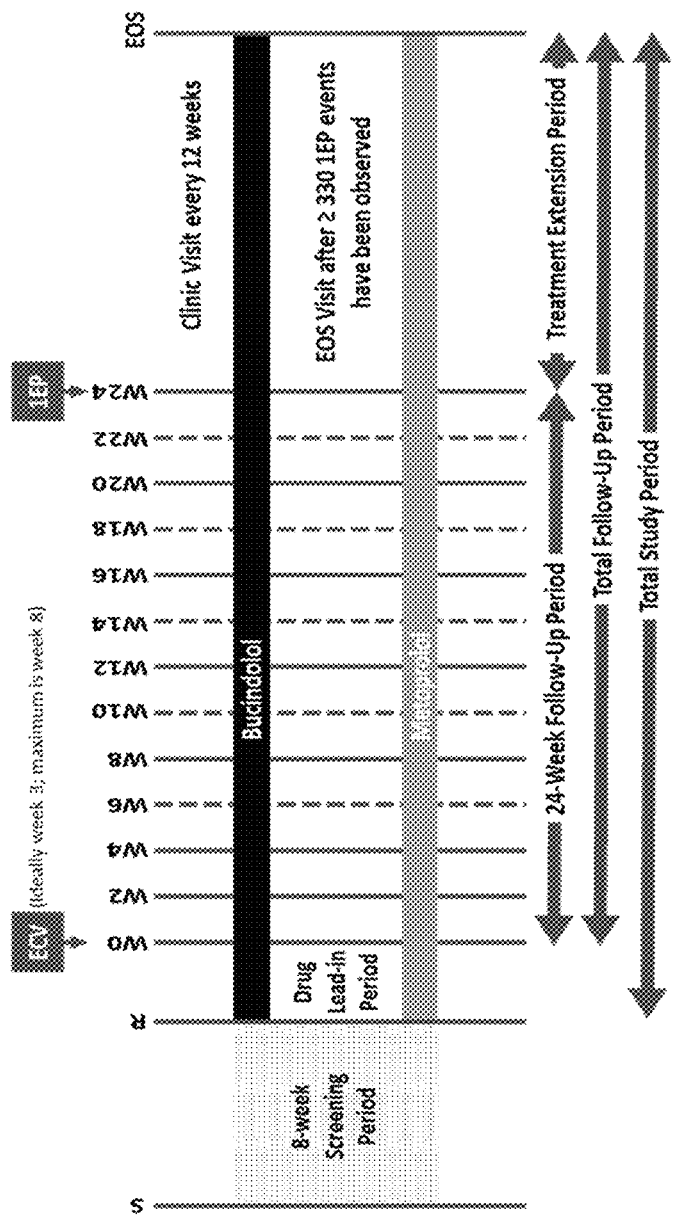
FIG. 2. Schedule of major operational events in GENETIC-AF.

Following up-titration, electrical cardioversion (ECV) was performed if needed to establish sinus rhythm prior to the start of follow-up. During the 24-week follow-up period, heart rhythm was monitored by 12 lead electrocardiogram (ECG) every 4 weeks (FIG. 2). A prospectively defined device substudy permitted continuous heart rhythm monitoring to assess AF burden. Substudy participants had a pre-existing Medtronic pacemaker or defibrillator with an atrial lead or were implanted with a Medtronic Reveal LINQ insertable cardiac monitor (ICM) prior to the start of follow-up. After week 24, patients continued to receive blinded study drug and had clinic visits every 12 weeks for assessments of efficacy and safety.

Patients had HFrEF with a LVEF <0.50 assessed in the past 12 months, symptomatic paroxysmal or persistent AF in the past 180 days and were receiving optimal anticoagulation therapy for stroke prevention. Patients were genotyped at screening and those who were ADRB1 Arg389Arg were eligible for randomization.

Exclusion criteria included New York Heart Association (NYHA) Class IV symptoms, clinically significant fluid overload, permanent AF (ongoing AF event >1 year), antiarrhythmic therapies in past 7 days, prior atrioventricular node ablation, high-grade atrioventricular block, catheter ablation for AF or atrial flutter (AFL) in past 30 days, and prior intolerance or contraindication to beta-blocker therapy. Details of the trial entry criteria have been previously reported (31).

The active comparator, metoprolol succinate (Toprol-XL), is a selective beta1-adrenergic receptor blocker indicated for the treatment of HF. Metoprolol was selected as the active comparator to ensure continuity with previous HF trials and because it has demonstrated effectiveness in preventing AF in HFrEF patients (12,93), but does not appear to confer enhanced benefits in patients with an ADRB1 Arg389Arg genotype (26,25).

Patients were randomized (1:1) to treatment with bucindolol or metoprolol, which was over-encapsulated to maintain blinding. Since bucindolol is administered twice-daily (bid), and metoprolol is given once-daily (qd), a placebo dose was included for the metoprolol arm and all study drugs were administered twice-daily. Randomization was centralized and stratified by HF etiology (ischemic, non-ischemic), LVEF (<0.35, ≥0.35), device type (ICM, pacemaker/defibrillator, no device), and rhythm at randomization (sinus rhythm, AF/AFL), using 16,000 randomly generated numbers and a block size of four. Study drug was titrated weekly to obtain a target dose of 100 mg bid (50 mg bid if <75 kg) for bucindolol (16) and 200 mg qd for metoprolol (15). For more details see Table 45. Patients experiencing AF/AFL during follow-up remained on blinded study drug and could undergo ECV, ablation, or initiate therapy with amiodarone or dofetilide.

ADRB1 Arg389Gly genotype was determined by RT-PCR in DNA extracted from whole blood. Systemic venous plasma norepinephrine was assayed by high-pressure liquid chromatography with electrochemical detection and venous plasma NT-proBNP was measured by electrochemiluminescence immunoassay.

Study design, conduct, and performance were overseen by a 11-member Steering Committee and was monitored by a 3-member Data and Safety Monitoring Committee (DSMB) who also performed the interim efficacy analysis. The protocol was approved by the Institutional Review Board/Ethics Committee and all patients provided written informed consent.

2. Statistical Analyses

For the interim analysis, the endpoint of interest was time to first event of AF/AFL or all-cause mortality (ACM) during a 24-week follow-up period. The primary endpoint for the planned Phase 3 study was time to symptomatic AF/AFL or ACM, with symptoms captured by a study-specific questionnaire. A clinical events committee, blinded to treatment assignment, adjudicated the first occurrence of the AF/AFL endpoint, including the association of new or worsening symptoms. Sample size for Phase 3 assumed a 60% event rate in the metoprolol arm, a 25% relative risk reduction with bucindolol, and accrual of 330 primary events in approximately 620 patients for 90% power at alpha=0.01.

The efficacy analysis was conducted according to intention-to-treat with censoring at 24 weeks for patients not experiencing an event. Hazard ratio (HR) and 95% confidence interval (CI) values were determined by Cox proportional hazards models with adjustment for the four randomization strata, and treatment as a covariate. Testing for superiority was performed using a 2-sided significance level of 0.05. Patients who died prior to start of follow-up and patients who failed to establish sinus rhythm post-ECV were assigned an event on day 1. Patients were censored on day 1 if they were in AF/AFL and the ECV procedure was not performed, or if they withdrew from the study prior to start of follow-up.

Variables identified in the GENETIC-AF Statistical Analysis Plan (SAP) that were potential predictors of the primary endpoint were investigated by precision therapeutic phenotyping. Hypothesis-based (e.g., AF duration, AF type, LVEF, NYHA Class, NT-proBNP, norepinephrine) and hypothesis-free (e.g. HF duration, initial study dose) elements were included in the multivariate methodology, which was applied to both obvious and non-obvious data to identify a therapeutic phenotype appropriate for investigating in Phase 3. To examine the relationship between HF duration and bucindolol effectiveness for reducing HF events, we analyzed data from the BEST trial (14) and pharmacogenetic substudy (17) for the endpoint of time to all-cause mortality or first HF hospitalization (ACM/HFH).

Time to first event of AF/AFL or ACM was assessed in the device substudy following similar methodology for the primary endpoint, with an AF/AFL event prospectively-defined as AF burden ≥6 hours per day as recorded by continuous monitoring. Six hours of AF burden has previously been shown to be associated with an increased rate of hospitalization for HF (18). Due to the smaller sample size in the substudy, treatment effect estimates were determined based on Cox proportional hazards models with no adjustment for randomization strata.

Normally distributed continuous variables were analyzed by t-tests or ANOVA where appropriate. Neurohormonal changes from baseline and DTRI data were analyzed by the Wilcoxon signed rank test, and between group differences by the Wilcoxon rank sum test. Categorical variable differences were assessed by Chi square or Fisher's exact test.

An interim analysis examined data from the initial Phase 2B population. If the DSMB determined that the data were consistent with pre-trial assumptions, the trial was to seamlessly proceed to Phase 3 (see SAP). To aid in signal detection, Bayesian predictive probability of success estimates (94,95) were generated and compared to prespecified thresholds for each potential outcome (i.e., Phase 3 transition, Phase 2B completion, or futility). Based on the interim analysis the DSMB recommended completion of Phase 2B, and the data from this population are presented below.

B. Results

1. Population and Baseline Characteristics

Figure 20:
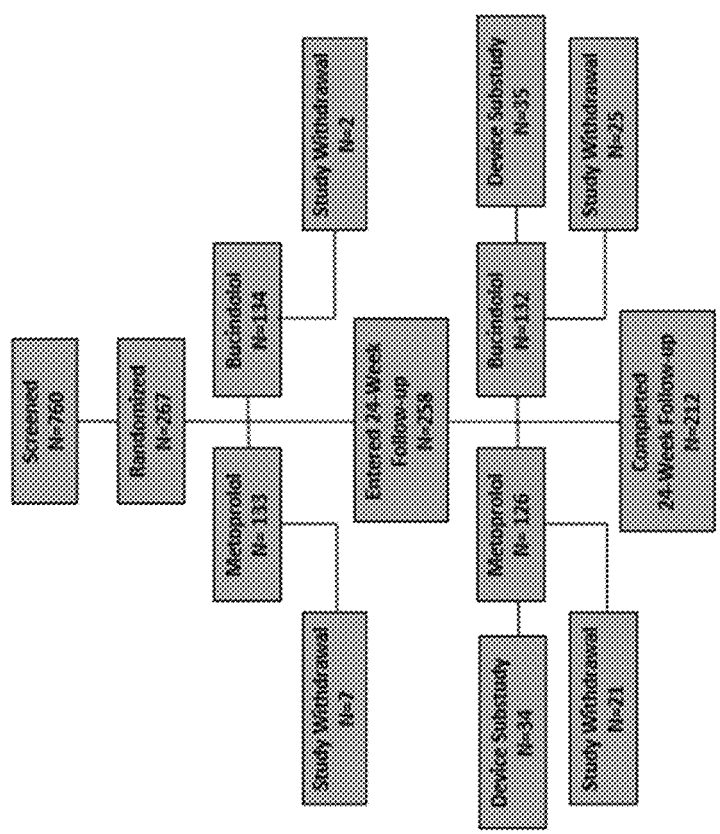
FIG. 20. Consort Diagram

The trial was conducted in 92 centers in 6 countries (Canada, Hungary, The Netherlands, Poland, Serbia, and the United States) between April 2014 and December 2017. A total of 760 patients were screened (FIG. 20); 362 (48%) failed screening due to genotype, 73 (9.6%) did not meet other eligibility criteria, and 58 (7.6%) failed due to other reasons (e.g., withdrawal of consent, lost to follow-up). The remaining 267 patients were randomized to study drug and up-titrated to target doses. Compliance was >90% in both groups, with a higher proportion of patients attaining target dose for bucindolol compared to metoprolol (84% and 72%, respectively; p=0.035).

Baseline characteristics were well-balanced between treatment groups (Table 42). Mean LVEF was 0.36±0.10, 72% had NYHA II or III symptoms at baseline, 51% had persistent AF, and plasma NT-proBNP were elevated at baseline (median=801 pg/ml; inter quartile range (IQR): 384, 1420). ECV was required in 46% of patients to establish sinus rhythm prior to follow-up start. About half (48%) of all patients had implanted monitoring devices, which included ICMs inserted for the trial (16%) and pre-existing pacemakers or defibrillators (32%).

Figure 21:
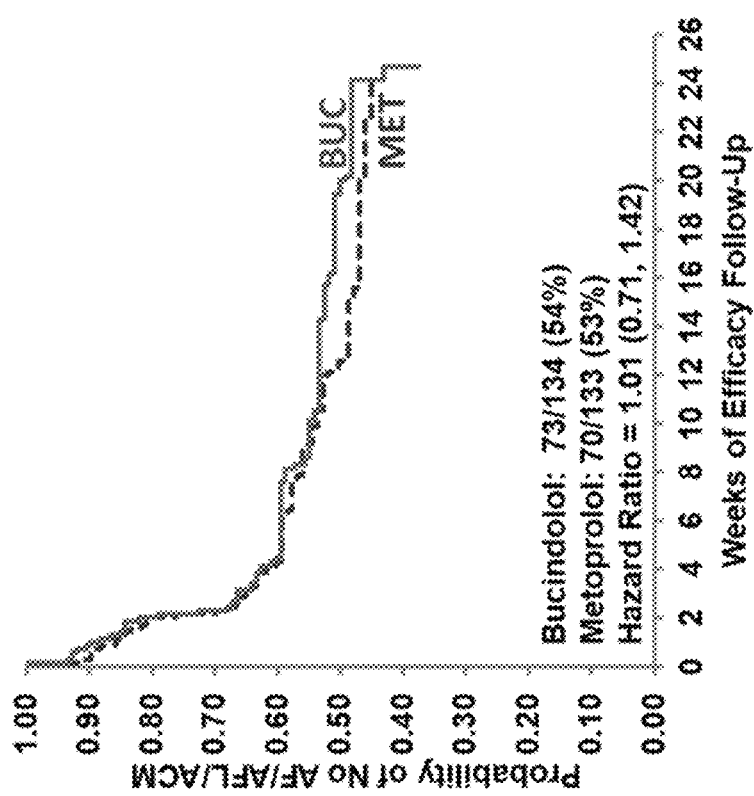
FIG. 21. Time to First AF/AFL/ACM Event. Cox proportional hazards model adjusted for the four randomization strata. Non-stratified analysis: Hazard Ratio=0.96 (95% CI: 0.69, 1.33). Stratified analysis including adjustment for previous use of class III anti-arrhythmic drugs (yes/no): HR=0.92 (95% CI: 0.63, 1.33).

121; 94%). Event rates were similar for the bucindolol and metoprolol groups (54% and 53%, respectively), with a HR of 1.01 (95% CI: 0.71, 1.42) for the covariate-adjusted Cox proportional hazards model (FIG. 21). In a prespecified analysis (Statistical Analysis Plan and Phase 2B Amend-

TABLE 42

Baseline Characteristics

| | Entire Study | | | Device Substudy | | |
|---|---|---|---|---|---|---|
| Parameter | All Patients N = 267 | Bucindolol N = 134 | Metoprolol N = 133 | All Patients N = 69 | Bucindolol N = 35 | Metoprolol N = 34 |
| Age, years | 65.6 ± 10.1 | 65.8 ± 10.3 | 65.5 ± 10.0 | 66.1 ± 10.7 | 65.5 ± 11.5 | 66.8 ± 9.9 |
| Male/Female, % | 82/18 | 83/17 | 81/19 | 93/7 | 94/6 | 91/9 |
| Race: W/B/A/O, % | 96/2/1/1 | 96/1/1/2 | 96/2/1/1 | 96/1/1/2 | 94/0/3/3 | 97/3/0/0 |
| LVEF | 0.36 ± 0.10 | 0.36 ± 0.10 | 0.36 ± 0.10 | 0.34 ± 0.08 | 0.33 ± 0.08 | 0.36 ± 0.09 |
| NYHA I/II/III, % | 28/57/15 | 30/60/10 | 26/54/20 | 23/57/20 | 29/49/23 | 18/65/18 |
| Ischemic/Non-Ischemic HF, % | 32/68 | 31/69 | 33/67 | 28/72 | 29/71 | 26/74 |
| Randomized in AF/Not in AF, % | 51/49 | 49/51 | 52/48 | 65/35 | 63/37 | 68/32 |
| Persistent/Paroxysmal AF, % | 51/49 | 51/49 | 51/49 | 64/36 | 63/37 | 65/35 |
| HF DxT Duration, days | 1153 ± 1909 | 1252 ± 2070 | 1054 ± 1733 | 1168 ± 1723 | 1208 ± 1880 | 1126 ± 1572 |
| AF DxT Duration, days | 1306 ± 2240 | 1431 ± 2271 | 1180 ± 2209 | 1355 ± 1984 | 1444 ± 1997 | 1263 ± 1995 |
| Systolic blood pressure, mm Hg | 123.3 ± 15.3 | 124.7 ± 14.9 | 121.8 ± 15.7 | 123.3 ± 15.1 | 122.4 ± 15.7 | 124.2 ± 14.5 |
| Diastolic blood pressure, mmHg | 75.3 ± 10.8 | 75.8 ± 11.0 | 74.8 ± 10.6 | 75.0 ± 10.1 | 73.7 ± 9.9 | 76.3 ± 10.3 |
| Heart Rate, bpm | 76.3 ± 17.8 | 76.5 ± 17.9 | 76.0 ± 17.7 | 78.4 ± 17.2 | 76.8 ± 16.4 | 80.1 ± 18.1 |
| Previous ECV/AF Ablation/Type III AAD, % | 49/21/48 | 49/21/50 | 50/20/46 | 55/13/54 | 57/17/57 | 53/9/50 |
| Device Type: ICM/PM/ICD, % | 16/17/15 | 17/15/18 | 15/20/12 | 62/22/16 | 66/20/14 | 59/24/18 |
| Norepinephrine, pg/ml | 673 ± 353 | 682 ± 348 | 664 ± 359 | 706 ± 368 | 710 ± 398 | 702 ± 339 |
| NT-proBNP, pg/ml, median (IQR) | 801 (384, 1420) | 777 (355, 1326) | 861 (420, 1607) | 996 (457, 1645) | 923 (365, 1506) | 1013 (537, 1806) |

W/B/A/O = White/Black/Asian/Other.
HF DxT Duration = time from HF diagnosis to randomization.
AF DxT Duration = time from AF diagnosis to randomization.
ECV = electrical cardioversion.
AAD = antiarrhythmic drug.
ICM = insertable cardiac monitor.
ICD = implanted cardiac defibrillator.
PM = pacemaker.
IQR = interquartile range.
Note:
mean ± standard deviations are presented unless otherwise specified.

2. Efficacy Outcomes

A total of 143 events were observed for the efficacy endpoint, including 121 AF/AFL events, 19 ECV failures, and 3 deaths. Nearly all AF/AFL events were adjudicated as symptomatic by a blinded clinical events committee (114/ ment) of regional subgroups (Table 43, FIG. 26), a trend for bucindolol benefit compared to metoprolol was observed in the U.S. subgroup (HR=0.70; 95% CI: 0.41, 1.19), which was not seen in Canada (HR=1.52; 95% CI: 0.68, 3.43) or in Europe (HR=1.01; 95% CI: 0.48, 0.48, 2.14).

TABLE 43

Treatment Emergent Adverse Events

| | | | | | | | | Time to AF/AFL/ACM | |
|---|---|---|---|---|---|---|---|---|---|
| | HF DxT (years) | | AF DxT (years) | | DTRI (years) | | | Stratified | |
| Cohort | Mean | Median | Mean | Median | Mean | Median | P value* | HR (95% CI) | Non-stratified HR (95% CI) |
| U.S. (N = 127) | 4.5 | 1.5 | 3.4 | 1.0 | 1.1 | 0.0 | — | 0.70 (0.41, 1.19) | 0.77 (0.48, 1.22) |

TABLE 43-continued

Treatment Emergent Adverse Events

| Cohort | HF DxT (years) | | AF DxT (years) | | DTRI (years) | | P value* | Time to AF/AFL/ACM | |
| --- | --- | --- | --- | --- | --- | --- | --- | --- | --- |
| | Mean | Median | Mean | Median | Mean | Median | | Stratified HR (95% CI) | Non-stratified HR (95% CI) |
| Non-U.S. (N = 140) | 2.0 | 0.4 | 3.8 | 0.9 | −1.8 | 0.0 | 0.0005 | 1.34 (0.79, 2.28) | 1.22 (0.76, 1.96) |
| Canada (N = 59) | 2.5 | 0.5 | 3.4 | 0.6 | −0.9 | 0.0 | 0.024 | 1.52 (0.68, 3.43) | 1.42 (0.72, 2.79) |
| Europe (N = 81) | 1.6 | 0.4 | 4.0 | 1.7 | −2.4 | 0.0 | 0.0009 | 1.01 (0.48, 2.14) | 1.06 (0.55, 2.07) |
| Hungary (N = 33) | 1.5 | 0.3 | 7.5 | 4.1 | −5.9 | −2.8 | <0.0001 | 2.90 (0.71, 11.8) | 3.57 (0.99, 12.9) |
| Poland (N = 23) | 1.6 | 0.9 | 1.4 | 0.7 | 0.3 | 0.0 | 0.590 | 0.25 (0.03, 2.22) | 0.28 (0.07, 1.14) |
| Serbia (N = 21) | 0.4 | 0.3 | 0.9 | 0.4 | −0.5 | 0.0 | 0.175 | 0.42 (0.08, 2.18) | 0.59 (0.15, 2.36) |
| Netherlands (N = 4) | 8.0 | 7.1 | 6.4 | 3.8 | 1.6 | −0.1 | ND | ND | ND |

AF DxT = time from AF diagnosis to randomization.
HF DxT = time from HF diagnosis to randomization.
DTRI = diagnosis to randomization index;
DTRI = HF DxT − AF DxT.
*Wilcoxon rank sum test for comparison to U.S. Cohort.

3. Device Substudy

The device substudy included 69 patients from the U.S. (N=42), Canada (N=21), and Europe (n=6) who underwent continuous atrial rhythm monitoring. Cardiac monitors were inserted in 43 patients for the trial, whereas, 26 patients had pre-existing pacemakers or implantable cardioverter defibrillators (ICDs). The baseline characteristics of the substudy were well-balanced between the two groups and were generally similar to the overall population (Table 42); however, the substudy had a higher proportion of males (93% vs. 82%), persistent AF (64% vs. 51%), and AF at the time of randomization (65% vs. 51%), compared to the overall population.

Figures 22A, 22B:
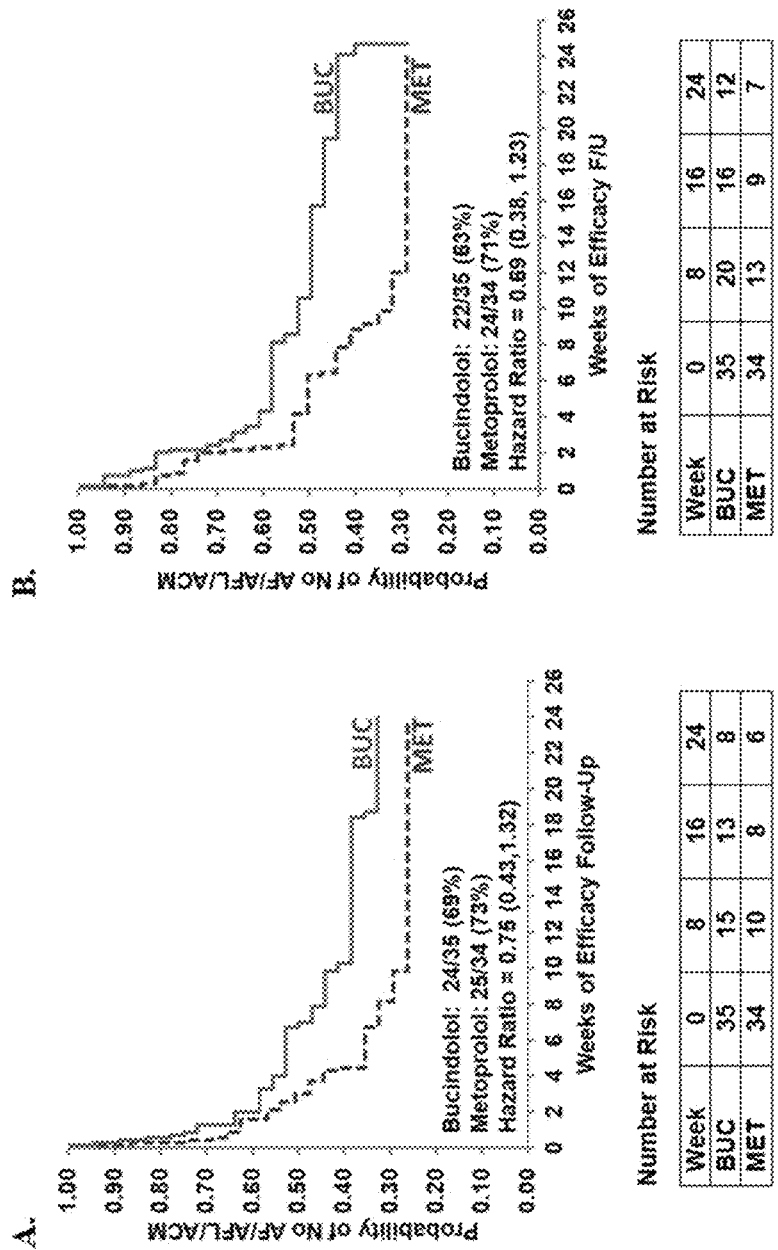
FIG. 22A-22B. Time to First Event of AF/AFL/ACM in the Device Substudy. 22A., Device-based detection. 22B., ECG-based detection. For device-based detection an AF/AFL event was defined as AF burden ≥6 hours per day. Non-stratified Cox proportional hazards model.

An analysis of time to first event of AF/AFL or ACM was conducted in the device substudy following similar methodology for the primary endpoint. As shown in FIG. 22, a trend for bucindolol benefit compared to metoprolol was observed by device-based detection (HR=0.75; 95% CI: 0.43, 1.32). Similar results were observed when the substudy population was assessed by intermittent, clinic-based 12-lead ECGs (HR=0.69; 95% CI: 0.38, 1.23); however, the device-detected endpoint generally occurred earlier than the ECG-based endpoint (median=6.5 days; p<0.0001). For detection of subsequent ECG-determined AF, AF burden ≥6 hours had a sensitivity of 100%, a specificity of 87% and an accuracy of 96%.

4. Patient Characteristics and Treatment Response by Region

The differences in treatment response observed in the U.S. and non-U.S. cohorts prompted examination of baseline characteristics by region (Table 46). In general, the non-U.S. cohort had less severe HF compared to the U.S. cohort, as demonstrated by significantly higher LVEF (0.39 vs. 0.33), systolic blood pressure (126 v. 120 mmHg), and NYHA class I symptoms (39% vs. 17%), as well as significantly lower plasma NT-proBNP (1135 vs. 1380 pg/mL) and NYHA class III symptoms (5% vs. 26%). Notably, patients in the non-U.S. cohort had a more recent diagnosis of HF (Table 43), with a mean time from HF diagnosis to randomization that was less than half of that in the U.S. group (2.0 vs. 4.5 years); whereas, mean time from AF diagnosis to randomization was similar between the two groups (3.8 vs. 3.4 years).

TABLE 46

Baseline Characteristics by Region

| Parameter | U.S. Cohort N = 127 | Non-U.S. Cohort N = 140 | P-value |
| --- | --- | --- | --- |
| Age, years | 66.3 ± 10.7 | 65.1 ± 9.5 | 0.516 |
| Male/Female, % | 87/13 | 78/22 | 0.079 |
| Race: W/B/A/O, % | 93/4/1/2 | 99/0/1/0 | 0.017 |
| LVEF | 0.33 ± 0.09 | 0.39 ± 0.09 | <0.001 |
| NYHA I/II/III, % | 17/57/26 | 39/56/5 | <0.001 |
| Ischemic/Non-Ischemic HF, % | 31/69 | 33/67 | 0.896 |
| Randomized in AF/Not in AF, % | 59/41 | 43/57 | 0.010 |
| Persistent/Paroxysmal AF, % | 52/48 | 50/50 | 0.807 |
| AF DxT Duration, days | 1236 ± 2192 | 1370 ± 2288 | 0.517 |
| HF DxT Duration, days | 1627 ± 2306 | 724 ± 1326 | <0.001 |
| Systolic blood pressure, mmHg | 119.9 ± 15.7 | 126.3 ± 14.4 | 0.001 |
| Diastolic blood pressure, mmHg | 73.8 ± 11.3 | 76.6 ± 10.2 | 0.024 |
| Heart Rate, bpm | 78.4 ± 19.4 | 74.4 ± 16.0 | 0.118 |
| Previous ECV, % | 55 | 44 | 0.041 |
| Previous AF Ablation, % | 17 | 24 | 0.373 |
| Previous Type III A AD use, % | 47 | 49 | 0.902 |
| Device Type: ICM/PM/ICD, % | 19/15/21 | 14/20/9 | 0.002 |
| Norepinephrine, pg/ml | 657 ± 373 | 687 ± 335 | 0.389 |

TABLE 46-continued

Baseline Characteristics by Region

| Parameter | U.S. Cohort N = 127 | Non-U.S. Cohort N = 140 | P-value |
|---|---|---|---|
| NT-proBNP, pg/ml, median (IQR) | 953 (488, 1506) | 678 (143, 1252) | 0.045 |

W/B/A/O = White/Black/Asian/Other.
AF DxT = time from AF diagnosis to randomization.
HF DxT = time from HF diagnosis to randomization.
ECV = electrical cardioversion.
AADs = antiarrhythmic drugs.
ICM = insertable cardiac monitor.
ICD = implanted cardiac defibrillator.
PM = pacemaker.
IQR = interquartile range.
Note:
mean ± standard deviations are presented unless otherwise specified.
Wilcoxon Rank Sum Test for continuous values and Fishers Exact Test for categorical values.

To quantify the relationship between the initial development of HF and AF, an index termed the diagnosis to randomization index (DTRI) was derived from information provided in case report forms. This index represents the differences between the HF duration (i.e., the time of HF diagnosis to randomization) and the AF duration (i.e., the time of AF diagnosis to randomization), with positive values representing HF onset prior to AF and negative values representing AF onset prior to HF. As shown in Table 43, the U.S. and non-U.S. cohorts had significant differences in the relative timing of HF and AF onset as measured by mean DTRI (p<0.0005). The U.S. cohort, on average, had HF for more than a year prior to developing AF; whereas, the non-U.S. cohort had a diagnosis of AF for nearly 2 years prior to developing HF. Interestingly, bucindolol response for the primary endpoint correlated with mean DTRI (0=0.93, p=0.020), with poor response seen in populations having long-standing AF prior to the development of HF (i.e., Hungary and Canada) and good response in populations with concurrent or previous onset of HF prior to the development of AF (i.e., U.S., Poland, and Serbia).

5. Baseline Characteristics Predicting Endpoint Frequency and/or Interaction with Treatment Cox proportional hazards regression modeling was performed to explore prespecified variables (SAP) that were potential predictors of the primary endpoint (Table 47). Three variables violated the Cox model proportionality of hazards assumption. Of these, atrial rhythm at randomization was previously addressed by randomization stratification, as was heart rate, which generally correlates with atrial rhythm. The third variable, prior treatment with class III anti-arrhythmic drugs, was not previously identified and was included as a covariate in all subsequent analyses to account for non-proportional influence on baseline hazard.

TABLE 47

Cox Proportional Hazards Regression Modeling for Time to First AF/AFL/ACM Event

| | Two Predictor Model | | Three Predictor Model | | |
|---|---|---|---|---|---|
| Predictor | Treatment | Predictor | Treatment | Predictor | Treatment x Predictor |
| Rhythm at randomization[†] | 0.83 | <0.001* | 0.66 | <0.001* | 0.51 |
| Baseline heart rate[†] | 0.80 | <0.001* | 0.96 | 0.042* | 0.99 |
| AF type | 0.72 | 0.001* | 0.77 | 0.06 | 0.49 |
| Baseline systolic blood pressure | 0.84 | 0.006* | 0.15 | 0.63 | 0.15 |
| HF DxT | 0.77 | 0.007* | 0.66 | 0.63 | 0.73 |
| Initial study dose | 0.39 | 0.017* | 0.79 | 0.89 | 0.35 |
| Prior ECV count | 0.76 | 0.018* | 0.37 | 0.78 | 0.30 |
| HF etiology | 0.81 | 0.023* | 0.91 | 0.04* | 0.53 |
| Baseline NT-proBNP | 0.91 | 0.040* | 0.48 | 0.75 | 0.28 |
| Baseline NYHA class | 0.99 | 0.043* | 0.59 | 0.91 | 0.57 |
| AF DxT | 0.83 | 0.07 | 0.18 | 0.14 | 0.025** |
| Device strata | 0.72 | 0.11 | 0.98 | 0.77 | 0.77 |
| Prior ECV or ablation | 0.79 | 0.13 | 0.51 | 0.13 | 0.52 |
| Region | 0.82 | 0.09 | 0.87 | 0.16 | 0.33 |
| Baseline diastolic blood pressure | 0.71 | 0.28 | 0.18 | 0.09 | 0.16 |
| Previous use of class III AAR[†] | 0.76 | 0.35 | 0.58 | 0.32 | 0.64 |
| Beta blocker prior to randomization | 0.84 | 0.42 | 0.66 | 0.68 | 0.98 |
| Baseline creatinine | 0.82 | 0.48 | 0.30 | 0.19 | 0.26 |
| Total prior ECV or ablation | 0.74 | 0.52 | 0.75 | 0.64 | 0.93 |
| Prior ablation | 0.78 | 0.62 | 0.83 | 0.14 | 0.19 |
| LVEF | 0.80 | 0.66 | 0.79 | 0.96 | 0.84 |
| LVEF strata | 0.80 | 0.68 | 0.74 | 0.89 | 0.82 |
| CYP2D6 | 0.98 | 0.93 | 0.21 | 0.29 | 0.17 |
| Baseline norepinephrine | 0.73 | 0.99 | 0.63 | 0.73 | 0.72 |

*P < 0.05 for prediction of primary endpoint.
**P < 0.05 for treatment x predictor interaction.
[†]Violation of proportionality of hazards assumption (p < 0.05).
AF DxT = time from initial AF diagnosis to randomization.
HF DxT = time from initial HF diagnosis to randomization.
ECV = electrical cardioversion.
AAR = antiarrhythmic drug.
LVEF = left ventricular ejection fraction.
CYP = cytochrome p450.

On multivariate analysis, ten variables predicted the occurrence of the primary endpoint. In addition to the initial dose of study drug, which was based on beta blocker therapy prior to enrollment, the two-predictor model identified five variables related to the degree or duration of HF (i.e., systolic blood pressure, HF duration, HF etiology, NT-proBNP, and NYHA Class) and four variables related to heart rhythm (i.e., rhythm at randomization, baseline heart rate, AF type, and the number of prior ECVs). The only predictor by treatment interaction variable having a p-value <0.05 was duration of time from initial AF diagnosis to randomization (i.e., AF DxT).

Figure 26:
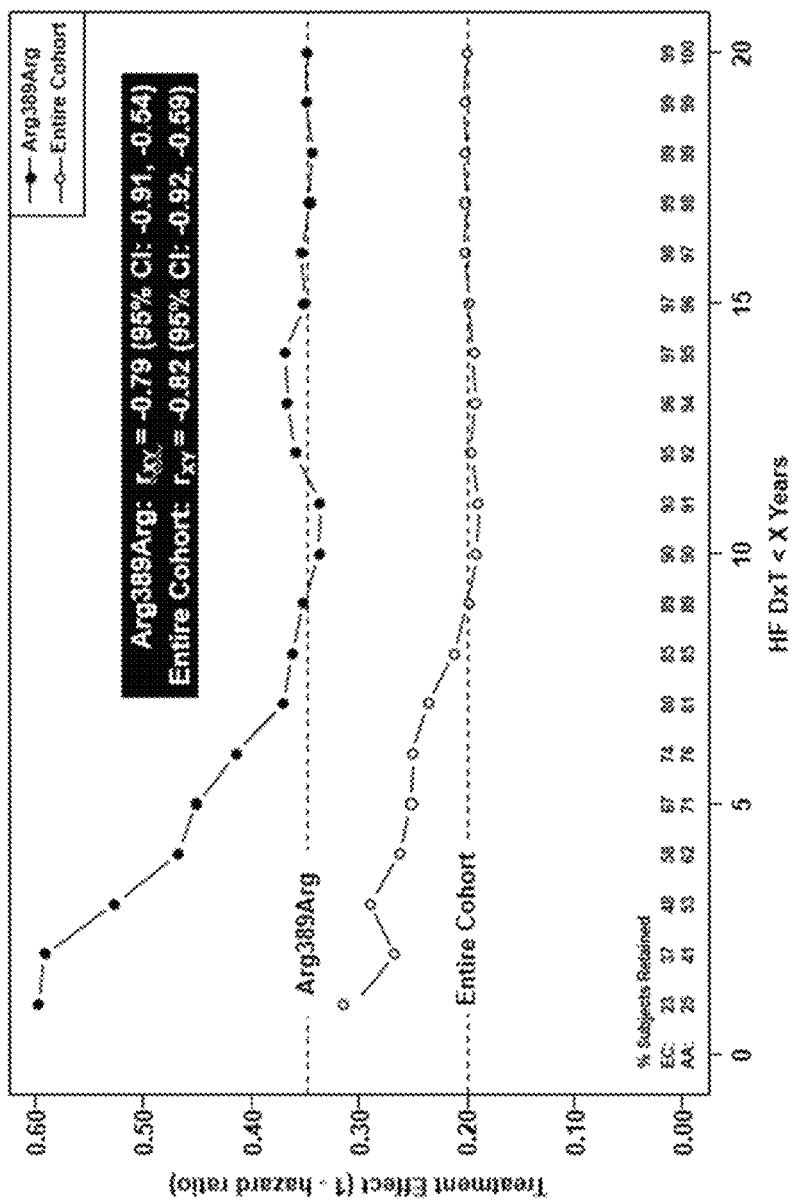
FIG. 26. Treatment Effect and the Duration of HF in the BEST HF Trial. Entire cohort (open circles, n=2708) and ADRB1 Arg389Arg subgroup (closed circles, n=493). Hazard ratio is for time to first heart failure hospitalization or death for bucindolol and placebo. HF DxT=time from initial HF diagnosis to randomization. Rxy=correlation coefficient. Arg389Arg=patients homozygous for ADRB1 Arg389.

The time from initial HF diagnosis to randomization (i.e., HF DxT) was a significant predictor for the occurrence of primary endpoint but did not predict treatment or treatment by predictor interactions in Cox modeling of the primary endpoint (Table 47). However, since AF DxT predicted bucindolol response for the prevention of AF recurrence, we examined data from the placebo-controlled BEST HF trial (14) to determine whether HF DxT had a similar relationship to bucindolol response for the HF endpoint, ACM or first HF hospitalization (HFH). As shown in FIG. 26, an attenuation of treatment response for the BEST ACM/HFH endpoint is observed in cohorts with greater values of HF DxT upper bound (i.e., inclusion of long-standing HF prior to randomization). This strong, negative correlation was observed in both the entire cohort (N=2708; r=−0.82; 95% CI: −0.92, −0.59) and for the ADRB1 Arg389Arg subgroup (N=493; r=0.79; 95% CI: −0.91, −0.54).

6. Effect of Duration and Relative Onset of AF and HF on Treatment Effect

Figures 23A, 23B:
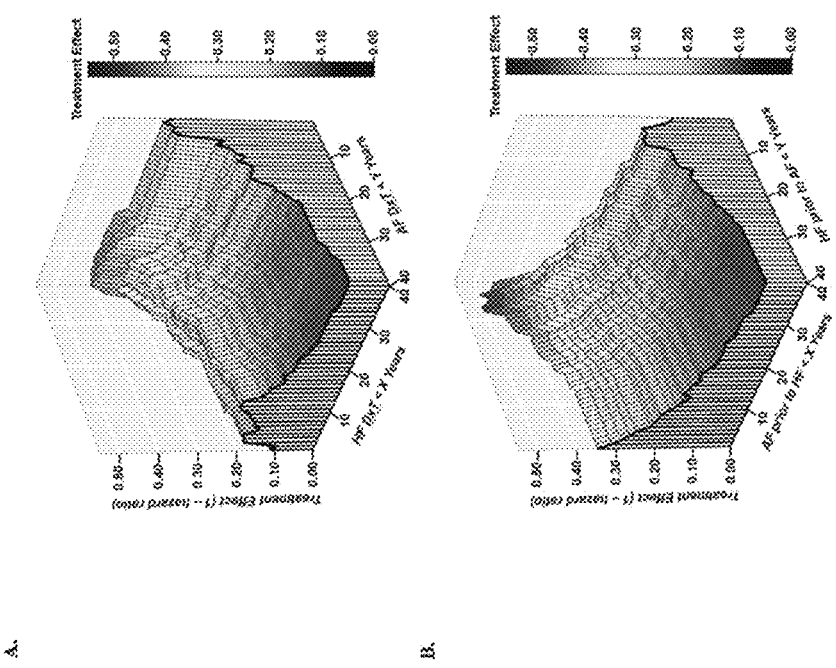
FIG. 23A-23B. Treatment Effect by Duration and Relative Onset of AF and HF prior to Randomization 23A. 3-dimensional plot of HF DxT (x-axis) and AF DxT (y-axis) versus treatment effect (z-axis). 23B. 3-dimensional plot of AF onset prior to HF (x-axis) and HF onset prior to AF (y-axis) versus treatment effect (z-axis). Hazard ratio is for time to AF/AFL/ACM endpoint. AF DxT=time from initial AF diagnosis to randomization. HF DxT=time from initial HF diagnosis to randomization. DTRI (Diagnosis to Randomization Index)=HF DxT−AF DxT. AF onset prior to HF=absolute value of DTRI lower bound. HF onset prior to AF=DTRI upper bound.
Figure 27:
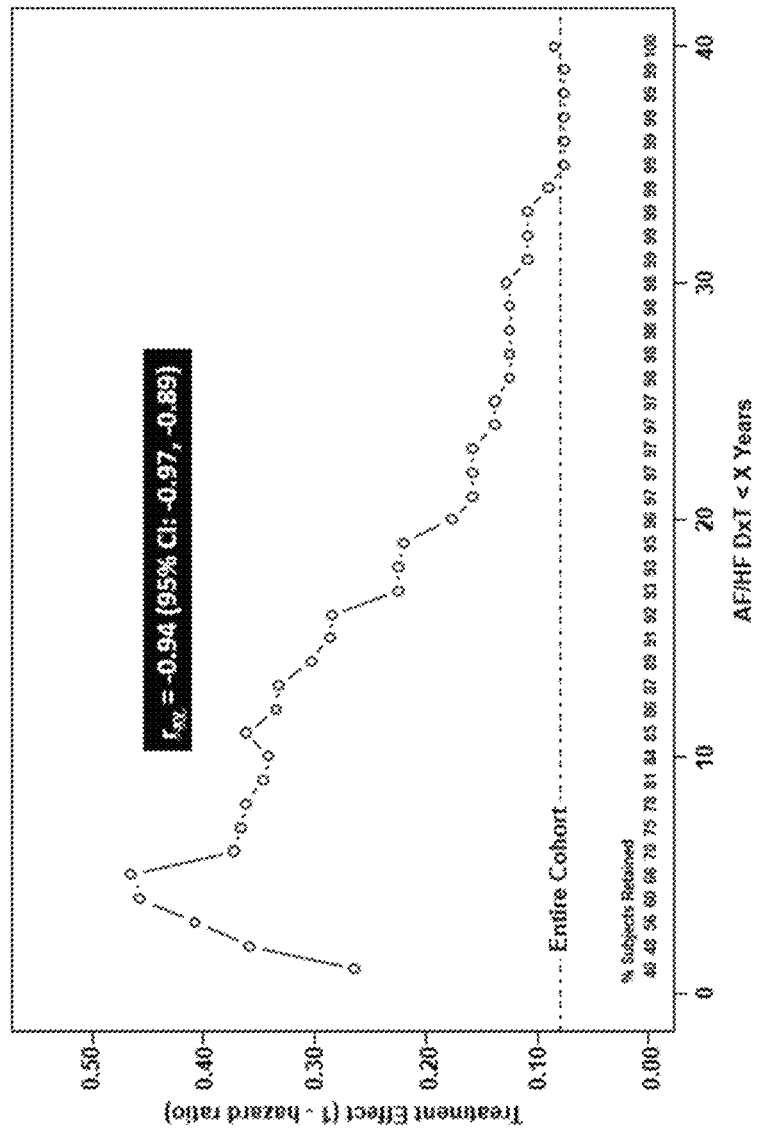
FIG. 27. Treatment Effect by AF and HF Duration. Treatment effect versus AF/HF DxT (i.e., both HF DxT and AF DxT<X years). Hazard ratio is for time to AF/AFL/ACM endpoint. AF/HF DxT=time from initial AF and HF diagnosis to randomization.

To further examine the effects of AF and HF duration identified in the above analyses, a 3 dimensional plot was constructed with treatment effect (i.e., 1-hazard ratio) for the GENETIC-AF primary endpoint as the dependent variable (z-axis), and HF DxT (x-axis) and AF DxT (y-axis) as independent variables. As shown in FIG. 23A, an attenuation of treatment effect was associated with increasing values of both AF and HF DxT. When equivalent DxT values (both HF and AF DxT values had to be <the timepoint duration on the x axis) were used to examine the combined effects of AF and HF duration (FIG. 27), a strong negative correlation was observed (r=−0.94; 95% CI: 0.97, −0.89), with substantial attenuation of treatment effect seen with the inclusion of a small proportion of patients with both AF and HF durations greater than 12-15 years.

Figure 28A:
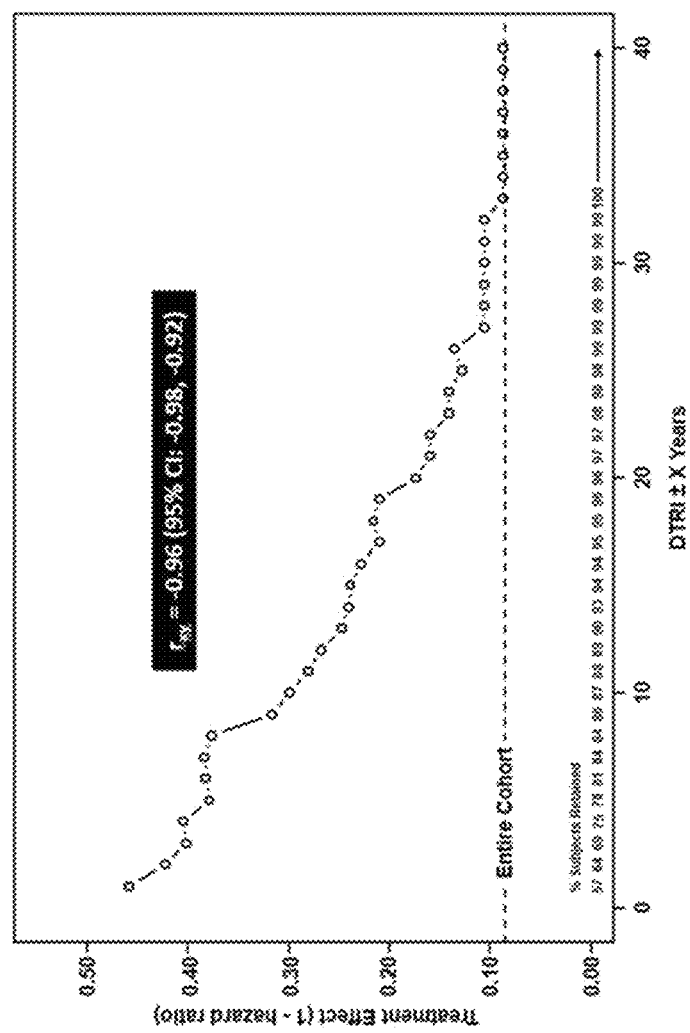
FIG. 28A-28B. Treatment Effect Relationship to Relative Onset of AF and HF (DTRI). 28A. Treatment effect versus absolute value of DTRI upper and lower bounds. 28B. Histogram of DTRI distribution for DxT12 cohort and cohort excluded by DxT12 criteria. Hazard ratio is for time to AF/AFL/ACM endpoint. DTRI=Diagnosis to Randomization Index. DxT12=cohort with <12 years of AF and HF prior to randomization. X-axis is in 2-year intervals.

To examine the effects of the relative onset of AF and HF on treatment effect, a 3 dimensional plot was constructed with treatment effect as the dependent variable (z-axis), and the absolute value of DTRI lower bound (i.e., years of AF prior to HF) and DTRI upper bound (i.e., years of HF prior to AF) and as independent variables. As shown in FIG. 23B, there is an attenuation of treatment effect associated with increasing absolute values of DTRI lower and upper bound (i.e., increasing time between the initial presentations of AF and HF). When equivalent absolute values for DTRI lower and upper bounds were used to examine the concept of contemporaneous AF and HF development (FIG. 28A), there was a nearly linear, negative correlation with treatment effect (r=−0.96; 95% CI: −0.98, −0.92).

7. Prevention of AF Recurrence in the Precision Therapeutic Selected Phenotype

Duration and relative onset of AF and HF are indirectly related characteristics that may have additive and/or overlapping effects. Therefore, we examined their use in combination to identify a precision therapeutic phenotype appropriate for further study.

Figure 29:
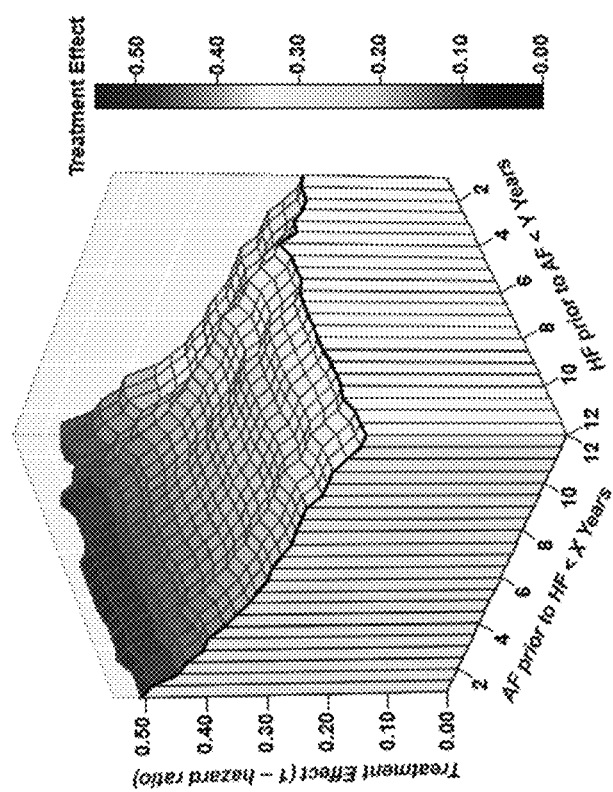
FIG. 29. Treatment Effect and the Relative Onset of AF and HF in DxT12 Cohort. 3-dimensional plot of AF onset prior to HF (x-axis) and HF onset prior to AF (y-axis) versus treatment effect (z-axis) in DxT12 Cohort. Hazard ratio is for time to AF/AFL/ACM endpoint. DTRI (Diagnosis to Randomization Index)=HF DxT−AF DxT. AF onset prior to HF=absolute value of DTRI lower bound. HF onset prior to AF=DTRI upper bound. DxT12=cohort with <12 years of AF and HF prior to randomization.

In the example presented below, we selected a population with an AF and HF DxT<12 years (i.e., DxT12 cohort), as this cutoff retained a high proportion (86%) of the overall population while minimizing attenuation of the observed treatment effect. We then applied a DTRI lower bound of −2 years (i.e., AF not preceding HF by more than 2 years; DxT12/DTRI-2 cohort), as this cutoff retained 85% of the DxT12 cohort. As shown in FIG. 29, restriction of DTRI upper bound (i.e., years of HF prior to AF) was not required when examined in a DxT12 background.

Figure 28B:
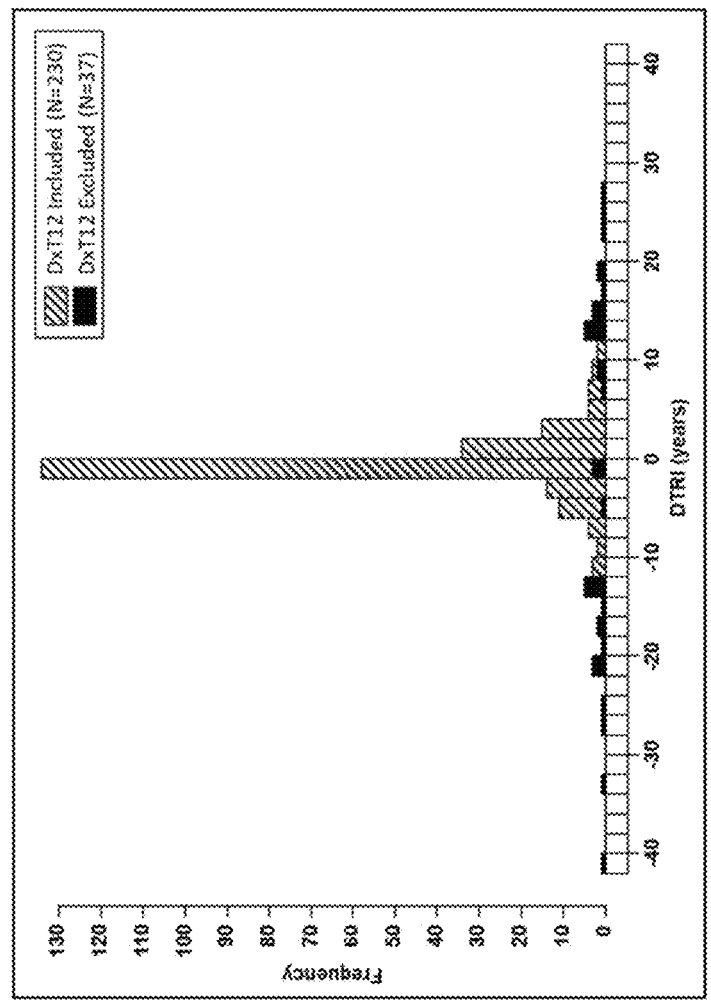

Patient characteristics of the DxT12 and DxT12/DTRI-2 cohorts are shown in Table 48a. Additional characterization of the patient population is set forth in Table 48b. Patients excluded by the DxT12 criteria had characteristics consistent with longstanding AF and HF; whereas the population excluded by the DTRI >−2 years criteria had characteristics consistent with longstanding AF as primary diagnosis and treatment history, with primarily mild left ventricular dysfunction. Of note, patients who had contemporaneous development of both AF and HF (i.e., DTRI values within 2 years of zero) are the majority of those included in the 230 patient DxT12 cohort ("DTRI included"); whereas DTRI patients with values±2 years are conspicuously absent from the 37 patient cohort excluded by the DxT12 criteria, i.e. those with the first diagnosis of both AF and HF ≥12 years prior to randomization (FIG. 28B). The accumulation of a substantial number (>10) of patients with DTRI values±2 years does not occur until the DxT cutoff is restricted to <6 years (data not shown).

TABLE 48a

Baseline Characteristics for Selected Phenotypes

| Parameter | AF12/HF12 | | | AF12/HF12/DTRI-2 | | |
|---|---|---|---|---|---|---|
| | Included N = 230 | Excluded N = 37 | p-value | Included N = 196 | Excluded N = 34 | p-value |
| Age, years | 64.9 ± 10.2 | 70.1 ± 8.4 | 0.012 | 65.2 ± 9.9 | 63.1 ± 11.8 | 0.435 |
| Male/Female, % | 80/20 | 95/5 | 0.036 | 80/20 | 79/21 | 1.000 |
| Race: W/B/A/O, % | 97/2/0/1 | 95/0/0/5 | 0.087 | 96/2/1/1 | 97/3/0/0 | 0.728 |
| LVEF | 36.6 ± 9.4 | 33.4 ± 10.5 | 0.104 | 36.0 ± 9.3 | 39.8 ± 9.6 | 0.010 |
| NYHA I/II/III, % | 30/57/13 | 6/59/24 | 0.099 | 28/57/15 | 41/56/3 | 0.074 |
| Ischemic/Non-Ischemic HF, % | 30/70 | 43/57 | 0.132 | 32/68 | 21/79 | 0.227 |
| Randomized in AF/Not in AF, % | 47/53 | 73/27 | 0.004 | 48/52 | 41/59 | 0.577 |
| Persistent/Paroxysmal AF, % | 49/51 | 62/38 | 0.159 | 48/52 | 56/44 | 0.459 |
| AF DxT, days | 770 ± 983 | 4642 ± 4201 | <0.001 | 539 ± 787 | 2098 ± 955 | <0.001 |
| HF DxT, days | 698 ± 1012 | 3988 ± 3289 | <0.001 | 778 ± 1064 | 231 ± 402 | <0.001 |
| Systolic blood pressure, mm Hg | 124.0 ± 15.0 | 118.9 ± 16.7 | 0.094 | 123.9 ± 15.4 | 124.5 ± 13.1 | 0.827 |
| Diastolic blood pressure, mmHg | 75.7 ± 10.2 | 72.6 ± 13.7 | 0.090 | 75.3 ± 10.4 | 78.0 ± 9.3 | 0.093 |
| Heart rate, bpm | 76.2 ± 18.3 | 76.6 ± 14.3 | 0.61 | 75.7 ± 18.5 | 79.4 ± 16.9 | 0.223 |
| Previous ECV (0, 1, 2+), % | 51/28/20 | 46/22/32 | 0.263 | 52/31/18 | 50/15/35 | 0.032 |
| Previous AF ablation (0, 1, 2+), % | 82/13/5 | 62/27/11 | 0.017 | 85/11/4 | 65/24/12 | 0.010 |
| Previous class I AAD use: Y/N, % | 8/92 | 8/92 | 1.000 | 6/94 | 21/79 | 0.008 |
| Previous class III AAD use: Y/N, % | 46/54 | 59/41 | 0.157 | 42/58 | 71/29 | 0.003 |

TABLE 48a-continued

Baseline Characteristics for Selected Phenotypes

| | AF12/HF12 | | | AF12/HF12/DTRI-2 | | |
|---|---|---|---|---|---|---|
| Parameter | Included N = 230 | Excluded N = 37 | p-value | Included N = 196 | Excluded N = 34 | p-value |
| Device type: None/ILR/TD, % | 55/18/27 | 32/3/65 | <0.001 | 55/17/28 | 53/26/21 | 0.347 |
| Norepinephrine, pg/ml | 646 ± 311 | 839 ± 519 | 0.030 | 656 ± 316 | 585 ± 278 | 0.243 |
| NT-proBNP, pg/ml, median (IQR) | 769 (372, 1338) | 1044 (528, 1983) | 0.043 | 790 (392, 1387) | 588 (263, 1147) | 0.266 |

AF12/HF12 = AF DxT and HF DxT <12 years.
AF12/HF12/DTRI-2 = AF12/HF12 and DTRI >−2 years.
W/B/A/O = White/Black/Asian/Other.
ECV = electrical cardioversion.
AAD = antiarrhythmic drug.
ILR = implanted loop recorder.
TD = therapeutic device (implanted cardiac defibrillator or pacemaker).
IQR = interquartile range.
AF DxT = time from initial AF diagnosis to randomization.
HF DxT = time from initial HF diagnosis to randomization.
DTRI = Diagnosis to Randomization Index.
Note:
mean ± standard deviations are presented unless otherwise specified. Wilcoxon Rank Sum Test for continuous values and Fishers Exact Test for categorical values.

TABLE 48b

Baseline Characteristics for the HFmrEF and HFlrEF Subpopulations

| Parameter (± SD) | HFmrEF 40% ≤ LVEF < 50% N = 126 | HFlrEF LVEF < 40% N = 141 | P-value |
|---|---|---|---|
| Age, years | 65.9 ± 0.88 | 65.4 ± 0.87 | 0.600 |
| Male/Female, % | 76/24 | 87/13 | 0.025 |
| Race: W/B/A/O, % | 99/1/0/0 | 94/3/1/2 | 0.231 |
| LVEF | 44.7 ± 0.3 | 28.5 ± 0.5 | <0.001 |
| NYHA I/II/III, % | 42/52/6/0 | 16/62/23/0 | <0.001 |
| Ischemic/Non-Ischemic HF, % | 29/71 | 35/65 | 0.361 |
| Randomized in AF/Not in AF, % | 44/56 | 57/43 | 0.037 |
| Persistent/Paroxysmal AF, % | 50/50 | 52/48 | 0.807 |
| AF Dx Duration, days | 1398 ± 202 | 1224 ± 186 | 0.032 |
| HF Dx Duration, days | 678 ± 141 | 1578 ± 174 | <0.001 |
| DTRI, days | −720 ± 238 | 355 ± 213 | <0.001 |
| Systolic blood pressure, mm Hg | 127.1 ± 1.2 | 119.9 ± 1.3 | <0.001 |
| Diastolic blood pressure, mmHg | 77.1 ± 1.0 | 73.7 ± 0.9 | 0.005 |
| Heart Rate, bpm | 74.0 ± 1.5 | 78.3 ± 1.5 | 0.034 |
| Previous ECV, % | 52 | 48 | 0.796 |
| Previous AF Ablation, % | 23 | 18 | 0.433 |
| Previous Type I AAD use, % | 14 | 2 | <0.001 |
| Previous Type III AAD use, % | 49 | 47 | 0.714 |
| Previous Entresto use, % | 1 | 7 | 0.011 |
| Entresto use during study, % | 4 | 14 | 0.005 |
| Device Type: ILR/CRT/ICD/PM, % | 16/3/6/15 | 16/12/23/4 | <0.001 |
| Norepinephrine, pg/ml | 653 ± 27 | 692 ± 33 | 0.588 |
| NT-proBNP, pg/ml | 872 ± 88 | 1599 ± 172 | <0.001 |

W/B/A/O = White/Black/Asian/Other.
ECV = electrical cardioversion.
AADs = anti arrhythmic drugs.
ILR = implanted loop recorder.
CRT = cardiac resynchronization therapy.
ICD = implanted cardiac defibrillator.
PM = pacemaker.
Note:
mean ± standard deviations are presented unless otherwise specified. Wilcoxon Rank Sum Test for continuous values and Fishers Exact Test for categorical values.

Figures 24A, 24B:
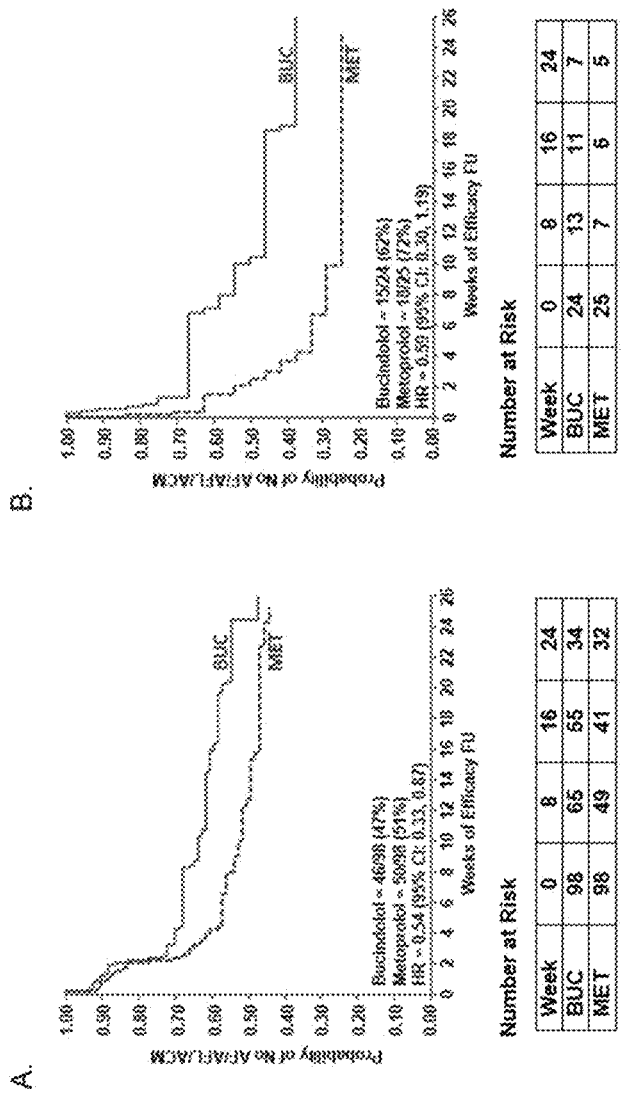
FIG. 24A-24B. Time to First Event of AF/AFL/ACM in DxT12/DTRI-2 Cohort 24A. ECG-based detection in the entire cohort. 24B. Device-based detection in the substudy cohort. For device-based detection an AF/AFL event=AF burden ≥6 hours per day. HR=hazard ratio. FU=follow-up FIG. 25A-25C. Time to First AF/AFL/ACM Event by Region 25A., U.S. cohort; 25B., Canada cohort; 25C., Europe cohort. Cox proportional hazards model adjusted for the four randomization strata.
Figures 25A, 25B, 25C:
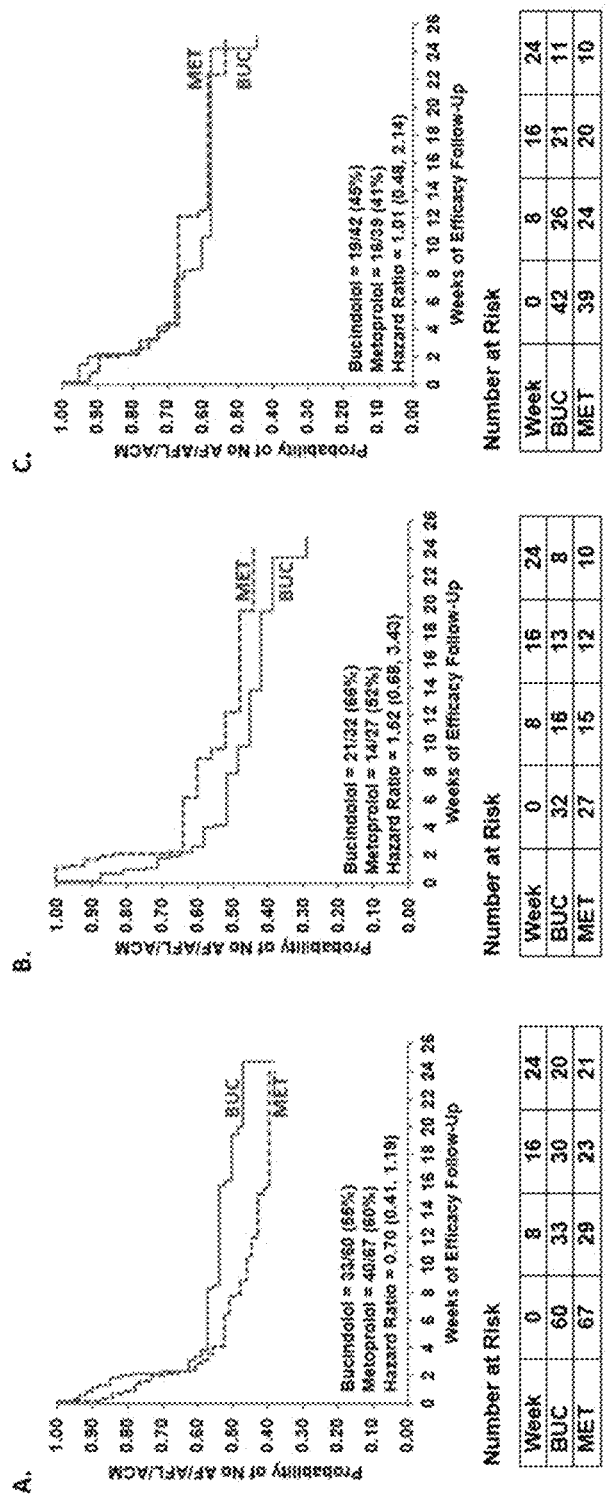

The primary endpoint of time to first event of AF/AFL/ACM for the DxT12/DTRI-2 cohort (N=196) is shown in FIG. 24. In HFrEF patients (LVEF <0.50) the HR was 0.54 (95% CI: 0.33, 0.87) by ECG-based detection, with similar results observed by device-based detection (HR=0.59; 95% CI: 0.30, 1.19; N=49). In HF patients with mid-range ejection fraction (HFmrEF; LVEF ≥0.40 and <0.50) the HR was 0.42 (95% CI: 0.21, 0.86; p=0.017) and in HF patients with lower-range ejection fraction (HFlrEF; LVEF<0.40) the HR was 0.69 (95% CI: 0.33, 1.43; p=0.32). Device-based estimate for HFmrEF and HFlrEF are not presented due to the small sample size. See Table 49 for more details.

TABLE 49

Time to First Event of AF/AFL/ACM for Subgroups by LVEF

| Cohort | HFrEF LVEF < 0.50 N(%) | HFrEF LVEF < 0.50 HR (95% CI) | HFmrEF 0.40 ≤ LVEF < 0.50 N(%) {% of Cohort} | HFmrEF 0.40 ≤ LVEF < 0.50 HR (95% CI) | HFlrEF LVEF < 0.40 N (%) {% of Cohort} | HFlrEF LVEF < 0.40 HR (95% CI) |
|---|---|---|---|---|---|---|
| All Patients | 267 (100) | 0.92 (0.63, 1.33) | 128 (100) {48} | 0.78 (0.45, 1.33) | 139 (100) {52} | 1.03 (0.58, 1.83) |
| AF12/HF12 | 230 (86) | 0.68 (0.45, 1.02) | 113 (88) {49} | 0.61 (0.34, 1.10) | 117 (84) {51} | 0.74 (0.38, 1.44) |
| AF12/HF12/ DTRI-2 | 196 (73) | 0.54 (0.33, 0.87) | 91 (71) {46} | 0.42 (0.21, 0.86) | 107 (77) {54} | 0.69 (0.33, 1.43) |

AF12/HF12 = AF/HF DxT <12 years;
12/12/DTRI-2 = AF/HF DxT <12 years and DTRI >−2 years.
HFrEF = HF with reduced LVEF;
HFmrEF = HF with mid-range LVEF;
HFlrEF = HF with lower-range LVEF.
DTRI = Diagnosis to Randomization Index.

8. Effects on Norepinephrine and NT-ProBNP

Plasma norepinephrine at baseline was similar in the bucindolol (682±348 pg/ml, n=128) and metoprolol (664±359 pg/ml, n=134) groups. At 4 weeks, there was a significant decrease from baseline in the bucindolol group (−124±26 pg/ml; p<0.001) that was not observed in the metoprolol group (36±32 pg/ml; p=0.30). The change from baseline at 4 weeks was significantly different between the two groups (p=0.012).

Plasma NT-proBNP was non-normally distributed in both groups, and median values at baseline were similar (777 and 861 pg/ml, p=0.38; Table 50). There was a significant decrease from baseline in the bucindolol group at week 4 (96 pg/ml; p=0.003) and week 12 (96 pg/ml; p=0.002) that was not observed in the metoprolol group. At week 24, significant decreases relative to baseline values were observed in both the bucindolol (197 pg/ml; p=0.005) and metoprolol (−100 pg/ml; p=0.014) groups, but the change from baseline was not significantly different between the two groups (p=0.220).

TABLE 50

NT-proBNP values (pg/ml)‡

| Parameter | Metoprolol N = 123 | Bucindolol N = 125 |
|---|---|---|
| Baseline | 861 (420, 1607) | 777 (355, 1326) |
| P value vs. Met† | NA | 0.378 |
| ΔWeek 4 | −35 (−384, 246) | −96 (−431, 70) |
| P value vs. Bsl* | 0.320 | 0.003 |
| P value vs. Met† | NA | 0.300 |
| ΔWeek 12 | −50 (−610, 303) | −96 (−482, 69) |
| P value vs. Bsl* | 0.198 | 0.002 |
| P value vs. Met† | NA | 0.051 |
| ΔWeek 24 | −100 (−634, 117) | −197 (−613, 115) |
| P value vs. Bsl* | 0.014 | 0.005 |
| P value vs. Met† | NA | 0.220 |

‡Median and interquartile range presented due to non-normal distribution; *Wilcoxon signed rank test;
†Wilcoxon rank sum test;
Δ = change from baseline.

9. Safety

The proportion of patients experiencing adverse events (AEs) was similar in the two groups (Table 44). More patients in the metoprolol group had symptomatic bradycardia or bradycardia leading to dose reduction or discontinuation of study drug compared to the bucindolol group (9.0% vs. 3.0%; p=0.042). Three (2.3%) patients in each group died while receiving study drug or within 30 days of their last dose. All deaths in the metoprolol group occurred during the primary endpoint period (worsening HF—day 25; sudden cardiac death—day 43; motor vehicle accident—day 77). All deaths in the bucindolol group occurred during the long-term extension period (respiratory failure—day 385; sudden death—day 535; cardiac tamponade—day 779). Rates of HF hospitalization (7.5% vs. 8.3%) and ACM/HF hospitalization (8.2% vs. 9.0%) were similar for the bucindolol and metoprolol groups, respectively. There were no strokes in either treatment group, with 93% of patients receiving oral anticoagulants prior to randomization.

TABLE 44

Treatment Emergent Adverse Events

| Endpoint | Bucindolol (N = 134) | Metoprolol (N = 133) |
|---|---|---|
| Any adverse event (AE) | 100 (74.6%) | |
| AE possible/probably related to study drug | 32 (23.9%) | 40 (30.1%) |
| AE leading to permanent study drug discontinuation | 11 (8.2%) | 11 (8.3%) |
| AE leading to study withdrawal (excluding death) | 2 (1.5%) | 2 (1.5%) |
| AE of symptomatic bradycardia or bradycardia leading to dose reduction or discontinuation of study drug | 4 (3.0%) | 12 (9.0%) |
| Any serious adverse event | 34 (25.4%) | 27 (20.3%) |
| AE leading to death | 3 (2.3%) | 3 (2.3%) |

Data presented from randomization through 30 days after last dose of study drug.

C. Analysis

The GENETIC-AF trial was designed as an adaptive, randomized, controlled trial that was powered for a full Phase 3 investigational comparison if evidence from the Phase 2B study suggested efficacy was likely on expansion to the Phase 3 sample size (19). In the Phase 2B analysis, pharmacogenetic-guided bucindolol did not reduce the recurrence of AF/AFL/ACM compared to metoprolol in the overall population. However, trends for bucindolol benefit were observed in key subgroups, particularly in those without long-standing and heavily treated AF prior to the development of HF. A lower proportion of patients with long-standing AF diagnosed prior to the development of HF likely contributed to the favorable bucindolol treatment effect in U.S. and device substudy patients, who were majority U.S. enrolled. In addition to the findings relevant to the investigational drug, this study also has several important findings relative to detection of AF in clinical trials.

GENETIC-AF also represents several firsts in the conduct of pharmacogenetic studies in cardiovascular disease and AF in particular. It is the first pharmacogenetically-targeted, randomized, controlled trial of rhythm control therapy in AF. Moreover, it is the first pharmacogenetic trial for prevention of recurrent AF in HFrEF, defined as HF with any decrease in LVEF (98). It is also the first study to compare AF burden to symptomatic AF/AFL as determined by adjudication of symptoms and ECG data. Finally, it represents the first comparative beta-blocker trial to include HF patients with mid-range ejection fraction (HFmrEF), defined as a LVEF $\geq 0.40$ and $<0.50$ (99).

There are several important findings from GENETIC-AF regarding AF in this HFrEF population. For example, nearly all patients who experienced AF recurrence had symptomatic AF, defined as new or worsening symptoms as adjudicated by a blinded clinical events committee. Recently, there has also been considerable interest in methods of AF diagnosis in clinical practice, including telemetry and device-based technologies (96,97). Our device substudy defined an AF/AFL event as AF burden $\geq 6$ hours per day because this amount of burden had previously been shown to be associated with an increased rate of hospitalization for HF (34). We found that AF burden $\geq 6$ hours per day as recorded by continuous monitoring exhibited high predictive accuracy for clinically symptomatic AF/AFL and tended to identify these events earlier than intermittent ECG monitoring.

Approximately half of patients screened for this trial had the ADRB1 Arg389Arg genotype, consistent with previous findings (17,19,13,26). In this genotype only norepinephrine high affinity beta1 Arg389 receptors are present, providing a substrate for the favorable effect of sympatholysis (19) that was again observed for bucindolol. Bucindolol lowered plasma norepinephrine levels after 4 weeks of treatment, which was not observed for metoprolol. Plasma NT-proBNP levels also decreased significantly with bucindolol treatment but not with metoprolol. These data indicate that the pharmacodynamic profile that contributes to the pharmacogenetic differentiation of bucindolol was operative in the trial.

It is also notable there were no safety concerns identified with bucindolol. Similar rates of death and hospitalization were observed in both treatment arms, though power was limited for detection of uncommon events. Interestingly, bradycardia was significantly lower in the bucindolol arm, suggesting that bucindolol may lead to less bradycardia than metoprolol in patients with the ADRB1 Arg389Arg genotype.

A major goal of a Phase 2 clinical trial is to further refine the study population that will be investigated in Phase 3. To this end we conducted an exercise in precision therapeutic phenotyping, or "individual treatment effect modeling" (98), designed to identify both prespecified obvious as well as nonobvious variables associated with a beneficial treatment effect of bucindolol. Exploration of factors contributing to the heterogeneity in response observed for regional subgroups led us to examine the timing of AF and HF onset prior to randomization and relative to one another. This led us to identify two variables that were strongly associated with an attenuation of bucindolol response: 1) the interval of time from the initial diagnosis of HF and AF to randomization (i.e., DxT), and; 2) the onset of AF relative to initial HF diagnosis (i.e., DTRI). AF duration has previously been reported to modulate response for other drug therapies post-ECV (99) and for catheter ablation (38). Less well appreciated is how the HF duration may impact medical therapy, and how these two variables interact in HF patients with concomitant AF. It should also be noted that GENETIC-AF compared two members of a drug class that had been administered chronically to this population, in some cases for years, prior to randomization. As such, a survivor effect due to loss of patients who develop AF and HF within a few years of each other, potentially due to adverse effects on mortality with the combination (2), may be responsible for altering the composition of certain subpopulations (i.e., those with longstanding AF/HF DxT, FIG. 28B) in a manner that influences treatment response (FIG. 29). If a contemporaneous relationship between the onset of AF and HF is optimal for bucindolol to maintain sinus rhythm, potentially related to higher levels of adrenergic activity when both conditions manifest in some proximity (13, 3), then this would explain the phenotype identified in our analysis. Alternatively, or in addition, it is also possible that the DTRI effect has a biological origin based on differences in atrial and ventricular pathophysiology when AF precedes or dominates over HF, the major difference residing in chamber interstitial fibrosis being a more prominent feature in AF (100, 72).

For comparative efficacy studies that seek to observe a differential response between two drugs in the same drug class it is critical to identify a study population with high potential for overall response to the drug class. This is necessary because a differential response is, by definition, a fraction of the overall response to a specific drug and, therefore, is more difficult to observe in a given study population. In this exploratory Phase 2 trial with limited sample size and statistical power, we identified HF populations who respond differentially to two beta-blockers based on genetic targeting. This approach circumvents potential issues associated with conventional subset analyses by evaluating monotonicity and consistency of trends across the full continuum of candidate variables such that the classifiers are readily conducive to numerical calibration. We propose that increasing the permissible limits of variation (i.e., tolerance) for the phenotype selection criteria increases the likelihood of reproducibility of these results in future studies.

D. Conclusion

In the first trial of a pharmacogenetic-guided rhythm control intervention, bucindolol did not reduce the recurrence of AF/AFL or ACM compared to metoprolol in the overall population. However, precision therapeutic phenotyping identified a large population of HF patients with an ADRB1 Arg389Arg genotype who display a differential response to bucindolol compared to metoprolol for the prevention of AF/AFL. This experience underscores the utility of performing relatively large Phase 2 studies comprised of heterogeneous populations in order to generate the data necessary to identify appropriate therapeutic phenotypes suitable for Phase 3 investigation.

E. Clinical Perspectives

The intersection of atrial fibrillation (AF) and heart failure (HF) is common, worsens the prognosis of each disorder and lacks effective, easily administered and safe drug therapy. In the BEST trial pharmacogenetic substudy, against placebo in patients with an ADRB1 Arg389Arg genotype the 4th generation beta-blocker bucindolol reduced the risk of developing AF by 74%, leading to design and performance of the Phase 2 trial GENETIC-AF where 267 high AF risk HFrEF patients were randomized to bucindolol vs. the conventional, 2nd generation compound metoprolol succinate. Overall there was no difference in effectiveness (hazard ratio (HR) 1.01; 95% CI: 0.71, 1.42), but a trend for benefit with bucindolol was observed in the U.S. subgroup (N=127; HR=0.70; 95% CI: 0.41, 1.19) and in patients with implanted devices (N=69; HR=0.75; 95% CI: 0.43, 1.32). The trial exhibited marked regional heterogeneity, which was attributed to 2 countries predominately enrolling patients whose AF diagnosis preceded HF by many years; in countries that enrolled patients with a more contemporaneous presentation of AF and HF bucindolol was associated with a positive efficacy signal.

F. Translational Outlook

The theoretical basis for bucindolol's advantage over conventional beta-blockers for preventing AF and reducing HF events in HFrEF patients who are genotype ADRB1 Arg389Arg is its more powerful inhibition of the higher functioning Arg389 polymorphic variant of the $beta_1$-adrenergic receptor. The ADRB1 Arg389Gly polymorphism is not present in other species but can be and has been investigated by transgenic overexpression in mice. In terms of the potential for reverse translation, precision therapeutic phenotyping in GENETIC-AF identified a group of patients in whom AF developed many years prior to HF who did not respond favorably to bucindolol, suggesting different pathophysiology compared to patients who develop AF and HF contemporaneously. This putative pathophysiologic difference and its impact on therapy, potentially related to a greater burden of atrial and ventricular fibrosis associated with longstanding AF, could be translationally investigated in animal models of AF and HF.

Example 7

Statistical Analysis Plan for Example 6 Study

A. Definitions of Analysis Populations and Endpoint Follow-Up Periods

The efficacy analysis will follow the intent-to-treat (ITT) principle and all patients randomized to study treatment will be included regardless of (1) the success of the treatment titration process and (2) result of electrical cardioversion (ECV) aimed at converting atrial fibrillation (AF) to sinus rhythm (SR). As an additional sensitivity analysis, testing of the primary and secondary endpoints will be repeated on a protocol-compliant subpopulation. Further sensitivity analyses specific to endpoints are described below. The safety analyses will include all patients that received at least one dose of blinded study treatment. The screened population includes any patient who signs informed consent for the study. The screen failure population is a subpopulation of the screened population who are not randomized to study drug for any reason.

Four follow-up periods will be defined for inclusion of each patient's results in endpoint calculations:

Drug Titration Period: starts on the day of randomized treatment initiation and extends for six weeks after randomization.

24-Week Follow-up Period: starts on the day of 1) the first ECG that establishes stable SR (defined in Section 3.2.1), or; 2) the last ECV attempt for patients who fail to convert to stable SR, or; 3) the Week 0 Visit, for patients in AF who do not undergo ECV for any reason. Ends on the day of the Week 24 Visit or the End of Study (EOS) Visit, if patient discontinues prior to Week 24 Visit.

Total Follow-up Period: starts on the same day as the 24-Week Follow-up Period and extends until the EOS Visit.

Total Study Period: starts on the day of the Randomization Visit and extends until the EOS Visit.

B. Patient Characteristics.

1. Screen Failure

Screen failure reasons will be tabulated in order of frequency. These reasons are collected on the eCRF DEMOG form.

2. Randomization

Randomized treatment assignment is centralized and in versions 1 and 2 of the protocol was stratified by: 1) HF etiology (ischemic/non-ischemic); 2) LVEF (<0.35/≥0.35) and; 3) type of Medtronic device (Reveal/Non-Reveal/No Device). In protocol version 3 a fourth strata was added: rhythm status at randomization: (SR vs AF). The count of patients randomized by strata within each treatment group will be tabulated by site and overall. The randomization process will be described in full detail.

3. Baseline Characteristics

The treatment groups will be examined for comparability with respect to demographics, cardiovascular history, AF risk factors, current disease state, HF and AF therapies, physical exam abnormalities, CYP2D6 and α2C genotyping, vital signs, ECG and laboratory parameters using descriptive statistics. Continuous variables will be analyzed with a mean, standard error, standard deviation, median, minimum, maximum and n=count of results available. Categorical variables will be described with n=count of results available and percentage of study population, with a clear explanation of the denominators provided in footnotes when necessary.

4. Treatment Exposure and Compliance

The treatment groups will be examined for comparability with respect to the outcome of the titration period (broken down by pre-study beta blocker usage), the attainment of target dose and the days of double blind treatment by dose level and overall. Elapsed days and days of treatment exposure during the four follow-up periods will also be described by treatment group.

Compliance since the previous visit is reported by the sites on the VISREC eCRF form. Overall compliance rates for the 24-Week Follow-up Period and the Total Study Period will be calculated for each patient and compared between the two treatment groups with descriptive statistics. Note that if a patient discontinues study treatment, compliance is calculated through the date of discontinuation.

5. Concomitant Medications

Patients must be receiving optimal anticoagulation therapy for stroke prevention. A tabulation of anticoagulant drug usage by treatment group will be generated. For warfarin users, INR is collected on the LAB eCRF as the following ranges: <1, ≥1 and <2, ≥2 and <3, ≥3 and <4, ≥4. A tabulation of these reported ranges by treatment group will be generated for each of the study visits in which reporting is required.

Reported usage of all concomitant medications during the study will be standardized with preferred name and Anatomical Therapeutic Classification (ATC) using the WHODrug dictionary for tabulation by treatment group.

6. Metrics for Key Study Procedures

Metrics for the following study procedures and medical interventions will be presented with descriptive statistics by randomized treatment group:

The cardiac rhythm status of every patient at both the Randomization Visit and at the start of the 24-Week Follow-up Period will be tabulated as follows.
Patients in Stable SR at Week 0 who did not require ECV
Pts in SR at Randomization
Pts in AF at Randomization
Patients in Stable SR at Week 0 who did require ECV
Pts in SR at Randomization
Pts in AF at Randomization
Patients in AF/AFL at Week 0
Pts in SR at Randomization
Pts in AF at Randomization
Death/Loss to Follow-up (LTF) prior to Week 0
Pts in SR at Randomization
Pts in AF at Randomization
Elapsed days on treatment prior to ECV.
Outcome of ECV.
Compliance with procedures for collection of transtelephonic monitoring (TTM) results, and
Compliance with procedures for collection of Medtronic device results.

7. Final Study Disposition

The disposition of patients screened and randomized into the study will be tabulated by treatment group and displayed with a flow diagram. This will include the counts of screens, screen failures, re-screens, randomizations, completion of the Week 24 Visit, reasons for permanent discontinuation of study treatment and reasons for discontinuation of study follow-up (broken down by pre/post Week 24 Visit). Note that all patients classified as completing the Week 24 Visit will have all components of the primary and secondary endpoints ascertained through the entire 24-Week Follow-up Period.

8. Protocol Deviations

ARCA Clinical Operations maintains an Excel spreadsheet of protocol deviations reported during the study. Each protocol deviation is classified as being Major or Minor, based on its potential impact on clinical results per ARCA SOP CLIN-005. Tabulations and listings of the reported protocol deviations will be provided for both treatment groups.

C. Efficacy Analysis

1. General Methodology i.) Time-to-Event Analysis Methodology

Time-to-event is calculated as the date of the event minus the date of initiation of efficacy follow-up, with 1 added in order to include both the start date and end date of the interval.

For all endpoints, follow-up will be censored when a patient receives a cardiac transplant, is declared to be permanently lost to follow-up or withdraws consent. The follow-up periods and specific censoring rules are identified in the endpoint descriptions.

These analyses will be a two-tailed comparison of bucindolol and metoprolol, using the log rank statistic with the exact variance calculation stratified by the randomized treatment assignment strata: 1) HF etiology (ischemic/non-ischemic); 2) LVEF (<0.35/≥0.35); 3) type of Medtronic device (Reveal/Non-Reveal/No Device); and 4) rhythm status at randomization: (SR vs AF). Note that patients enrolled under versions 1 and 2 of the protocol were not stratified by rhythm status however their rhythm status is known due to inclusion criteria (all were in AF). The calculations will be performed with the SAS® LIFETEST procedure, with the stratification variables specified in the STRATA statement and the TEST statement used to specify the treatment group comparator and any covariates being examined. Cox's proportional hazards model will be used to calculate estimated hazard ratios and 95% confidence intervals. The calculations will be performed with the SAS PHREG procedure, with the stratification variables specified in the STRATA statement and the treatment group comparator and any covariates being examined specified in the MODEL statement. For the primary endpoint, the appropriateness of assuming proportional hazards will be explored by the graphing of log (−log(survival function)) over follow-up for each treatment group.

Where appropriate, Kaplan-Meier survival curves for bucindolol versus metoprolol will be generated to provide a graphical comparison of the two treatment groups.

Follow-up for the time-to-event endpoints will generally end either at the Week 24 Visit or the EOS Visit for the Total Follow-up Period or Total Study Period endpoints. If the Week 24 Visit falls later than day 180, follow-up will be censored on day 180.

ii.) Components of Combined Endpoints

This report will contain many endpoints that involve the time to the first occurrence of multiple events, such as AF/AFL onset, mortality or hospitalization. For these endpoints, the count of first events provided by each component will be tabulated. In addition, each component of the combined endpoints will be analyzed separately with a time-to-first-event analysis following the same methodologies used for the combined statistic.

iii.) Adjudication

A Clinical Events Classification (CEC) group will adjudicate the primary endpoint, first symptomatic AF/AFL event or death during the 24-Week Follow-up Period. As part of the adjudication process for the primary endpoint, the CEC will also evaluate the secondary endpoint of first AF/AFL event (i.e., symptomatic or asymptomatic). Specifically, the ECGs for the first report of AF/AFL will be reviewed and adjudicated for the presence of AF/AFL regardless of the symptom status. If the first protocol-defined AF/AFL event is not considered a symptomatic AF/AFL event, the triggering process will continue for that patient until the first symptomatic AF/AFL event is identified for the primary endpoint. The CEC over-read of ECG tracings will be used in the calculation of other pertinent study endpoints (such as non-symptomatic AF/AFL within the 24-Week Follow-up Period). More details can be found in the CEC Charter.

iv.) Core Lab and Transtelephonic Monitoring

In the original study protocol, an Electrophysiology Core Lab (Agility Centralized Research Services) provided a centralized ECG interpretation of the individual ECGs performed at the clinic site and the transtelephonic monitors (TTM) worn by the patients, both during the 24-Week Follow-up Period. In version 4 of the protocol, the collection of these two sources of data was discontinued. The CEC adjudication process was not in production mode at that time point, so it was decided the CEC would perform their own interpretation (over-reads) of the site ECG tracings and not use any of the Core Lab interpretations. Further, the CEC adjudication would make use of available TTM data.

v.) Hospitalization

Many of the efficacy endpoints involve hospitalization. Only non-voluntary, overnight hospital admissions will be included in these endpoints; emergency room visits will not be included. Patients in this study will often have scheduled hospital admissions for treatment of their AF and/or HF. Examples include ablation procedures, Tikosyn induction, placement/replacement of implanted devices, and IV drug treatment. These will not be included in the endpoints. The eCRF specifically collects the investigator's assessment of hospitalization causation, which includes assessments of non-CV, CV and HF hospitalizations. In addition to the investigator assessment of causation, the data will be reviewed by the Sponsor via a blinded listing review prior to database lock to confirm which hospitalizations are considered voluntary, overnight admissions.

vi.) Data Collection Cut-off at End of Study

The protocol states the study will end with approximately 620 randomized patients and accrual of at least 330 primary endpoint events, presuming the sample size and target event counts are not altered due to the Phase 3 interim analysis (see DSMB Charter). At this point, any patients still participating in the 24-Week Follow-up Period will remain on blinded study treatment until they complete the Week 24 Visit. Those patients in the Extension Period will be called in for an EOS Visit.

vii.) Missing Data Due to Withdrawal or Loss to Follow-up

The rate of withdrawal or loss to follow-up prior to the Week 24 Visit is expected to be low. If a withdrawal or loss to follow-up occurs prior to the Week 24 Visit, all time-to-event endpoints will be censored as of the last completed visit. Note that patients that withdraw from the study will be requested to consent to have their vital status checked via phone calls. If deaths are detected by this procedure the date of death will be incorporated into the efficacy and safety datasets and analyses.

viii.) P-value Adjustment for Interim Analysis

The goals and operational details for the interim efficacy analysis and ongoing safety monitoring can be found in the DSMB Charter and the DSMB SAP.

At the end of Phase 3, the alpha level for the primary endpoint will be reduced to 0.04989 to adjust for the Phase 2B ($\alpha=0.00001$) and Phase 3 ($\alpha=0.0001$) interim analyses.

2. Efficacy Endpoints i.) Primary Efficacy Endpoint

The primary endpoint is elapsed time-to-first-event of symptomatic AF/AFL or all-cause mortality (ACM) during the 24-Week Follow-up Period. This is a time-to-event endpoint censored at the end of the 24-Week Follow-up Period. The identification of first event of symptomatic AF/AFL or death is provided by the CEC. The CEC does not distinguish between the presence of AF or AFL so a component analysis will not be possible.

The following definitions apply to this endpoint:

Stable SR on study drug is defined as any of the following:

SR confirmed ≥1 hour after ECV.

SR confirmed ≥1 hour after spontaneous conversion from AF/AFL.

SR confirmed ≥1 hour at the Week 0 Visit for patients randomized in SR.

An AF/AFL event is defined as AF or AFL observed on two consecutive measures separated by at least 10 minutes as assessed by ECG/TTM.

A symptomatic AF/AFL event is defined as an AF/AFL event that is associated with a clinically relevant change in patient-reported symptoms, as determined by the CEC examination of blinded data.

The CEC charter and associated documents describe the "triggers" that are established to identify events for their consideration and the data sources to be used in their adjudication proceedings. The charter also describes their approach for identifying an AF event as symptomatic and for identifying the onset date and time of the event since that is needed for this time-to-event endpoint. Note that version 3 of the protocol involved a comprehensive change to the symptoms collected, with 6 of the original 8 symptoms having their descriptions modified and 2 new symptoms being added. Also the symptom characteristics were clarified with addition of a 'frequency' field to the collection form. All of these changes were made to give the CEC more specific information to support their identifying symptoms that were new or worsened in association with AF onset. Since these changes were implemented after only 12 patients were randomized (2% of the planned 620) and the identification of overall symptom onset/worsening is an adjudicated decision, no modification of analysis methodology is planned.

AF/AFL will be assessed at scheduled and unscheduled clinic visits via 12-lead ECG. Patients will be queried at the time of each ECG assessment to determine if they have experienced any change in symptoms that could be potentially related to AF.

The vast majority of patients will either be in SR or successfully convert from AF to SR after one or two ECV procedures around three weeks after they begin randomized treatment. However, there are several scenarios that depart from this norm and the methodology for establishing the start of efficacy follow-up and censoring for the primary endpoint is described below:

1. Spontaneous conversion to stable SR prior to the planned cardioversion. For these patients, the day of the first ECG assessment that meets the definition of stable SR, as defined above, will be designated as Day 1 of the 24-Week Follow-up Period.
2. Failure to attain stable SR because the ECV procedure was not performed due to drop out or any reason other than those described below. These patients will be included in the analysis as censored on Day 1 of the 24-Week Follow-up Period.
3. Failure to attain stable SR, either spontaneously or following ECV. These patients will be included in the endpoint calculation as experiencing the event on Day 1 of the 24-Week Follow-up Period.
4. Deaths occurring after randomization and prior to conversion to stable SR will be counted as events on Day 1 of the 24-Week Follow-up Period.
5. Patients with AF/AFL stopped at the Week 0 visit by any means other than ECV will be censored on Day 1 of the 24-Week Follow-up Period. An example is the performance of AV nodal ablation at the Week 0 visit.

The primary endpoint analysis will also be performed within the following prospectively identified subgroups based on pathophysiological or clinical importance:

1) Started the 24-Week Follow-up Period in SR vs AF; 2) LVEF strata at randomization: ≤0.35 vs. >35; 3) Gender; 4) Ischemic etiology vs. nonischemic; 5) Age above/below median; 6) Duration of AF diagnosis above and below median.; 7) Baseline norepinephrine above and below median; 8) Baseline NT-proBNP; 9) $\alpha_{2C}$ AR polymorphisms (i.e., Del carriers vs. $\alpha_{2C}$ wild type homozygotes).

In exploratory analyses, the following covariates will be included as potentially relevant explanatory variables in the Cox regression models: 1) Initial study treatment dose level; 2) Baseline NYHA Class; 3) Gender; 4) Race; 5) Age; 6) Baseline serum creatinine; 7) Baseline norepinephrine level;

8) Baseline heart rate; 9) Baseline systolic blood pressure; 10) History of diabetes; 11) Duration of AF diagnosis; 12) Previous amiodarone use (both historical and stopped just prior to randomization); 13) Ablation procedure prior to study; 14) Therapeutic device type: CRT, ICD, single ventricular lead pacemaker; 15) For the subset of patients in AF at baseline, type of rhythm abnormality: (paroxysmal AF or persistent AF); 16) For the subset of patients in SR at baseline: the time since last attaining SR, the type of previous rhythm abnormality, and the intervention that ended the previous AF episode; 17) Elapsed days of treatment from randomization date to start of the 24-Week Follow-up Period; 18) CYP2D6 metabolizer status; 19) $\alpha_{2C}$ AR polymorphisms (i.e., Del carriers vs. $\alpha_{2C}$ wild type homozygotes); 20) Country in which clinic site is located; 21) Other clinically significant AF risk factors.

Additional exploratory analyses will include the following:
A qualitative analysis of the symptoms associated with the primary endpoint events. The symptoms will be classified as arrhythmia-related (palpitations or lightheadedness/dizziness) HF-related (fatigue or tiredness, weakness or problems exercise, weight gain or swelling of both legs and/or feet), or both.
For patients with primary endpoint events of symptomatic AF/AFL, how many had prior events of asymptomatic AF/AF that progressed into symptomatic.

The following sensitivity analyses will be performed:
A subpopulation analysis including only those patients beginning the 24-Week Follow-up Period in SR.
In the per-protocol analysis, endpoint events and deaths that occur more than 30 days after permanent discontinuation of study treatment are omitted.
All Week 24 Visits included (ie—no exclusion of events observed at Week 24 Visits after day 180).
Patients that have not previously reverted to AF/AFL that withdraw or are lost to follow-up prior to the Week 24 Visit, will be assigned an AF/AFL event at the first missed clinic visit or scheduled TTM.
Patients that withdraw or are lost to follow-up prior to the Week 24 Visit are omitted from the analysis.

ii.) Secondary Efficacy Endpoints

The following endpoints will be tested for superiority of bucindolol benefit relative to metoprolol by fixed sequence provided that bucindolol is found to be significantly superior in the primary endpoint. The time-to-event endpoint methodology described in Sections 3.1.1 and 3.2.1 for events involving AF/AFL recurrence will be used unless otherwise noted:

Time-to-first-event of AF/AFL (i.e., symptomatic or asymptomatic) or ACM during the 24-Week Follow-up Period.
Supportive Analyses:
Events accrued during the Total Follow-up Period.
For patients with events based on symptomatic AFL, the rate of patients subsequently progressing to AF. Also for these patients, the elapsed time from symptomatic AFL to AF.
Data Source:
ECG (over-read by CEC for first 24 weeks)
TTM (first 24 weeks only)
Proportion of patients with VT, VF, or symptomatic supraventricular tachycardia (SVT) during the 24-Week Follow-up Period. Includes VF and symptomatic SVT events of any duration, VT events ≥15 seconds, and VT events that result in appropriate firing of an ICD. It will be tested with a Cochran-Mantel-Haenszel statistic to control for the four stratification variables.
Supportive Analyses:
Events accrued during the Total Follow-up Period.
Data Source:
The CVEVENT eCRF form is the source of all components of these compound endpoints.
Total all-cause hospitalization days per patient during the Total Study Period. The count of hospitalization days will be normalized for the total number of days of follow-up prior to testing with the Wilcoxon Rank Sum statistic.
Supportive Analyses:
Number of heart failure hospitalization days per patient.
All-cause hospitalization days through first recurrence of AF/AFL versus days after recurrence, normalized for days of follow-up within each period. The comparison will take place within treatment group and across treatment.
All-cause hospitalization days for patients with ventricular rate control (VRR) control compared to those without VRR control. The comparison will take place within treatment group and across treatment.
Data Source:
The HOSP eCRF form provides the number of hospitalization days and the reason for hospitalization.
The ECG and AE eCRF will be used to identify the patients in AF with VRR control at the end of the study.
Time-to-first-event of AF/AFL (i.e., symptomatic or asymptomatic), HF hospitalization (as assessed by the Investigator), or ACM during the Total Follow-up Period. As in the primary endpoint, any incidence of ACM prior to start of the 24-Week Follow-up Period will be analyzed as an event on Day 1. Hospitalization prior to Week 0 are not included, but those are included in the safety analyses.
Supportive Analyses:
Events accrued during the 24-Week Follow-up Period. Combinations of each component ((i.e., AF/AFL+ ACM, AF/AFL+HFH, HFH+ACM).
Data Source:
ECG (over-read by CEC for first 24 weeks), HOSP and DEATH eCRF forms.
TTM (first 24 weeks only).
Proportion of patients with adequate ventricular rate control (VRR) in the setting of AF/AFL. Adequate VRR in setting of AF/AFL is defined as follows: 1) the presence of AF or AFL; 2) a VRR between 40 and 80 beats per minute (bpm) at rest; and 3) the absence of symptoms associated with bradycardia. Thus this is a subset analysis only involving patients with AF/AFL recurrence. The endpoint is evaluated for the last tracing demonstrating AF/AFL during the 24-Week Follow-up Period prior to intervention (eg: ablation, ECV, initiation of anti-arrhythmic drugs). Will be tested with a Cochran-Mantel-Haenszel statistic to control for the four stratification variables.
Supportive Analyses:
Evaluated for the last tracing demonstrating AF/AFL when the patient is still on study treatment during the 24-Week Follow-up Period.

Data Source:
ECG and AE eCRF form (for symptomatic bradycardia).

iii.) Tertiary Efficacy Endpoints

The following endpoints will be tested for superiority of bucindolol benefit relative to metoprolol. The time-to-event endpoint methodology described in Section 3.1.1 and 3.2.1 for events involving AF/AFL recurrence will be used unless otherwise noted:

Time-to-first-event of VT/VF or ACM during the Total Follow-up Period. Includes VF events of any duration, VT events of ≥15 seconds, and VT events that result in appropriate firing of an ICD.

Supportive Analyses:
Events accrued during the 24-Week Follow-up Period.

Data Source:
CVEVENT and DEATH eCRF forms.

Time-to-first-event of AF/AFL (i.e., symptomatic or asymptomatic), CV-related hospitalization (as assessed by the Investigator), or ACM during the Total Study Follow-up Period.

Supportive Analyses:
Events accrued during the 24-Week Follow-up Period.
Combinations of each component (i.e., AF/AFL+ACM, AF/AFL+CVH, CVH+ACM).

Data Source:
ECG (over-read by CEC during the 24-Week Follow-up Period), HOSP and DEATH eCRF forms.
TTM (24-Week Follow-up Period).

Proportion of patients with stroke or systemic embolism during the Total Follow-up Period. Stroke is defined as a focal neurologic deficit from a non-traumatic ischemic, hemorrhagic, or uncertain cause lasting at least 24 hours (as assessed by the Investigator). Tested with a Cochran-Mantel-Haenszel statistic to control for the four stratification variables.

Data Source:
CVEVENT eCRF form.

Proportion of patients randomized with AF/AFL who convert to stable SR (spontaneous or post-ECV) and enter the 24-Week Follow-up Period. Tested with a Cochran-Mantel-Haenszel statistic to control for the four stratification variables.

Supportive Analyses:
Subset of patients with spontaneous conversion.

Data Source:
FUSTART eCRF form.

Total number of ECV procedures per patient during the Total Study Period. This count will be normalized for the total number of days of follow-up prior to testing with the Wilcoxon Rank Sum statistic.

Data Source:
ECV eCRF form.

Proportion of patients at Week 24 Visit who are receiving study drug and have not had an AF/AFL event. Tested with a Cochran-Mantel-Haenszel statistic to control for the four stratification variables.

Data Source:
ECG (over-read by CEC), DRUGLOG and EOT eCRF forms.
TTM (24-Week Follow-up Period).

Change in NT-proBNP, assessed relative to baseline (Randomization Visit). Change from baseline will be tested for greater reduction in the bucindolol treatment group with the Wilcoxon Rank Sum test because of the expected lack of normality of this measure.

Data source:
LabCorp vendor dataset.

Change in norepinephrine, assessed relative to baseline (Randomization Visit). Change from baseline will be tested for greater reduction in the bucindolol treatment group with the Wilcoxon Rank Sum test because of the expected lack of normality of this measure.

Data source:
LabCorp vendor dataset.

The EQ-5D questionnaire has 5 dimensions (mobility, self-care, usual activities, pain/discomfort and anxiety/depression) and each is self-rated by the patient as no problems, some problems, or severe problems. The results for each dimension will be analyzed individually at both time points. The change from randomization to each visit will be categorized as improved or no change/worsened and the proportions of these categories in both treatment groups will be tabulated with a 2 by 2 table. The bucindolol treatment group will be tested for superior response using a Cochran-Mantel-Haenszel statistic to control for the four stratification variables.

Data source:
EQ-5D eCRF form.

Pharmacoeconomic modeling of healthcare utilization. Details of this analysis will be prespecified in a separate analysis plan.

D. Safety Analysis

The following four periods are established for analysis of safety endpoints:

24-Week On-Drug Period: starts at day of randomization and extends to latest visit attended through Week 24 Visit. For patients that discontinue treatment early, data collected through 30 days after the final dose of study treatment are included.

24-Week On-Study Period: starts at day of randomization and extends to latest visit attended through Week 24 Visit. For patients that discontinue the study prior to Week 24, data collected through 30 days after the final study visit are included. Study treatment status is not considered for data inclusion.

Total Study On-Drug Period: starts at day of randomization and extends through 30 days after the final dose of study treatment.

Total Study On-Study Period: starts at day of randomization and extends through 30 days after final clinic visit attended. Study treatment status is not considered for data inclusion.

Analysis of SAEs will be performed for all four timeframes. For the other safety endpoints, the 24-Week On-Study and Total Study On-Study Periods will be used. If treatment group imbalances are observed for an endpoint, it will be further analyzed with the other data inclusion timeframes.

The results for the following safety endpoints will be compared with descriptive statistics between the treatment groups for all patients receiving study treatment. Results collected from first dose of study drug to 30 days after the last dose for each patient will be included in the assessments of safety. Results specific to scheduled visits will be included in the by-visit analyses if they were collected within a ±7-day window for the prescribed visit study day.

Incidence of ACM during the Total Study Period.

Supportive Analyses:
The association of VRR control with mortality will be examined using the final heart rate measurement available for each patient (comparisons will be within the treatment groups).

Data Source:
  DEATH eCRF form.
Incidence of ACM, CV-related hospitalization (as assessed by the Investigator), or withdrawal of study drug due to an AE during the Drug Titration Period.
Data source:
  DEATH, HOSP, EOS and AE eCRF forms.
Incidence of symptomatic heart block during the Total Study Period. Symptomatic Heart
Block is defined as the first of any of the following: 1) 3rd degree heart block (complete heart block); 2) any 2nd degree heart block with the presence of symptoms attributable to, and temporally correlated with the occurrence of heart block which include any of the following: Near-fainting or fainting (syncope)/Dizziness; Weakness or Fatigue; Shortness of breath; Chest pain; or 3) 2nd or 3rd degree heart block requiring implantation of a permanent pacemaker (with or without defibrillator).
Data source:
  CVEVENT and AE eCRF forms.
Overall incidence and severity of treatment-emergent AEs/SAEs over time during the Total Study Period. Also events associated with device implantation. The events will have standardized MedDRA preferred terms and System Organ Classes assigned to them for tabulation.
Supportive analyses:
  Incidence of AEs leading to reduction, interruption or permanent discontinuation of study treatment.
  Incidence of AEs associated with device implantation.
  Incidence of AEs by CYP2D6 metabolizer status.
  Incidence of AEs by α2C AR polymorphisms.
Data source:
  AE eCRF form.
Incidence of neoplasm-related AEs during the Total Study Period. The AEs of special interest will be tabulated according to the following characteristics.
  Development of treatment-emergent neoplastic conditions.
  Progression or worsening of pre-study neoplastic conditions.
  Progression or worsening of treatment-emergent neoplastic conditions.
Data source:
  AE, NEOPLHX and NEOPLAS eCRF forms.
Clinical Chemistry and Hematology.
  Visit collection: screen, start of follow-up Week 0 (protocol versions 1 and 2), Week 4 (protocol versions 3 and 4), Week 12 (protocol versions 3 and 4), Week 24, every 24 weeks during extension, end of treatment and end of study. Screen results will serve as the pre-treatment baseline.
  Change from baseline to each planned study visit of collection will be calculated and analyzed with descriptive statistics.
  The numbers and percentages of patients with values exceeding the bounds of normal ranges will be tabulated for scheduled visits.
  The numbers and percentages of patients with values exceeding the panic bounds each visit.
  Data source:
    LabCorp vendor-supplied dataset.
ECG quantitative parameters.
  Measured at every visit. Randomization Visit measurement prior to first dose will serve as the baseline. Will be analyzed at Week 0, 4, 12 and 24 visits as well as end of treatment and end of study.
  Change from baseline to each analysis visit will be calculated and analyzed with descriptive statistics.
  The numbers and percentages of patients with QTc increase from baseline exceeding 60 ms at any time point during the study.
  Data source:
    ECG eCRF form.
Vital signs and weight (data source: VITALS eCRF form).
  Measured at every in-clinic visit. Randomization Visit measurement prior to first dose will serve as the baseline. Will be analyzed at Week 0, 4, 12 and 24 visits as well as end of treatment and end of study.
  Change from baseline to each analysis visit will be calculated and analyzed with descriptive statistics.
  Data source:
    VITALS eCRF form.
Proportion of patients attaining target study drug dose during the Drug Titration Period. Will be calculated for all patients, those receiving β-blocker therapy prior to randomization and those not previously receiving β-blocker therapy.
  Data Sources:
    VISREC and DRUGLOG eCRF forms.
E. Measurement of Interest and Substudies
1. AF Burden (AFB) Substudy.

In this optional substudy, AFB, defined as the amount of time per day that a patient is in AF/AFL, is measured by implanted Medtronic devices, including cardiac monitors, pacemakers, cardioverter-defibrillators, and cardiac resynchronization therapy. These devices also measure VRR during periods of AF. Approximately 50% of the study participants are expected to participate in the AFB substudy.

The distribution of device types will be presented by treatment group, by patient baseline characteristics, by disease severity, by treatment exposure prior to device implantation and elapsed days to start of the 24-Week Follow-up Period. AFB will be presented as hours/day in graphical displays for each patient with the dates of randomization and initial ECV and other interventions annotated.

The treatment efficacy endpoint will be the time to first device-detected event or ACM, with an event defined as at least 6 hours of AFB in a single day. This endpoint will be analyzed through the Week 24 Visit with the same methodology used for the study primary endpoint. Patients with no AFB data available after the start of the 24-Week Follow-up Period will be excluded. Patients with an implanted therapeutic device that produces paced rhythm which confounds the measurement of AFB will also be excluded.

2. Supportive Analyses

Time to device detected AF/AFL event during the Total Follow-up Period.

The proportion of patients with VRR on the last day demonstrating AF/AFL during the 24-Week Follow-up Period. Will be tested using a Cochran-Mantel-Haenszel statistic to control for the four stratification variables.

The percent of follow-up days in AFB, calculated as the number of days with AFB of at least six hours divided by the total number of days in the 24-Week Follow-up Period. Statistical testing will be performed with the Wilcoxon Rank Sum Statistic. A sensitivity analysis will be performed on the subset of patients beginning the 24-Week Follow-up Period in SR.

3. Data Sources
  i.) Medtronic Vendor-Supplied Dataset
  DNA Bank, with collection at time of screening, for patients who agree to participate in the substudy. No analysis of these data have been pre-planned.

Sparse sampling of bucindolol hydrochloride plasma concentrations for population pharmacokinetic analysis. The analysis plan for the substudy will be prepared separately prior to unblinding.

F. GENETIC-AF Clinical Trial. Phase 2B Statistical Analysis Plan Amendment

1. Rationale for Phase 2B statistical Analysis Plan

On the pre-specified first interim analysis of the GENETIC-AF trial conducted on Aug. 7, 2017, based on application of pre-defined Bayesian predictive probability of success (PPoS) modeling of the "modified primary endpoint" data, the GENETIC-AF Data and Safety Monitoring Board (DSMB) recommended completing the trial in Phase 2B rather than immediately stopping for futility or "seamlessly" transitioning to Phase 3. Shortly thereafter, the Sponsor informed the trial investigators of the DSMB decision and instructed sites to complete follow-up of all randomized patients by Dec. 31, 2017. This implies that 267 patients will constitute the final Phase 2B population, with nearly all of them having completed the planned 24 weeks of follow-up or having reached the Phase 2B modified primary endpoint (hereafter referred to as the Phase 2B primary endpoint) of time to symptomatic or asymptomatic atrial fibrillation/atrial flutter (AF/AFL) or all-cause mortality (ACM).

The DSMB Phase 2B interim analysis, conducted and reported to the Sponsor on Aug. 7, 2017 was based on 103 AF/AFL/ACM events from 215 patients randomized through Jun. 19, 2017 including 162 who had attained full follow-up or experienced the Phase 2B primary endpoint. In contrast, the completed Phase 2B dataset on 267 patients will likely include approximately 50% more Phase 2B primary endpoint events. Currently the patients are attending final study visits and all data are being subjected to full monitoring QA during close-out of each site. ARCA expects to receive the final data and treatment assignments in February of 2018.

The GENETIC-AF Statistical Analysis Plan (SAP)1, which focused primarily on analyses pertinent to the Phase 3 population, was completed on Mar. 15, 2017 and submitted to FDA on Mar. 30, 2017. In the Phase 3 SAP, the primary efficacy endpoint is time to symptomatic AF/AFL or ACM, which was powered based on an expectation of 330 events from a total of approximately 620 patients. As this study is now stopping at Phase 2B, ARCA estimates that the total number of events will be less than half of what was planned for the full Phase 3 study. As such, the prespecified analysis described in the SAP for the Phase 3 primary endpoint is not expected to provide adequate guidance to the Sponsor regarding the utility of conducting a reasonably sized Phase 3 trial based on a time to AF/AFL/ACM primary endpoint.

The DSMB charter2 was approved on Oct. 13, 2015 and submitted to FDA on Oct. 16, 2015. In the charter, the DSMB acknowledges that a traditional time-to-first AF/AFL/ACM event analysis would have very low statistical power for a population of 200-250 patients; therefore, the DSMB charter and an accompanying white paper3 outlined a Bayesian methodology for the interim analysis that would be more informative for the Phase 2B population. More specifically, the DSMB charter identified time to first event of symptomatic or asymptomatic AF/AFL or ACM as the primary efficacy endpoint for the Phase 2B interim analysis, since this more inclusive endpoint was expected to have significantly more events than the Phase 3 primary endpoint (i.e., symptomatic AF/AFL or ACM). ARCA's ongoing review of blinded data supports this conclusion, with approximately 75% of first AF/AFL events being adjudicated as symptomatic and 25% of events being adjudicated as asymptomatic.

Therefore, Sponsor plans to conduct the primary efficacy analysis of this Phase 2B study in a similar manner, following the Bayesian methodology that was prespecified in the DSMB charter for the Phase 2B interim analysis. As described below, these analyses will model the Phase 2B data to generate Bayesian predictive probability of success (PPoS) values for a discrete Phase 3 trial with 620 randomized patients who have accrued 330 events (i.e., symptomatic or asymptomatic AF/AFL or ACM). Additional Bayesian modeling will also be performed for Phase 3 planning purposes but these analyses will be secondary to the Phase 2B primary efficacy analysis described above. ARCA will also perform all analyses described in the GENETIC-AF SAP, recognizing that most of these endpoints (e.g., symptomatic AF/AFL, hospitalizations, mortality) will be significantly under powered and primarily hypothesis-generating in nature.

2. Description of Phase 2B Statistical Analyses

As described in the DSMB Charter2, the of time to first event of AF/AFL or ACM endpoint will be subjected to Bayesian modeling for derivation of PPoS estimates by Berry Consultants, Austin Tex. (Dr. Ben Saville, Project Lead). The PPoS bands and boundaries, identical to those described in the first interim analysis, are given in FIG. 2 and will be used to inform/guide the Sponsor. The primary efficacy analysis will be based on Bayesian modeling of the Phase 2B data assuming a discrete Phase 3 population of 620 patients with 330 events (i.e., symptomatic or asymptomatic AF/AFL or ACM).

A secondary analysis will also be performed based on Bayesian modeling of the Phase 2B data assuming a discrete Phase 3 population of 820 patients with 440 events (i.e., symptomatic or asymptomatic AF/AFL or ACM). This secondary analysis reflects what ARCA believes is the approximate upper bounds of clinical feasibility for a Phase 3 trial, and was the final sample size planned for the current study if the second (Phase 3) interim analysis described in the DSMB Charter2 indicated that the data was in the "promising zone"4.

As described in Section 3.2.1 of the GENETIC-AF SAP1, sensitivity analyses will be performed on both the primary and secondary models described above for the subset of patients who began the 24-week Follow-up Period in sinus rhythm. Additional exploratory analyses may also be performed with other sample sizes and event rates, as necessary.

All analyses described above will also be repeated for the symptomatic AF/AFL or ACM endpoint; however, since there are significantly fewer events for this endpoint these analyses are considered exploratory and the PPoS boundaries in FIG. 2 do not directly apply.

To determine if modification of inclusion/exclusion criteria could improve the design of a future Phase 3 trial, exploratory Bayesian analyses will be conducted following the primary (i.e., 620 patients/330 events) and secondary (i.e., 820 patients/440 events) models described above to explore treatment effects in various subgroups.

1) Subgroups of interests are prespecified in Section 3.2.1 of the GENETIC-AF SAP[1]. For the Phase 2B analysis, the following subgroups have been prioritized in order of importance based on pathophysiological and/or clinical relevance:

a) Randomized in sinus rhythm versus AF/AFL
b) LVEF at randomization: ≤0.35 versus >0.35
c) History of persistent AF versus paroxysmal AF
d) Geographic region (USA, Canada, or Europe)

Due to well-known issues associated with inflated false positive rates with subgroup analyses, these analyses will focus on estimation rather than hypothesis testing, and will incorporate Bayesian hierarchical methods to shrink estimated treatment effects in subgroups toward the respective estimate in the overall study population. The GENETIC-AF Steering Committee, which consists of AF and heart failure experts will review the subgroup analyses and determine whether there exists sufficient biologic or clinical plausibility to support further development in any of the subgroups.

3. Classification of Heart Failure by LVEF.

The definition of heart failure with reduced LV ejection fraction based on a lower limit of normal of 0.50 (104, 105) was used to define HFrEF (LVEF <0.50 and a history of HF). HFrEF patients were subdivided into HFmrEF (HF with mid-range LVEF) according to Ponikowski et al. as HF with an LVEF ≥0.40 and <0.50 (3), and HFlrEF (HF with "lower-range" LVEFs <0.40).

4. Modeling of Variables and Selection of Optimal Boundaries for Therapeutic Phenotypes In this exploratory Phase 2 trial with limited sample size and statistical power, we employed precision therapeutic phenotyping to identify HF populations who respond differentially to two beta-blockers based on genetic targeting. This approach circumvents potential issues associated with conventional subset analyses by evaluating monotonicity and consistency of trends across the full continuum of candidate variables. The benefit of deriving these therapeutic phenotype characteristics from continuous variables is that the classifiers are readily conducive to numerical calibration. With discrete and/or categorical classifiers, a hypothetical predictor variable is either correct or not, with limited or no gradation possible as a hedge against spuriousness. For the calibration of the continuous variable DxT and DTRI, one could select more restrictive criteria such as DxT10/DTRI-1 (i.e., <10 years of AF and HF with AF not preceding HF by more than 1 year), which yields a similar treatment effect estimate (HR=0.51; 95% CI: 0.30, 0.85) compared to DxT12/DTRI-2 (HR=0.54; 95% CI: 0.33, 0.87); whereas, more inclusive criteria such as DxT15/DTRI-3 results in only a slight loss of signal (HR=0.63; 95% CI: 0.40, 0.98). We propose that increasing the permissible limits of variation (i.e., tolerance) for the phenotype selection criteria increases the likelihood of reproducibility of these results in future studies.

Example 8

Precision AF Phase 3 Trial

This Example describes a proposed Phase 3 trial.

A. Study Overview

Rationale: Most anti-arrhythmic agents currently approved for the treatment of atrial fibrillation (AF) and atrial flutter (AFL) are either contraindicated or have label warnings for use in heart failure (HF) patients with reduced left ventricular ejection fraction (LVEF) due to an increased risk of mortality in this patient population.

Bucindolol hydrochloride (bucindolol) is a nonselective β-adrenergic receptor (AR) blocking agent with mild vasodilator properties, which was previously studied in the BEST Phase 3 HF trial. In a large pharmacogenomic substudy of the BEST trial, bucindolol was shown to interact with AR polymorphism in such a way that targeting specific genotypes of these variants could improve therapeutic index. Specifically, HF patients who have a β1-AR 389 arginine homozygous genotype (i.e., ADRB1 Arg389Arg) had more efficacious treatment responses to bucindolol, as assessed by HF clinical outcomes and the reduction of new onset AF, compared to patients with ADRB1 389Gly homozygous or heterozygous genotypes (i.e., ADRB1 389Gly carriers). These pharmacogenetic effects are thought to be due to two unique pharmacologic properties of bucindolol, sympatholysis (i.e., lowering of plasma norepinephrine) and $\beta_1$-AR inverse agonism (i.e., inhibition of constitutively active receptors).

GENETIC-AF was a Phase 2B trial conducted in the U.S., Canada, and Europe that compared bucindolol to metoprolol succinate (Toprol-XL) for the prevention of recurrent AF/AFL or ACM in HF patients with the ADRB1 Arg389Arg genotype. The trial randomized HF patients with mid-range LVEFs (≥0.40 and <0.50, "HFmrEF") and HF patients with lower-range LVEFs (<0.40, "HFlrEF"). Similar results were observed in the overall population for the primary endpoint based on intermittent ECG monitoring (N=267; HR=1.01; 95% CI: 0.71, 1.42), but a trend for bucindolol benefit was observed in a prespecified analysis of the U.S. subgroup (N=127; HR=0.70; 95% CI: 0.41, 1.19). In a substudy of patients who underwent continuous heart rhythm monitoring with implanted devices, a trend for bucindolol benefit was observed in the overall substudy population (N=69; HR=0.75; 95% CI: 0.43, 1.32) and in the U.S. substudy cohort (N=42; HR=0.50; 95% CI: 0.17, 1.42) for a prospectively-defined time to first AF/AFL event endpoint based on ≥6 hours per day of device-detected AF burden. In a post-hoc analysis of the GENETIC-AF primary endpoint that excluded patients with long-standing AF or HF >12 years, strong trends for bucindolol benefit were observed (N=230; HR=0.68; 95% CI: 0.45, 1.02), which achieved statistical significance when this population was restricted to patients who did not have AF more than 2 years prior to developing HF (N=196; HR=0.54; 95% CI: 0.33, 0.87; p=0.011). In this population, a significant reduction in the primary endpoint was also observed for bucindolol compared to metoprolol in the HFmrEF cohort (N=91; HR=0.42; 95% CI: 0.21, 0.86; p=0.017); whereas, a non-significant trend was observed in the HFlrEF cohort (N=105; HR=0.69; 95% CI: 0.33, 1.43).

Metoprolol succinate (Toprol-XL) is the active comparator for the trial. Metoprolol succinate is a $\beta_1$-AR selective β-blocker that is FDA approved for the treatment of stable, symptomatic (NYHA Class II or III) HF of ischemic or non-ischemic origin. Metoprolol succinate has demonstrated mild efficacy for the prevention of new onset AF in a HF with reduced ejection fraction (HFrEF) patient population and is often used off-label in this setting (Class IIa indication with a "C" level of evidence for AF prevention per ACC/AHA/ESC Joint Guidelines). In a previous study, metoprolol succinate decreased the incidence of AF recurrence, compared to placebo, in patients with AF who had recently undergone electrical cardioversion (ECV) to sinus rhythm (SR). In contrast to bucindolol, metoprolol succinate does not appear to confer added clinical benefits in HFrEF patients that have a ADRB1 Arg389Arg genotype. In addition, limited data from the MERIT-HF DNA substudy did not indicate any evidence of a ADRB1 Arg389Gly polymorphism differential effect for preventing AF. Finally, metoprolol succinate does not lower norepinephrine and is not a $\beta_1$-AR inverse agonist.

Objectives: The primary objective of this study is to compare the effects of bucindolol and metoprolol succinate on AF events in a genotype-defined ADRB1 Arg389Arg HFmrEF population at risk for AF recurrence.

The secondary objectives of this study are to compare the effects of bucindolol and metoprolol on patient reported symptoms and HF clinical outcomes, as well as AF burden and ventricular response rate (VRR) in a subgroup of patients participating in the continuous monitor (CM) substudy. The safety and tolerability of bucindolol and metoprolol will also be evaluated.

Design: PRECISION-AF is a double-blind, two-arm, genotype-directed, active-controlled, superiority study that compares the effects of bucindolol and metoprolol succinate on the time to first AF event in a genotype-defined ADRB1 Arg389Arg HFmrEF population at risk for AF recurrence.

Patients must have an initial HF diagnosis documented within the past 12 years, a LVEF ≥0.40 and <0.50 for their most recent assessment in the past 12 months, and no contraindication for β-blocker therapy. Patients must have an initial AF diagnosis documented within the past 12 years and the date of the initial AF diagnosis cannot precede the date of the initial HF diagnosis by more than 2 years. Patients must have current or recent history of persistent or paroxysmal AF and be clinically indicated for ECV if not in SR. Patients will be genotyped for ADRB1 Arg389Gly at screening and those who are ADRB1 Arg389Arg (~50% of patients) will be eligible for the trial.

A subset of patients participating in the trial will have their cardiac rhythm continuously monitored to assess AF burden (AFB). AFB monitoring will be done via Medtronic insertable cardiac monitors (ICM) or other pre-existing Medtronic devices that can measure AFB. Patients who agree to have a Medtronic device inserted for the trial may do so at the Randomization Visit or at any time prior to the start of the 26-week Follow-up Period.

Eligible patients will be randomized (1:1) to blinded treatment with bucindolol or metoprolol (i.e., study drug) and up-titrated weekly to a target dose of 200 mg per day of bucindolol (100 mg BID) or metoprolol (200 mg QD). Randomization will be centralized and stratified by: 1) rhythm at randomization (SR vs. AF); 2) previous class III anti-arrhythmic drug use (Yes vs. No); 3) previous ablation (Yes vs. No); 4) implanted device (Yes vs. No).

Patients who are in SR after the 4-week Drug Lead-in Period will start the 26-week Follow-up Period at the Week 0 Visit. Patients in AF after the 4-week Drug Lead-in Period will undergo ECV at the Week 0 Visit to establish SR on study drug prior to start of the 26-week Follow-up Period. The first ECV attempt may be performed up to 8 weeks after randomization if, in the opinion of the Investigator, additional time is needed to attain the appropriate dose of study drug or to adjust anticoagulation status prior to ECV. ECV procedures performed before completion of the 4-week Drug Lead-in Period are discouraged and require pre-approval by the Sponsor or its designee.

The primary endpoint (i.e., time to first AF/AFL event) will be assessed during the 26-week Follow-up Period after establishment of SR on study drug. For patients requiring ECV, establishment of SR on study drug will be confirmed by electrocardiogram (ECG) at least 30 minutes following ECV. Patients who do not demonstrate SR following the first ECV procedure will undergo a second ECV procedure within two weeks of the initial attempt to establish baseline SR prior to the start of efficacy follow-up unless, in the opinion of the Investigator, it would not be the best course of treatment for the patient. The 26-week Follow-up Period will begin on the day of the ECG that establishes SR on study drug or on the day of the last ECV procedure for patients who fail to convert to SR on study drug prior to the start of follow-up.

During the 26-week Follow-up Period, heart rhythm will be assessed by 12-lead ECG at each clinic visit. At the time of each ECG assessment, patients will be queried for symptoms potentially related to AF/AFL. Patients will be queried for symptoms potentially related to AF/AFL at all unscheduled clinic visits during the 26-week Follow-up Period and a 12-lead ECG must be collected if new or worsening symptoms are reported. Patients experiencing an AF/AFL event will be encouraged to remain on blinded study drug and may undergo subsequent procedures or medical interventions as clinically indicated.

After the Week 26 Visit, patients will enter the Treatment Extension Period and continue to receive blinded study drug. Follow-up will continue until at least 400 patients have been randomized and 235 primary endpoint events have been observed in the 26-week Follow-up Period. At this time, all patients will complete the 26-week Follow-up Period or return to the clinic for an End of Study Visit if already in the Treatment Extension Period. At the end of the study, patients will discontinue study drug and transition to commercially-available β-blocker therapy per Investigator discretion. Investigators and patients will not be informed of the treatment assignment at the time of transition off study drug.

The trial utilizes an interim analysis/adaptive design methodology that will examine preliminary results from an initial population (N=250) with evaluable data for the primary endpoint. The interim efficacy analysis has three potential outcomes: 1) early termination of the trial for futility; 2) completion of the trial at the planned sample size of 400 patients, or; 3) completion of the trial with an expanded sample size of 550 patients if conditional power calculations are within promising zone boundaries.

Number of Patients: The trial is designed to randomize approximately 400 patients, with a possible increase to 550 patients if dictated by "promising zone" conditional power calculations on interim analysis. The ADRB1 Arg389Arg genotype is expected in approximately 50% of screened patients and a 65% screen-fail rate is assumed for the study (15% for general criteria and a 50% screen-fail rate due to genotype). Therefore, it is estimated that approximately 1150 patients will be screened to randomize 400 patients.

Number of Centers: Approximately 100 centers will be included in this global study. For the planned sample size of 400 patients, a maximum of 40 randomized patients per center is permitted (i.e., 10% of total enrollment).

Treatment Duration: Patients will be eligible to receive study drug for a minimum of 30 weeks and will continue to receive study drug until at least 400 patients have been randomized and 235 primary endpoint events have been observed in the 26-week Follow-up Period (currently estimated to require 3.5 years from the time of first patient randomization).

Inclusion Criteria: Patients must meet all of the following inclusion criteria to be eligible for randomization in this study.
1. Age ≥18 years and ≤85 years at the Screening Visit.
2. Weight ≥40 kg at the Randomization Visit.
3. Possess the ADRB1 Arg389Arg genotype.
4. History of HF with initial diagnosis documented <12 years prior to the Screening Visit.
5. Documented history of the following <12 years prior to the Screening Visit:

a. HF symptoms (e.g. breathlessness, fatigability, paroxysmal nocturnal dyspnea, orthopnea) and/or HF signs (e.g. evidence of volume overload)
b. At least one of the following:
   i. BNP ≥100 pg/ml
   ii. NT-proBNP ≥125 pg/ml (age ≤75 years) or ≥400 pg/ml (age >75 years).
   iii. HF hospitalization.
6. LVEF ≥0.40 and <0.50 per most recent assessment <12 months prior to the Screening Visit.
   a. Heart rate <120 bpm at time of assessment for LVEF ≥0.45 and <0.50 if evaluated in AF/AFL.
7. History of AF with initial diagnosis documented <12 years prior to the Screening Visit.
8. At least one symptomatic paroxysmal or persistent AF episode ≤120 days of the Screening Visit.
   a. Qualifying AF episode documented by ECG, Holter, TTM, ECG patch, or implanted device. Documentation by implanted device requires a single episode ≥60 minutes in duration.
   b. Must have experienced new or worsening symptoms related to the qualifying AF episode, in the opinion of the Investigator.
   c. Atrial flutter in the absence of AF is not a qualifying AF episode.
9. Clinically indicated for ECV and willing to undergo ECV if not in SR at the Week 0 Visit.
10. Receiving guideline indicated oral anticoagulation therapy considered optimal for stroke prevention in the opinion of the Investigator, at the Randomization Visit and throughout the study unless contraindicated.
11. Systolic blood pressure >90 mmHg and <150 mmHg at the Randomization Visit.
12. Female of childbearing potential must have a negative serum pregnancy test at screening, a negative urine pregnancy test at randomization, and must agree to use highly effective contraception for the duration of the trial and for at least 30 days following the last dose of study drug.
    a. Female who is surgically sterile or post-menopausal for at least 12 months is not considered to be of childbearing potential.
13. Must agree not to participate in a clinical study involving another investigational drug or device throughout the duration of this study.
    a. Exception for non-experimental registries allowing participation in a randomized trial.
14. Must be competent to understand the information given in the Institutional Review Board (IRB) or Independent Ethics Committee (IEC) approved informed consent form (ICF). Must sign the ICF prior to the initiation of any study procedure and not withdraw consent prior to the Randomization Visit.

Exclusion Criteria: Patients who meet any of the following exclusion criteria are not eligible for randomization in this study.
1. NYHA Class IV symptoms at the Randomization Visit.
2. Significant fluid overload at the Randomization Visit, in the opinion of the Investigator.
Evidence of significant fluid overload may include:
   a. Mean jugular venous pressure above the clavicle at 90°.
   b. Liver congestion.
   c. Moist pulmonary rales post-cough.
   d. Peripheral edema beyond 1+ pedal not explained by local factors.
3. Initial AF diagnosis >2 years (730 days) prior to the initial HF diagnosis.
4. Permanent AF at the Screening Visit.
   a. Permanent AF is defined as an ongoing AF event 1 year or longer in duration with no intervening evidence of SR and no intent for rhythm control interventions.
5. More than two ECV procedures ≤6 months of the Randomization Visit or if the most recent ECV ≤6 months of the Randomization Visit failed to produce SR.
6. History of an AF or AFL ablation ≤30 days of the Randomization Visit.
7. Use of any of the following at the Randomization Visit:
   a. Amiodarone, disopyramide, dofetilide, dronedarone, flecainide, propafenone, sotalol,
   non-dihydropyridine calcium channel blockers, daily NSAIDS (e.g., ibuprofen, celecoxib), thiazolidinediones, or frequent use of short acting nitroglycerin (e.g., >6 sublingual tablets/week).
8. Use of strong inhibitors of cytochrome P450 CYP2D6 (e.g., fluoxetine, paroxetine, propafenone, quinidine, or ritonavir) at the Randomization Visit for patients who were not receiving β-blocker therapy during the screening period.
9. Evidence of an appropriate firing of an ICD device for ventricular tachycardia (VT) or ventricular fibrillation (VF) ≤90 days of the Randomization Visit.
   a. Exception: does not include anti-tachycardia pacing.
10. History of a successful atrioventricular node ablation.
11. History of untreated second-degree Mobitz II or third-degree heart block.
12. History of untreated symptomatic bradycardia or if symptomatic bradycardia is likely on full dose of study drug in the opinion of the Investigator.
13. Heart rate <60 beats per minute at the Randomization Visit for patients who were not receiving β-blocker therapy during the screening period.
14. Contraindication to β-blocker therapy or history of intolerance to low-dose β-blocker therapy (e.g., 25 mg QD metoprolol or equivalent).
15. Myocardial infarction, unstable angina, acute coronary syndrome cardiac surgery (including PTCA or stent placement), or evidence of new ischemic changes as assessed by ECG ≤90 days of the Randomization Visit.
16. History of pulmonary hypertension, defined as a systolic pulmonary arterial pressure ≥70 mmHg at rest, as assessed by echocardiography or right heart catheterization.
17. Known reversible causes of AF such as alcohol intoxication, pulmonary embolism, hyperthyroidism, acute pericarditis, or hypoxemia.
18. Untreated thyroid disease, in the opinion of the Investigator, at the Randomization Visit.
19. Serum potassium <3.5 mmol/L at the Screening Visit.
    a. Assessed by the central lab at the Screening Visit. Any exclusionary results must be corrected prior to randomization as documented by either the central or local lab.
20. Renal failure requiring dialysis, serum creatinine >2.5 mg/dL, or an estimated creatinine clearance <30 mL/min (Cockcroft-Gault) at the Screening Visit.
    a. Assessed by the central lab at the Screening Visit. Any exclusionary results must be corrected prior to randomization as documented by either the central or local lab.

21. Significant intrinsic liver disease or a total bilirubin >2.5 mg/dL at the Screening Visit.
   a. Assessed by the central lab at the Screening Visit. Any exclusionary results must be corrected prior to randomization as documented by either the central or local lab.
22. Participation in a clinical study or treatment with an investigational drug or device within 30 days of the Screening Visit (or 5 half-lives of the investigational agent, whichever is longer).
   a. Exception for non-experimental registries allowing participation in a randomized trial.
23. Comorbid condition or illness which, in the opinion of the Investigator, may limit life expectancy to less than 1 year.
24. Serious or active medical or psychiatric condition which, in the opinion of the Investigator, may interfere with treatment, assessment, or compliance with the protocol.
25. Treatment for a malignancy within 2 years of screening, the presence of a treated malignancy that has evidence of disease progression, or the presence of a malignancy expected to require radiation therapy, chemotherapy, hormonal treatment, or surgical intervention during the study.
   a. Exceptions for localized resectable skin carcinomas, in situ carcinomas of the cervix, and lowgrade prostate cancers.
26. History of alcohol, drug, or chemical abuse that, in the opinion of the Investigator, could impair or limit the patient's full participation in the study.

Randomized Treatment:
Patients not receiving β-blocker therapy at randomization will initiate study drug at 25 mg per day bucindolol (12.5 mg BID) or Toprol-XL (25 mg QD) and will be up-titrated in a blinded manner to the target dose. Study drug will be administered twice-daily to maintain the blind.
Patients receiving β-blocker therapy during screening will discontinue treatment at the time of randomization, initiate study drug at a daily dose equivalent to 50% of the commercial dose, and up-titrate in a blinded manner to the target dose.
Study drug should be up-titrated to the target dose for all patients unless a clinical contraindication is documented. Target dose for study drug is 200 mg per day bucindolol or Toprol-XL
Investigators should make every reasonable attempt to up-titrate study drug on a weekly schedule but can delay up-titration if required clinically (e.g., up-titration at a two-week interval). Up-titration intervals shorter than one week require prior approval from the Sponsor or its designee.
Study drug may continue to be up-titrated after the start of the 26-week Follow-up Period.
Study drug dose may be reduced at any time in the event of documented intolerance.
At the end of the study, patients will discontinue study drug and transition to commercially-available β-blocker therapy per Investigator discretion. Transition to commercial β-blocker therapy is recommended to occur in a similar manner as described for initiation of blinded β-blocker therapy.

Figure 32:
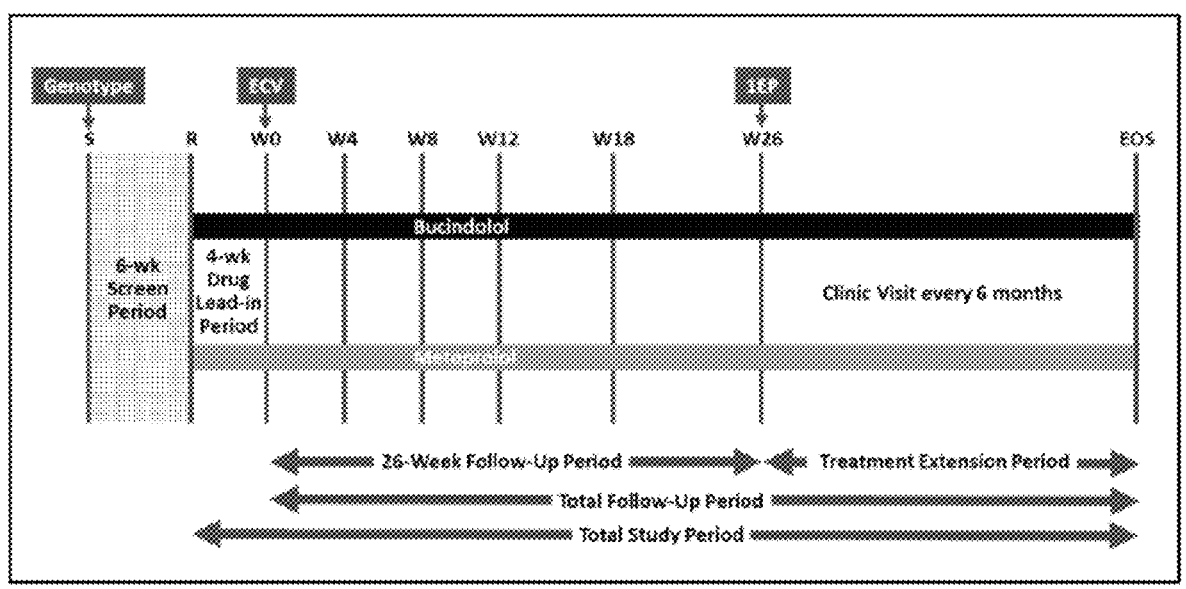
FIG. 32. Visit schedule for proposed Precision AF Phase 3 Trail.

Visit Schedule (See FIG. 32):
There is a maximum of 6 weeks between the Screening Visit and the Randomization Visit.
During the Drug Lead-in Period, up-titration of study drug will be managed via Titration Visits. The number and timing of these Titration Visits will vary by patient to provide flexibility for optimal patient management. After the Week 0 Visit, Investigators may continue to up-titrate study drug at scheduled or unscheduled clinic visits.
If needed, the first ECV should occur 4 weeks after randomization, but may be performed up to 8 weeks after randomization if, in the opinion of the Investigator, additional time is needed to attain the appropriate dose of study drug or to achieve appropriate anticoagulation status prior to ECV. ECV procedures performed before completion of the 4-week drug lead-in period are discouraged and require pre-approval by the Sponsor or its designee.
During the 26-week Follow-up Period, patients will return to the clinic at scheduled intervals for routine assessments of efficacy and safety (Weeks 4, 8, 12, 18, and 26).
During the Treatment Extension Period, patients will return to the clinic every 6 months for routine assessments of efficacy and safety.
Follow-up will continue until at least 400 patients have been randomized and 235 primary endpoint events have been observed in the 26-week Follow-up Period. After this event, all patients will complete the 26-week Follow-up Period or return to the clinic for an End of Study Visit if already in the Treatment Extension Period.

Primary Endpoint:
Time to first AF/AFL or ACM event during a 26-week Follow-up Period, defined as any of the following:
   Symptomatic AF/AFL as assessed by 12-lead ECG
      Associated with a clinically relevant change in patient-reported symptoms
   Clinical intervention for AF/AFL, defined as clinical evidence of AF/AFL and any of the following:
      Initiation of any anti-arrhythmic drug for pharmacological cardioversion
      Electrical cardioversion (ECV)
      Ablation
   All-cause mortality
Potential AF/AFL events will be adjudicated by a blinded Clinical Events Committee (CEC).

Secondary Endpoints:
Percent experiencing symptomatic bradycardia or bradycardia leading to dose reduction or discontinuation of study drug during the 26-week Follow-up Period.
Percent attaining target study drug dose during the Drug Titration Period.
Change from baseline in the overall score of the Atrial Fibrillation Effect on QualiTy-of-life (AFEQT) Questionnaire.
Time to first event of HF hospitalization or cardiovascular mortality (CVM) during the Total Study Period (as assessed by the Investigator).

Safety Endpoints:
Incidence of ACM during the Total Study Period.
Incidence of CVM, cardiovascular-related hospitalization (as assessed by the Investigator), or withdrawal of study drug due to a serious adverse event (SAE) during the Drug Titration Period.
Incidence of stroke, TIA, or other thromboembolism during the Total Study Period.
Incidence and severity of SAEs during the Total Study Period.

Incidence of neoplasm-related SAEs during the Total Study Period.

Change from baseline in clinical laboratory tests over time during the Total Study Period.

Change from baseline in vital signs and weight over time during the Total Study Period.

Relationship of CYP2D6 poor metabolizers to SAEs.

Substudies and Other Endpoints:

Change from baseline in the overall score of the Minnesota Living with Heart Failure (MLHF) Questionnaire.

Change from baseline in the EQ-5D Questionnaire.

Population Pharmacokinetic Analysis.

Pharmacoeconomic modeling of healthcare utilization.

AFB for patients who agree to participate in the optional continuous monitor (CM) substudy.

AFB is defined as the amount of time per day that a patient is in AF/AFL, as measured by a Medtronic implanted device.

VRR during periods of AF/AFL, as collected by implanted Medtronic devices.

Optional DNA Bank for patients who agree to participate in the DNA substudy.

B. Treatment of Atrial Fibrillation in Heart Failure

Most anti-arrhythmic agents with AF indications are either contraindicated or have significant label warnings for use in HF patients due to an increased risk of mortality, particularly in HFlrEF. In the United States, drug therapy is confined to the Class 3 antiarrhythmic agents, amiodarone and dofetilide, and amiodarone is not approved for this indication. In addition, amiodarone has multiple toxicities, is proarrhythmic, and likely increases mortality in HFlrEF.25, 26 Although the pro-arrhythmia of dofetilide can be reduced by in-hospital monitoring of QT interval on institution of therapy, this requirement of dofetilide use does not preclude drug induced Torsades de Pointes. Considering these safety concerns, as well as the negative clinical consequences of AF in HF patients, there is a clear unmet medical need for a drug that is effective in preventing AF in HF.

β-blockers, which are currently indicated for the treatment of HFlrEF, have demonstrated mild efficacy for the prevention of new onset AF and are often used off-label in this setting (Class IIa indication with a "C" level of evidence for AF prevention per ACC/AHA/ESC Guidelines). In a meta-analysis of HF trials comparing beta blocker against placebo, the mean relative risk for developing AF was 0.73 (0.61, 0.86).

HFmrEF is a recently defined population of HF patients for whom there are no guidelines/indications for beta-blockers or other HF therapies. Data on the efficacy of β-blockers in HFmrEF is very limited and has been explored largely through analysis of β-blocker HF trials or registries that have included left ventricular ejection fraction in the mid-range (40-49%). In a meta-analysis of 575 HFmrEF patients, there was a trend for reduction in CVM or CVH with β-blockers in sinus rhythm (HR 0.83; 95% CI: 0.60, 1.13) but not in AF (HR 1.06; 95% CI: 0.58, 1.94), which is similar to what has been reported in HFlrEF. The efficacy of β-blockers for prevention of AF in HFmrEF patients has not been reported.

In a meta-analysis by Nasr et al, the annualized event rate for the development of AF was 5.3% for placebo and 3.8% for β-blocker treatment. This low order event rate would dictate a very large sample size (i.e., >4,000 patients) if new onset AF was the primary endpoint for a HF clinical trial. However, there is a patient population in which the onset of AF is much higher in frequency—patients with paroxysmal or persistent AF who have recently undergone electrical cardioversion (ECV) to SR. In the latter setting, approximately 50% of patients will experience a recurrence of AF within 6 months of ECV to SR, even with the use of Class I and Class III anti-arrhythmic drugs.38 In study populations that included both HF and non-HF patients, β-blockers have demonstrated a reduction in risk (effect size) for the recurrence of AF on the order of 30%, which is similar to the effects observed in major β-blocker HF trials for new onset AF.30 In one study, patients with symptomatic persistent AF were treated with metoprolol (n=83) or placebo (n=85) and underwent ECV to SR approximately one week after treatment initiation. At the end of the 6-month follow-up period, the incidence of AF recurrence was significantly lower ($p<0.01$) in the metoprolol group (52%) compared to the placebo group (74%), with significant differences observed between the groups as early as one week post-ECV ($p<0.05$). Earlier studies in similar patient populations (i.e., persistent AF recently converted to SR) have shown similar event rates for the recurrence of AF following ECV. For example, Katritsis et al compared the effects of carvedilol (n=43) and bisoprolol (n=47) in patients with persistent AF recently converted to SR and observed AF recurrence rates of 32% and 46%, respectively. Similarly, Plewan et al compared the effects of sotalol (n=64) and bisoprolol (n=64) in patients with persistent AF recently converted to SR and observed AF recurrence rates of 41% and 42%, respectively. In both of these studies, nearly all AF events occurred during the first 6 months post-ECV. In contrast to the lower event rates observed for new onset AF, the event rates expected for recurrent symptomatic AF would allow for adequately-powered and wellcontrolled comparative studies to be conducted in a reasonable timeframe.

C. Study Design

PRECISION-AF is a double-blind, two-arm, genotype-directed, active-controlled, superiority study that compares the effects of bucindolol and metoprolol succinate on the time to first AF/AFL event in a genotype-defined ADRB1 Arg389Arg HFmrEF population at risk for AF recurrence.

Patients must have an initial HF diagnosis documented within the past 12 years, a LVEF ≥0.40 and <0.50 for their most recent assessment in the past 12 months, and no contraindication for β-blocker therapy. Patients must have an initial AF diagnosis documented within the past 12 years and the date of the initial AF diagnosis cannot precede the date of the initial HF diagnosis by more than 2 years. Patients must have a current or recent history of persistent or paroxysmal AF and be clinically indicated for ECV if not in SR. Patients will be genotyped for ADRB1 Arg389Gly at screening and those who are ADRB1 Arg389Arg (~50% of patients) will be eligible for the trial. FIG. 31 shows an analysis of the likelihood of success of the phase 3 trial based on the entry criteria. A high likelihood of success is achieved based on these entry criteria.

A subset of patients participating in the trial will have their cardiac rhythm continuously monitored to assess AF burden (AFB). AFB monitoring will be done via Medtronic insertable cardiac monitors (ICM) or other pre-existing Medtronic devices that can measure AFB. Patients who agree to have a Medtronic device inserted for the trial may do so at the Randomization Visit or at any time prior to the start of the 26-week Follow-up Period.

Eligible patients will be randomized (1:1) to blinded treatment with bucindolol or metoprolol (i.e., study drug) and up-titrated weekly to a target dose of 200 mg per day of bucindolol (100 mg BID) or metoprolol (200 mg QD). Randomization will be centralized and stratified by: 1) rhythm at randomization (SR vs. AF); 2) previous class III anti-arrhythmic drug use (Yes vs. No); 3) previous ablation (Yes vs. No); 4) implanted device (Yes vs. No).

Patients who are in SR after the 4-week Drug Lead-in Period will start the 26-week Follow-up Period at the Week 0 Visit. Patients in AF after the 4-week Drug Lead-in Period will undergo ECV at the Week 0 Visit to establish SR on study drug prior to start of the 26-week Follow-up Period. The first ECV attempt may be performed up to 8 weeks after randomization if, in the opinion of the Investigator, additional time is needed to attain the appropriate dose of study drug or to adjust anticoagulation status prior to ECV. ECV procedures performed before completion of the 4-week Drug Lead-in Period are discouraged and require pre-approval by the Sponsor or its designee.

The primary endpoint (i.e., time to first AF/AFL event) will be assessed during the 26-week Follow-up Period after establishment of SR on study drug. For patients requiring ECV, establishment of SR on study drug will be confirmed by ECG at least 30 minutes following ECV. Patients who do not demonstrate SR following the first ECV procedure will undergo a second ECV procedure within two weeks of the initial attempt to establish baseline SR prior to the start of efficacy follow-up unless, in the opinion of the Investigator, it would not be the best course of treatment for the patient. The 26-week Follow-up Period will begin on the day of the ECG that establishes SR on study drug or on the day of the last ECV procedure for patients who fail to convert to SR on study drug prior to the start of follow-up.

During the 26-week Follow-up Period, heart rhythm will be assessed by 12-lead ECG at each clinic visit. At the time of each ECG assessment, patients will be queried for symptoms potentially related to AF/AFL. Patients will be queried for symptoms potentially related to AF/AFL at all unscheduled clinic visits during the 26-week Follow-up Period and a 12-lead ECG must be collected if new or worsening symptoms are reported. Patients experiencing an AF/AFL event will be encouraged to remain on blinded study drug and may undergo subsequent procedures or medical interventions as clinically indicated.

After the Week 26 Visit, patients will enter the Treatment Extension Period and continue to receive blinded study drug. Follow-up will continue until at least 400 patients have been randomized and 235 primary endpoint events have been observed in the 26-week Follow-up Period. At this time, all patients will complete the 26-week Follow-up Period or return to the clinic for an End of Study Visit if already in the Treatment Extension Period. At the end of the study, patients will discontinue study drug and transition to commercially-available β-blocker therapy per Investigator discretion. Investigators and patients will not be informed of the treatment assignment at the time of transition off study drug.

The trial utilizes an interim analysis/adaptive design methodology that will examine preliminary results from an initial population (N=250) with evaluable data for the primary endpoint. The interim efficacy analysis has four potential outcomes: 1) early termination of the trial for futility; 2) completion of the trial at the planned sample size of 400 patients, or; 3) completion of the trial with an expanded sample size of 550 patients if conditional power calculations are within promising zone boundaries.

D. Visit Schedule

There is a maximum of 6 weeks between the Screening Visit and the Randomization Visit.

During the Drug Lead-in Period, up-titration of study drug will be managed via Titration Visits. The number and timing of these Titration Visits will vary by patient to provide flexibility for optimal patient management. After the Week 0 Visit, Investigators may continue to up-titrate study drug at scheduled or unscheduled clinic visits.

If needed, the first ECV should occur 4 weeks after randomization, but may be performed up to 8 weeks after randomization if, in the opinion of the Investigator, additional time is needed to attain the appropriate dose of study drug or to achieve appropriate anticoagulation status prior to ECV. ECV procedures performed before completion of the 4-week Drug Lead-in Period are discouraged and require pre-approval by the Sponsor or its designee.

During the 26-week Follow-up Period, patients will return to the clinic at scheduled intervals for routine assessments of efficacy and safety (Weeks 4, 8, 12, 18, and 26).

During the Treatment Extension Period, patients will return to the clinic every 6 months for routine assessments of efficacy and safety.

Follow-up will continue until at least 400 patients have been randomized and 235 primary endpoint events have been observed in the 26-week Follow-up Period. After this event, all patients will complete the 26-week Follow-up Period or return to the clinic for an End of Study Visit if already in the Treatment Extension Period.

E. Patient Population

Number of Patients and Study Centers: The trial is designed to randomize approximately 400 patients, with a possible increase to 550 patients if dictated by "promising zone" conditional power calculations on interim analysis.56

The ADRB1 Arg389Arg genotype is expected in approximately 50% of screened patients and a 65% screen-fail rate is assumed for the study (15% for general criteria and a 50% screen-fail rate due to genotype). Therefore, it is estimated that approximately 1150 patients will be screened to randomize 400 patients.

Approximately 100 centers will be included in this global study. For the planned sample size of 400 patients, a maximum of 40 randomized patients per center is permitted (i.e., 10% of total enrollment).

Patient Characteristics and Screening Procedures: Patients must meet all of the inclusion criteria and none of the exclusion criteria listed above to be eligible for randomization in this study. Any patient who fails screening for any reason (other than genotype) may be re-screened two additional times. Patients who are re-screened will be assigned a new screening number and will sign a new informed consent form (ICF). Each screening must be adequately documented in the source documents. Previous screening tests completed within 6 weeks of randomization that still meet the study entry criteria do not need to be repeated for patients who are being re-screened.

F. Dose Rationale

The starting dose of bucindolol will be 25 mg per day (12.5 mg BID) with weekly dose titrations as tolerated until the target dose of 200 mg per day (100 mg BID) is achieved. This is similar to the dosing protocol employed in a previous Phase 2 HF trial in a NYHA Class II-III HF population (dose range: 12.5 to 100 mg BID) and the BEST trial (dose range: 6.25 to 100 mg BID), where on average patients had clinical HF that was more advanced (NYHA Class III-IV) than is anticipated to be the case for the current protocol (i.e., NYHA Class I-III). Bucindolol was well tolerated in GENETIC-AF, with nearly all patients (89%) attaining the protocol-specified target dose (i.e., 50 mg BID for patients <75 kg, and 100 mg BID for patients ≥75 kg). As in GENETIC-AF, most patients randomized in PRECISION-AF are expected to be receiving commercial β-blocker therapy prior to randomization.

The dosing of metoprolol is consistent with the prescribing information for HFrEF, which is based on the methods used in the MERIT-HF trial. Specifically, the starting dose is 25 mg per day (25 mg QD) with weekly dose titrations as tolerated until the target dose of 200 mg per day (200 mg QD) is achieved. Although metoprolol has lower affinity for the human $\beta_1$-AR than bucindolol, metoprolol has a higher bioavailability and much lower protein binding, allowing for equivalent daily target doses of the two study drugs.

Blinding of study drug will be achieved by over-encapsulation of bucindolol and metoprolol tablets using the same capsule size and color.

Patients who are not receiving β-blocker therapy at randomization will initiate study drug at 25 mg per day bucindolol or Toprol-XL and will be up-titrated in a blinded manner to the target dose (Table 51). Patients receiving β-blocker therapy during screening will discontinue treatment at the time of randomization, initiate study drug at a daily dose equivalent to 50% of the commercial dose, and up-titrate in a blinded manner to the target dose.

One capsule of study drug should be taken twice daily (BID), in the morning and then approximately 12 hours later in the evening, unless instructed otherwise. Study drug can be taken with or without food.

The first dose of study drug should be administered in the clinic on the day of randomization after all protocol-specified assessments are completed. Patients receiving commercial β-blocker therapy during the screening period should be instructed to withhold this medication on the day of the Randomization Visit. Patients who do not qualify for randomization may immediately reinitiate their commercial β-blocker therapy per the Investigator's discretion.

For all randomized patients, the first evening dose of study drug should be taken approximately 12 hours after the first dose, but no earlier than 6 hours after the first dose of study drug. If this is not possible, then the patient should skip the Day 1 evening dose and take the first Day 2 dose the following morning. Similarly, if a patient does not withhold their morning dose of commercial β-blocker therapy on the day of the Randomization Visit, they should be instructed to skip the first morning dose of study drug and take the first evening dose approximately 12 hours, but no earlier than 6 hours, after their last dose of commercial β-blocker therapy.

Study drug should be up-titrated to the target dose for all patients unless a clinical contraindication is documented. Target dose for study drug is 200 mg per day of bucindolol or Toprol-XL. Investigators should make every reasonable attempt to up-titrate study drug on a weekly schedule but can delay up-titration if required clinically (e.g., up-titration at a two-week interval). Up-titration intervals shorter than one week require prior approval from the Sponsor or its designee. Study drug dose may be reduced at any time in the event of documented intolerance. The goal of up-titration is to reach the target dose of study drug within 4 weeks of randomization. For patients who are in AF requiring ECV, the Drug Lead-in Period may be prolonged (i.e. Week 0 Visit delayed) if they have not attained target dose within 4 weeks of randomization. If ECV cannot be delayed and/or a patient cannot tolerate the target dose, it is recommended to reach at least 100 mg per day of study drug prior to ECV. Patients who cannot reach target dose by the time of ECV should have up-titration continued to target levels after SR is achieved, as achievement of SR may improve study drug tolerability.

Patients who forget to take a dose of study drug by more than 6 hours should be instructed to skip that dose and take the subsequent dose of study drug at the next designated interval. Patients who experience dose interruptions of more than 2 days (i.e., 4 doses) should contact the site to determine if dose adjustment is necessary prior to re-initiation of study drug.

At the end of the study, patients will discontinue study drug and transition to commercially-available β-blocker therapy per Investigator discretion. Transition to commercial β-blocker therapy is recommended to occur in a similar manner as the dosing algorithm described for initiation of blinded β-blocker therapy. If commercial β-blocker therapy is not being considered at the end of the study, then transition off study drug will require down-titration over several weeks. This will be accomplished via unscheduled visits prior to the final visit.

Formulation: Clinical supplies of study drug, which include the investigational medicinal product (bucindolol hydrochloride) and the active comparator (metoprolol succinate), are supplied by the Sponsor. The metoprolol succinate used in this study is Toprol-XL (AstraZeneca). Blinding is achieved by over-encapsulation of bucindolol and metoprolol tablets using the same capsule size and color. Since bucindolol is administered twice daily, and metoprolol is

TABLE 51

Study Drug Titration Schedule

| Previous Commercial β-blocker[1] Daily Dose (mg per day) | | | | | | | | | | | | Study Drug Daily Dose (mg per day) | |
|---|---|---|---|---|---|---|---|---|---|---|---|---|---|
| Metoprolol XL/CR/IR | | Carvedilol CR | | Carvedilol IR | | Bisoprolol | | Sotolol | | Nebivolol | | Bucindolol | Toprol-XL |
| > | ≤ | > | ≤ | > | ≤ | > | ≤ | > | ≤ | > | ≤ | = | = |
| — | 50 | — | 20 | — | 12.5 | — | 2.5 | — | 160 | — | 1.25 | 25 | 25 |
| 50 | 100 | 20 | 40 | 12.5 | 25 | 2.5 | 5 | 160 | 240 | 1.25 | 2.5 | 50 | 50 |
| 100 | 200 | 40 | 80 | 25 | 50 | 5 | 10 | 240 | 320 | 2.5 | 5 | 100 | 100 |
| 200[2] | — | 80[2] | — | 50[2] | — | 10[2] | — | 320[2] | — | 5 | 10[2] | 200 | 200 |
| Transition to Starting Dose of Study Drug ➡➡➡ | | | | | | | | | | | | Up-titration ⬇ | |

[1]Transition from β-blockers other than those above requires approval from Sponsor or its designee prior to randomization.
[2]Patients receiving commercial β-blocker doses higher than those currently approved will require pre-approval from the Sponsor or its designee prior to randomization.

given once per day, a placebo capsule has been manufactured for the active comparator arm.

Over-encapsulated bucindolol is provided in the following dosage strengths: 12.5, 25, 50 and 100 mg. Over-encapsulated metoprolol is provided in the following dosage strengths: 25, 50, 100, and 200 mg.

Small quantities of microcrystalline cellulose have been added to the study drug capsules as part of the over-encapsulation process to backfill the remaining void space. Placebo capsules for the metoprolol arm of the study have been prepared by filling the over-capsules with microcrystalline cellulose.

G. Randomization and Blinding

The Sponsor or a specified designee will prepare the randomization code. Only persons not involved in the day-to-day conduct of the study will know the randomization code before unblinding. The randomization will be performed with the use of an Interactive Web Response System (IWRS) via the internet. Randomization will be centralized and stratified by: 1) rhythm at randomization (SR vs. AF); 2) previous class III anti-arrhythmic drug use (Yes vs. No); 3) previous ablation (Yes vs. No); 4) implanted device (Yes vs. No).

Blinding will be accomplished by providing study drug in capsules that are visually indistinguishable and provided in numbered kits. Only the numbers of the kits to be administered to a given patient, and not the identity of the study drug, will be provided to sites. Investigators, site personnel, and patients will not be informed of the blinded study drug assignment at the time of transition off study drug.

In the case of a medical emergency, the Investigator may request unblinding of the study drug assignment for a patient via the IWRS. Unblinding should only be done if diagnosis or treatment of the medical emergency is dependent on knowledge of study drug received. The Sponsor or its designee must be contacted immediately and provided the rationale for the unblinding events. Once unblinded, the patient may be required to discontinue from study drug, but he/she should continue to participate in all other study-related activities including assessments of efficacy. The Sponsor or its designee will document any patient who is unblinded, including the rationale for and date of unblinding.

H. Statistical Considerations

Definitions of Analysis Populations and Endpoint Follow-Up Periods

The efficacy analysis will follow the intent-to-treat (ITT) principle and all patients randomized to study treatment will be included regardless of the success of the titration process. As an additional sensitivity analysis, the efficacy endpoint testing will be performed on a protocol-compliant subpopulation. The safety analyses will include those patients who received at least one dose of blinded study treatment. The screened population includes any patient who signs informed consent for the study. The screen failure population is a subpopulation of the screened population who are not randomized to study drug for any reason.

Four follow-up periods will be defined for inclusion of each patient's results in endpoint calculations:

Drug Titration Period: Starts on the day of randomized treatment initiation and extends for 6 weeks after randomization.

26-week Follow-up Period: Starts on the day of the ECG that establishes SR or the last ECV procedure for patients who fail to convert to stable SR. Follow-up will be censored at the time of the Week 26 Visit for the primary endpoint and all other 26-week endpoints for patients who have not experienced an event by this visit.

Total Follow-up Period: Starts on the same day as the 26-week Follow-up Period and extends until the final study visit.

Total Study Period: Starts on the day of randomized treatment initiation and extends until the final study visit.

Study Population Analyses

Screen failure reasons will be tabulated, ordered by frequency.

The distributions of the following characteristics will be summarized for the randomized treatment groups with descriptive statistics (e.g., mean, standard error, standard deviation, median, minimum, maximum and patient count for continuous variables, and counts with percentages for categorical variables):

Demographics

Cardiovascular disease history and AF risk factors

Baseline results for $CHADS_2$ score, NYHA functional class, vital signs, ECG and laboratory parameters Other bucindolol-related genes (e.g., ADRA2C Ins322-325Del and CYP2D6)

Final study disposition categories

Treatment exposure, by
  Patients attaining target dose
  Length and outcome of titration period
  Days of double blind treatment by dose and overall
  Compliance Concomitant medication usage at baseline and throughout study Protocol deviations Metrics for several key study procedures will be presented with descriptive statistics by randomized treatment group:

Type/manufacturer of implanted device

Elapsed days on treatment prior to start of 26-week Follow-up Period

Elapsed days on treatment prior to ECV

Outcome of ECV

Primary Endpoint

The primary endpoint is elapsed time to first AF event during a 26-week Follow-up Period.

This is a time to event endpoint censored at 26 weeks of follow-up after establishment of SR on study drug. The Cox proportional hazards model will be used for calculation of an estimated hazard ratio and 95% confidence interval, stratified by the pre-specified randomization strata: 1) rhythm at randomization (SR vs. AF); 2) previous class III anti-arrhythmic drug use (Yes vs. No); 3) previous ablation (Yes vs. No); 4) implanted device (Yes vs. No). The analysis methodology will also be applied separately to each component of this composite endpoint (i.e., Symptomatic AF/AFL, Clinical intervention for AF, and ACM). The following definitions apply to this endpoint:

SR on study drug is defined as any of the following:
  SR confirmed by ECG ≥30 minutes after ECV.
  SR confirmed by two consecutive ECGs collected at least 30 minutes apart for patients completing the Drug Lead-in Period who do not require ECV (e.g., SR confirmed at the Randomization and Week 0 Visits).
  SR confirmed by two consecutive ECGs collected at least 30 minutes apart for patients who spontaneously convert from AF to SR prior to completing the Drug Lead-in Period.

An AF event is defined as any of the following:
  Symptomatic AF/AFL, defined as AF or AFL as assessed by 12-lead ECG that is associated with a clinically relevant change in patient-reported symptoms, as determined by the CEC examination of blinded data
  Clinical intervention for AF, defined as clinical evidence of AF and any of the following:
    Initiation of any anti-arrhythmic drug for pharmacological cardioversion
    ECV
    Ablation
  All-cause mortality (included in the primary endpoint to account for competing risk).

Potential AF events will be adjudicated by a blinded Clinical Events Committee (CEC). The CEC charter will describe their approach for determining AF events and for identifying the onset date and time of the AF event.

The following scenarios are possible for a small subgroup of patients:
1. Failure to attain SR on study drug because the ECV procedure was not performed due to drop out or any other reason other than those described below. These patients will be included in the analysis as censored on Day 1 of follow-up.
2. Failure to attain SR on study drug following ECV. These patients will be included in the endpoint calculation as experiencing the event on Day 1 of follow-up.
3. Deaths occurring after randomization and prior to conversion to SR on study drug will be counted as events on Day 1.

In exploratory analyses, covariates and stratification variables will be included as potentially relevant explanatory variables in the Cox regression models. These variables will be prespecified in the SAP prior to the collection of a significant amount (e.g., <25%) of data and prior to the interim analysis.

Secondary Endpoints

The following endpoints will be tested for superiority of bucindolol benefit relative to metoprolol by fixed sequence provided that bucindolol meets the superiority criteria on the primary endpoint. The following statistical analysis methodologies for the study will be described in further detail in the Statistical Analysis Plan.

Percent experiencing symptomatic bradycardia or bradycardia leading to dose reduction or discontinuation of study drug during the 26-week Follow-up Period. This endpoint will be tested with a Cochran-Mantel-Haenszel statistic to control for the four stratification variables. A supportive analysis will also be performed to evaluate this endpoint at the time of study drug discontinuation.
  Percent attaining target study drug dose during the Drug Titration Period. This endpoint will be tested with a Cochran-Mantel-Haenszel statistic to control for the four stratification variables. A supportive analysis will also be performed to evaluate this endpoint at the time of study drug discontinuation. Supportive analyses will also be performed for the subpopulations receiving and not receiving previous β-blocker therapy at randomization.
  Change from baseline in the overall score of the Atrial Fibrillation Effect on QualiTy-of-life (AFEQT) Questionnaire. A supportive analysis will examine change from baseline in the symptom subscale score.
  Time to first event of HF hospitalization or cardiovascular mortality (CVM) during the Total Study Period (as assessed by the Investigator). A supportive analysis will involve the same analysis methodology applied to each component (i.e., HFH, CVM).

Safety Endpoints

The results for the following safety endpoints will be compared with descriptive statistics between the treatment groups for all patients receiving study treatment. All results collected from first dose of study drug to within 30 days of the last dose for each patient will be included in the assessments of safety unless otherwise stated. Exploratory analyses will also examine polymorphisms in other bucindolol-related genes (i.e., ADRA2C Ins322-325Del and CYP2D6) and their relationship to the safety endpoints.

Incidence of ACM during the Total Study Period.
  Incidence of CVM, cardiovascular-related hospitalization (as assessed by the Investigator), or withdrawal of study drug due to a SAE during the Drug Titration Period. The components will also be examined individually.
  Incidence of stroke, TIA, or other thromboembolism during the Total Study Period.
  Incidence and severity of SAEs during the Total Study Period.
  Incidence of neoplasm-related SAEs during the Total Study Period. These SAEs of special interest will be tabulated according to the following characteristics:
    Development of treatment-emergent neoplastic conditions.
    Progression or worsening of pre-study neoplastic conditions.
    Progression or worsening of treatment-emergent neoplastic conditions.
  Change from baseline in clinical laboratory tests over time during the Total Study Period. For clinical laboratory tests, the numbers and percentages of patients with values exceeding the bounds of normal ranges.
  Change from baseline in vital signs and weight over time during the Total Study Period.
  Relationship of CYP2D6 poor metabolizers to SAEs Substudies and Other Endpoints
  Change from baseline in the overall score of the Minnesota Living with Heart Failure (MLHF) Questionnaire
  Change from baseline in the EQ-5D questionnaire
    The EQ-5D questionnaire has 5 dimensions (mobility, self-care, usual activities, pain/discomfort and anxiety/depression) and each is self-rated by the patient as no problems, some problems, or severe problems. The bucindolol treatment group will be tested for superior response using a Cochran-Mantel-Haenszel statistic to control for the four stratification variables.
  Population Pharmacokinetic Analysis.
    Sparse sampling data will be combined with other bucindolol studies to examine the potential effects of intrinsic and extrinsic variables on exposure-response relationships for efficacy and safety. Polymorphisms in CYP2D6, the enzyme primarily responsible for the metabolism of bucindolol, will be examined as a covariate of special interest.
    Details of this analysis will be prespecified in a separate analysis plan and submitted prior to the end of patient follow-up and unblinding of randomized treatment assignments.
  Pharmacoeconomic modeling of healthcare utilization.
    Details of this analysis will be prespecified in a separate analysis plan and submitted prior to the end of patient follow-up and unblinding of randomized treatment assignments.

AFB for patients who agree to participate in the substudy.
AFB is defined as the amount of time per day that a patient is in AF/AFL, as measured by a Medtronic implanted device.

The primary endpoint of the CM substudy will be measured through the Week 26 Visit. It will be a time to first event analysis, with an AF/AFL event defined as at least 6 hours of AFB in a single day. It will be analyzed with the same methodology as the primary endpoint.

AFB will be presented as hours/day with descriptive statistics and graphical displays.

Additional analyses will examine all available AFB data, including VRR during periods of AF/AFL as collected by implanted Medtronic devices.

DNA Bank
For patients who agree to participate in the optional DNA substudy.

Power and Sample Size

GENETIC-AF was a Phase 2B trial conducted in the U.S., Canada, and Europe that compared bucindolol to metoprolol succinate (Toprol-XL) for the prevention of recurrent AF/AFL or ACM in HF patients with the ADRB1 Arg389Arg genotype. The trial randomized HF patients with mid-range LVEF ≥0.40 and <0.50 (HFmrEF) and HF patients with lower-range LVEF <0.40 (HFlrEF).

Similar results were observed in the overall population for the primary endpoint based on intermittent ECG monitoring (N=267; HR=1.01; 95% CI: 0.71, 1.42), but a trend for bucindolol benefit was observed for a prespecified analysis of the U.S. subgroup (N=127; HR=0.70; 95% CI: 0.41, 1.19). In a substudy of patients who underwent continuous heart rhythm monitoring with implanted devices, a trend for bucindolol benefit was observed in the overall substudy population (N=69; HR=0.75; 95% CI: 0.43, 1.32) and in the U.S. substudy cohort (N=42; HR=0.50; 95% CI: 0.17, 1.42) for a prospectively-defined time to first AF/AFL event endpoint based on ≥6 hours per day of device-detected AF burden.

In a post-hoc analysis of the GENETIC-AF primary endpoint that excluded patients with long-standing AF and HF >12 years, strong trends for bucindolol benefit were observed (N=230; HR=0.68; 95% CI: 0.45, 1.02), which achieved statistical significance when this population was restricted to patients who did not have AF more than 2 years prior to developing HF (N=196; HR=0.54; 95% CI: 0.33, 0.87; p=0.011). In this population, a significant reduction in the primary endpoint was observed for bucindolol compared to metoprolol in the HFmrEF cohort (N=91; HR=0.42; 95% CI: 0.21, 0.86; p=0.017); whereas, a non-significant trend was observed in the HFlrEF cohort (N=105; HR=0.69; 95% CI: 0.33, 1.43).

Based on a Special Protocol Agreement with the U.S. FDA, a single Phase 3 trial may be sufficient for regulatory approval if the primary endpoint is significant with a p-value ≤0.01. Therefore, estimates of power for the primary endpoint are provided below at an alpha level of 0.01 and 0.05 for a variety of metoprolol event rate and bucindolol treatment effect assumptions. Metoprolol event rate estimates are based on Phase 2B data, which was 55% for the HFmrEF population for 24 weeks of follow-up. Bucindolol treatment effect estimates range from 30% to 50%, corresponding to a HR range of approximately 0.50 to 0.70.

As shown in Table 52, a 400-patient study would have >90% power to achieve a p-value ≤0.05 for a bucindolol treatment effect size of 40% and a metoprolol event rate of 55% at 26 weeks. For the same assumptions, the trial would have >80% power to achieve a p-value ≤0.05 for a bucindolol treatment effect size of 35%.

TABLE 52

Power for Primary Endpoint: 400 Patients and Alpha = 0.05

| Metoprolol Event Rate | Treatment Effect of Bucindolol | | | | |
|---|---|---|---|---|---|
| | 30% | 35% | 40% | 45% | 50% |
| 45% | 61.2% | 76.3% | 88.0% | 95.1% | 98.5% |
| 50% | 65.9% | 80.7% | 91.1% | 96.8% | 99.2% |
| 55% | 70.3% | 84.5% | 93.6% | 98.0% | 99.6% |
| 60% | 74.3% | 87.7% | 95.5% | 98.8% | 99.8% |
| 65% | 77.9% | 90.3% | 96.8% | 99.3% | 99.9% |

As shown in Table 53, a 400-patient study would have >90% power to achieve a p-value ≤0.01 for a bucindolol treatment effect size of 45% and a metoprolol event rate of 55% at 26 weeks. For the same assumptions, the trial would have >80% power to achieve a p-value 0.01 for a bucindolol treatment effect size of 40%.

TABLE 53

Power for Primary Endpoint: 400 Patients and Alpha = 0.01

| Metoprolol Event Rate | 1. Treatment Effect of Bucindolol | | | | |
|---|---|---|---|---|---|
| | 2. 30% | 3. 35% | 4. 40% | 5. 45% | 6. 50% |
| 7. 45% | 8. 37.0% | 9. 53.9% | 10. 71.1% | 11. 85.0% | 12. 93.9% |
| 13. 50% | 14. 41.9% | 15. 60.0% | 16. 76.8% | 17. 89.3% | 18. 96.3% |
| 19. 55% | 20. 46.8% | 21. 65.6% | 22. 81.8% | 23. 92.6% | 24. 97.8% |
| 25. 60% | 26. 51.4% | 27. 70.7% | 28. 85.9% | 29. 95.0% | 30. 98.8% |
| 31. 65% | 32. 56.1% | 33. 75.3% | 34. 89.3% | 35. 96.7% | 36. 99.3% |

Interim Analyses

Blinded safety data (e.g., group A and group B) will be summarized for inspection by an independent DSMB and will be reviewed at regular intervals. The DSMB Chair will also monitor a subset of safety data at periodic intervals during the study (e.g., monthly). If a clinically significant imbalance in the groups is observed at any time, the DSMB Chair may request an unblinded analysis.

In addition to these routine safety reviews, the DSMB will perform an interim efficacy analysis that will examine preliminary results from an initial population (N=250) with evaluable data for the primary endpoint. The interim efficacy analysis has four potential outcomes: 1) early termination of the trial for futility; 2) completion of the trial at the planned sample size of 400 patients, or; 3) completion of the trial with an expanded sample size of 550 patients.

If the futility criteria are not met and the DSMB determines that the preliminary data are consistent with pre-trial assumptions (i.e., event rate, treatment effect, and power), the trial will proceed to the planned sample size of 400 patients. If the DSMB determines that an expansion of the total sample size is warranted to maintain adequate power for the final analysis, the trial will proceed to completion with a total sample size of 550 patients. The potential increase in sample size is a methodological strategy known as a "promising zone" design, which is well-documented in the statistical literature.[56,67] The specific criteria determining sample size adjustment will not be provided to Investigators, but these criteria will be prespecified in the DSMB charter and will be selected to maintain the type-1 error rate.

Power estimates for the primary endpoint given a variety of metoprolol event rate and treatment benefit assumptions are shown below for the expanded sample size of 550 patients. Metoprolol event rate estimates range from 45% to 65% and bucindolol treatment effect estimates range from 30% to 50%, corresponding to a HR range of approximately 0.50 to 0.70.

As shown in Table 54, a 550-patient study would have >90% power to achieve a p-value ≤0.05 for a bucindolol treatment effect size of 35% and a metoprolol event rate of 55% at 26 weeks. For the same assumptions, the trial would have >80% power to achieve a p-value ≤0.05 for a bucindolol treatment effect size of 30%.

TABLE 54

Power for Primary Endpoint: 550 Patients and Alpha = 0.05

| Metoprolol Event Rate | Treatment Effect of Bucindolol | | | | |
|---|---|---|---|---|---|
| | 30% | 35% | 40% | 45% | 50% |
| 45% | 74.9% | 88.0% | 95.6% | 98.9% | 99.8% |
| 50% | 79.4% | 91.3% | 97.3% | 99.4% | 99.9% |
| 55% | 83.3% | 93.7% | 98.3% | 99.7% | 99.9% |
| 60% | 86.5% | 95.5% | 99.0% | 99.9% | 99.9% |
| 65% | 89.2% | 96.9% | 99.4% | 99.9% | 99.9% |

As shown in Table 55, a 550-patient study would have >90% power to achieve a p-value ≤0.01 for a bucindolol treatment effect size of 40% and a metoprolol event rate of 55% at 26 weeks. For the same assumptions, the trial would have >80% power to achieve a p-value ≤0.01 for a bucindolol treatment effect size of 35%.

TABLE 55

Power for Primary Endpoint: 550 Patients and Alpha = 0.01

| Metoprolol Event Rate | Treatment Effect of Bucindolol | | | | |
|---|---|---|---|---|---|
| | 30% | 37. 35% | 38. 40% | 39. 45% | 40. 50% |
| 45% | 52.2% | 71.3% | 86.4% | 95.1% | 98.8% |
| 50% | 58.2% | 77.1% | 90.4% | 97.1% | 99.4% |
| 55% | 63.6% | 82.0% | 93.4% | 98.4% | 99.7% |
| 60% | 68.7% | 86.0% | 95.6% | 99.1% | 99.9% |
| 65% | 73.3% | 89.4% | 97.1% | 99.5% | 99.9% |

Therefore, this adaptive interim analysis strategy maintains sufficient power across a range of potential treatment effects to test the hypothesis that bucindolol is superior to metoprolol for the prevention of AF in the target HF population with the ADRB1 Arg389Arg genotype. Further details of the interim efficacy analyses will be available in the DSMB charter, which will be finalized prior to enrollment of 10% of the target sample size.

Significance

At the end of the trial, the alpha level for the primary endpoint will be reduced to adjust for the alpha spend for the interim analysis (α=0.00001). Therefore, a significant result for the primary endpoint will be claimed for a p-value ≤0.04999.

Based on a Special Protocol Agreement with the U.S. FDA, a single Phase 3 trial may be sufficient for regulatory approval if the primary endpoint is significant with a p-value ≤0.01, which corresponds to p≤0.00999 when adjusted for the alpha spend at the interim analysis.

Deviation Reporting

All patients with protocol deviations will be included in the ITT analyses; a limited per-protocol analysis will be performed separately. During study initiation, sites will receive instructions on the reporting of protocol deviations. In addition, sites will be responsible for reporting such occurrences to their respective IRB/IEC as required. If protocol deviations are identified during monitoring visits, education of the offending sites will occur and repeat offenders may be suspended from enrolling additional patients. Differences in protocol deviations between treatment groups will be analyzed.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

APPENDIX

Δ Norepinephrine (NE) and NT-ProBNP Data

TABLE 27

| | | Norepinephrine, pg/ml | | | | | | | | |
|---|---|---|---|---|---|---|---|---|---|---|
| | | Entire Cohort (n = 267) | | U.S. (n = 127) | | Canada (n = 59) | | Hungary (n = 33) | | Europe excluding Hungary (n = 48) | |
| Parameter | | Met 128/133 | Buc 134/134 | Met 64/67 | Buc 60/60 | Met 26/27 | Buc 32/32 | Met 15/15 | Buc 18/18 | Met 23/24 | Buc 24/24 |
| Baseline Mean ± SD | | 664 ± 359 | 682 ± 349 | 664 ± 386 | 650 ± 362 | 674 ± 429 | 642 ± 341 | 627 ± 258 | 767 ± 270 | 675 ± 250 | 753 ± 375 |
| Baseline Median | | 590 | 607 | 599 | 598 | 541 | 522 | 571 | 792 | 592 | 691 |
| | | | | | | Week 4 data are in Table 10 | | | | | |
| Week 12 Mean ± SD | | 605 ± 266 | 570 ± 275 | 576 ± 246 | 529 ± 267 | 577 ± 273 | 528 ± 252 | 716 ± 308 | 638 ± 254 | 640 ± 283 | 683 ± 318 |

TABLE 27-continued

| | Norepinephrine, pg/ml | | | | | | | | | |
|---|---|---|---|---|---|---|---|---|---|---|
| | Entire Cohort (n = 267) | | U.S. (n = 127) | | Canada (n = 59) | | Hungary (n = 33) | | Europe excluding Hungary (n = 48) | |
| Parameter | Met 128/133 | Buc 134/134 | Met 64/67 | Buc 60/60 | Met 26/27 | Buc 32/32 | Met 15/15 | Buc 18/18 | Met 23/24 | Buc 24/24 |
| Week 12 Median | 566 | 520 | 560 | 466 | 563 | 484 | 590 | 690 | 614 | 611 |
| ΔWeek 12 Mean ± SEM | −64 ± 30 | −118 ± 27 | −100 ± 43 | −128 ± 49 | −111 ± 57 | −133 ± 48 | 144 ± 89 | −172 ± 63 | −52 ± 65 | −34 ± 51 |
| ΔWeek 12 Median | −57 | −100 | −66 | −86 | −85 | −100 | 37 | −171 | −76 | −55 |
| P value vs. Bsl*/vs. Met† | 0.023 | <0.0001/ 0.18 | 0.07 | 0.011/ 0.52 | 0.061* | 0.016/ 0.80 | 0.20 | 0.022/ 0.008 | 0.26 | 0.57/ 0.69 |
| Week 24 Mean ± SD | 690 ± 414 | 631 ± 329 | 639 ± 472 | 585 ± 336 | 722 ± 303 | 623 ± 276 | 716 ± 301 | 711 ± 267 | 904 ± 348 | 798 ± 459 |
| Week 24 Median | 586 | 545 | 519 | 498 | 690 | 564 | 668 | 736 | 924 | 729 |
| ΔWeek 24 Mean ± SEM | 2 ± 33 | −64 ± 31 | −46 ± 40 | −86 ± 40 | 18 ± 75 | −38 ± 54 | 148 ± 336 | −132 ± 296 | 105 ± 126 | 56 ± 152 |
| ΔWeek 24 Median | −24 | −47 | −46 | −46 | −10 | −21 | −42 | −193 | 232 | −82 |
| P value vs. Bsl*/vs. Met† | 0.90 | 0.012/ 0.16 | 0.17 | 0.058/ 0.74 | 0.83 | 0.72/ 0.58 | 0.43 | 0.034/ 0.065 | 0.64 | 0.70/ 0.33 |

*Wilcoxon signed rank test for within group changes;
†Wilcoxon signed rank sum test on between group changes

TABLE 28

| | NT-proBNP (pg/ml) | | | | | | | | | |
|---|---|---|---|---|---|---|---|---|---|---|
| | Entire Cohort (n = 267) | | U.S. (n = 127) | | Canada (n = 59) | | Hungary (n = 33) | | Europe excluding Hungary (n = 48) | |
| Parameter | Met 123/133 | Buc 125/134 | Met 62/67 | Buc 55/60 | Met 26/27 | Buc 29/32 | Met 14/15 | Buc 17/18 | Met 21/24 | Buc 24/24 |
| Baseline Mean ± SD | 1343 ± 1846 | 1159 ± 1306 | 1499 ± 2033 | 1245 ± 1332 | 1646 ± 2303 | 1314 ± 1503 | 781 ± 458 | 989 ± 1428 | 883 ± 880 | 893 ± 849 |
| Baseline Median | 861 | 777 | 982 | 904 | 913 | 790 | 785 | 567 | 521 | 600 |
| | | | | | Week 4 data are in Table 11 | | | | | |
| Week 12 Mean ± SD | 1134 ± 1197 | 1052 ± 1923 | 1224 ± 1240 | 1383 ± 2538 | 1338 ± 1504 | 674 ± 767 | 864 ± 876 | 1095 ± 1929 | 867 ± 885 | 782 ± 1256 |
| Week 12 Median | 652 | 470 | 661 | 561 | 845 | 432 | 593 | 446 | 526 | 376 |
| ΔWeek 12 Mean ± SEM | −135 ± 124 | −108 ± 133 | −63 ± 190 | +130 ± 262 | −482 ± 355 | −602 ± 232 | +45 ± 190 | +40 ± 170 | −70 ± 184 | −101 ± 164 |
| ΔWeek 12 Median | −50 | −96 | −99 | −81 | −36 | −176 | +75 | −96 | −20 | −92 |
| P value vs. Bsl*/ vs. Met† | 0.198 | 0.002/ 0.051† | 0.38 | 0.36/ 0.40 | 0.25 | 0.001/ 0.105 | 0.70 | 0.64/ 0.54 | 0.68 | 0.029/ 0.30 |
| Week 24 Mean ± SD | 1334 ± 1732 | 1135 ± 1632 | 1374 ± 1839 | 1124 ± 1516 | 1382 ± 1974 | 831 ± 961 | 1150 ± 784 | 1244 ± 2515 | 1108 ± 962 | 1859 ± 2282 |
| Week 24 Median | 661 | 502 | 547 | 653 | 623 | 425 | 1019 | 244 | 765 | 593 |

TABLE 28-continued

NT-proBNP (pg/ml)

| Parameter | Entire Cohort (n = 267) | | U.S. (n = 127) | | Canada (n = 59) | | Hungary (n = 33) | | Europe excluding Hungary (n = 48) | |
|---|---|---|---|---|---|---|---|---|---|---|
| | Met 123/133 | Buc 125/134 | Met 62/67 | Buc 55/60 | Met 26/27 | Buc 29/32 | Met 14/15 | Buc 17/18 | Met 21/24 | Buc 24/24 |
| ΔWeek 24 Mean ± SEM | −206 ± 176 | −92 ± 136 | −158 ± 258 | −163 ± 161 | −489 ± 361 | −442 ± 223 | +201 ± 219 | +41 ± 276 | −133 ± 153 | +983 ± 712 |
| ΔWeek 24 Median | −100 | −197 | −135 | −315 | −106 | −271 | +150 | −176 | −101 | −48 |
| P value vs. Bsl*/vs. Met† | 0.014 | 0.005/0.22 | 0.024 | 0.031/0.91 | 0.18 | 0.057/0.45 | 0.47 | 0.102/0.113 | 0.47 | 0.92/0.92 |

*Wilcoxon signed rank test;
†/Wilcoxon signed rank sum test

Δ Safety During Total Follow-Up

TABLE 29

Treatment-Emergent Adverse Events (All SOCs and AEs ≥ 3% in any Group)

| Endpoint | Metoprolol (N = 133) | Bucindolol (N = 134) |
|---|---|---|
| ANY ADVERSE EVENT | 95 (71.4%) | 100 (74.6%) |
| CARDIAC DISORDERS | 35 (26.3%) | 32 (23.9%) |
| CARDIAC FAILURE CONGESTIVE | 9 (6.8%) | 6 (4.5%) |
| BRADYCARDIA | 9 (6.8%) | 5 (3.7%) |
| CARDIAC FAILURE | 5 (3.8%) | 6 (4.5%) |
| SINUS BRADYCARDIA | 8 (6.0%) | 0 (0.0%) |
| INFECTIONS AND INFESTATIONS | 29 (21.8%) | 36 (26.9%) |
| UPPER RESPIRATORY TRACT INFECTION | 6 (4.5%) | 7 (5.2%) |
| NASOPHARYNGITIS | 4 (3.0%) | 4 (3.0%) |
| BRONCHITIS | 4 (3.0%) | 2 (1.5%) |
| INFLUENZA | 3 (2.3%) | 4 (3.0%) |
| PNEUMONIA | 1 (0.8%) | 4 (3.0%) |
| MUSCULOSKELETAL AND CONNECTIVE TISSUE DISORDERS | 18 (13.5%) | 33 (24.6%) |
| ARTHRALGIA | 3 (2.3%) | 7 (5.2%) |
| PAIN IN EXTREMITY | 2 1.5%) | 5 (3.7%) |
| BACK PAIN | 4 (3.0%) | 3 (2.2%) |
| GASTROINTESTINAL DISORDERS | 24 (18.0%) | 28 (20.9%) |
| DIARRHOEA | 6 (4.5%) | 6 (4.5%) |
| NAUSEA | 5 (3.8%) | 5 (3.7%) |
| CONSTIPATION | 2 (1.5%) | 8 (6.0%) |
| NERVOUS SYSTEM DISORDERS | 24 (18.0%) | 24 (17.9%) |
| DIZZINESS | 3.8%) | 5 (3.7%) |
| HEADACHE | 5 (3.8%) | 6 (4.5%) |
| SYNCOPE | 4 (3.0%) | 4 (3.0%) |
| GENERAL DISORDERS AND ADMINISTRATION SITE CONDITIONS | 23 (17.3%) | 18 (13.4%) |
| FATIGUE | 7 (5.3%) | 6 (4.5%) |
| OEDEMA PERIPHERAL | 5 (3.8%) | 3 (2.2%) |
| CHEST PAIN | 4 (3.0%) | 2 (1.5%) |
| VASCULAR DISORDERS | 18 (13.5%) | 19 (14.2%) |
| HYPOTENSION | 10 (7.5%) | 13 (9.7%) |
| METABOLISM AND NUTRITION DISORDERS | 15 (11.3%) | 18 (13.4%) |
| GOUT | 4 (3.0%) | 3 (2.2%) |
| HYPOMAGNESAEMIA | 0 (0.0%) | 4 (3.0%) |
| RESPIRATORY, THORACIC AND MEDIASTINAL DISORDERS | 13 (9.8%) | 21 (15.7%) |
| DYSPNOEA | 6 (4.5%) | 3 (2.2%) |
| COUGH | 3 (2.3%) | 4 (3.0%) |
| EPISTAXIS | 0 (0.0%) | 4 (3.0%) |
| INJURY, POISONING AND PROCEDURAL COMPLICATIONS | 16 (12.0%) | 14 (10.4%) |
| LACERATION | 4 (3.0%) | 1 (0.7%) |
| INVESTIGATIONS | 10 (7.5%) | 16 (11.9%) |
| RENAL AND URINARY DISORDERS | 12 (9.0%) | 13 (9.7%) |
| ACUTE KIDNEY INJURY | 5 (3.8%) | 6 (4.5%) |
| SKIN AND SUBCUTANEOUS TISSUE DISORDERS | 8 (6.0%) | 11 8.2%) |
| PSYCHIATRIC DISORDERS | 12 (9.0%) | 2 (1.5%) |
| DEPRESSION | 4 (3.0%) | 1 (0.7%) |
| EYE DISORDERS | 3 2.3%) | 8 (6.0%) |
| NEOPLASMS BENIGN, MALIGNANT AND UNSPECIFIED | 8 (6.0%) | 3 (2.2%) |
| EAR AND LABYRINTH DISORDERS | 5 (3.8%) | 3 (2.2%) |
| HEPATOBILIARY DISORDERS | 3 (2.3%) | 4 (3.0%) |
| BLOOD AND LYMPHATIC SYSTEM DISORDERS | 3 (2.3%) | 4 (3.0%) |
| ENDOCRINE DISORDERS | 4 (3.0%) | 2 (1.5%) |
| REPRODUCTIVE SYSTEM AND BREAST DISORDERS | 4 (3.0%) | 0 (0.0%) |
| PRODUCT ISSUES | 1 (0.8%) | 2 (1.5%) |
| IMMUNE SYSTEM DISORDERS | 1 (0.8%) | 1 (0.7%) |

Notes:

Incidence rates are presented as the number (%) of patients. Patients are counted once for each preferred term, once within each SOC (system organ class), and once for the overall total of patients with any adverse event. Events with onset within 30 days of final study visit are included. Source: Table S04.

TABLE 30

Treatment-Emergent Serious Adverse Events
(All SOCs and AEs ≥ 3% in any Group)

| Endpoint | Metoprolol (N = 133) | Bucindolol (N = 134) |
|---|---|---|
| ANY ADVERSE EVENT | 26 (19.5%) | 33 (24.6%) |
| CARDIAC DISORDERS | 13 (9.8%) | 12 (9.0%) |
| CARDIAC FAILURE CONGESTIVE | 7 (5.3%) | 2 (1.5%) |
| INFECTIONS AND INFESTATIONS | 4 (3.0%) | 6 (4.5%) |
| RESPIRATORY, THORACIC AND MEDIASTINAL DISORDERS | 2 (1.5%) | 7 (5.2%) |
| VASCULAR DISORDERS | 4 (3.0%) | 3 (2.2%) |
| RENAL AND URINARY DISORDERS | 2 (1.5%) | 4 (3.0%) |
| GASTROINTESTINAL DISORDERS | 2 (1.5%) | 2 (1.5%) |
| GENERAL DISORDERS AND ADMINISTRATION SITE CONDITIONS | 2 (1.5%) | 2 (1.5%) |
| HEPATOBILIARY DISORDERS | 1 (0.8%) | 3 (2.2%) |
| INJURY, POISONING AND PROCEDURAL COMPLICATIONS | 1 (0.8%) | 2 (1.5%) |
| METABOLISM AND NUTRITION DISORDERS | 1 (0.8%) | 2 (1.5%) |
| NEOPLASMS BENIGN, MALIGNANT AND UNSPECIFIED | 3 (2.3%) | 1 (0.7%) |
| NERVOUS SYSTEM DISORDERS | 2 (1.5%) | 2 (1.5%) |
| PRODUCT ISSUES | 1 (0.8%) | 2 (1.5%) |
| MUSCULOSKELETAL AND CONNECTIVE TISSUE DISORDERS | 0 (0.0%) | 2 (1.5%) |
| EAR AND LABYRINTH DISORDERS | 1 (0.8%) | 0 (0.0%) |

Notes:
Incidence rates are presented as the number (%) of patients. Patients are counted once for each preferred term, once within each SOC (system organ class), and once for the overall total of patients with any adverse event. Events with onset within 30 days of final study visit are included.

TABLE 31

Selected Events Occurring During Total Study Period

| Endpoint | Metoprolol (N = 133) | Bucindolol (N = 134) |
|---|---|---|
| Any serious adverse event | 26 (20%) | 33 (25%) |
| Cardiovascular serious adverse event | 13 (10%) | 12 (9%) |
| All-cause mortality | 3 (2%) | 3 (2%) |
| Cardiovascular mortality | 2 (2%) | 1 (1%) |
| Heart failure mortality | 1 (1%) | 0 (0%) |
| All-cause hospitalization | 20 (15%) | 27 (20%) |
| Cardiovascular hospitalization | 14 (11%) | 17 (13%) |
| Heart failure hospitalization | 10 (8%) | 9 (7%) |
| Any bradycardia | 16 (12%) | 5 (4%) |
| Symptomatic bradycardia | 7 (5%) | 5 (4%) |
| Asymptomatic bradycardia | 10 (8%) | 0 (0%) |
| Incidence of Cr > 3.0 | 1 (1%) | 1 (1%) |
| Incidence of bilirubin > 2.0 | 2 (2%) | 1 (1%) |

Note:
Events with onset more than 30 days after treatment discontinuation are omitted. Patients are counted once for each endpoint.

TABLE 32

Treatment Emergent Bradycardia Adverse Events

| Endpoint | Metoprolol (N = 133) | Bucindolol (N = 134) |
|---|---|---|
| Any bradycardia event | 16 (12%) | 5 (4%) |
| Asymptomatic bradycardia event | 10 (8%) | 0 (0%) |
| Symptomatic bradycardia event | 7 (5%) | 5 (4%) |
| Bradycardia event leading to study drug discontinuation | 1 (1%) | 1 (1%) |
| Bradycardia event leading to study drug dose reduction | 11 (8%) | 3 (2%) |
| Bradycardia event leading to study drug dose interruption | 2 (2%) | 0 (0%) |

Note:
Patients are counted once for each characteristic.

TABLE 33

Rhythm-Related Events and Cardiovascular Events

| Endpoint | Metoprolol (N = 133) | Bucindolol (N = 134) |
|---|---|---|
| Additional ECV After Successful SR | 30 (23%) | 37 (28%) |
| Ablation | 18 (14%) | 21 (16%) |
| Anti-Arrhythmic Therapy | 44 (33%) | 46 (34%) |
| Rate Control Therapy | 15 (11%) | 20 (15%) |
| Pacemaker Implantation | 3 (2%) | 1 (1%) |
| ICD Implantation | 7 (5%) | 5 (4%) |
| CAD | 1 (1%) | 8 (6%) |
| Stroke | 0 (0%) | 0 (0%) |
| TIA | 1 (1%) | 0 (0%) |
| Non-CNS Embolism | 0 (0%) | 0 (0%) |
| Ventricular Flutter | 1 (1%) | 1 (1%) |
| Symptomatic SVT | 1 (1%) | 0 (0%) |
| VT >=15 sec or Required Therapy | 0 (0%) | 3 (2%) |
| Heart block (Mobitz I/II, 2:1, or $3^{rd}$ degree) | 0 (0%) | 0 (0%) |
| Appropriate Firing of on ICD | 1 (1%) | 0 (0%) |
| Catheterization | 1 (1%) | 5 (4%) |
| CV Surgery | 0 (0%) | 0 (0%) |

Notes:
Patients with at least one post randomization visit are included. Bradycardia appears in endpoint tables.

TABLE 34

Systolic Blood Pressure and Heart Rate by Scheduled Collection Visit

| | Systolic Blood Pressure (mmHg) | | Heart Rate (bpm) | |
|---|---|---|---|---|
| Endpoint | Metoprolol (N = 133) | Bucindolol (N = 134) | Metoprolol (N = 133) | Bucindolol (N = 134) |
| Baseline | | | | |
| N | 133 | 134 | 131 | 134 |
| Mean ± SEM | 121.8 ± 1.4 | 124.7 ± 1.3 | 76.0 ± 1.5 | 76.5 ± 1.5 |
| Min, Max | 90.0, 149 | 86.0, 154 | 43.0, 119 | 38.0, 135 |

TABLE 34-continued

Systolic Blood Pressure and Heart Rate by Scheduled Collection Visit

| Endpoint | Systolic Blood Pressure (mmHg) | | Heart Rate (bpm) | |
|---|---|---|---|---|
| | Metoprolol (N = 133) | Bucindolol (N = 134) | Metoprolol (N = 133) | Bucindolol (N = 134) |
| Week 4 Change from Baseline | | | | |
| N | 119 | 125 | 121 | 125 |
| Mean ± SEM | 0.8 ± 1.3 | −0.3 ± 1.5 | −4.1 ± 1.7 | 0.1 ± 1.6 |
| Min, Max | −30, 44.0 | −39, 51.0 | −57, 60.0 | −75, 34.0 |
| Week 12 Change from Baseline | | | | |
| N | 116 | 124 | 117 | 122 |
| Mean ± SEM | 1.8 ± 1.4 | −0.5 ± 1.8 | −7.3 ± 1.5 | −1.5 ± 1.8 |
| Min, Max | −34, 54.0 | −67, 56.0 | −55, 29.0 | −76, 55.0 |
| Week 24 Change from Baseline | | | | |
| N | 103 | 106 | 104 | 106 |
| Mean ± SEM | 1.4 ± 1.6 | −1.1 ± 1.5 | −6.4 ± 1.9 | 0.1 ± 2.3 |
| Min, Max | −33, 40.0 | −39, 42.0 | −54, 74.0 | −78, 93.0 |

Note:
Heart rate determined by ECG.

Δ CYP2D6 Genetic Variation Effects on Adverse Events

TABLE 35

Treatment-Emergent Adverse Events (All SOCs and AEs ≥ 3% in any Group), CYP2D6 genotypes

| Endpoint | Extensive/Ultra Metabolizer (N = 216) | | Poor Metabolizer (N = 20) | |
|---|---|---|---|---|
| | N | % | N | % |
| ANY ADVERSE EVENT | 161 | 75% | 16 | 80% |
| CARDIAC DISORDERS | 58 | 27% | 7 | 35% |
| CARDIAC FAILURE CONGESTIVE | 11 | 5% | 3 | 15% |
| BRADYCARDIA | 12 | 6% | 1 | 5% |
| CARDIAC FAILURE | 9 | 4% | 0 | 0% |
| SINUS BRADYCARDIA | 5 | 2% | 2 | 10% |
| INFECTIONS AND INFESTATIONS | 53 | 25% | 5 | 25% |
| UPPER RESPIRATORY TRACT INFECTION | 11 | 5% | 1 | 5% |
| NASOPHARYNGITIS | 5 | 2% | 1 | 5% |
| BRONCHITIS | 6 | 3% | 0 | 0% |
| INFLUENZA | 6 | 3% | 1 | 5% |
| PNEUMONIA | 3 | 1% | 2 | 10% |
| MUSCULOSKELETAL AND CONNECTIVE TISSUE DISORDERS | 35 | 16% | 7 | 35% |
| ARTHRALGIA | 6 | 3% | 2 | 10% |
| PAIN IN EXTREMITY | 3 | 1% | 2 | 10% |
| BACK PAIN | 5 | 2% | 1 | 5% |
| GASTROINTESTINAL DISORDERS | 41 | 19% | 4 | 20% |
| DIARRHOEA | 12 | 6% | 0 | 0% |
| NAUSEA | 9 | 4% | 0 | 0% |
| CONSTIPATION | 4 | 2% | 3 | 15% |
| NERVOUS SYSTEM DISORDERS | 39 | 18% | 3 | 15% |
| DIZZINESS | 9 | 4% | 0 | 0% |
| HEADACHE | 10 | 5% | 0 | 0% |
| SYNCOPE | 7 | 3% | 1 | 5% |
| GENERAL DISORDERS AND ADMINISTRATION SITE CONDITIONS | 30 | 14% | 4 | 20% |
| FATIGUE | 8 | 4% | 1 | 5% |
| OEDEMA PERIPHERAL | 5 | 2% | 1 | 5% |
| CHEST PAIN | 4 | 2% | 1 | 5% |
| VASCULAR DISORDERS | 30 | 14% | 1 | 5% |
| HYPOTENSION | 19 | 9% | 0 | 0% |
| METABOLISM AND NUTRITION DISORDERS | 23 | 11% | 2 | 10% |
| GOUT | 5 | 2% | 0 | 0% |
| HYPOMAGNESAEMIA | 3 | 1% | 0 | 0% |
| RESPIRATORY, THORACIC AND MEDIASTINAL DISORDERS | 26 | 12% | 2 | 10% |
| DYSPNOEA | 5 | 2% | 0 | 0% |
| COUGH | 5 | 2% | 1 | 5% |
| EPISTAXIS | 3 | 1% | 1 | 5% |
| INJURY, POISONING AND PROCEDURAL COMPLICATIONS | 27 | 13% | 2 | 10% |
| LACERATION | 5 | 2% | 0 | 0% |
| INVESTIGATIONS | 22 | 10% | 1 | 5% |
| RENAL AND URINARY DISORDERS | 22 | 0% | 1 | 5% |
| ACUTE KIDNEY INJURY | 11 | 5% | 0 | 0% |
| CHRONIC KIDNEY DISEASE | 4 | 2% | 0 | 0% |
| HAEMATURIA | 3 | 1% | 0 | 0% |
| SKIN AND SUBCUTANEOUS TISSUE DISORDERS | 14 | 6% | 4 | 20% |
| PSYCHIATRIC DISORDERS | 10 | 5% | 0 | 0% |
| DEPRESSION | 5 | 2% | 0 | 0% |
| EYE DISORDERS | 8 | 4% | 1 | 5% |
| NEOPLASMS BENIGN, MALIGNANT AND UNSPECIFIED | 10 | 5% | 0 | 5% |
| EAR AND LABYRINTH DISORDERS | 6 | 3% | 1 | 5% |
| HEPATOBILIARY DISORDERS | 5 | 2% | 1 | 5% |
| BLOOD AND LYMPHATIC SYSTEM DISORDERS | 7 | 3% | 0 | 0% |
| ENDOCRINE DISORDERS | 6 | 3% | 0 | 0% |
| REPRODUCTIVE SYSTEM AND BREAST DISORDERS | 1 | 0% | 1 | 5% |
| PRODUCT ISSUES | 3 | 1% | 0 | 0% |
| IMMUNE SYSTEM DISORDERS | 2 | 1% | 0 | 0% |

Notes:
Incidence rates are presented as the number (%) of patients. Patients are counted once for each preferred term, once within each SOC (system organ class), and once for the overall total of patients with any adverse event. Events with onset within 30 days of final study visit are included. AEs are identical to those shown in Supplement, Table.

TABLE 36

Treatment-Emergent Adverse Events by Treatment (All SOCs and AEs ≥ 3% in any Group)

| Endpoint | Extensive/Ultra Metabolizer | | Poor Metabolizer | |
|---|---|---|---|---|
| | Metoprolol (N = 111) | Bucindolol (N = 105) | Metoprolol (N = 8) | Bucindolol (N = 12) |
| ANY ADVERSE EVENT | 80 (72.1%) | 81 (77.1%) | 7 (87.5%) | 9 (75.0%) |
| CARDIAC DISORDERS | 27 (24.3%) | 29 (27.6%) | 4 (50.0%) | 3 (25.0%) |
| CARDIAC FAILURE CONGESTIVE | 7 (6.3%) | 4 (3.8%) | 1 (12.5%) | 2 (16.7%) |
| BRADYCARDIA | 7 (6.3%) | 5 (4.8%) | 1 (12.5%) | 0 (0.0%) |
| CARDIAC FAILURE | 3 (2.7%) | 6 (5.7%) | 0 (0.0%) | 0 (0.0%) |
| SINUS BRADYCARDIA | 5 (4.5%) | 0 (0.0%) | 2 (25.0%) | 0 (0.0%) |
| INFECTIONS AND INFESTATIONS | 23 (20.7%) | 30 (28.6%) | 1 (12.5%) | 4 (33.3%) |
| UPPER RESPIRATORY TRACT INFECTION | 5 (4.5%) | 6 (5.7%) | 0 (0.0%) | 1 (8.3%) |
| NASOPHARYNGITIS | 3 (2.7%) | 2 (1.9%) | 0 (0.0%) | 1 (8.3%) |
| BRONCHITIS | 4 (3.6%) | 2 (1.9%) | 0 (0.0%) | 0 (0.0%) |
| INFLUENZA | 3 (2.7%) | 3 (2.9%) | 0 (0.0%) | 1 (8.3%) |
| PNEUMONIA | 0 (0.0%) | 3 (2.9%) | 1 (12.5%) | 1 (8.3%) |
| MUSCULOSKELETAL AND CONNECTIVE TISSUE DISORDERS | 12 (10.8%) | 23 (21.9%) | 3 (37.5%) | 4 (33.3%) |
| ARTHRALGIA | 1 0.9%) | 5 (4.8%) | 2 (25.0%) | 0 (0.0%) |
| PAIN IN EXTREMITY | 1 (0.9%) | 2 (1.9%) | 1 (12.5%) | 0 (0.0%) |
| BACK PAIN | 4 (3.6%) | 1 (1.0%) | 0 (0.0%) | 1 (8.3%) |
| GASTROINTESTINAL DISORDERS | 18 (16.2%) | 23 (21.9%) | 2 (25.0%) | 2 (16.7%) |
| DIARRHOEA | 6 (5.4%) | 6 (5.7%) | 0 (0.0%) | 0 (0.0%) |
| NAUSEA | 4 3.6%) | 5 (4.8%) | 0 (0.0%) | 0 (0.0%) |
| CONSTIPATION | 0 (0.0%) | 4 (3.8%) | 1 (12.5%) | 2 (16.7%) |
| NERVOUS SYSTEM DISORDERS | 20 (18.0%) | 19 (18.1%) | 1 (12.5%) | 2 (16.7%) |
| DIZZINESS | 4 (3.6%) | 5 (4.8%) | 0 (0.0%) | 0 (0.0%) |
| HEADACHE | 5 (4.5%) | 5 (4.8%) | 0 (0.0%) | 0 (0.0%) |
| SYNCOPE | 4 (3.6%) | 3 (2.9%) | 0 (0.0%) | 1 (8.3%) |
| GENERAL DISORDERS AND ADMINISTRATION SITE CONDITIONS | 17 (15.3%) | 13 (12.4%) | 3 (37.5%) | 1 (8.3%) |
| FATIGUE | 5 (4.5%) | 3 (2.9%) | 0 (0.0%) | 1 (8.3%) |
| OEDEMA PERIPHERAL | 3 (2.7%) | 2 (1.9%) | 1 (12.5%) | 0 (0.0%) |
| CHEST PAIN | 3 (2.7%) | 1 (1.0%) | 1 (12.5%) | 0 (0.0%) |
| VASCULAR DISORDERS | 16 (14.4%) | 14 (13.3%) | 0 (0.0%) | 1 (8.3%) |
| HYPOTENSION | 9 (8.1%) | 10 (9.5%) | 0 (0.0%) | 0 (0.0%) |
| METABOLISM AND NUTRITION DISORDERS | 11 (9.9%) | 12 (11.4%) | 1 (12.5%) | 1 (8.3%) |
| GOUT | 3 (2.7%) | 2 (1.9%) | 0 (0.0%) | 0 (0.0%) |
| HYPOMAGNESAEMIA | 0 (0.0%) | 3 (2.9%) | 0 (0.0%) | 0 (0.0%) |
| RESPIRATORY, THORACIC AND MEDIASTINAL DISORDERS | 10 (9.0%) | 16 (15.2%) | 0 (0.0%) | 2 (16.7%) |
| DYSPNOEA | 3 (2.7%) | 2 (1.9%) | 0.0 | 0 (0.0%) |
| COUGH | 2 (1.8%) | 3 (2.9%) | 0 (0.0%) | 1 (8.3%) |
| EPISTAXIS | 0 (0.0%) | 3 (2.9%) | 0 (0.0%) | 1 (8.3%) |
| INJURY, POISONING AND PROCEDURAL COMPLICATIONS | 13 (11.7%) | 14 (13.3%) | 2 (25.0%) | 0 (0.0%) |
| LACERATION | 4 3.6%) | 1 (1.0%) | 0 (0.0%) | 0 (0.0%) |
| INVESTIGATIONS | 9 (8.1%) | 13 (12.4%) | 0 (0.0%) | 1 (8.3%) |
| RENAL AND URINARY DISORDERS | 11 (9.9%) | 11 10.5%) | 0 (0.0%) | 1 (8.3%) |
| ACUTE KIDNEY INJURY | 5 (4.5%) | 6 (5.7%) | 0 (0.0%) | 0 (0.0%) |
| CHRONIC KIDNEY DISEASE | 1 (0.9%) | 3 (2.9%) | 0 (0.0%) | 0 (0.0%) |
| HAEMATURIA | 0 (0.0%) | 3 (2.9%) | 0 (0.0%) | 0 (0.0%) |
| SKIN AND SUBCUTANEOUS TISSUE DISORDERS | 6 (5.4%) | 7.6%) | 1 (12.5%) | 3 (25.0%) |
| PSYCHIATRIC DISORDERS | 8 (7.2%) | 2 (1.9%) | 0 (0.0%) | 0 (0.0%) |
| DEPRESSION | 4 (3.6%) | 1 (1.0%) | 0 (0.0%) | 0 (0.0%) |
| EYE DISORDERS | 4 (3.6%) | 5 (4.8%) | 0 (0.0%) | 1 (8.3%) |
| NEOPLASMS BENIGN, MALIGNANT AND UNSPECIFIED | 7 (6.3%) | 3 (2.9%) | 0 (0.0%) | 0 (0.0%) |
| EAR AND LABYRINTH DISORDERS | 4 (3.6%) | 2 (1.9%) | 0 (0.0%) | 1 (8.3%) |
| HEPATOBILIARY DISORDERS | 2 (1.8%) | 3 (2.9%) | 1 (12.5%) | 0 (0.0%) |
| BLOOD AND LYMPHATIC SYSTEM DISORDERS | 3 (2.7%) | 4 (3.8%) | 0 (0.0%) | 0 (0.0%) |
| ENDOCRINE DISORDERS | 4 (3.6%) | 2 (1.9%) | 0 (0.0%) | 0 (0.0%) |
| REPRODUCTIVE SYSTEM AND BREAST DISORDERS | 1 (0.9%) | 0 (0.0%) | 1 (12.5%) | 0 (0.0%) |
| PRODUCT ISSUES | 1 (0.9%) | 2 (1.9%) | 0 (0.0%) | 0 (0.0%) |
| IMMUNE SYSTEM DISORDERS | 1 (0.9%) | 1 (1.0%) | 0 (0.0%) | 0 (0.0%) |

Notes:

Incidence rates are presented as the number (%) of patients. Patients are counted once for each preferred term, once within each SOC (system organ class), and once for the overall total of patients with any adverse event. Events with onset within 30 days of final study visit are included. AEs are identical to those shown in Supplement 7.7, Table.

TABLE 37

Miscellaneous Time-to-First Event Efficacy Endpoints: Patients with LVEF <0.39 or LVEF 0.39-0.49 With HF Duration - AF Duration >= −30 Days

| Endpoint | MET + PM (N = 98) | BUC + PM (N = 107) | MET − PM (N = 90) | BUC − PM (N = 97) |
|---|---|---|---|---|
| All-cause mortality (ACM), 24-week f/u | 3 (3%) | 0 (0.0%) | 2 (2%) | 0 (0.0%) |
| ACM, total f/u (11.3 mos) | 3 (3%) | 2 (2%) | 2 (2%) | 2 (2%) |
| HF hospitalization 24-week f/u | 2 (2%) | 4 (4%) | 2 (2%) | 4 (4%) |
| HF hospitalization total f/u | 10 (10%) | 8 (7%) | 9 (10%) | 8 (8%) |
| ACM or HF hospitalization 24-wk f/u | 5 (5%) | 4 (4%) | 4 (4%) | 4 (4%) |
| ACM or HF hospitalization total f/u | 12 (12%) | 9 (8%) | 11 (12%) | 9 (9%) |
| CV hospitalization 24-wk f/u | 7 (7%) | 6 (6%) | 6 (7%) | 6 (6%) |
| CV hospitalization total f/u | 14 (14%) | 15 (14%) | 13 (14%) | 15 (15%) |

TABLE 38

Trough bucindolol (B) and metoprolol (M) plasma concentrations and human $\beta_1$-adrenergic receptor (AR) occupancies, CYP2D6 genetic variants at 4 weeks of efficacy follow-up.

| CYP2D6 Variant (N) | Bucindolol plasma concentration, ng/ml Mean | Median | P value vs. PM | Metoprolol plasma concentration, ng/ml Mean | Median | P value vs. PM | P vs Buc, w/in variant |
|---|---|---|---|---|---|---|---|
| EM (90B, 92M) | 14.1 ± 37.2 | 3.4 | <0.0001 | 73.9 ± 93.6 | 54.8 | 0.006 | <0.0001 |
| IM (6B, 8M) | 18.5 ± 21.0 | 9.1 | 0.007 | 212.8 ± 154.4 | 205.5 | 0.37 | 0.005 |
| PM (10B, 6M)) | 175.9 ± 142.4 | 137.8 | — | 130.7 ± 46.0 | 130.0 | — | 0.91 |

Estimated bucindolol $\beta_1$-AR receptor occupancies: EM/UM, 90.7%; IM, 92.2%; PM, 99.2%
Estimated metoprolol $\beta_1$-AR receptor occupancies: EM/UM, 86.2; IM, 94.7%; PM, 91.6%

40

Δ
Δ PI Subspecialties by Country

TABLE 39

Investigators and Patients by Subspecialty and Country in GENETIC-AF

| Region | | U.S. (N = 43) | Canada (N = 18) | Hungary (N = 7) | Poland (N = 6) | Serbia (N = 4) | Netherlands (N = 4) | Total (N = 82) |
|---|---|---|---|---|---|---|---|---|
| Investigator by Subspecialty | EP | 23 (53%) | 12 (67%) | 5 (71%) | 1 (17%) | 0 (0%) | 0 (0%) | 41 (50%) |
| | HF | 13 (30%) | 0 (0%) | 0 (0%) | 1 (17%) | 0 (0%) | 0 (0%) | 18 (22%) |
| | GC/I | 6 (14%) | 3 (17%) | 0 (0%) | 4 (66%) | 3 (75%) | 4 (100%) | 20 (24%) |
| | Intvn | 1 (2%) | 1 (11%) | 1 (14%) | 0 (0%) | 1 (25%) | 0 (0%) | 4 (5%) |
| | Crt Cr | 0 (0%) | 1 (6%) | 1 (14%) | 0 (0%) | 0 (0%) | 0 (0%) | 2 (2%) |

| Region | | U.S. (N = 127) | Canada (N = 59) | Hungary (N = 33) | Poland (N = 23) | Serbia (N = 21) | Netherlands (N = 4) | Total (N = 267) |
|---|---|---|---|---|---|---|---|---|
| Patients by Subspecialty | EP | 77 (61%) | 47 (80%) | 26 (79%) | 9 (39%) | 0 (0%) | 0 (0%) | 159 (60%) |
| | HF | 32 (25%) | 0 (0%) | 0 (0%) | 4 (17%) | 0 (0%) | 0 (0%) | 36 (13%) |
| | GC/I | 15 (12%) | 9 (15%) | 0 (0%) | 10 (43%) | 20 (95%) | 4 (100%) | 58 (22%) |
| | Intvn | 3 (2%) | 2 (2%) | 6 (18%) | 0 (0%) | 1 (5%) | 0 (0%) | 12 (4%) |
| | Crt Cr | 0 (0%) | 1 (2%) | 1 (3%) | 0 (0%) | 0 (0%) | 0 (0%) | 2 (1%) |

EP = electrophysiologist;
HF = heart failure or HF/transplant;
GC/I = general cardiology &/or imaging;
Intvn = interventional;
Crt Cr = critical care Δ Numbers of Patients Excluded by Criteria (LVEF ≥39 and DTRI <−30 Days)

TABLE 40

| | Patients Excluded by Criteria (LVEF ≥ 0.39 and DTRI < −30 days) | | |
|---|---|---|---|
| Country | Entire Cohort | # Remaining | # Excluded (%) |
| All | 267 | 205 | 62 (23%) |
| USA | 127 | 108 | 19 (15%) |
| Canada | 59 | 46 | 13 (22%) |
| Hungary | 33 | 13 | 20 (61%) |
| Poland | 23 | 18 | 5 (22%) |
| Serbia | 21 | 17 | 4 (19%) |
| Netherlands | 4 | 3 | 1 (25%) |

TABLE 41 xTAG CYP2D6 Kit v3 Alleles and SNPs

| *Genotype | SNPs detected by xTAG CYP2D6 Kit v3 | Frequency in the U.S. Caucasian population[4] | Frequency in the African American population[4] | Predicted Enzyme Activity |
|---|---|---|---|---|
| *1 | None | 37 to 40% | 29 to 35% | Normal |
| *2 | −1584 > G, 1661G > C, 2850C > T, 4180G > C | 26 to 33% | 18 to 27% | Normal |
| *3 | 2549A > del | 1% | 0.2 to 0.6% | None |
| *4 | 100C > T, 1661G > C, 1846G > A, 4180G > C, 2850C > T | 18 to 20% | 6 to 9% | None |
| *5 | deletion | 2 to 4% | 6 to 7% | None |
| *6 | 1707T > del, 4180G > C | 1% | 0.5% | None |
| *7 | 2935A > C | Not known | Not known | None |
| *8 | 1661G > C, 1758G > T, 2850C > T, 4180G > C | Not known | Not known | None |
| *9 | 2613delAGA | 2 to 3% | 0.3% | Reduced |
| *10 | 100C > T, 1661G > C, 4180G > C | 2 to 8% | 0.3 to 0.4% | Reduced |
| *11 | 883G > C, 1661G > C, 2850C > T, 4180G > C | Not known | Not known | None |
| *15 | 138insT | Not known | Not known | None |
| *17 | 1023C > T, 1661G > C, 2850C > T, 4180G > C | 0.2 to 0.3% | 15 to 26% | Reduced |
| *29 | 1659G > A, 1661G > C, 2850C > T, 3183G > A, 4180G > C | Not known[5] | Not known[5] | Reduced |
| *35 | −1584C > G, 31G > A, 1661G > C, 2850C > T, 4180G > C | 7.4%[6] | 1%[6] | Normal |
| *41 | 1661G > C, 2850C > T, 2988G > A, 4180G > C | 9%[6] | 11%[6] | Reduced |
| DUP | duplication | | | |

1. Tramadol Therapy and CYP2D6 Genotype. Medical Genetic Summaries (Internet). Cited 2017 October. Available from: https://www.ncbi.nlm.nih.gov/books/NBK31S9SO/.
2. Becquemont L (June 2009). Pharmacogenomics 10 (6): 961-9.
3. xTAG CYP2D6 Kit v3 Package Insert
[4]Bradford L D. CYP2D6 allele frequency in European Caucasians, Asians, Africans and their descendants. Pharmacogenomics 2002; 3(2): 229-43.
[5]Wennerholm A, Johansson f. et at. Characterization of the CYP2D6 '29 allele commonly present in a black Tanzanian population causing reduced catalytic activity. Pharmacogenetics 2001; 11(5): 417-427.
[6]Gaedigk A, Ryder D L. CYP2D6 poor metabolizer status can be ruled out by a single genotyping assay for the -1584G promoter polymorphism. Clin Chem 2003, 49(6 Pt 1): 1008-11.

REFERENCES

The following references and the publications referred to throughout the specification, to the extent that they provide exemplary procedural or other details supplementary to those set forth herein, are specifically incorporated herein by reference.

1. Benjamin E J, Blaha M J, Chiuve S E, Cushman M, Das S R, Deo R, de Ferranti S D, Floyd J, Fornage M, Gillespie C, Isasi C R, Jiménez M C, Jordan L C, Judd S E, Lackland D, et al. Heart disease and stroke statistics-2017 Update: A report from the American Heart Association. *Circulation.* 2017; 135:e146-e603.
2. Wang T J, Larson M G, Levy D, Vasan R S, Leip E P, Wolf P A, D'Agostino R B, Murabito J M, Kannel W B, Benjamin E J. Temporal relations of atrial fibrillation and congestive heart failure and their joint influence on mortality: the Framingham Heart Study. *Circulation.* 2003; 107:2920-25
3. Aleong R G, Sauer W H, M D, Davis G, Bristow M R. New onset atrial fibrillation predicts heart failure progression. *Am J Med.* 2014; 127:963-71.
4. Kotecha D, Banerjee A, Lip G Y. Increased stroke risk in atrial fibrillation patients with heart failure: does ejection fraction matter? *Stroke.* 2015; 46:608-9.
5. Kotecha D, Piccini J P. Atrial fibrillation in heart failure: what should we do? *Eur Heart J.* 2015; 36:3250-7.
6. Bardy G H, Lee K L, Mark D B, Poole J E, Packer D L, Boineau R, Domanski M, Troutman C, Anderson J, Johnson G, McNulty S E, Clapp-Channing N, Davidson-Ray L D, Fraulo E S, Fishbein D P, Luceri R M, Ip J H; Sudden Cardiac Death in Heart Failure Trial (SCD-HeFT) Investigators. Amiodarone or an implantable cardioverter-defibrillator for congestive heart failure. *N Engl J Med.* 2005; 352:225-37.
7. Torp-Pedersen C, Metra M, Spark P, Lukas M A, Moullet C, Scherhag A, Komajda M, Cleland J G, Remme W, Di Lenarda A, Swedberg K, Poole-Wilson P A; COMET Investigators. *J Cardiac Fail.* 2005; 13:340-5.
8. Torp-Pedersen C, Møller M, Bloch-Thomsen P E, Kober L, Sandøe E, Egstrup K, Agner E, Carlsen J, Videbaek J, Marchant B, Camm A J. Dofetilide in patients with congestive heart failure and left ventricular dysfunction. Danish Investigations of Arrhythmia and Mortality on Dofetilide Study Group. *N Engl J Med.* 1999; 341:857-65.
9. Tikosyn prescribing information 10. Banchs J E, Wolbrette D L, Samii S M, Penny-Peterson E D, Patel P P, Young S K, Gonzalez M D, Naccarelli G V. Efficacy and safety of dofetilide in patients with atrial fibrillation and atrial flutter. *J Intery Card Electrophysiol.* 2008; 23:111-5.

11. Nasr I A, Bouzamondo A, Hulot J S, Dubourg O, Le Heuzey J Y, Lechat P. Prevention of atrial fibrillation onset by beta-blocker treatment in heart failure: a meta-analysis. *Eur Heart J.* 2007; 28:457-462.

12. van Veldhuisen D J, Aass H, El Allaf D, Dunselman P H, Gullestad L, Halinen M, et al. Presence and development of atrial fibrillation in chronic heart failure. Experiences from the MERIT-HF Study. *Eur J Heart Fail.* 2006; 8(5):539-46.

13. Aleong R G, Sauer W H, Davis G, Murphy G A, PhD, Port J D, PhD, Abraham W T, Liggett S B, Bristow M R. Prevention of atrial fibrillation by bucindolol is dependent on the beta-1 389 Arg/Gly adrenergic receptor polymorphism. *JACC Heart Fail.* 2013; 1:338-44.

14. BEST Investigators. A trial of the beta-adrenergic blocker bucindolol in patients with advanced heart failure. *New Engl J Med.* 2001; 344:1659-67.

15. MERIT-HF Investigators. Effect of metoprolol CR/XL in chronic heart failure: Metoprolol CR/XL Randomised Intervention Trial in Congestive Heart Failure (MERIT-HF). *Lancet.* 1999; 353:2001-7.

16. Mason D A, Moore J D, Green S A, Liggett S B. A gain-of-function polymorphism in a G-protein coupling domain of the human beta1-adrenergic receptor. *J Biol Chem.* 1999; 274:12670-12674.

17. Liggett S B, Mialet-Perez J, Thaneemit-Chen S, Weber S A, Greene S M, Hodne D, Nelson B, Morrison J, Domanski M J, Abraham W T, Anderson J L, Carlquist J F, Krause-Steinrauf H J, Lazzeroni L C, Port J D, Lavori P W, Bristow M R. A polymorphism within a highly conserved beta1-adrenergic receptor motif alters beta-blocker response in multiple models and human heart failure. *Proc Natl Acad Sci.* 2006; 103:11288-11293.

18. Sandilands A J, O'Shaughnessy K M, Brown M J. Greater inotropic and cyclic AMP responses evoked by noradrenaline through Arg389 $\beta_1$-adrenoceptors versus Gly389 $\beta_1$-adrenoceptors in isolated human atrial myocardium. *Br J Pharmacol.* 2003; 138:386-392.

19. O'Connor C M, Fiuzat M, Carson P E, Anand I, Plehn J F, Gottlieb S S, Silver M A, Lindenfeld J, Miller A B, White M, Walsh R, Nelson P B, Medway A M, Davis G, Robertson A D, Port J D, Carr J, Murphy G A, Lazzeroni L C, Abraham W T, Liggett S B, Bristow M R. Combinatorial pharmacogenetic interactions of bucindolol and $\beta_1$, $\alpha_{2C}$ adrenergic receptor polymorphisms. *PLoS One.* 2012; 7:e44324.

20. Mialet Perez J, Rathz D A, Petrashevskaya N N, Hahn H S, Wagoner L E, Schwartz A, Dorn G W, Liggett S B. Beta 1-adrenergic receptor polymorphisms confer differential function and predisposition to heart failure. *Nat Med.* 2003; 9:1300-5.

21. Bristow M R, Abraham W T, Yoshikawa T, White M, Hattler B G, Crisman T S, Lowes B D, Robertson A D, Larrabee P, Gilbert E M. Second- and third-generation beta-blocking drugs in chronic heart failure. *Cardiovasc Drugs Ther.* 1997; 11:291-96.

22. Bristow M R, Krause-Steinrauf H, Nuzzo R, Liang Cheng-Seng, Lindenfeld J, Lowes B D, Hattler B, Abraham W T, Olson L, Krueger S, Thaneemit-Chen S, Hare J M, Domanski M J, Eichhorn E J, Lavori P, Zelis R. Effect of Baseline or changes in adrenergic activity on clinical outcomes in the beta-blocker evaluation of survival trial (BEST). *Circulation.* 2004; 110:1437-42.

23. Aleong R G, Sauer W H, Robertson A D, Liggett S B, Bristow M R. Adrenergic receptor polymorphisms and prevention of ventricular arrhythmias with bucindolol in patients with chronic heart failure. *Circ Arrhythm Electrophysiol.* 2013; 6:137-43.

24. Kao D P, Davis G, M S, Aleong R, O'Connor C M, Mona Fiuzat M, Carson P E, Anand I S, Plehn J F, Gottlieb S S, Silver M A, Lindenfeld J, Miller A B, White M, Murphy G A, Sauer W, M D, Bristow MR. Effect of bucindolol on heart failure outcomes and heart rate response in patients with reduced ejection fraction heart failure and atrial fibrillation. *Eur J Heart Fail.* 2013; 15:324-33.

25. White H L, de Boer R A, Maqbool A, Greenwood D, van Veldhuisen D J, Cuthbert R, Ball S G, Hall A S, Balmforth A J. An evaluation of the beta-1 adrenergic receptor Arg389Gly polymorphism in individuals with heart failure: a MERIT-HF sub-study. *Eur J Heart Fail.* 2003; 5:463-468.

26. Sehnert A J, Daniels S E, Elashoff M, Wingrove J A, Burrow C R, Horne B, Muhlestein J B, Donahue M, Liggett S B, Anderson J L, Kraus W E. Lack of association between adrenergic receptor genotypes and survival in heart failure patients treated with carvedilol or metoprolol. *J Am Coll Cardiol.* 2008; 52:644-651.

27. Cresci S, Kelly R J, Cappola T P, et al. Clinical and genetic modifiers of long-term survival in heart failure. *J Am Coll Cardiol.* 2009; 54:432-44.

28. Kotecha D, Holmes J, Krum H, Altman D G, Manzano L, Cleland J G, Lip G Y, Coats A J, Andersson B, Kirchhof P, von Lueder T G, Wedel H, Rosano G, Shibata M C, Rigby A, Flather M D; Beta-Blockers in Heart Failure Collaborative Group. Efficacy of β blockers in patients with heart failure plus atrial fibrillation: an individual-patient data meta-analysis. *Lancet.* 2014; 384:2235-43.

29. Bristow M R, Murphy G A, Krause-Steinrauf H, et al. An alpha2C-adrenergic receptor polymorphism alters the norepinephrine-lowering effects and therapeutic response of the beta-blocker bucindolol in chronic heart failure. *Circ Heart Fail.* 2010; 3:21-8.

30. GENETIC-AF Clinical Trial (BUC-CLIN-303), ClinicalTrials.gov

31. Piccini J P, Connolly S J, Abraham W T, Healey J S, Steinberg B A, Al-Khalidi H R, Dignacco P, van Veldu-isen D J, Sauer W H, Dufton C, Marshall D A, Aleong R G, Davis G W, Clark R L, Emery L L, Bristow M R. A Genotype-directed comparative Effectiveness TrIal of buCindolol and Toprol-XL for prevention of symptomatic Atrial Fibrillation/Atrial Flutter in patients with heart failure: Rationale and design of the GENETIC-AF Trial. *Am Heart J*, in press.

32. Bristow M R, Kao D P, Breathett K K, Altman N L, M D, Gorcsan J 3$^{rd}$, Gill E A, M D, Lowes B D, Gilbert E M, Quaife R A, Mann D L. Structural and functional phenotyping of the failing heart: Is the left ventricular ejection fraction obsolete? *JACC-Heart Fail.* 2017; 5:772-81.

33. Ponikowski P, Voors A A, Anker S D et al. 2016 ESC Guidelines for the diagnosis and treatment of acute and chronic heart failure. *Eur Heart J.* 2016; 37:2129-200.

34. Sarkar S, Koehler J, Crossley G H, Tang W H, Abraham W T, Warman E N, Whellan D J. Burden of atrial fibrillation and poor rate control detected by continuous monitoring and the risk for heart failure hospitalization. *Am Heart J.* 2012; 164:616-24.

35. Bretz F, Schmidli H, Konig F, Racine A, Maurer W. Confirmatory seamless phase II/III clinical trials with hypotheses selection at interim: general concepts. *Biom J.* 2006; 48:623-34.
36. GENETIC-AF DSMB Charter Version 2.0 and appended White Paper, Submitted to IND 118934, Serial Amendment 037 on Oct. 16, 2015.
37. Chen Y H J, DeMets D L and Lan K K G. Increasing the sample size when the unblinded interim result is promising. *Stat Med.* 2004; 23:1023-38.
38. Bunch T J, May H T, Bair T L, Johnson D L, Weiss J P, Crandall B G, Osborn J S, Anderson J L, Muhlestein J B, Lappe D L, Day J D. Increasing time between first diagnosis of atrial fibrillation and catheter ablation adversely affects long-term outcomes. *Heart Rhythm.* 2013; 10:1257-62.
39. Hussein A A, Saliba W I, Barakat A, Bassiouny M, Chamsi-Pasha M, Al-Bawardy R, Hakim A, Tarakji K, Baranowski B, Cantillon D, Dresing T, Tchou P, Martin D O, Varma N, Bhargava M, Callahan T, Niebauer M, Kanj M, Chung M, Natale A, Lindsay B D, Wazni O M. Radiofrequency Ablation of persistent atrial fibrillation: diagnosis-to-ablation time, markers of pathways of atrial remodeling, and outcomes. *Circ Arrhythm Electrophysiol.* 2016; 9:e003669.
40. Arya A, Silberbauer J, Teichman S L, Milner P, Sulke N, Camm A J. A preliminary assessment of the effects of ATI-2042 in subjects with paroxysmal atrial fibrillation using implanted pacemaker methodology. *Europace.* 2009 April; 11(4):458-64.
41. Werner Jung, Vlada Zvereva, Andreas Rillig, Birge Roggenbuck, Gholam Sadeghzadeh, Johannes Kohler. How to use implantable loop recorders in clinical trials and hybrid therapy. *J Intern Card Electrophysiol.* 2011 December; 32(3): 227-232.
42. Chen-Scarabelli, Scarabelli T M Ellenbogen K A, Halperin J L. Device-detected atrial fibrillation: what to do with asymptomatic patients. *J Am Coll Cardiol.* 2015 Jan. 27; 65(3):281-94.
43. Turakhia M P, Ziegler P D, Schmitt S K, Chang Y, Fan J, Than C T, Keung E K, Singer D E. Atrial Fibrillation Burden and Short-Term Risk of Stroke: Case-Crossover Analysis of Continuously Recorded Heart Rhythm From Cardiac Electronic Implanted Devices. *Circ Arrhythm Electrophysiol.* 2015 October; 8(5): 1040-7.
44. Eduardo N. Warman, PhD, Andrea Grammatico, PhD, Luigi Padeletti, M D. Sample size estimates for atrial fibrillation endpoints, *Heart Rhythm* (2004) 1, B58-B63.
45. Kaplan R M, Ziegler P D, Koehler J, Glotzer T V, Passman R S. Atrial fibrillation variability on long-term monitoring of implantable cardiac rhythm management devices. *Clin Cardiol.* 2017; 40:1044-48.
46. Yoshizawa A, Yoshikawa T, Nakamura I, Satoh T, Moritani K, Suzuki M, Baba A, Iwanaga S, Mitamura H, Ogawa S. Brain natriuretic peptide response is heterogeneous during beta-blocker therapy for congestive heart failure. *J Card Fail.* 2004; 10:310-5.
47. Frantz R P, Lowes B D, Grayburn P A, White M, Krause-Steinrauf H, Krishnan V, Uyeda L, Burnett J C; BEST Neurohumoral Substudy Investigators. Baseline and serial neurohormones in patients with congestive heart failure treated with and without bucindolol: results of the neurohumoral substudy of the Beta-Blocker Evaluation of Survival Study (BEST). *J Card Fail.* 2007; 13:437-44.
48. Lowes B D, Gilbert E M, Abraham W T, Minobe W A, Larrabee P, Ferguson D, Wolfel E E, Lindenfeld J, Tsvetkova T, Robertson A D, Quaife R A, Bristow M R. Myocardial gene expression in dilated cardiomyopathy treated with beta-blocking agents. *New Engl J Med.* 2002; 346:1357-65.
49. Kao D P, Lowes B D, Gilbert E M, Minobe W, Epperson L E, Meyer L K, Ferguson D A, Volkman A K, Zolty R, Borg C D, Quaife R A, Bristow M R. Therapeutic molecular phenotype of beta-blocker associated reverse remodeling in nonischemic dilated cardiomyopathy. *Circ Cardiovasc Genet.* 2015; 8:270-83.
50. Ohta Y, Shimada T, Yoshitomi H, Inoue S, Murakami Y, Shimizu H, Nakamura K, Ohta T, Katoh H, Ishibashi Y. Drop in plasma brain natriuretic peptide levels after successful direct current cardioversion in chronic atrial fibrillation. *Can J Cardiol.* 2001; 17:415-20.
51. Tsuchida K, Tanabe K. Influence of paroxysmal atrial fibrillation attack on brain natriuretic peptide secretion. *J Cardiol.* 2004; 44:1-11.
52. Yanagisawa S, Inden Y, Kato H, Fujii A, Mizutani Y, Ito T, Kamikubo Y, Kanzaki Y, Hirai M, Murohara T. Decrease in B-Type Natriuretic Peptide Levels and Successful Catheter Ablation for Atrial Fibrillation in Patients with Heart Failure. *Pacing Clin Electrophysiol.* 2016; 39:225-34
53. Rossi A, Enriquez-Sarano M, Burnett J C Jr, Lerman A, Abel M D, Seward J B. Natriuretic peptide levels in atrial fibrillation: a prospective hormonal and Doppler-echocardiographic study. *J Am Coll Cardiol.* 2000; 35:1256-62.
54. Massie B M, Cleland J G, Armstrong P W, Horowitz J D, Packer M, Poole-Wilson P A, Ryden L. Regional differences in the characteristics and treatment of patients participating in an international heart failure trial. The Assessment of Treatment with Lisinopril and Survival (ATLAS) Trial Investigators. *J Card Fail.* 1998; 4:3-8.
55. Pitt B, Pfeffer M A, Assmann S F, Boineau R, Anand I S, Claggett B, Clausell N, Desai A S, Diaz R, Fleg J L, Gordeev I, Harty B, Heitner J F, Kenwood C T, Lewis E F, O'Meara E, Probstfield J L, Shaburishvili T, Shah S J, Solomon S D, Sweitzer N K, Yang S, McKinlay S M; TOPCAT Investigators. *N Engl J Med.* 2014; 370(15): 1383-92
56. Pfeffer M A, Claggett B, Assmann S F, Boineau R, Anand I S, Clausell N, Desai A S, Diaz R, Fleg J L, Gordeev I, Heitner J F, Lewis E F, O'Meara E, Rouleau J L, Probstfield J L, Shaburishvili T, Shah S J, Solomon S D, Sweitzer N K, McKinlay S M, Pitt B. Regional variation in patients and outcomes in the Treatment of Preserved Cardiac Function Heart Failure With an Aldosterone Antagonist (TOPCAT) trial. *Circulation.* 2015; 131:34-42.
57. Bristow M R, Enciso J S, Gersh B J, Grady C, Rice M M, Singh S, Greenberg B H. Detection and management of geographic disparities in the TOPCAT trial: Lessons learned and derivative recommendations. *J Am Coll Cardiol Basic Transl Sci.* 2016; 1:180-89.
58. Wedel H, DeMets D, Deedwania P, et al. Challenges of subgroup analyses in multinational clinical trials: experiences from the MERIT-HF trial. *Am Heart J.* 2001; 142:502-11.
59. O'Connor C M, Fiuzat M, Caron M F, Davis G, Karl Swedberg K, Peter E. Carson P E, Koch B, Bristow M R. Influence of global region on outcomes in large heart failure β-Blocker trials. *J Am Coll Cardiol* 58:915-922, 2011.
60. Yusuf S, Wittes J. Interpreting Geographic Variations in Results of Randomized, Controlled Trials. *N Engl J Med.* 2016; 375:2263-71.

61. Pocock S, Calvo G, Marrugat J, Prasad K, Tavazzi L, Wallentin L, Zannad F, Alonso Garcia A. International differences in treatment effect: do they really exist and why? *Eur Heart J.* 2013; 34:1846-52
62. Committee for Proprietary Medicinal Products (CPMP): points to consider on adjustment for baseline covariates. *Stat Med.* 2004; 23(5):701-9.
63. FDA Complete Response Letter to NDA 22-313, dated May 29, 2009.
64. Bristow M R. Beta-adrenergic receptor blockade in chronic heart failure. *Circulation.* 2000; 101:558-69.
65. Toprol XL package insert. Södertälje, Sweden: AstraZeneca: 2012.
66. Bucindolol Hydrochloride Clinical Study Report Phase 1 Study S1457 "Pharmacokinetics of Orally and Intravenously Administered Bucindolol" dated 30 Jun. 1998.
67. Burstein B, Nattel S. Atrial fibrosis: mechanisms and clinical relevance in atrial fibrillation. *J Am Coll Cardiol.* 2008; 51:802-9
68. Corradi D. Atrial fibrillation from the pathologist's perspective. *Cardiovasc Pathol.* 2014; 23:71-84.
69. Aleong R G, Kao D P, Lowes B D, Minobe W, Gilbert E M, Bristow M R. Ventricular myocardial gene expression in HFrEF patients with atrial fibrillation (AF) vs. no AF, and changes in response to beta-blockade. *Circulation.* 2017; 136 Supp 1 A17316.
70. Braunwald E, Bristow M R. *Circulation.* 2000; 102(20 Suppl 4):IV14-23.
71. Wakili R, Voigt N, Kääb S, Dobrev D, Nattel S. Recent advances in the molecular pathophysiology of atrial fibrillation. *J Clin Invest.* 2011; 121:2955-68.
72. Dzeshka M S, Lip G Y, Snezhitskiy V, Shantsila E. Cardiac fibrosis in patients with atrial fibrillation: Mechanisms and clinical implications. *J Am Coll Cardiol.* 2015; 66:943-59.
73. Abhayaratna W P, Seward J B, Appleton C P, Douglas P S, Oh J K, Tajik A J, Tsang T S. Left atrial size: physiologic determinants and clinical applications. *J Am Coll Cardiol.* 2006; 47:2357-63.
74. Lowes B D, Minobe W A, Abraham W T, Rizeq M N, Bohlmeyer T J, Quaife R A, Roden R L, Dutcher D L, Robertson A D, Voelkel N F, Badesch D B, Groves B M, Gilbert E M, Bristow M R. Changes in gene expression in the intact human heart: down-regulation of alpha-myosin heavy chain in hypertrophied, failing ventricular myocardium. *J Clin Invest.* 1997; 100:2315-24.
75. Abraham W T, Fisher W G, Smith A L, Delurgio D B, Leon A R, Loh E, Kocovic D Z, Packer M, Clavell A L, Hayes D L, Ellestad M, Trupp R J, Underwood J, Pickering F, Truex C, McAtee P, Messenger J; MIRACLE Study Group. Multicenter InSync Randomized Clinical Evaluation. Cardiac resynchronization in chronic heart failure. *N Engl J Med.* 2002; 346:1845-53.
76. Bristow M R, Saxon L A, Feldman A M, Mei C, M D, Anderson S A, DeMets D L. Lessons learned and insights gained in the design, analysis and outcomes of the COMPANION trial. *JACC-Heart Fail.* 2016; 4:521-35.
77. Bristow M R, O'Connell J B, Gilbert E M, French W J, Leatherman G, Kantrowitz N E, Orie J, Smucker M L, Marshall G, Kelly P, Deitchman D, Anderson J L, for the Bucindolol Investigators. Dose-response of chronic beta-blocker treatment in heart failure from either idiopathic dilated or ischemic cardiomyopathy. *Circulation.* 1994; 89:1632-42.
78. Hein L, Altman J D, Kobilka B K. Two functionally distinct alpha2-adrenergic receptors regulate sympathetic neurotransmission. *Nature.* 1999; 402:181-84.
79. Taylor M R, Sun A Y, Davis G, Fiuzat M, Liggett S B, Bristow M R. Race, genetic variation, and therapeutic response disparities in heart failure. *JACC Heart Fail.* 2004; 2:561-72.
80. Small K M, Forbes S L, Rahman R F, Bridges K M, Liggett S B. A four amino acid deletion polymorphism in the third intracellular loop of the human $\alpha_{2C}$-adrenergic receptor confers impaired coupling to multiple effectors. *J Biol Chem.* 2000; 275:23059-64.
81. Bristow M R, Murphy G A, Krause-Steinrauf H, Anderson J L, Carlquist J F, Thaneemit-Chen S, Krishnan V, Abraham W T, Lowes B D, Port J D, Davis G W, Lazzeroni L C, Robertson A D, Lavori P W, and Liggett S B. An $\alpha_{2C}$-adrenergic receptor polymorphism alters the norepinephrine lowering effects and therapeutic response of the beta blocker bucindolol in chronic heart failure. *Circ Heart Fail.* 2010; 3:21-8.
82. Cohn J N, Pfeffer M A, Rouleau J, Sharpe N, Swedberg K, Straub M, Wiltse C, Wright T J; MOXCON Investigators. Adverse mortality effect of central sympathetic inhibition with sustained-release moxonidine in patients with heart failure (MOXCON). *Eur J Heart Fail.* 2003; 5:659-67.
83. Rienstra M, Damman K, Mulder B A, Van Gelder I C, McMurray J J, Van Veldhuisen D J. Beta-blockers and outcome in heart failure and atrial fibrillation: a meta-analysis. *JACC Heart Fail.* 2013; 1(1):21-8.
84. Bristow M R, Aleong R G. Treatment of the heart failure patient with atrial fibrillation: A major unmet need. *JACC Heart Fail.* 2013; 1:29-30.
85. Xenotech hepatic microsme in vitro bucindolol metabolism study (Parkinson Sr Au)
86. Eichhorn E J, Bristow M R. Medical therapy can improve the biologic properties of the chronically failing heart: A new era in the treatment of heart failure. *Circulation.* 94:2285-96.
87. Anderson J L, Gilbert E M, O'Connell J B, Renlund D, Yanowitz F, Murray M, Roskelley M, Mealey P, Volkman K, Deitchman D, Bristow M R. Long-term (2 year) beneficial effects of beta-adrenergic blockade with bucindolol in patients with idiopathic dilated cardiomyopathy. *J Am Coll Cardiol.* 1991; 17:1373-81.
88. Healey J S, Connolly S J, Gold M R, Israel C W, Van Gelder I C, Capucci A, Lau C P, Fain E, Yang S, Bailleul C, Morillo C A, Carlson M, Themeles E, Kaufman E S, Hohnloser S H; ASSERT Investigators. Subclinical atrial fibrillation and the risk of stroke. *N Engl J Med.* 2012 Jan. 12; 366(2):120-9.
89. Trulock K M, Narayan S M, Piccini J P. Rhythm control in heart failure patients with atrial fibrillation: contemporary challenges including the role of ablation. *J Am Coll Cardiol* 2014; 64:710-21.
90. Olsson L G, Swedberg K, Ducharme A et al. Atrial fibrillation and risk of clinical events in chronic heart failure with and without left ventricular systolic dysfunction: results from the Candesartan in Heart failure-Assessment of Reduction in Mortality and morbidity (CHARM) program. *J Am Coll Cardiol* 2006; 47:1997-2004.
91. Turagam M K, Garg J, Whang W et al. Catheter Ablation of Atrial Fibrillation in Patients With Heart Failure: A Meta-analysis of Randomized Controlled Trials. Ann Intern Med. 2019; 170(1):41-50.
92. Marrouche N F, Brachmann J, Andresen D et al. Catheter Ablation for Atrial Fibrillation with Heart Failure. *N Engl J Med* 2018; 378:417-427.

93. Nergårdh A K, Rosenqvist M, Nordlander R, Frick M. Maintenance of sinus rhythm with metoprolol C R initiated before cardioversion and repeated cardioversion of atrial fibrillation: a randomized double-blind placebo-controlled study. Eur Heart J 2007; 28:1351-7.
94. Spiegelhalter D J, Freedman L S, Blackburn P R. Monitoring clinical trials: conditional or predictive power? Control Clin Trials. 1986; 7(1):8-17.
95. Berry S M, Spinelli W, Littman G S, Liang J Z, Fardipour P, Berry D A, Lewis R J, Krams M. A Bayesian dose-finding trial with adaptive dose expansion to flexibly assess efficacy and safety of an investigational drug. Clin Trials. 2010; 7:121-35.
96. Steinhubl S R, Waalen J, Edwards A M et al. Effect of a Home-Based Wearable Continuous ECG Monitoring Patch on Detection of Undiagnosed Atrial Fibrillation: The mSToPS Randomized Clinical Trial. JAMA 2018; 320:146-155.
97. Turakhia M P, Desai M, Hedlin H et al. Rationale and design of a large-scale, app-based study to identify cardiac arrhythmias using a smartwatch: The Apple Heart Study. Am Heart J 2019; 207:66-75.
98. Wilson F P, Parikh C R. Translational Methods in Nephrology: Individual Treatment Effect Modeling. Am Soc Nephrol. 2018; 29:2615-18.
99. Toso E, Blandino A, Sardi D, Battaglia A, Garberoglio L, Miceli S, Azzaro G, Capello A L, Gaita F. Electrical cardioversion of persistent atrial fibrillation: acute and long-term results stratified according to arrhythmia duration. Pacing Clin Electrophysiol 2012; 35:1126-34.
100. Li D, Fareh S, Leung T K, Nattel S. Promotion of atrial fibrillation by heart failure in dogs: atrial remodeling of a different sort. Circulation 1999; 100:87-95.
101. GENETIC-AF Phase 3 Statistical Analysis Plan submitted to FDA on Mar. 30, 2017
102. DSMB Charter Version 2.0 submitted to FDA on Oct. 16, 2015
103. DSMB Charter White Paper submitted to FDA on Oct. 16, 2015
104. Davis B R, Kostis J B, Simpson L M, Black H R, Cushman W C, Einhorn P T, et al. and the ALLHAT Collaborative Research Group. Heart failure with preserved and reduced left ventricular ejection fraction in the antihypertensive and lipid-lowering treatment to prevent heart attack trial. Circulation. 2008; 118:2259-67.
105. Gupta D K, Shah A M, Castagno D, Takeuchi M, Loehr L R, Fox E R, Butler K R, Mosley T H, Kitzman D W, Solomon S D. Heart failure with preserved ejection fraction in African Americans: The ARIC (Atherosclerosis Risk In Communities) study. JACC Heart Fail. 2013 April; 1(2):156-63.
106. Butler J, et al. Developing Therapies for Heart Failure with Preserved Ejection Fraction: Current State and Future Directions. JACC Heart Fail. 2014 April; 2(2):97-112.
107. Butler J, et al. Exploring New Endpoints for Patients with Heart Failure with Preserved Ejection Fraction. Circ. Heart Fail. 2016; 9:e00358. DOI: 10.1161/CIRCHEARTFAILURE.116.003358
108. Kotecha, D, et al., Heart Failure With Preserved Ejection Fraction and Atrial Fibrillation. JACC 2016. 68(20): 2217-28.
109. Yancy, C W, et al., 2013 ACCF/AHA Guideline for the Management of Heart Failure. 2013, DOI: 10.1161/CIR.0b013e31829e8776.
110. Kirchof, P, et al., 2016 ESC Guidelines for the management of atrial fibrillation developed in collaboration with EACTS. Eur. Heart J. 2016. 37:2893-62.
Sara Goodwin, John D. McPherson and W. Richard McCombie, Coming of age: ten years of next-generation sequencing technologies, 17 Nature Revs. Genetics 333 (2016).
Camilla L. C. Ip et al., MinION Analysis and Reference Consortium: Phase 1 data release and analysis [version 1; referees: 2 approved], F1000Research.com 1 (Oct. 15, 2015), (f1000researchdata. s3.amazonaws.com/manuscripts/7757/69f3a63b-b808-447d-a1ca-f4548ce9fc57_7201_-_Camilla_Ip.pdf?doi=10.12688/f1000research.7201.1)
Jeffrey M. Perkel, Peter A. Fung, 2016 Next-Gen Sequencing Buyer's Guide, Biocompare.com (Aug. 30, 2016), (biocompare.com/190681-2016-NGS-Buyer-s-Guide/)
Oxford Nanopore Technologies, About us, Nanoporetech.com, (nanoporetech.com/about-us).
Daniel R. Garalde et al., Highly parallel direct RNA sequencing on an array of nanopores, BioR$_x$iv.org (Aug. 12, 2016) (biorxiv.org/content/biorxiv/early/2016/08/12/068809.full.pdf)

What is claimed is:

1. A method of maintaining a normal sinus rhythm in a patient, the method comprising administering an effective amount of bucindolol to a patient diagnosed with heart failure and atrial fibrillation who (a) has been tested and found to have a left ventricle ejection fraction greater than 0.40 and no more than 0.6; (b) has been genotyped as homozygous for Arg389 in the $\beta_1$AR gene.

2. The method of claim 1, wherein the atrial fibrillation is new onset, recurrent, ongoing, persistent, or paroxysmal atrial fibrillation.

3. The method of claim 1, wherein the patient has been tested and found to have a left ventricle ejection fraction of 0.45 or higher.

4. The method of claim 3, wherein the patient has been tested and found to have a left ventricle ejection fraction of 0.50-0.60.

5. The method of claim 1, wherein the patient has been tested and found to have a left ventricle ejection fraction of no more than 0.55.

6. The method of claim 3, wherein the patient has been tested and found to have a left ventricle ejection fraction of no more than 0.55.

7. The method of claim 4, wherein the patient has been tested and found to have a left ventricle ejection fraction of no more than 0.55.

8. The method of claim 1, wherein the patient is administered about 12.5 to 200 mg of bucindolol per day.

9. The method of claim 8, wherein the patient is administered bucindolol in 50 or 100 mg doses.

10. The method of claim 9, wherein the patient is administered bucindolol twice per day.

11. The method of claim 1, wherein the patient is administered about 0.15 to 5 mg/kg of bucindolol per day.

12. A method of maintaining a normal sinus rhythm in a patient previously diagnosed with heart failure and atrial fibrillation, the method comprising administering bucindolol after the patient is both measured as having a left ventricle ejection fraction of greater than 0.40 and no more than 0.55 and genotyped to be homozygous for Arg389 in the $\beta_1$AR gene.

13. The method of claim 12, wherein the atrial fibrillation is new onset, recurrent, ongoing, persistent, or paroxysmal atrial fibrillation.

14. The method of claim 12, wherein the patient has been measured as having a left ventricle ejection fraction of at least 0.45.

15. The method of claim 14, wherein the patient has been measured as having a left ventricle ejection fraction of at least 0.50.

16. The method of claim 15, wherein the patient is administered bucindolol in 50 or 100 mg doses.

17. The method of claim 16, wherein the patient is administered bucindolol twice per day.

18. The method of claim 12, wherein the patient is administered about 0.15 to 5 mg/kg of bucindolol per day.

19. A method of reducing atrial fibrillation burden in a patient, the method comprising administering 12.5 to 200 mg of bucindolol per day to a patient diagnosed with heart failure and atrial fibrillation and who (a) has been tested and found to have a left ventricle ejection fraction of greater than 0.4 and no more than 0.6; and (b) has been genotyped as homozygous for Arg389 in the $\beta_1 AR$ gene.

20. The method of claim 19 wherein the atrial fibrillation is new onset, recurrent, ongoing, persistent, or paroxysmal atrial fibrillation.

21. A method of maintaining a normal sinus rhythm in a heart failure patient, the method comprising administering 12.5 to 200 mg of bucindolol per day to a patient previously diagnosed with heart failure and atrial fibrillation and who (a) has been tested and found to have a left ventricle ejection fraction of 0.50-0.55; and (b) has been genotyped as homozygous for Arg389 in the $\beta_1 AR$ gene.

22. The method of claim 21, wherein the atrial fibrillation is new onset, recurrent, ongoing, persistent, or paroxysmal atrial fibrillation.

23. The method of claim 21, wherein the patient receives 50 or 100 mg of bucindolol twice per day.

24. The method of claim 19, wherein the administering reduces the atrial fibrillation burden in the patient.

* * * * *